United States Patent
Cioanta et al.

(10) Patent No.: US 10,888,715 B2
(45) Date of Patent: Jan. 12, 2021

(54) ACOUSTIC PRESSURE SHOCK WAVES USED FOR PERSONALIZED MEDICAL TREATMENT OF TISSUE CONDITIONS

(71) Applicant: SANUWAVE, INC., Suwanee, GA (US)

(72) Inventors: Iulian Cioanta, Milton, GA (US); Cary McGhin, Sugar Hill, GA (US); John Jackson, Buford, GA (US)

(73) Assignee: SANUWAVE, INC., Suwanee, GA (US)

( * ) Notice: Subject to any disclaimer, the term of this patent is extended or adjusted under 35 U.S.C. 154(b) by 499 days.

(21) Appl. No.: 15/858,458

(22) Filed: Dec. 29, 2017

(65) Prior Publication Data

US 2018/0221688 A1     Aug. 9, 2018

Related U.S. Application Data

(60) Provisional application No. 62/441,184, filed on Dec. 31, 2016.

(51) Int. Cl.
| | |
|---|---|
| A61N 7/00 | (2006.01) |
| G05B 13/02 | (2006.01) |
| G16H 40/63 | (2018.01) |
| A61N 5/06 | (2006.01) |
| A61N 5/067 | (2006.01) |

(Continued)

(52) U.S. Cl.
CPC ............. *A61N 7/00* (2013.01); *G05B 13/026* (2013.01); *G16H 40/63* (2018.01); *A61B 18/26* (2013.01); *A61B 2018/266* (2013.01); *A61N 5/0616* (2013.01); *A61N 2005/063* (2013.01); *A61N 2005/067* (2013.01); *A61N 2007/006* (2013.01); *A61N 2007/0017* (2013.01); *A61N 2007/0039* (2013.01); *G16H 20/40* (2018.01)

(58) Field of Classification Search
CPC .............. A61B 18/26; A61B 2018/266; A61N 2005/063; A61N 2005/067; A61N 2007/0017; A61N 2007/0039; A61N 2007/006; A61N 5/0616; A61N 7/00; G05B 13/026; G16H 20/40; G16H 40/63
See application file for complete search history.

(56) References Cited

U.S. PATENT DOCUMENTS

| 5,595,178 A | 1/1997 | Voss et al. |
|---|---|---|
| 6,080,119 A | 6/2000 | Schwarze et al. |
| 6,390,995 B1 | 5/2002 | Ogden et al. |

(Continued)

FOREIGN PATENT DOCUMENTS

WO     2016172433 A1     10/2016

OTHER PUBLICATIONS

International Search Report and the Written Opinion of the International Searching Authority; dated May 1, 2018; distributed by Lee W. Young of the ISA/US.

(Continued)

*Primary Examiner* — Michael T Rozanski
(74) *Attorney, Agent, or Firm* — Polsinelli PC; Eric J. Hanson, Esq.

(57) ABSTRACT

A system for individualized treatment of a tissue condition with acoustic pressure shocks includes personalized determination and automatic adjustment of a shock wave treatment regimen or shock wave dosage to be administered for personalized treatment based on factors such as a patient's comorbidities, state of the tissue condition, individual physical characteristics and lifestyle parameters.

26 Claims, 72 Drawing Sheets

(51) Int. Cl.
  *G16H 20/40* (2018.01)
  *A61B 18/26* (2006.01)

(56) References Cited

U.S. PATENT DOCUMENTS

| | | | |
|---|---|---|---|
| 6,413,230 | B1 | 7/2002 | Haupt et al. |
| 7,189,209 | B1 | 3/2007 | Ogden et al. |
| 8,961,441 | B2 | 2/2015 | Cioanta et al. |
| 9,198,825 | B2 | 12/2015 | Katragadda et al. |
| 2008/0033287 | A1 | 2/2008 | Schwarze et al. |
| 2008/0033323 | A1 | 2/2008 | Meirer et al. |
| 2012/0330194 | A1 | 12/2012 | Britva et al. |
| 2015/0005679 | A1 | 1/2015 | Becse et al. |
| 2016/0082290 | A1 | 3/2016 | Hart |

OTHER PUBLICATIONS

Measurement of Transcutaneous Oxygen Pressure in Normal and Ischaemic Skin, by G.S.E. Dowd et al, the Journal of Bone and Joint Surgery, vol. 65-B, No. 1, pp. 79-83, 1983.
The Pathogenesis of Burn Wound Conversion, by V. Singh et al, Annals of Plastic Surgery, vol. 59, No. 1, pp. 109-115, 2007.
Extracorporeal Shock Wave Therapy for Management of Chronic Ulcers in the Lower Extremities, by R. Saggini et al, Ultrasound in Medicine and Biology, vol. 34, No. 8, pp. 1261-1271, 2008.
Extracorporeal Shock Wave Treatment Modulates Skin Fibroblast Recruitment and Leukocyte Infiltration for enhancing Extended Skin-Flap Survival, by YR. Kuo et al, Wound Repair and Regeneration, vol. 17, No. 1, pp. 80-87, 2009.
Shock Wave Treatment Reduces Necrotic Flap Zones and Induces VEGF Expression in Animal Epigastric Skin Flap Model, by R. Meirer et al, Journal of Reconstructive Microsurgery, vol. 23, No. 4, pp. 231-236, 2007.
Pulsed Acoustic Cellular Treatment Induces Expression of Proangiogenic Factors and Chemokines in Muscle Flaps, by L. Krokowicz, et al, Journal of Trauma, Injury, Infection, and Critical Care, vol. 69, No. 6, pp. 1448-1456, 2010.
Pressure Ulcers: What Clinicians Need to Know, by W.T. Wake, the Permanente Journal, vol. 14, No. 2, pp. 56-60, 2010.
Factors Affecting Wound Healing, by S. Guo and L.A. DiPietro, Journal of Dentistry Research, vol. 89, No. 3, pp. 219-229, 2010.
Impact of Alcoholism and Alcohol Induced Disease on America, by Research Society on Alcoholism, 2011.
Pulsed Acoustic Cellular Expression as a Protective Therapy against I/R Injury in a Cremaster Muscle Flap Model, by L. Krokowicz, et al, Microvascular Research, vol. 83, No. 2, pp. 213-222, 2012.
Ankle Brachial Index and Transcutaneous Partial Pressure of Oxygen as Predictors of Wound Healing in Diabetic Foot Ulcers, by C.V. Lalithambika et al, the Journal of Diabetic Foot Complications, vol. 6, No. 4, pp. 54-59, 2014.
Burn Wound Healing and Treatment: Review and Advancements, by M.P. Rowan et al, Critical Care, pp. 1-12, 2015.
Extended European Search Report dated Jul. 30, 2020 in corresponding European Patent Application No. 17886438.5.

| Study Visit | ≥ 50% Wound Area Reduction | | | | | | $\chi^2$ p-value |
|---|---|---|---|---|---|---|---|
| | Shock Wave Treated | | | Sham Control | | | |
| | N | n | % | N | n | % | |
| Week 0 | 172 | 5 | 2.91 | 164 | 5 | 3.05 | 0.939 |
| Week 2 | 172 | 74 | 43.02 | 164 | 57 | 34.76 | 0.120 |
| Week 4 | 172 | 88 | 51.16 | 164 | 67 | 40.85 | 0.058 |
| Week 6 | 172 | 99 | 57.56 | 164 | 78 | 47.56 | 0.067 |
| Week 8 | 172 | 105 | 61.05 | 164 | 84 | 51.22 | 0.069 |
| Week 10 | 172 | 112 | 65.12 | 164 | 91 | 55.49 | 0.071 |
| Week 12 | 172 | 115 | 66.86 | 164 | 93 | 56.71 | 0.055 |
| Week 14 | 172 | 117 | 68.02 | 164 | 98 | 59.76 | 0.115 |
| Week 16 | 172 | 119 | 69.19 | 164 | 99 | 60.37 | 0.090 |
| Week 18 | 172 | 119 | 69.19 | 164 | 100 | 60.98 | 0.114 |
| Week 20 | 172 | 121 | 70.35 | 164 | 101 | 61.59 | 0.089 |
| Week 22 | 172 | 121 | 70.35 | 164 | 101 | 61.59 | 0.089 |
| Week 24 | 172 | 121 | 70.35 | 164 | 101 | 61.59 | 0.089 |

Figure 4

| Demographic | | Shock Wave Treated | | | Sham Control | | | p-value |
|---|---|---|---|---|---|---|---|---|
| | | N | n | % | N | n | % | |
| Age (years) | < 65 | 120 | 45 | 37.5 | 129 | 33 | 25.6 | 0.043 |
| | ≥ 65 | 52 | 20 | 38.5 | 35 | 10 | 28.6 | 0.341 |
| Sex | Male | 137 | 55 | 40.1 | 132 | 33 | 25.0 | 0.008 |
| | Female | 35 | 10 | 28.6 | 32 | 10 | 31.3 | 0.811 |
| Smoking Status | Non-Users | 146 | 54 | 37.0 | 133 | 35 | 26.3 | 0.056 |
| | Users | 26 | 11 | 42.3 | 31 | 8 | 25.8 | 0.188 |
| BMI (kg/m$^2$) | < 32 | 84 | 38 | 45.2 | 87 | 22 | 25.3 | 0.006 |
| | ≥ 32 | 88 | 27 | 30.7 | 77 | 21 | 27.3 | 0.631 |
| Weight (pounds) | < 220 | 86 | 35 | 40.7 | 78 | 21 | 26.9 | 0.063 |
| | ≥ 220 | 86 | 30 | 34.9 | 86 | 22 | 25.6 | 0.184 |
| Height (inches) | < 70 | 72 | 20 | 27.8 | 72 | 25 | 34.7 | 0.369 |
| | ≥ 70 | 100 | 45 | 45.0 | 92 | 18 | 19.6 | 0.0002 |
| Ulcer Age (months) | < 6 | 91 | 44 | 48.4 | 75 | 27 | 36.0 | 0.109 |
| | ≥ 6 | 81 | 21 | 25.9 | 89 | 16 | 18.0 | 0.210 |
| HbA1c | < 7 | 55 | 20 | 11.6 | 46 | 14 | 8.5 | 0.581 |
| | ≥ 7 | 115 | 45 | 26.2 | 116 | 29 | 17.7 | 0.021 |

Figure 7

ACOUSTIC PRESSURE SHOCK WAVES USED FOR PERSONALIZED MEDICAL TREATMENT OF TISSUE CONDITIONS

CROSS-REFERENCE TO RELATED APPLICATIONS

This application claims the benefit of priority of U.S. provisional application No. 62/441,184, filed Dec. 31, 2016, which is incorporated herein by reference in its entirety.

BACKGROUND OF THE INVENTION

The present invention shows methods and devices that use acoustic pressure shock waves or acoustic pressure waves for treating acute or chronic tissue conditions (for both humans and animals) by using a personalized approach based on patient's comorbidities and other aspects, such as health conditions, personal parameters and the like, that might influence the successful outcome of the treatment. Practically, the dosage of acoustic pressure shock waves used for treatment of skin is adjusted via an algorithm that employs specific factors that take into account patient's comorbidities and other parameters related to state of damaged tissue.

Common tissue conditions can be categorized as skin discolorations (red birthmarks, hemangiomas, moles, freckles, melisma, and skin tags), chronic skin problems (eczema, psoriasis, acne, rosacea, porphyria, pyodema gangrenosum, and skin ulcers), acute skin problems (cold sores, plantar and palmer warts, hair loss, blisters, chafing, corns and calluses, sunburn, burns, ingrown hair, gangrene, rashes, dermatitis, itching, cysts, skin lumps, urticarial, alopecia areata, vitiligo, varicose veins, spider veins, intertrigo, lice, scabies, bruises, epidermoid cysts, and keloids), tissue infections (can be bacterial as leprosy, carbuncles, staph infection as impetigo, boils, pilonidal cysts, abscess, also fungal as fungal skin infections, tinea, athlete's foot, candidiasis, sporotrichosis, fungal nail infection, and finally viral as molluscum contagiosum, shingles, and chickenpox), and skin cancer (melanoma and carcinoma).

The etiology of the above mentioned tissue conditions can be diverse (environmental, genetic, immunologic, bacterial, viral, fungal, etc.). However, some of the most common chronic tissue conditions are produced due to ischemic disorders or in general due to poor blood circulation in the affected area. Also, some of the acute tissue conditions can degenerate from acute to a chronic situation due to infections and ischemia or poor blood circulation. In clinical studies conducted in animal and humans, acoustic pressure shock waves demonstrated positive results in treating different soft or hard tissues with ischemic conditions and for healing diverse chronic wounds (diabetic foot ulcers (DFUs), arterial ulcers, venous ulcers, pressure sores, to name a few). Furthermore, the acoustic pressure shock waves showed very promising results in treating acute conditions where the skin is breached as with traumatic wounds, burns, reconstructive skin flaps, surgical wounds, etc. Some treatments that involve the use of acoustic pressure shock waves for bone defects and chronic wounds have also been patented.

For example, U.S. Pat. No. 5,595,178 shows the use of extracorporeal acoustic pressure shock waves in the treatment of chronic bone gaps by producing mechanical vibrations into the tissues around the bone gap and thus filling the gap and accelerating the healing. Bone gaps non-unions are generated by poor healing process produced by ischemic conditions.

U.S. Pat. No. 6,390,995 presents a method of treating an ischemic condition associated with soft tissue adjacent to a musculoskeletal environment that involves applying acoustic pressure shock waves to cause micro-disruptions, non-osseous tissue stimulation, increased vascularization, and circulation and induction of growth factors to induce or accelerate the body's natural healing processes and responses.

Also, U.S. Pat. No. 7,189,209 describes a method of treating pathological conditions associated with bone and musculoskeletal environments and soft tissues that involves applying acoustic pressure shock waves to cause localized trauma, including micro-disruptions, non-osseous tissue stimulation, increased vascularization, and circulation and induction of growth factors to induce or accelerate the body's natural healing processes and responses. The specific claims of the patent refer to the application of acoustic pressure shock waves for the treatment of diabetic foot ulcers and pressure sores.

Acoustic pressure shock waves are also known to have antibacterial effects demonstrated in vitro and in vivo against bacteria under both static and dynamic growth conditions. The acoustic pressure shock waves have similar action on viruses, funguses and other harmful micro-organisms that may be the origin of different tissue conditions. Thus the tissue conditions categorized as skin infections can also be treated with acoustic pressure shock waves, as presented in patent application PCT/US 16/2877. For some of the chronic and acute tissue conditions that are the subject of described treatment solutions, infections can occur and the antibacterial effect of the acoustic pressure shock waves can assist the healing process of the respective skin/tissue condition during its treatment with acoustic pressure shock waves.

SUMMARY OF THE INVENTION

The acoustic pressure shock waves and treatment methodologies described herein demonstrated positive results in treating different soft or hard tissues with ischemic conditions and for healing diverse chronic wounds (diabetic foot ulcers—DFUs, arterial ulcers, venous ulcers, pressure sores, to name a few). Furthermore, the acoustic pressure shock waves and treatments provided very promising results in treating acute conditions where the skin is breached as with traumatic wounds, burns, reconstructive skin flaps, surgical wounds, etc.

For tissue conditions (both chronic and acute), in general conventional acoustic pressure shock wave treatment regimens are fixed/predetermined (number of pulses, frequency, energy setting, and total number of treatments) for each specific skin condition and do not take into account a patient's comorbidities, medical history, biometrics or personal habits (smoking, drinking, etc.). For example, patients with significant cardio-vascular problems would respond much slower to any type of treatment related to chronic tissue conditions. Poor blood circulation and ischemic conditions will impair the healing process, due to the lack of nutrients in the affected area. The same can be said about the patients that have diabetes mellitus. To address these shortcomings, the present invention teaches the use of acoustic pressure shock waves for treating acute or chronic tissue conditions (for both humans and animals) in a personalized/tailored manner that takes into account the general health status, personal habits, and biometrics of the patient and the status of damaged skin tissue to provide personalized and more effective treatment with acoustic pressure shock waves.

In general for tissue conditions, these conventional fixed/predetermined treatment regimens that employ acoustic pressure shock waves are calculated based on the total area of the affected zone that needs to be treated with fixed/predetermined parameters. The treatment area can include one wound or multiple wounds and it is also traced/determined with extra centimeters in each direction around the perimeter of the wound/wounds to be able to treat the chronic wound bed starting from healthy tissue/well-perfused tissue positioned adjacent to the targeted area (see FIG. 3).

The extracorporeal acoustic pressure shock waves produced by the proposed embodiments will have a compressive phase (produces high compressive pressures) and a tensile phase (produces cavitation bubbles that collapse with high speed jets) during one cycle of the acoustic pressure shock waves. This two synergetic effects work in tandem by acting at macro (compressive phase) and micro level (cavitation jets of the tensile phase), which is enhancing the effects of the acoustic pressure shock waves in the living tissue. The high mechanical tension and pressure found at the front of the acoustic pressure shock wave distinguishes the acoustic pressure shock waves from other kinds of sound waves, such as ultrasonic waves. The acoustic pressure shock waves generated for medical purposes consist of a dominant compressive pressure pulse, which climbs steeply up to maximum one hundred Mega-Pascals (MPa; 1 MPa=10 bar) within a few nanoseconds and then falls back to zero within a few microseconds. The final portion of the acoustic pressure shock wave pressure profile is characterized by low negative pressures (tensile region of the acoustic pressure shock wave), with potential to generate cavitation in body fluids. The bubble diameter grows as the energy is delivered to the bubble. This energy is released from the bubble during its collapse (implosion) in the form of high speed pressure micro jets and localized/transient high temperature. The micro jets and elevated temperature are present within focal microscopic tissue volumes.

Acoustic pressure shock waves behave similarly to sound waves, with the main difference that the acoustic pressure shock waves possess more energy. An acoustic pressure shock wave can travel large distances easily, as long as the acoustic impedance of the medium remains the same. At the point where the acoustic impedance changes, energy is released and the acoustic pressure shock wave is reflected or transmitted with attenuation. Thus the greater the change in acoustic impedance between different substances, the greater the release of energy is generated. Based on this principle of energy deposition inside the leaving tissue when the acoustic impedance changes, the acoustic pressure shock waves are used in medical field to break kidney or gallbladder stones, to stimulate tissue growth, and to regenerate bones, muscle, skin, tendons, and the like.

For acoustic pressure shock waves or acoustic pressure waves to be effective in the clinical applications, they are usually focused or concentrated (semi-focused) or completely unfocused when sent towards the point at which treatment is to be provided. In the treated region in general there are two basic effects, with the first being characterized as direct generation of mechanical forces (primary effect from the positive, compressive high pressure rise), and the second being the indirect generation of mechanical forces (high velocity pressure micro jets) produced by cavitation (secondary effect from the negative, tensile pressure region).

In lithotripsy, cavitation is believed to be the primary cause of stone disintegration. In orthopedics, the acoustic pressure shock waves have been shown to positively affect bone and soft tissue, beginning a regeneration process, due to synergy between the high compressive pressures applied to the tissue (macro effect) and the collapse of the cavitation bubbles with high speed micro jets from the tensile phase (micro effect). For soft tissue treatment (as in pressure sores, chronic arterial and venous ulcers, diabetic foot ulcers, burns, etc.), the acoustic pressure shock waves are highly controlled to produce an energy output that will not produce any tissue injury. This is accomplished based on reflector geometry and material, energy setting (energy level of the acoustic pressure shock waves), and dosage (number of acoustic pressure shock waves and their frequency per second that dictates the total acoustic pressure shock waves delivered in one session). Reflector geometry directly shapes the focal volume and its position in space for the focused acoustic pressure shock waves.

The energy settings (energy input into acoustic pressure shock waves) directly affect the pressure output of the acoustic pressure shock waves and together with dosages (number of acoustic pressure shock waves and their frequency per second), determine the amount of energy deposited inside the tissue from the targeted treatment region. The peak positive compressive pressures of the acoustic pressure shock waves are concentrated to a specifically localized region causing a macro tissue disruption, movement or stretching of the tissue in the treatment region at amplitudes sufficient to disturb the tissue/cells but not cause damage, which initiates the cellular signaling for growth factors and other proteins. At the energy levels and dosages used in tissue regeneration, cavitation occurring in the negative pressure phase is also triggering cellular signaling without any damage. Pyrolysis produced by cavitation may be responsible for the observed Reactive Oxygen Species (ROS) expression as evidenced by up-regulation of endothelial constitutive nitric oxide synthase (eNOS). The negative pressure of the tensile phase may also release oxygen bound to plasma and hemoglobin and thus becoming a source of the immediate increased oxygenation, which attracts macrophages to the treatment site and begins the signaling for chemokines and cytokines, as observed in clinical studies.

These tissue (macro level) and cellular (micro level) disruptions are hypothesized to be the source of cellular expression seen in the laboratory and clinical work, when tissue is treated with acoustic pressure shock waves that provides the necessary triggering to start or re-start the body's natural healing process. The initial response to the acoustic pressure shock waves application promotes microcirculatory improvement. Continued effects after treatment include modulation of inflammatory and perfusion responses, an increase in capillary perfusion and vessel permeability, cellular signaling that initiates angiogenic growth factor and protein upregulation, and initiates proangiogenic growth factors (as vessel endothelial growth factor—VEGF) production leading to new vascularization. As a result, a chronic condition can be returned to an acute condition, jumpstarting the body's own healing response.

The increase in blood perfusion is important as it is by definition a decrease in the ischemia (lack of blood flow) that is often associated with impaired tissue conditions healing. As the cells of the microcirculatory system are disrupted by the acoustic pressure shock waves, there is an immediate change in local blood flow to the treated area, due to relaxation of local arterioles and increase in their diameter. This effect, in combination with unaltered blood flow, results in better perfusion and oxygenation. The vessel permeability index (VPI) simultaneously increases directly after acoustic pressure shock wave treatment This is a measure of the plasma or fluid content of the blood "leaking" from the vessel walls, and more fluid exchange increases the exchange of nutrients and gases between blood vessels and tissue cells in the treatment area. Thus the acoustic pressure shock waves show that more leukocytes (white blood cells) beginning to roll and stick to the blood vessel walls, finally transmigrating through the vessel wall and into the treatment region. Increasing leukocyte activation assists in the inflammatory phase of wound healing by triggering the release of pro-angiogenic factors. An inflammatory modulation response is apparent after acoustic pressure shock wave treatment. Down-regulation of inducible nitric oxide synthase (iNOS), which is an inflammatory marker, has also been demonstrated along with up-regulation of pro-inflammatory chemokines. The treatment is shown to blunt poly morphonuclear neutrophil and macrophage infiltration into the wound (burn model), which reduces the excessive inflammatory state of severe wounds. The chemokine driven, heightened inflammatory nature of difficult to heal wounds, and the favorable response to acoustic pressure shock waves provides a basis for the use of this technology in difficult to heal wounds. In addition to chemokine overproduction, the suppression of pro-inflammatory cytokines (IL-1β, IL-6, and TNFα) in response to acoustic pressure shock wave treatment is significant in that over-expression of these genes has been associated with impaired healing. Finally, acoustic pressure shock wave treatment is associated with downregulation of matrix metalloproteinases (MMPs) and TIMP-1 metallopeptidase inhibitor 1, which are remodeling proteins reported to be elevated in chronic wounds in comparison to acute wounds.

These factors effectively allow a wound to move through the inflammatory phase quickly and into the proliferation (cell growth) phase of healing. The shortened inflammatory phase noticed after acoustic pressure shock waves treatment may be beneficial to long term healing. During inflammation, undifferentiated collagen tissue is produced as the body attempts to simply cover and constrict an open wound. This necessary but hasty tissue formation results in scar formation, poor healing and constriction. By shortening this inflammatory phase, the scar tissue is less apparent, more subtle and does not constrict mobility.

Different factors can influence the healing process of tissue conditions such as presence of diabetes (determined via glycated hemoglobin HbA1c that is an average blood sugar levels have been over a period of weeks/months), location of the wound, occurrence of peripheral arterial disease (measured via ankle-brachial index—ABI), chronicity/age of skin condition (via age, grade/stage/degree and depth of the lesion produced by skin condition), patient degree of obesity (taken into account via body mass index—BMI, weight and height), tissue oxygenation around skin lesion (measured via transcutaneous monitoring of oxygen—$T_cP_{O2}$), reoccurrence of the skin condition, bacterial load, patient's smoker status, habits in consumption of alcohol or pre-existing conditions created by cancer, immunodeficiency, or steroids treatments. A short introduction to some of these factors is presented below.

The term HbA1c refers to glycated hemoglobin. It develops when hemoglobin, a protein within red blood cells that carries oxygen throughout the body, joins with glucose in the blood, becoming 'glycated'. By measuring glycated hemoglobin (HbA1c), clinicians are able to get an overall picture of what our average blood sugar levels have been over a period of weeks/months. For people with diabetes this parameter is important as the higher the HbA1c is the greater the risk of developing diabetes-related complications. When the body processes sugar, glucose in the bloodstream naturally attaches to hemoglobin. The amount of glucose that combines with the hemoglobin is directly proportional to the total amount of sugar that is in system at that time. Because red blood cells in the human body survive for 8-12 weeks before renewal, measuring glycated hemoglobin (or HbA1c) can be used to reflect average blood glucose levels over that duration, providing a useful longer-term gauge of blood glucose control. If the blood sugar levels are high over a period, then the HbA1c will also be greater. For diabetes mellitus patients, higher amounts of glycated hemoglobin, indicates poorer control of blood glucose levels, and it is associated with cardiovascular disease, nephropathy, neuropathy, and retinopathy. Monitoring by caregivers of HbA1c leads to changes in diabetes treatment and improvement of metabolic control compared to monitoring only of blood or urine glucose.

An important test that is used to predict the severity of peripheral arterial disease (PAD) is the ankle-brachial index (ABI). This test is done to check for peripheral arterial disease of the legs and is determined by measuring blood pressure at the ankle and in the arm while a person is at rest. Some people also do an exercise test. In this embodiment, the blood pressure measurements are repeated at both sites after a few minutes of walking on a treadmill. A slight drop in ABI with exercise means that the patient have PAD. This drop may be important, because PAD can be linked to a higher risk of heart attack or stroke. A lower ABI means that the patient might have PAD, which is a significant impediment in healing lesions produced by tissue conditions on legs and arms. ABI is also used to see how well a treatment is working (such as medical treatment, an exercise program, angioplasty, or surgery). This test might be done also to check patient's risk of heart attack and stroke. A normal resting ankle-brachial index is 1.0 to 1.4. This means that patient's blood pressure at ankle is the same or greater than the pressure at the arm, and suggests that the patient does not have significant narrowing or blockage of blood flow. Abnormal values for the resting ankle-brachial index are 0.9 or lower and 1.4 or higher. If the ABI is 0.91 to 1.00, it is considered borderline abnormal. Abnormal values might mean that the patient have a higher chance of having narrowed arteries in other parts of the body, which can increase the risk of a heart attack or stroke. Thus an ABI less than 0.9 indicates arterial disease and an ABI value of 1.4 or greater is also considered abnormal, and suggests calcification of the walls of the arteries and incompressible vessels, reflecting severe peripheral vascular disease.

The body mass index (BMI) is a value derived from the mass (weight) and height of an individual. The BMI is defined as the body mass divided by the square of the body height, and is universally expressed in units of $kg/m^2$, resulting from mass in kilograms and height in meters. The BMI is an attempt to quantify the amount of tissue mass (muscle, fat, and bone) in an individual, and then categorize that person as underweight, normal weight, overweight, or obese based on that value. However, there is some debate about where on the BMI scale the dividing lines between categories are preferably placed. Commonly accepted BMI ranges are underweight: under 18.5 $kg/m^2$, normal weight: 18.5 to 25, overweight: 25 to 30, obese: over 30.

The exponent in the denominator of the formula for BMI is arbitrary. The BMI depends upon weight and the square of height. Since mass increases to the $3^{rd}$ power of linear dimensions, taller individuals with exactly the same body shape and relative composition have a larger BMI. So short people are misled into thinking that they are thinner than they are, and tall people are misled into thinking they are fatter. This is why the weight and height of the patient are preferably taken into account besides the BMI, in order to determine if a person is obese or not.

Transcutaneous monitoring of oxygen ($T_cP_{O2}$) and carbon dioxide ($TcPCo_2$) originally developed for neonatal use, has become a routine measurement in several clinical areas including determination of peripheral vascular oxygenation, quantification of the degree of peripheral vascular disease, determination of the optimum level of amputation, evaluation of revascularization procedures, and selecting candidates for hyperbaric oxygen therapy and predicting non-responders to treatment. $T_cP_{O2}$ provides instant, continuous information about the body's ability to deliver oxygen to the tissue. $T_cP_{O2}$ is dependent on oxygen uptake in the respiratory system, the oxygen transport/capacity of the blood and the general status of the circulatory system. Any impairment of the organism's ability to deliver oxygen to the tissue will be revealed immediately since the skin is ranked very low in the body's system of oxygenation priority. Transcutaneous monitoring of oxygen ($T_cP_{O2}$) measurements usually require at least two or three sites to provide a good picture. The more sites assessed, the better the oxygenation picture. Technically, the electrode heats the underlying tissue to create a local hyperemia, which intensifies the blood perfusion, increasing the oxygen pressure. In addition, the heat will dissolve the lipid structure of the dead, keratinized cells in the epidermal layer making the skin permeable to gas diffusion. On its way the oxygen may be consumed by the cells, if the metabolism is high. Note that transcutaneous oxygen is not the same as the arterial oxygen pressure measured using standard pulse oximeters. Transcutaneous monitoring of oxygen ($T_cP_{O2}$) is a local, non-invasive measurement reflecting the amount of $O_2$ that has diffused from the capillaries, through the epidermis. Studies have shown that $T_cP_{O2}$ is related to the degree of ischemia. Some studies have shown that ABI has significant limitations for diagnosing and treating critical limb ischemia patients compared with $T_cP_{O2}$. Besides transcutaneous monitoring of oxygen ($T_cP_{O2}$) there are other methods to determine the oxygenation via blood analysis or specialized devices. For example, oxygen saturation is a term referring to the fraction of oxygen-saturated hemoglobin relative to total hemoglobin (unsaturated+saturated) in the blood. The human body requires and regulates a very precise and specific balance of oxygen in the blood. Normal blood oxygen levels in humans are considered 95-100 percent. If the level is below 90 percent, it is considered low resulting in hypoxemia. Thus it appears that a $T_cP_{O2}$ below 40 millimeters of mercury is preferably related to a severe circulatory disturbance in the cutaneous tissues related to impaired wound healing and a value less than 30 millimeters of mercury indicates critical limb ischemia. Values above 40 millimeters of mercury indicates normal values.

To determine oxygen saturation via blood analysis from the patient, the arterial oxygen saturation (SaO2) is determined by an arterial blood gas test, and a value below 60% causes hypoxemia (which can also be caused by anemia). Hypoxemia due to low SaO2 is indicated by cyanosis. Oxygen saturation can be measured in different tissues. Venous oxygen saturation (SvO2) is measured using blood analysis to see how much oxygen the body consumes. Under clinical treatment, a SvO2 below 90% indicates that the body is in lack of oxygen, and ischemic diseases occur. Another test that can be performed is the tissue oxygen saturation (StO2) that can be measured by near infrared spectroscopy (using non-invasive optical devices). Although the measurements are still widely discussed, they give an idea of tissue oxygenation in various conditions, which is very important to determine the optimal area that needs to be treated around the actual wound, as presented in FIG. 3. Finally, peripheral oxygen saturation (SpO2) is an estimation of the oxygen saturation level usually measured with a pulse oximeter device.

All of the above tests (individual or in combination) can be used to determine the level of oxygenation of the tissue bellow the skin lesion or around it and can substitute the transcutaneous monitoring of oxygen ($T_cP_{O2}$), which is used in the embodiments of this invention, as a measure of tissue oxygenation.

Besides the factors that influence the treatments regimen (as presented in the exemplary embodiments of this specification) other parameters can be added for each type of tissue condition to create new improved customized/personalized treatments, which means that this invention is not limited to the examples presented by the described embodiments.

In addition to number of acoustic pressure shock waves (also known as dosage) that are tailored/personalized to a certain patient (as presented in the exemplary embodiments), customized algorithms can be created to change the total number of treatments or the energy setting that are used during the treatment with acoustic pressure shock waves for tissue conditions.

Furthermore, closed-loop systems can be used that are monitoring biological conditions in real time and adjust the acoustic pressure shock wave therapy accordingly. In the case of skin damage treatments, the closed-loop systems can monitor the blood circulation, tissue oxygenations, etc.

Treatments with acoustic pressure shock waves is non-exclusive to other treatments and can be applied as an additional therapy that do not interfere with other treatments and be most likely to impart a synergistic effect that improves/expedites the healing process.

BRIEF DESCRIPTION OF THE DRAWINGS

FIG. 4 is table of the clinical data from a randomized double-blinded clinical trial for chronic wound care, using acoustic pressure shock waves as active treatment that shows in a tabular form the number of patients with 50% wound area reduction.

FIG. 7 is a tale of the clinical data from a randomized double-blinded clinical trial for chronic wound care, using acoustic pressure shock waves as active treatment, which shows in a tabular form the number of patients with complete wound closure for sub-groups based on age, sex, smoking status, BMI, weight, height, wound age and diabetes presence.

DETAILED DESCRIPTION OF THE INVENTION

Embodiments of the invention will be described with reference to the accompanying figures, wherein like numbers represent like elements throughout. Further, it is to be understood that the phraseology and terminology used herein is for the purpose of description and should not be regarded as limiting. The use of "including", "comprising", or "having" and variations thereof herein is meant to encompass the items listed thereafter and equivalents thereof as well as additional items. The terms "connected", and "coupled" are used broadly and encompass both direct and indirect mounting, connecting, and coupling. Further, "connected" and "coupled" are not restricted to physical or mechanical connections or couplings.

It is an objective of the present inventions to provide acoustic pressure shock waves generating devices that are modular, do not need high maintenance and can, if needed, be applied/used in conjunction with other devices, drugs, methods and existing treatments for tissue conditions (for both therapy and prophylactic use).

Figure 1A:
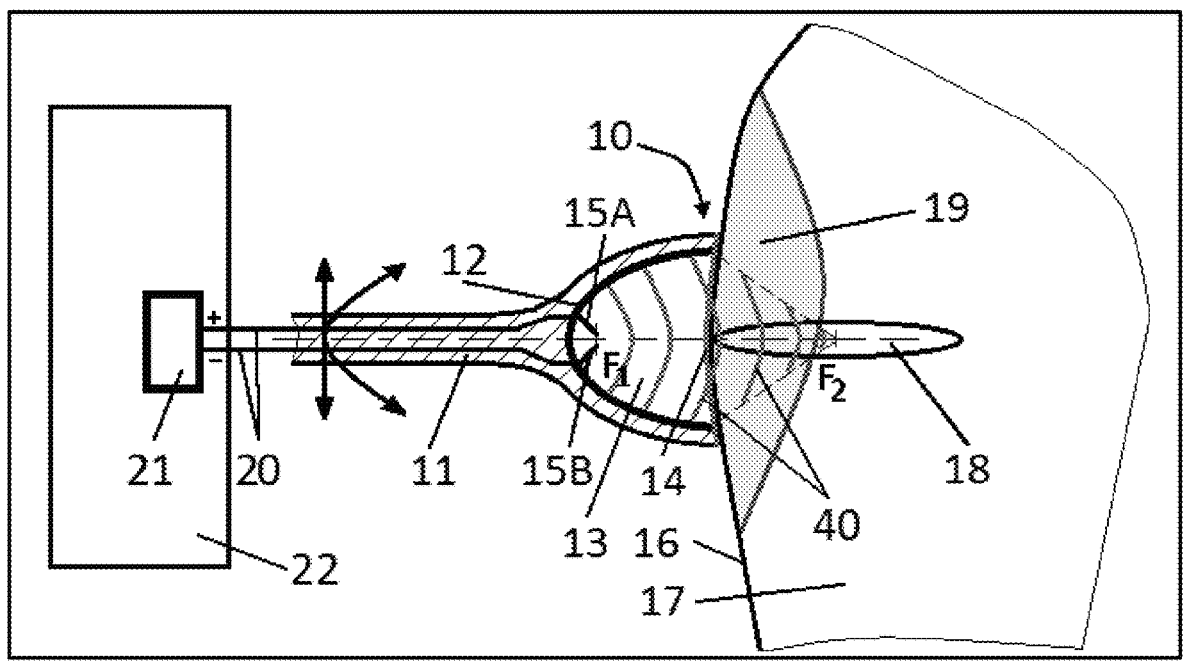
FIG. 1A is a schematic view of application of acoustic pressure shock waves to a tissue condition via electrohydraulic generators using discharges of high voltage spark-gap electrodes, according to one embodiment of the present invention.
Figure 1B:
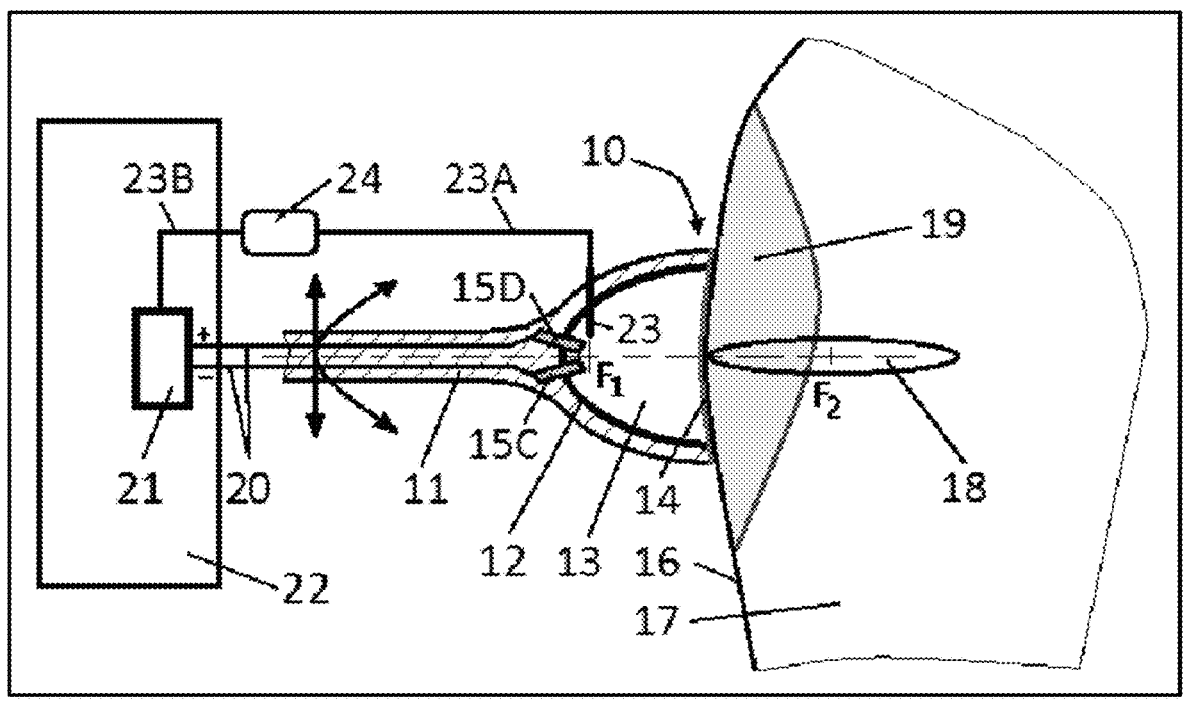
FIG. 1B is a schematic view of application of acoustic pressure shock waves to a tissue condition via electrohydraulic generators using one or multiple laser sources, according to one embodiment of the present invention.
Figure 1C:
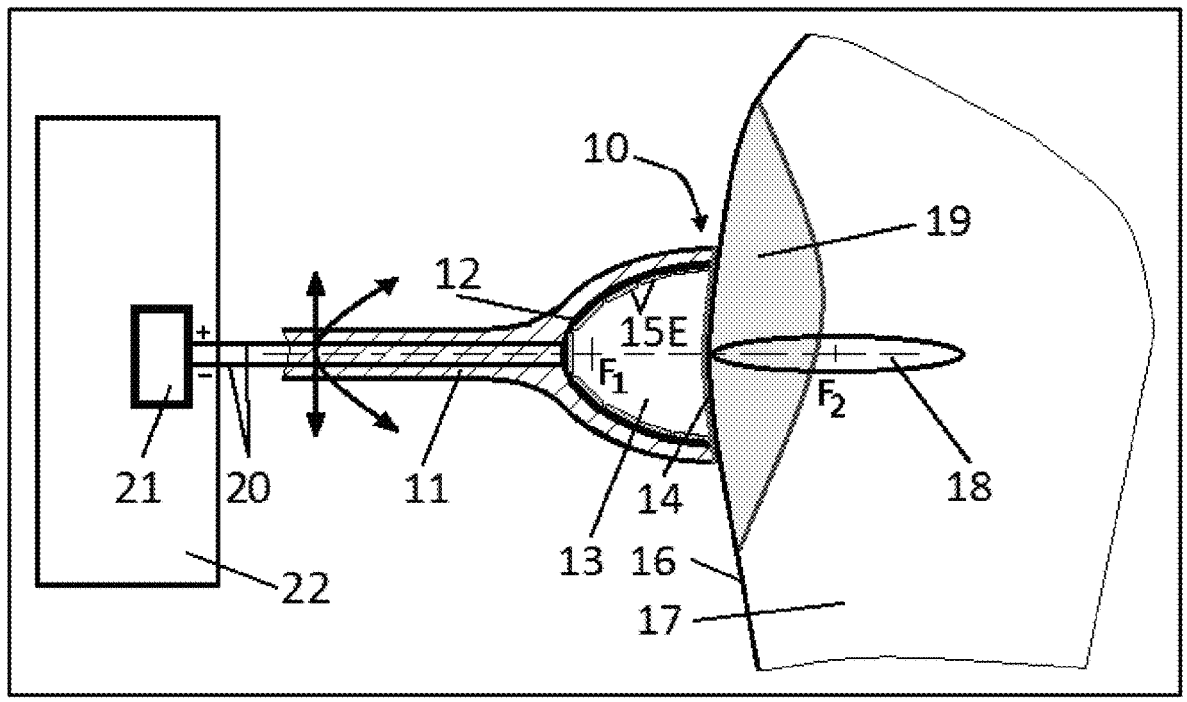
FIG. 1C is a schematic view of application of acoustic pressure shock waves to a tissue condition via piezoelectric generators using piezo crystals, according to one embodiment of the present invention.
Figure 1D:
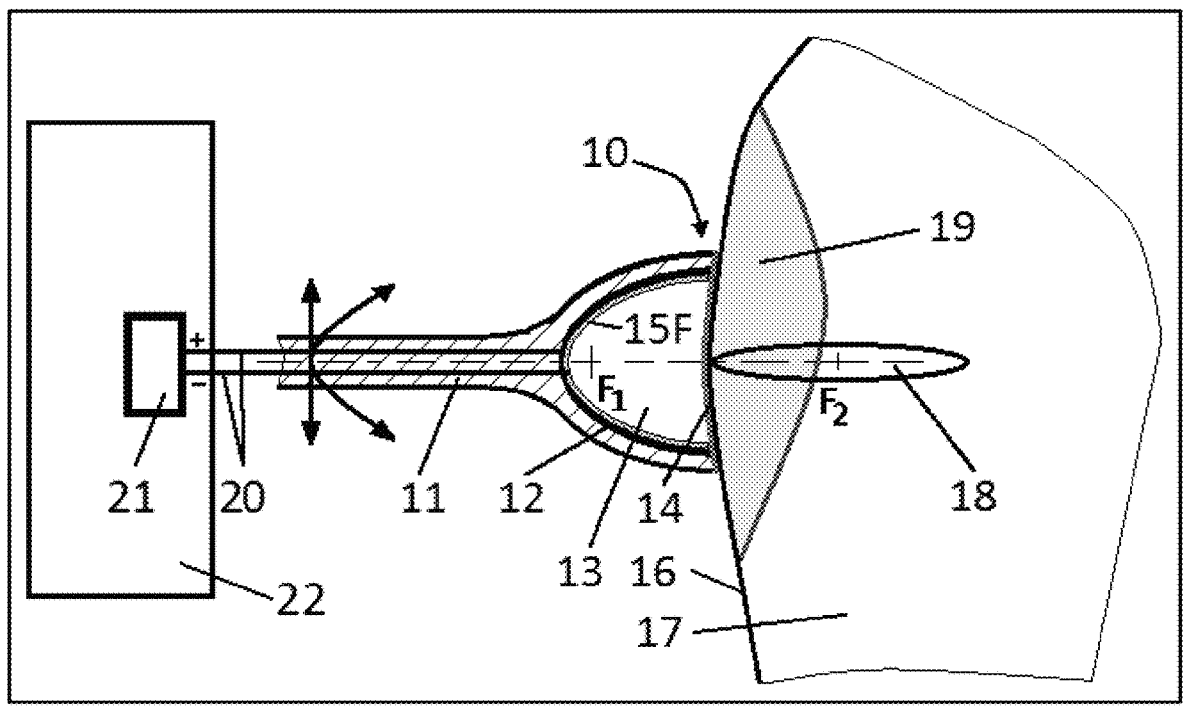
FIG. 1D is a schematic view of application of acoustic pressure shock waves to a tissue condition via piezoelectric generators using piezo fibers, according to one embodiment of the present invention.
Figure 1E:
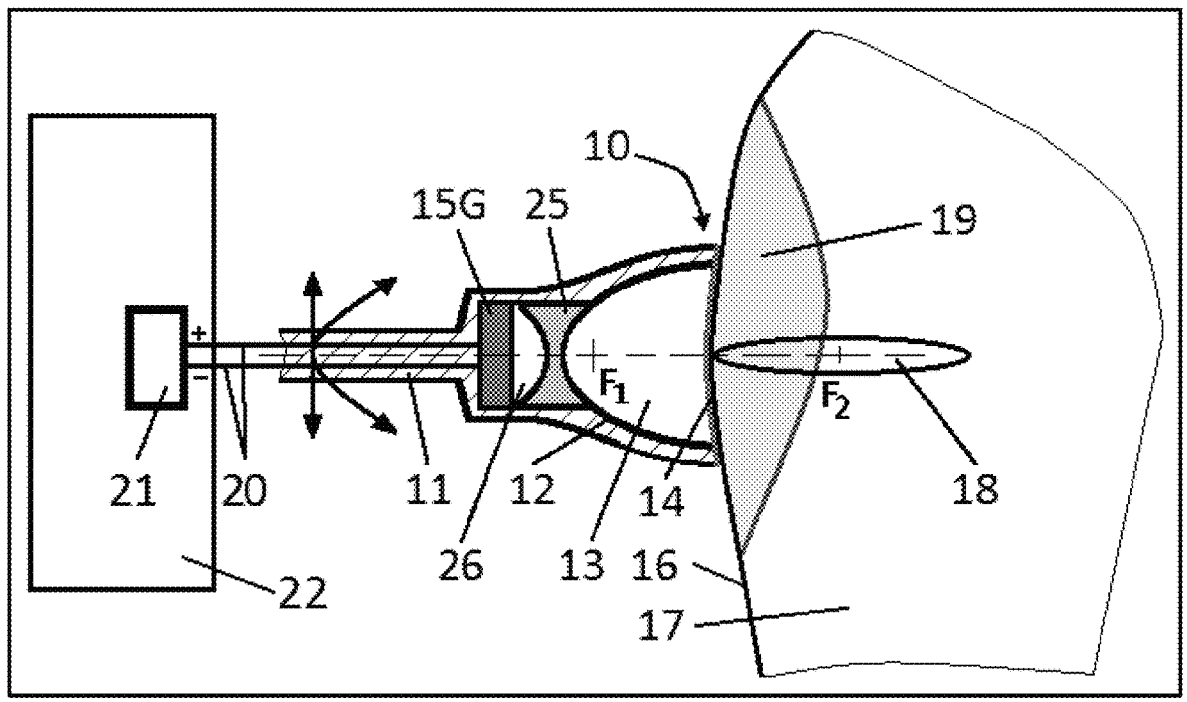
FIG. 1E is a schematic view of application of acoustic pressure shock waves to a tissue condition via electromagnetic generators using a flat coil and an acoustic lens, according to one embodiment of the present invention.
Figure 1F:
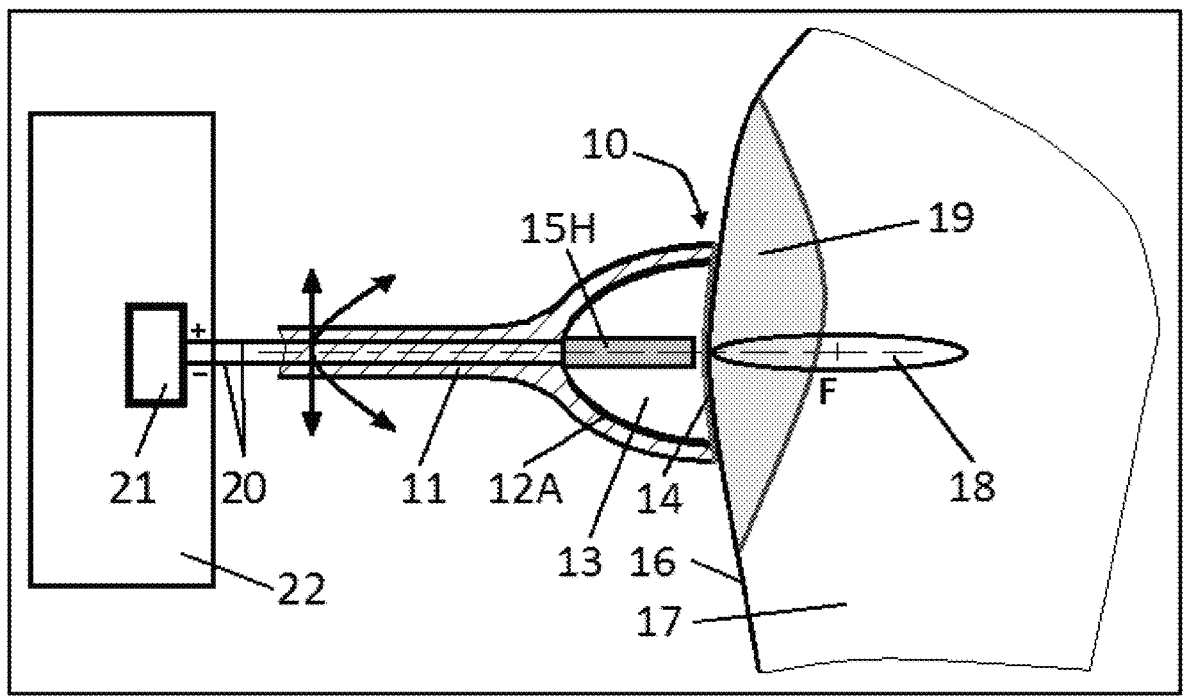
FIG. 1F is a schematic view of application of acoustic pressure shock waves to a tissue condition via electromagnetic generators using a cylindrical coil, according to one embodiment of the present invention.
Figure 1G:
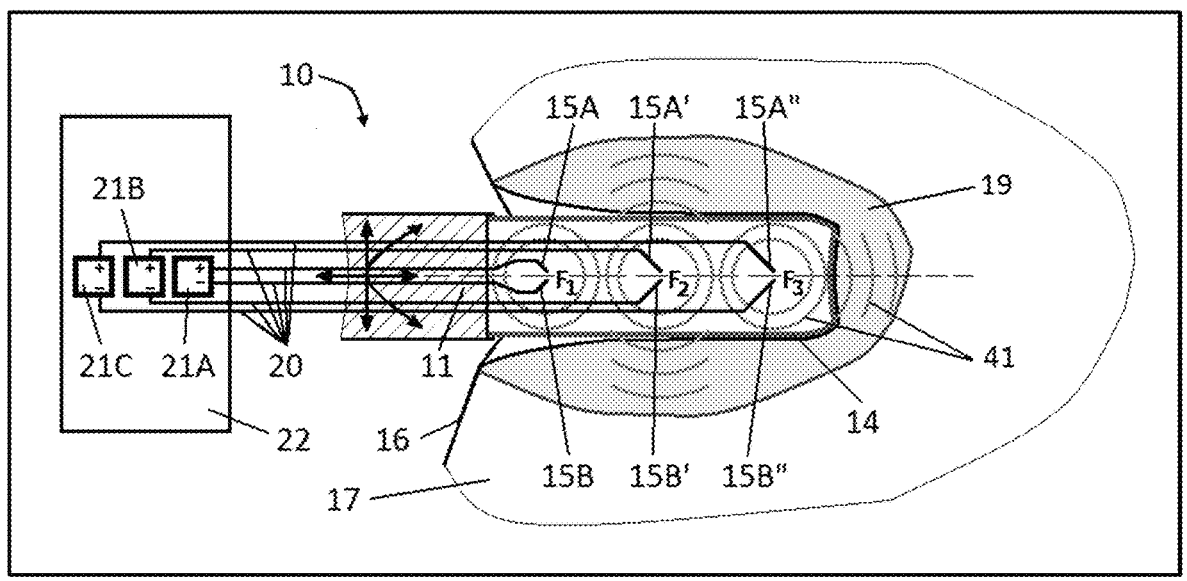
FIG. 1G is a schematic view of application of acoustic pressure shock waves to a tissue condition via electrohydraulic generators using multiple pairs of spark-gap electrodes, according to one embodiment of the present invention.
Figure 1H:
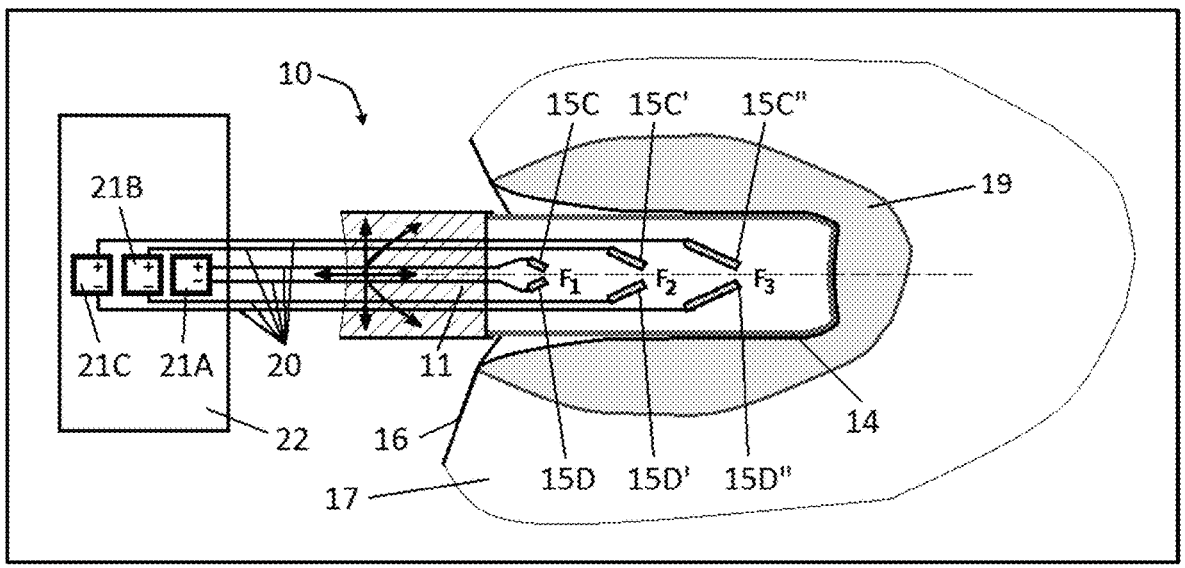
FIG. 1H is a schematic view of application of acoustic pressure shock waves to a tissue condition via electrohydraulic generators using multiple pairs of lasers, according to one embodiment of the present invention.
Figure 1I:
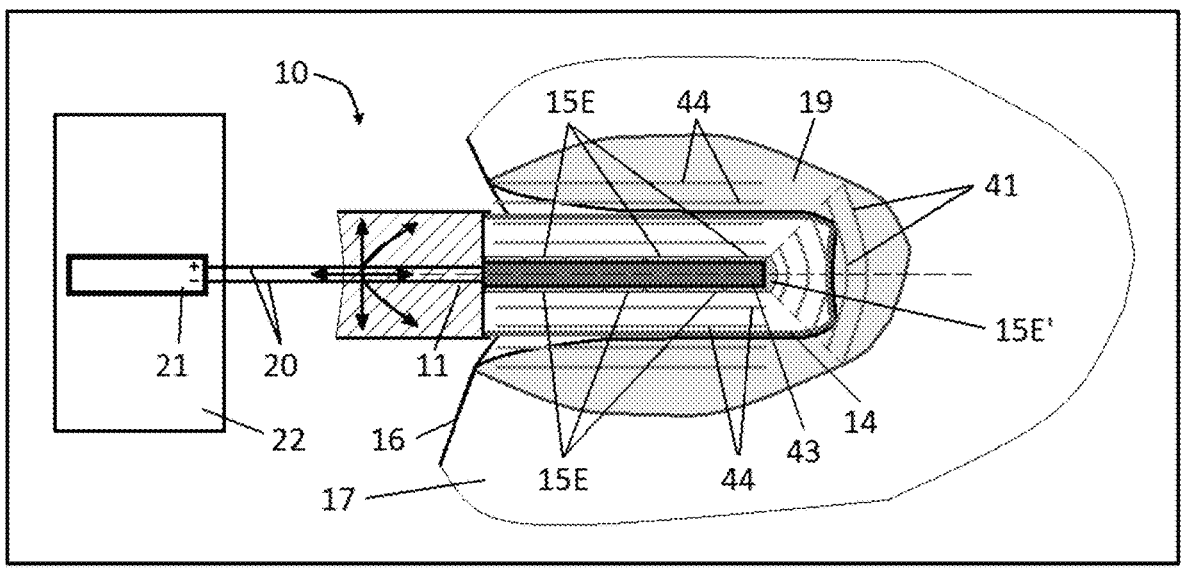
FIG. 1I is a schematic view of application of acoustic pressure shock waves to a tissue condition via piezoelectric generators using piezo crystals disposed on a cylindrical central core, according to one embodiment of the present invention.
Figure 1J:
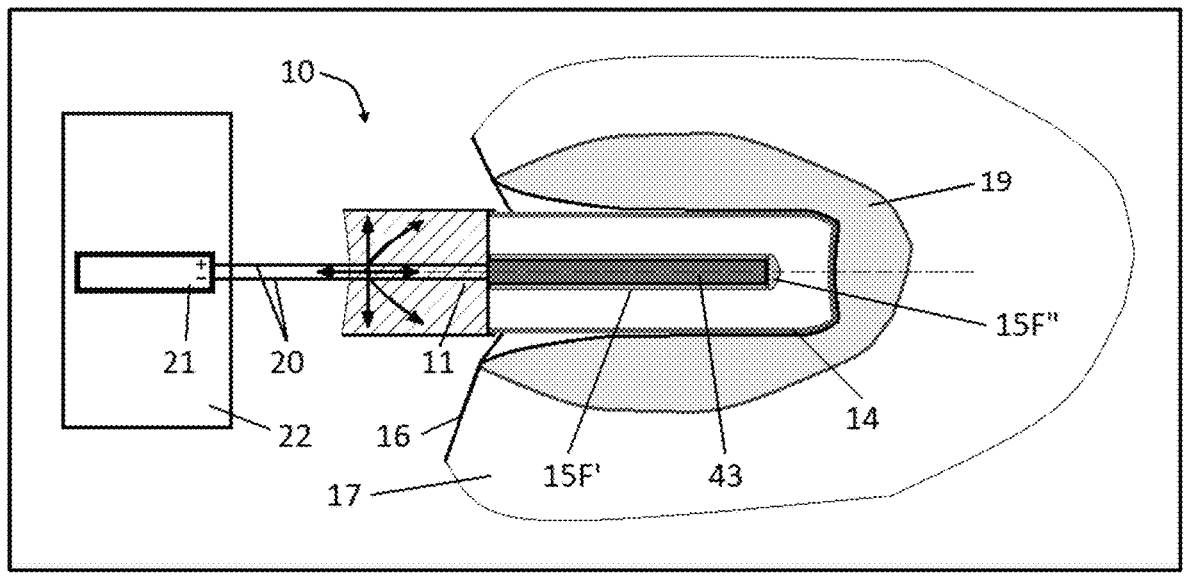
FIG. 1J is a schematic view of application of acoustic pressure shock waves to a tissue condition via piezoelectric generators using piezo fibers disposed on a cylindrical central core, according to one embodiment of the present invention.
Figure 1K:
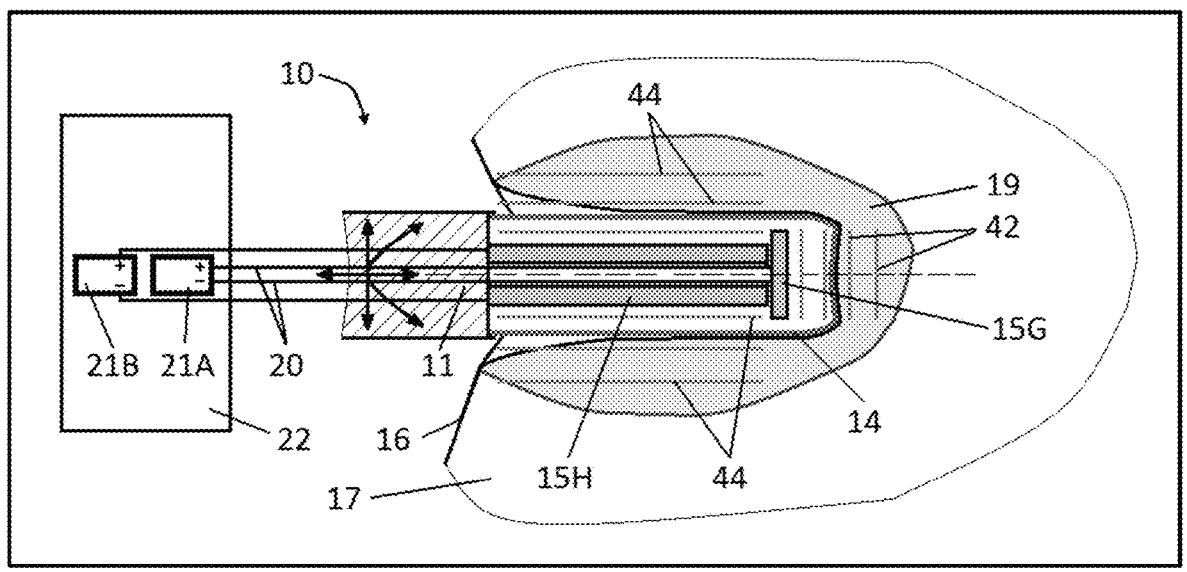
FIG. 1K is a schematic view of application of acoustic pressure shock waves to a tissue condition via electromagnetic generators using a combination of s cylindrical coil and a flat coil, according to one embodiment of the present invention.

It is a further objective of the present inventions to provide different methods of generating focused, unfocused, planar, pseudo-planar, cylindrical, or radial extracorporeal acoustic pressure shock waves for treating tissue conditions using specific devices that include the following acoustic pressure shock wave generators in various embodiments:

- electrohydraulic generators using one or multiple spark-gap high voltage discharges (as an example see FIG. 1A and FIG. 1G)
- electrohydraulic generators using one or multiple laser sources (as an example see FIG. 1B and FIG. 1H)
- piezoelectric generators using piezo crystals (as an example see FIG. 1C and FIG. 1I)
- piezoelectric generators using piezo fibers (as an example see FIG. 1D and FIG. 1J)
- electromagnetic generators using a flat coil and an acoustic lens (as an example see FIG. 1E) or a cylindrical coil (as an example see FIG. 1F) or a combination of them (as an example see FIG. 1K)

It is a further objective of the present inventions to provide a means of controlling the energy via the amount of energy generated from the acoustic pressure shock wave generators (energy setting), total number of the acoustic pressure shock waves/pulses or dosage, repetition frequency of the acoustic pressure shock waves, and special construction of the reflectors used in the acoustic pressure shock wave applicators.

It is a further objective of the present inventions to provide a variety of novel acoustic pressure shock wave applicator constructions and their capability to guide or focus acoustic pressure shock waves on the animal or human tissue target.

The inventions summarized below and defined by the enumerated claims are better understood by referring to the following detailed description, which is preferably read in conjunction with the accompanying drawing/figure. The detailed description of a particular embodiment, is set out to enable one to practice the invention, it is not intended to limit the enumerated claims, but to serve as a particular example thereof.

Also, the list of embodiments presented in this patent is not an exhaustive one and for those skilled in the art, new applications and optimization methods can be found within the scope of the invention.

The acoustic pressure shock waves or acoustic pressure waves produced by the proposed embodiments have a compressive phase (produces high compressive pressures) and a tensile phase (produces cavitation bubbles that collapse with high speed jets in the sub-millimeter range of action) during one cycle of the acoustic pressure shock waves or acoustic pressure waves. These two synergetic effects work in tandem, enhancing the acoustic pressure shock waves or acoustic pressure waves effects.

The acoustic pressure shock wave pulses incorporate frequencies ranging from 100 kHz to 20 MHz and will generally have a repetition rate of 1 to 20 Hz. The repetition rate is limited by cavitation, which represents the longest time segment (hundreds to thousands of microseconds) of the pressure pulse produced by acoustic pressure shock waves or acoustic pressure waves. To avoid any negative influence of a new in-coming pulse, cavitation bubbles need sufficient time to grow to their maximum dimension and then collapse with high speed jets that have velocities of more than 100 m/s. These jets, together with unidirectional nature of pressure fronts/forces created by acoustic pressure shock waves or acoustic pressure waves, play an important role in unidirectional actions on the treated tissue. If acoustic pressure shock wave pulses have too of a high repetition rate interference between subsequent shock wave pulses may result, which can negatively affect the cavitation period, hence reducing the desired effects of the acoustic pressure shock waves or acoustic pressure waves.

Embodiments from this present invention are designed to produce personalized or customized treatments for tissue conditions in general for both human and animals, and are further described in detail in the following paragraphs.

FIGS. 1A-1K show different embodiments for producing acoustic pressure shock waves to generally treat tissue conditions 19. FIGS. 1A-1F illustrate embodiments of the acoustic pressure shock wave applicator/treatment apparatus 10 having an applicator body 11 and inside of it resides an ellipsoidal reflector 12 or parabolic reflector 12A that defines the reflector cavity 13 together with an applicator/coupling membrane 14. In embodiments of the invention, the coupling membrane seals liquid inside the applicator body 11, wherein acoustic pressure shock waves are produced in and propagate through the liquid and exit through the membrane to a coupled treatment target area. The acoustic pressure shock waves generated by the devices shown in FIGS. 1A-1F are focused acoustic pressure shock waves 40 (specifically shown in FIG. 1A) that are directed towards a focal volume 18. For an efficient treatment of the tissue condition 19, the focal volume 18 preferably intersects the epidermis 16 and tissue condition 19. Embodiments from FIG. 1G-1K do not have a reflector of any type and generate radial acoustic pressure waves 41 (specifically shown in FIG. 1G and FIG. 1I), planar acoustic pressure waves 42 (specifically shown in FIG. 1K), or cylindrical acoustic pressure waves 44 (specifically shown in FIG. 1I and FIG. 1K). In these particular examples, the acoustic pressure shock waves are generated via different principles.

FIG. 1A shows focused acoustic pressure shock waves 40 generated via high voltage discharge produced between first electrode 15A and second electrode 15B (electrohydraulic principle using spark-gap high voltage discharges) in a fluid present inside the reflector cavity 13. The high voltage for the first electrode 15A and the second electrode 15B is provided by the power source 21 (included in control console/unit 22) via high voltage cable 20. The two electrodes 15A and 15B are positioned in the first focal point $F_1$ of the ellipsoidal reflector 12 and during their discharge they produce a plasma bubble that expands and collapses transforming the heat into kinetic energy in the form of acoustic pressure shock waves that reflects on the ellipsoidal reflector 12 and produces focused acoustic pressure shock waves 40, which are directed towards a focal volume 18.

FIG. 1B illustrates a device wherein focused acoustic pressure shock waves 40 (shown in FIG. 1A and not shown in FIG. 1B for simplicity) are generated via one or multiple laser sources (electrohydraulic principle using one or multiple lasers sources). In this embodiment the laser beams produced by first encased laser 15C and the second encased laser 15D in a fluid present inside the reflector cavity 13 generate the acoustic pressure shock waves, which are then focused via ellipsoidal reflector 12 towards the focal volume 18. The high voltage for the first encased laser 15C and the second encased laser 15D is provided by the power source 21 (included in control/console unit 22) via high voltage cable 20. The two laser sources are positioned in such way to intersect their beams in the first focal point $F_1$ of the ellipsoidal reflector 12 in order to produce a plasma bubble that expands and collapses transforming the heat into kinetic energy in the form of acoustic pressure shock waves, which are then focused via ellipsoidal reflector 12 towards the focal volume 18. FIG. 1B includes a means of monitoring the system performance by measuring the reaction temperature of the plasma bubble collapse using a method of optical fiber thermometry. An optical fiber tube assembly 23 extends into the $F_1$ region of the ellipsoidal reflector 12. The optical fiber tube assembly 23 transmits (via optical fiber 23A) specific spectral frequencies created from the sonoluminescence of the plasma reaction in the fluid present inside the reflector cavity 13 to the spectral analyzer 24. The loop is closed via feedback cable 23B that connects the spectral analyzer 24 with the power source 21. Basically, the spectral analysis provided by the spectral analyzer 24 is used to adjust accordingly the power generated by the power source 21, to ensure a proper laser discharge for the encased lasers 15C and 15D.

FIG. 1C shows a device wherein acoustic pressure shock waves are generated via piezo crystals 15E (piezoelectric principle using piezo crystals). In this embodiment the internal generation of a mechanical strain resulting from an applied electrical field to the piezo crystals/piezo ceramics 15E that are uniformly placed on the ellipsoidal reflector 12 generate the focused acoustic pressure shock waves 40 (shown in FIG. 1A and not shown in FIG. 1C for simplicity) in a fluid present inside the reflector cavity 13. The electrical field for the piezo crystals/piezo ceramics 15E is provided by the power source 21 (included in control console/unit 22) via high voltage cable 20.

Due to the parallelepiped geometry of the piezo crystals/piezo ceramics 15E, the crystals/ceramics may not conform well to the ellipsoidal reflector 12, which can result in problems with focusing. To overcome this issue, piezo fibers can be used as presented in FIG. 1D. The piezo fibers are integrated in a composite material with their longitudinal axis perpendicular to a solid surface as the ellipsoidal reflector 12 to form a piezo fiber reflector 15F. The advantage of the piezo fibers when compared to the piezo crystals/piezo ceramics 15E is their smaller dimension and cylindrical geometry that allows them to conform significantly better to the ellipsoidal geometry. Furthermore, the contacting of the piezo fibers may be realized by a common electrically conductive layer according to the interconnection requirements. Hence, the complex interconnection of a multitude of piezo crystals/piezo ceramics 15E (as presented in FIG. 1C) is no longer required. When an electrical field is provided by the power source 21 (included in control console/unit 22) via high voltage cable 20 to the piezo fiber reflector 15F, the piezo electric fibers will stretch in unison mainly in their lengthwise direction, which will create acoustic pressure shock waves that reflect on the ellipsoidal reflector 12 and produce focused acoustic pressure shock waves 40 (shown in FIG. 1A and not shown in FIG. 1D for simplicity). These focused acoustic pressure shock waves 40 are directed towards the focal volume 18. This represents the piezoelectric principle using piezo fibers to produce focused acoustic pressure shock waves.

FIG. 1E illustrates a device wherein acoustic pressure shock waves are generated via electromagnetic flat coil and plate assembly 15G and an acoustic lens 25 (electromagnetic principle using a flat coil and an acoustic lens). In this embodiment, an electromagnetic flat coil is placed in close proximity to a metal plate that acts as an acoustic source. When the electromagnetic flat coil is excited by a short electrical pulse provided by the power source 21 (included in control console/unit 22) via high voltage cable 20, the plate experiences a repulsive force and generates an acoustic pressure wave. Because the metal plate is flat, the resulting acoustic pressure wave is a planar acoustic pressure wave (not shown in FIG. 1E) moving in the fluid-filled cavity 26 towards the acoustic lens 25 that focuses the planar wave and thereby creates focused acoustic pressure shock waves 40 (shown in FIG. 1A and not shown in FIG. 1E for simplicity) towards the targeted area. The focusing effect of the acoustic lens 25 is given by its shape, which is a portion of an ellipsoidal surface in one embodiment.

FIG. 1F shows a device wherein acoustic pressure shock waves are generated via electromagnetic cylindrical coil and tube plate assembly 15H (electromagnetic principle using a cylindrical coil). In this embodiment, an electromagnetic cylindrical coil is excited by a short electrical pulse provided by power source 21 (included in control console/unit 22) via high voltage cable 20, and the plate is in the shape of a tube (thus creating an electromagnetic cylindrical coil and tube plate assembly 15H), which results in a cylindrical wave (not shown in FIG. 1F) that can be focused by a parabolic reflector 12A towards its focus point F in the targeted area through the fluid-filled reflector cavity 13, thus resulting in treatment with focused acoustic pressure waves 40 (shown in FIG. 1A and not shown in FIG. 1F for simplicity).

FIG. 1G illustrates a device wherein acoustic pressure waves are generated via multiple high voltage discharges (electrohydraulic principle using spark-gap high voltage discharges) produced on the longitudinal axis of the acoustic pressure shock wave applicator/treatment apparatus 10. As shown in FIG. 1G, there are three high voltage discharges produced in a fluid present inside the volume created between the applicator/coupling membrane 14 (shaped as a cylinder) and applicator body 11. The first spark-gap discharge in $F_1$ is produced between first electrode 15A and the second electrode 15B, the second spark-gap discharge in $F_2$ is produced between third electrode 15A' and the fourth electrode 15B', and the third spark-gap in $F_3$ is produced between fifth electrode 15A" and the sixth electrode 15B". The high voltage for each pair of electrodes is provided from independent power sources to allow a proper discharge without interference from the other pairs of electrodes. Thus the discharge in $F_1$ produced between first electrode 15A and the second electrode 15B is powered by the first power supply 21A, the discharge in $F_2$ produced between third electrode 15A' and the fourth electrode 15B' is powered by the second power supply 21B, and the discharge in $F_3$ produced between fifth electrode 15A" and the sixth electrode 15B" is powered by the third power supply 21C. The power sources 21A, 21B, and 21C are all included in the control console/unit 22 and are connected with the acoustic pressure shock wave applicator/treatment apparatus 10 via high voltage cable 20. There is no reflector present in this embodiment so when the spark-gap discharges are produced, the associated plasma bubbles expand and collapse transforming the heat into kinetic energy in the form of radial acoustic pressure waves 41. Due to the radial nature of the acoustic pressure waves produced by the acoustic pressure shock wave applicator/treatment apparatus 10 of this embodiment, the radial acoustic pressure waves 41 will propagate in all directions and thus penetrate and treat tissue condition 19 and/or epidermis 16 all around the applicator/coupling membrane 14. A coupling gel that is not specifically shown in FIG. 1G may preferably be applied between the membrane 14 and tissue to support propagation of the acoustic pressure shock waves. Being produced via electrohydraulic principle makes the radial acoustic pressure waves 41 more powerful when compared with radial pressure waves produced via pneumatic/ballistic means (see U.S. Pat. No. 6,413,230), which is a common method to produce medical radial acoustic pressure waves 41. Also the fact that the embodiment from FIG. 1G uses a soft or semi-hard applicator/coupling membrane 14 (shaped as cylinder) to send the radial acoustic pressure waves 41 towards tissue condition 19 and epidermis 16, are preferably better toler-ated by the patient when compared with the hard tip/coupler of pneumatic devices (see U.S. Pat. No. 6,413,230).

FIG. 1H shows a device wherein acoustic pressure shock waves are generated via multiple laser sources (electrohydraulic principle using multiple lasers sources) produced on the longitudinal axis of the acoustic pressure shock wave applicator/treatment apparatus 10. As shown in FIG. 1H, there are three pairs of encased lasers that produce laser beams in a fluid present inside the volume created between the applicator/coupling membrane 14 (shaped as a cylinder) and applicator body 11. The first encased laser 15C and the second encased laser 15D represent the first pair of encased lasers that produces laser beams in $F_1$, the third encased laser 15C' and the fourth encased laser 15D' represent the second pair of encased lasers that produces laser beams in $F_2$, and the fifth encased laser 15C" and sixth encased laser 15D" represent the third pair of encased lasers that produces laser beams in $F_3$. In one embodiment, the high voltage for each pair of encased lasers is provided from independent power sources. Thus the first encased laser 15C and the second encased laser 15D are powered by the first power supply 21A, the third encased laser 15C' and the fourth encased laser 15D' are powered by the second power supply 21B, and the fifth encased laser 15C" and sixth encased laser 15D" are powered by the third power supply 21C. In another embodiment all the lasers are powered by only one power source that uses laser splitters (not shown) to split energy between different encased lasers. Regardless of design, the power source or sources are included in the control console/unit 22 and are connected with the acoustic pressure shock wave applicator/treatment apparatus 10 via high voltage cable 20. To control and maintain good functionality of the lasers there are means of monitoring the system performance by measuring the reaction temperature of the plasma bubble collapse using a method of optical fiber thermometry, which are not specifically shown in FIG. 1H, but are shown in detail in FIG. 1B. Also in this embodiment there is no reflector present and so only radial acoustic pressure waves 41 are produced (shown in FIG. 1G and not shown in FIG. 1H for simplicity). Due to the radial nature of the acoustic pressure waves produced by the acoustic pressure shock wave applicator/treatment apparatus 10 of this embodiment, the radial acoustic pressure waves 41 will propagate in all directions and thus penetrate and treat tissue condition 19 and/or epidermis 16 all around the cylindrical applicator/coupling membrane 14. A coupling gel that is not specifically shown in FIG. 1H may be provided to couple the membrane 14 to the tissue to be treated.

FIG. 1I illustrates a device wherein the acoustic pressure shock waves are generated via piezo crystals 15E and convex piezo crystal/piezo ceramic 15E' (piezoelectric principle using piezo crystals). In this embodiment the internal generation of a mechanical strain resulting from an applied electrical field to the piezo crystals/piezo ceramics 15E uniformly placed on the cylindrical central core 43 produces cylindrical acoustic pressure waves 44 inside the fluid-filled applicator/coupling membrane 14. The electrical field applied to the convex piezo crystal/piezo ceramic 15E' placed on the distal end of the cylindrical central core 43 produces radial acoustic pressure waves 41. The electrical field for the piezo crystals/piezo ceramics 15E and convex piezo crystal/piezo ceramic 15E' is provided via high voltage cable 20 by the power source 21, which is included in control console/unit 22. The radial acoustic pressure waves 41 and cylindrical acoustic pressure waves 44 penetrate and treat tissue condition 19 and/or epidermis 16 all around the cylindrical applicator/coupling membrane 14, preferably, via a coupling gel that is not specifically shown in FIG. 1I.

Due to the parallelepiped geometry of the piezo crystals/piezo ceramics 15E, the crystals/ceramix may not conform very well to the cylindrical central core 43 of the embodiment presented in FIG. 1I, and to overcome this issue piezo fibers can be used as presented in FIG. 1J. The piezo fibers can be integrated in a composite material with their longitudinal axis perpendicular to the solid surface of the cylindrical central core 43, thus forming the piezo fibers cylindrical core 15F' and the piezo fibers convex disc cap 15F'''. The advantage of the piezo fibers when compared to the piezo crystals/piezo ceramics 15E is their smaller dimension and cylindrical geometry that allows them to confirm significantly better to the ellipsoidal geometry. Furthermore, the contacting of the piezo fibers may be realized by a common electrically conductive layer according to the interconnection requirements. Hence, the complex interconnection of a multitude of piezo crystals/piezo ceramics 15E (as presented in FIG. 1I) is no longer required. When an electrical field is provided by the power source 21 (included in control console/unit 22) via high voltage cable 20 to the piezo fibers cylindrical core 15F' and the piezo fibers convex disc cap 15F''', the piezo electric fibers will stretch in unison mainly in their lengthwise direction inside the fluid-filled applicator/coupling membrane 14, which will create the radial acoustic pressure waves 41 and cylindrical acoustic pressure waves 44 (shown in FIG. 1I and not shown in FIG. 1J for simplicity). The radial acoustic pressure waves 41 and cylindrical acoustic pressure waves 44 penetrate and treat tissue condition 19 and/or epidermis 16 all around the cylindrical applicator/coupling membrane 14, via a coupling gel that is not specifically shown in FIG. 1J.

FIG. 1K illustrates a device wherein acoustic pressure waves are generated via electromagnetic cylindrical coil and tube plate assembly 15H and electromagnetic flat coil and plate assembly 15G inside the fluid-filled applicator/coupling membrane 14 (electromagnetic principle using a cylindrical coil). In this embodiment, the electromagnetic cylindrical coil and tube plate assembly 15H is excited by short electrical pulses provided by the first power supply 21A and the electromagnetic flat coil and plate assembly 15G by the second power supply 21B. Both power supplies are included in the control console/unit 22 and they are connected with the acoustic pressure shock wave applicator/treatment apparatus 10 via high voltage cable 20. The electromagnetic cylindrical coil and tube plate assembly 15H create the cylindrical acoustic pressure waves 44 and the electromagnetic flat coil and plate assembly 15G produce planar acoustic pressure waves 42. The cylindrical acoustic pressure waves 44 and the planar acoustic pressure waves 42 penetrate and treat tissue condition 19 and/or epidermis 16 all around the cylindrical applicator/coupling membrane 14, preferably via a coupling gel that is not specifically shown in FIG. 1L.

Referring again to FIGS. 1A-1D, generated acoustic pressure shock waves are reflected/focused by the ellipsoidal reflector 12 towards the second focal point $F_2$ of the ellipsoid via the contact of the applicator/treatment apparatus 10 with a patient's epidermis 16. The coupling between applicator/treatment apparatus 10 and epidermis 16 is preferably accomplished with ultrasound gel, which is not specifically shown in FIGS. 1A-1K. In embodiments, ellipsoidal reflector 12 (FIGS. 1A-1D) is only a half of an ellipsoid in order to allow the transmission of the acoustic pressure shock waves inside the human and animal body 17, where the second focal point $F_2$ is preferably found. In this way, the acoustic pressure shock wave applicator/treatment apparatus 10 can be placed against the epidermis 16 of the human or animal body 17 via applicator/coupling membrane 14 and ultrasound coupling gel. With reference to FIG. 1E, the acoustic pressure shock waves are focused towards the targeted area by the acoustic lens 25 (it has the shape of a portion of an ellipsoidal surface). With reference to FIG. 1F, the focusing is realized by parabolic reflector 12A. Because different pressure fronts (direct or reflected) reach the second focal point $F_2$ (for ellipsoidal geometry of the reflector 12) or focus point F (for parabolic geometry of the reflector 12A) with certain small time differences, the acoustic pressure shock waves are in reality concentrated or focused on a three-dimensional space around second focal point $F_2$/focus point F, which is called the focal volume 18. Inside the focal volume 18 are found the highest pressure values for each focused acoustic pressure shock wave 40, which means that is preferable to position the targeted zone for the treatment in such way to intersect the focal volume 18 and if possible centered on the second focal point $F_2$ (for ellipsoidal geometries) or on the focus point F (for parabolic geometries). In order to be effective in the treatment of tissue conditions, the acoustic pressure shock wave applicator/treatment apparatus 10 and its components are designed in such way to ensure that the focal volume 18 (where acoustic pressure shock waves are focused) is positioned deep enough to allow its overlap with tissue condition 19 volume, as presented in FIG. 1A-1F.

Referring to FIGS. 1G-1K, the acoustic pressure waves are not focused but rather radial acoustic pressure waves 41 or planar acoustic pressure waves 42 or cylindrical acoustic pressure waves 44. Acoustic pressure waves generated in these embodiments head towards all directions in order to completely cover and treat tissue condition 19 and/or epidermis 16 of the human and animal body 17. Compared to the focused acoustic pressure shock wave 40 (see FIG. 1A), the radial acoustic pressure waves 41 or planar acoustic pressure waves 42 or cylindrical acoustic pressure waves 44 usually have limited penetration because the waves begin losing their energy immediately after getting into the tissue. As a result, the embodiments presented in FIGS. 1G-1K are preferable for treating superficial tissue conditions 19.

Referring again to FIGS. 1A-1E the penetration inside the human and animal body 17 and the geometry of the focal volume 18 is dictated by the energy settings for acoustic pressure shock waves or input energy, applicator/coupling membrane 14 geometry and dimensional characteristics of the ellipsoidal reflector 12 (dictated by the ratio of the large semi-axis and small semi-axis of the ellipsoid, and by its aperture defined as the dimension of the opening of the ellipsoidal reflector 12). Thus the ellipsoidal reflector 12 needs to have a geometry to allow a relatively deep second focal point $F_2$ inside the human and animal body 17 that can be positioned on the tissue condition 19. A relatively deep ellipsoidal reflector 12 is also advantageous because the larger the focusing area of the ellipsoidal reflector 12, then the larger the focal volume 18 will be, and consequently the larger the amount of energy associated that will result, which energy is ultimately deposited into the targeted zone of the tissue condition 19. In general, the ratio of the large semi-axis and small semi-axis of the ellipsoid (the axes dimensions are given by the largest and smallest lengths across the ellipsoid, with the semi-axis value being defined as half of the respective full dimension length) preferably have values between 1.1 and 1.6. For the parabolic reflector 12A (presented in FIG. 1F) its geometry are preferably chosen in such way that the focus point of the parabola F are preferably positioned deep enough to allow its overlap with the tissue condition 19. That means that the focal length (defined as distance between the bottom of the reflector where the parabola is most sharply curved and the focus point of the parabola F—see FIG. 1F) for the parabolic reflector 12A are preferably at least 5 cm (depending on the position of the tissue condition 19 inside the human and animal body 17).

Referring again to FIGS. 1G-1K, the penetration inside the human and animal body 17 is dictated only by the energy setting for acoustic pressure waves or input energy. Also, note that the cylindrical applicator/coupling membrane 14 and the unfocused nature of the radial acoustic pressure waves 41 or planar acoustic pressure waves 42 or cylindrical acoustic pressure waves 44 allow a uniform penetration into very large tissue conditions 19, such as for large pressure sores in the buttocks area, which are most difficult to heal. Sometimes getting focused shock waves 40 to a large tissue condition 19, like pressure sores, will not cover the entire wound bed properly. Acoustic pressure shock wave applicators/treatment apparatuses 10 as presented in FIGS. 1G-1K can preferably be initially used for very large tissue conditions 19 and where the depth of the wound is limited. After such initial treatment as presented by FIGS. 1G-1K, an acoustic pressure shock wave applicator/treatment apparatus 10 as shown in FIGS. 1A-1F that applies focused pressure shock waves may be used to intersect a focal volume 18 with desired targeted treatment areas.

The fluid present inside the acoustic pressure shock wave applicators/treatment apparatuses 10 presented in FIG. 1A-1K is preferably a mixture of degassed water with proprietary substance/particles/catalysts that promote a better discharge and recombination of free radicals back to water form, as presented in U.S. Pat. Nos. 6,080,119 and 9,198,825. Other fluids may also be employed, as will be appreciated by those of ordinary skill in the art, in order to provide suitable acoustic properties for producing and conducting focused acoustic pressure shock waves 40 or radial acoustic pressure waves 41 or planar acoustic pressure waves 42 or cylindrical acoustic pressure waves 44. Further, for all embodiments presented in FIGS. 1A-1K, the acoustic properties of the fluid are preferably similar to the acoustic properties of human and animal bodies 17, which allow transmission of the focused acoustic pressure shock waves 40 or radial acoustic pressure waves 41 or planar acoustic pressure waves 42 or cylindrical acoustic pressure waves 44 seamlessly between the acoustic pressure shock wave applicator/treatment apparatus 10 and human or animal bodies 17.

The quantity of energy deposited inside the tissue or tissue condition 19 during one treatment session by the acoustic pressure shock waves is dependent on the dosage, which includes the following elements:

Input energy delivered by the control console/unit 22 by the power source 21 or the first power supply 21A or the second power supply 21B or the third power supply 21C provided via high voltage cable 20 (see FIGS. 1A-1K)

Output energy inside the tissue or tissue condition 19 of each focused acoustic pressure shock waves 40 or radial acoustic pressure waves 41 or planar acoustic pressure waves 42 or cylindrical acoustic pressure waves 44, known as energy flux density or instantaneous intensity at a particular point inside the tissue condition 19

Frequency of repetition for acoustic pressure shock waves, defined as number of acoustic pressure shock waves per each second Total amount of focused acoustic pressure shock waves 40 or radial acoustic pressure waves 41 or planar acoustic pressure waves 42 or cylindrical acoustic pressure waves 44 delivered in one treatment The amount of energy deposited into the treatment zone is preferably sufficient to allow the therapy of the tissue conditions 19. In this regard, the voltage provided by the power source 21 via high voltage cable 20 is preferably in the range of 1 to 30 kV for the embodiments presented in FIGS. 1A-1K.

In the embodiments set forth in FIGS. 1A-1K, because hard materials have the tendency to reflect focused acoustic pressure shock waves 40 or radial acoustic pressure waves 41 or planar acoustic pressure waves 42 or cylindrical acoustic pressure waves 44 as compared with the surrounding soft tissue, there will be reflections at the bone/soft tissue. These reflections occur due to different acoustic properties of soft tissue and bone. In order to overcome these losses, the focused acoustic pressure shock waves 40 or radial acoustic pressure waves 41 or planar acoustic pressure waves 42 or cylindrical acoustic pressure waves 44 are preferably strong enough so that the transmitted component of the acoustic pressure shock waves at these interfaces to has sufficient energy at the targeted zone (output energy) to treat the tissue conditions 19. To accomplish the same, the energy flux density of each acoustic pressure shock wave is preferably in the range of 0.05 to 1.00 mJ/mm$^2$. However, depending on the characteristics of each device, the energy flux density is carefully chosen for each specific application in such way so as to not produce any damage to the targeted tissue from the tissue conditions 19.

For treating tissue conditions 19, cavitation plays a primary role in destroying the outer membrane of the pathogens present in the respective tissue conditions 19 or for stimulating tissue regeneration. In order to have maximum potential for the cavitation phase of focused acoustic pressure shock waves 40 or radial acoustic pressure waves 41 or planar acoustic pressure waves 42 or cylindrical acoustic pressure waves 44, the repetition rate or frequency is preferably in the range of 1 to 8 Hz. To not be negatively influenced by the new incoming acoustic pressure wave, the cavitation bubbles need sufficient time to grow to their maximum dimension and then collapse with high speed jets that have velocities of more than 100 m/s. This is why frequencies higher than 8 Hz are not usually preferable in the treatment of tissue conditions 19.

The total amount of focused acoustic pressure shock waves 40 or radial acoustic pressure waves 41 or planar acoustic pressure waves 42 or cylindrical acoustic pressure waves 44 is dependent on the status of the tissue condition 19 area. In order to effectively treat tissue conditions 19, the initial/fixed total number of focused acoustic pressure shock waves 40 or radial acoustic pressure waves 41 or planar acoustic pressure waves 42 or cylindrical acoustic pressure waves 44 (not customized/personalized to the patient, as presented later into this invention) is preferably from about 500 to about 3,000 generated waves, depending on the area of the tissue condition 19. If a large amount of focused acoustic pressure shock waves 40 or radial acoustic pressure waves 41 or planar acoustic pressure waves 42 or cylindrical acoustic pressure waves 44 is not feasible to be accomplished in a single session/treatment, then multiple sessions may be applied and spread over a certain period of time, such as twice a day or every day or every other day or two times per week, or one time per week, etc. In general, the initial/fixed number of treatments (not customized/personalized to the patient, as subsequently described herein) is preferably from four (4) to ten (10) sessions for each application (based on the severity of the tissue condition 19), followed by a resting period of from a few days to few weeks. If a tissue condition 19 is not completely resolved with the first round of sessions, after a resting period, the acoustic pressure shock waves can be administered again, preferably without producing any side effects.

Referring to the embodiment of FIG. 1G, the first pair of electrodes 15A and 15B, the second pair of electrodes 15A' and 15B', and the third pair of electrodes 15A" and 15B" can be activated simultaneously or sequentially, based on specific needs of the treatment. Similarly, for the embodiment from FIG. 1H the first pair of encased lasers 15C and 15D, the second pair of encased lasers 15C' and 15D', and the third pair of encased lasers 15C" and 15D" can be activated simultaneously or sequentially. Furthermore, only two pairs of electrodes or encased lasers can be used (or even only one of the pairs of electrodes or encased lasers can be activated), which allows for tailoring the treatment to deliver the radial acoustic pressure waves 41 to specific locations and different tissue penetrations. The same stands for the embodiment from FIG. 1I and FIG. 1J, where only specific piezo crystals/piezo ceramics 15E or the convex piezo crystal/piezo ceramic 15E' or segments of the piezo fibers cylindrical core 15F' or the piezo fibers convex disc cap 15F" can be selectively activated (concomitantly or sequentially) for a tailored treatment of specific zones from the tissue condition 19.

Moving up and down or around the tissue condition 19 (see arrows from FIGS. 1A-1F) or moving up and down or around or axially inside the tissue condition 19 (see arrows from FIGS. 1G-1K) will preferably allow for the proper treatment coverage the entire tissue condition 19 volume.

In order to transmit acoustic pressure shock waves inside the body, between the applicator/coupling membrane 14 of the acoustic pressure shock wave applicator/treatment apparatus 10 and the epidermis 16 of the patient, an acoustic coupling gel (ultrasound gel) is preferably used (not shown in FIGS. 1A-1F). The gel preferably has the same or nearly the same acoustic properties as animal/human soft tissue or skin/epidermis 16 and generally matches the acoustic impedance of the fluid enclosed inside the reflector cavity 13 of the acoustic pressure shock wave applicator/treatment apparatus 10. In this way the transmission of the focused acoustic pressure shock waves 40 or radial acoustic pressure waves 41 or planar acoustic pressure waves 42 or cylindrical acoustic pressure waves 44 is done without any losses. Caution must be taken, to not have air bubbles trapped inside the acoustic coupling gel, based on the fact that air can significant interfere with the propagation and potency/energy of the focused acoustic pressure shock waves 40 or radial acoustic pressure waves 41 or planar acoustic pressure waves 42 or cylindrical acoustic pressure waves 44, due to significant acoustic mismatch.

The focused acoustic pressure shock waves 40 or radial acoustic pressure waves 41 or planar acoustic pressure waves 42 or cylindrical acoustic pressure waves 44 can be transmitted in any angle possible relative to the targeted tissue condition 19 without any heat loss along the pathway (regardless of the distance traveled to the targeted area), can penetrate any type of tissue (hard, semi-hard, soft) and can treat superficial or profound seated tissue conditions 19, using an extracorporeal/non-invasive approach as presented in embodiments of FIGS. 1A-1K.

Figure 2A:
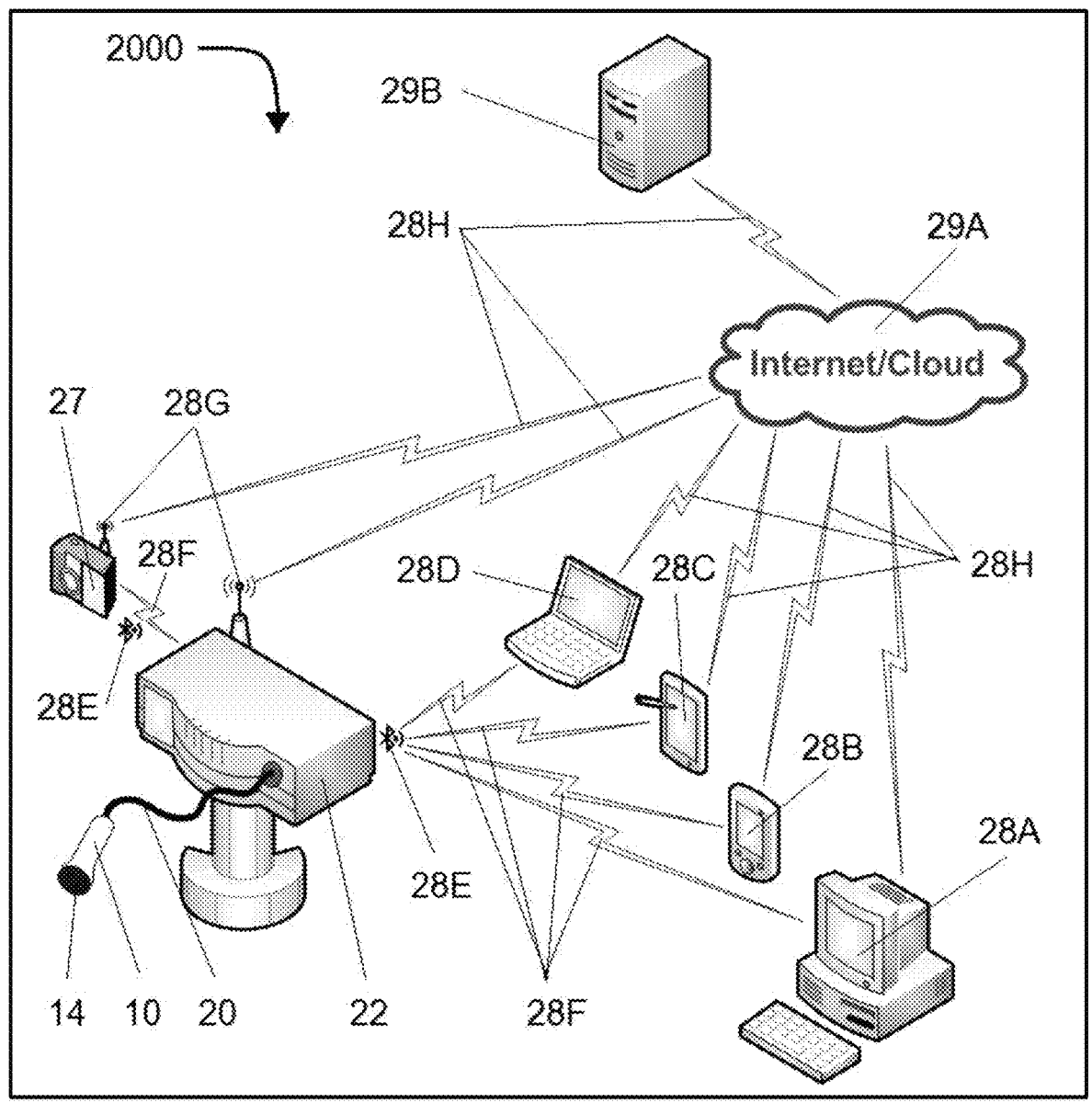
FIG. 2A is a schematic view of a medical treatment system using acoustic pressure shock wave devices and interconnectivity with other systems and a cloud network, according to one embodiment of the present invention.
Figure 2B:
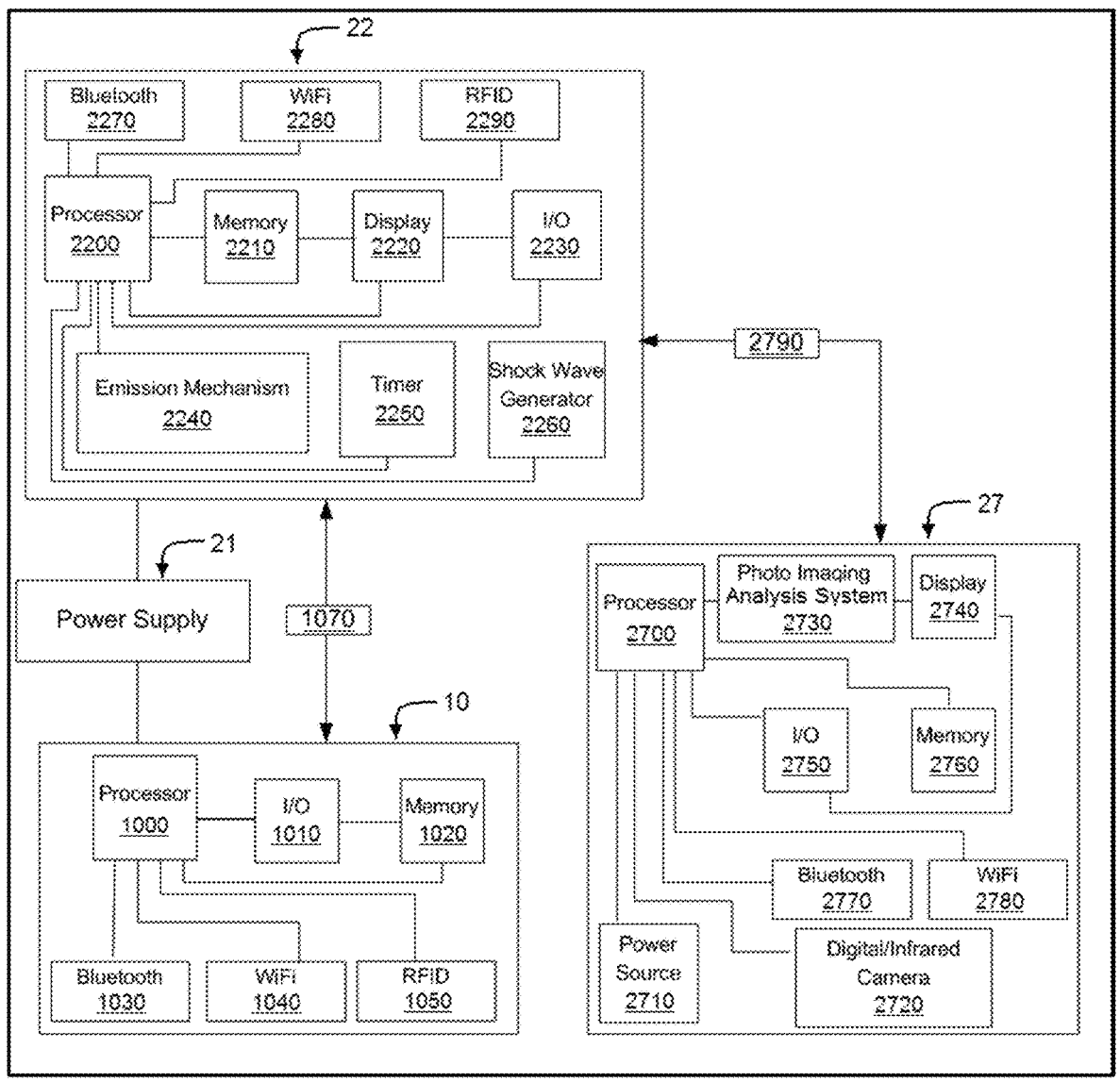
FIG. 2B is a relational block diagram of components of the acoustic pressure waves control console, applicator and artificial intelligence device of the medical treatment system of FIG. 2A, according to an embodiment of the present invention.

FIG. 2A is an illustration of a medical treatment system according to an embodiment of the invention. As shown in FIG. 2A, the medical treatment system 2000 includes multiple elements/components that work together to perform an optimized acoustic pressure shock wave treatment for the patient (not specifically shown in FIG. 2A). In some embodiments, various elements/components may be located proximate to or remote from other elements/components, and the communication network may be provided for transmitting and receiving information to and from one or more elements/components. In some embodiments, different devices and their components therein may also include electromechanical components, which are activated by sophisticated software and hardware components known to those skilled in the art. Each of the components may include hardware, software, or a combination of hardware and software configured to perform one or more functions associated with providing good functioning of the acoustic pressure shock wave applicator/treatment apparatus 10. The medical treatment system 2000 incorporates a control console/unit 22 that controls the functionality of the acoustic pressure shock wave applicator/treatment apparatus 10, which will be in contact with the patient with its applicator/coupling membrane 14. The control console/unit 22 is connected with the acoustic pressure shock wave applicator/treatment apparatus 10 via the high voltage cable 20 and thus producing acoustic pressure shock waves (not shown) in the treatment targeted area 30 (see FIG. 3). The control console/unit 22 can remotely control the acoustic pressure shock wave applicator/treatment apparatus 10 functioning and pairing using a control console/unit-applicator secured data transfer protocol 1070 (as shown in FIG. 2B) via a Bluetooth connection, Wi-Fi (wireless) connection, or an RFID connection. For simplicity, these connections and associated access ports/devices are not specifically shown in FIG. 2A. However, the internal components that perform these operations are presented in FIG. 2B.

For the medical treatment system 2000 presented in FIG. 2A, the assessment, monitoring and/or controlling of the treatment outcome is done by the artificial intelligence (A/I) device 27 that can be connected physically via a cable (not shown) to the control console/unit 22 or can communicate via a control console/unit-artificial intelligence (A/I) device secured data transfer protocol 2790 (as shown in FIG. 2B) by employing either a Bluetooth connection 28F, via the Bluetooth access port 28E, or a Wi-Fi (wireless) connection 28H (not shown in FIG. 2A), via the Wi-Fi access antenna 28G. In some embodiments, one or more components of medical treatment system 2000 may be located in a medical treatment facility (not shown) and communicatively coupled to any other component of the medical treatment system 2000. The one or more components may be coupled by optical, electrical, wireline or wireless media. In some embodiments, the components may be coupled by such mechanisms via a universal serial bus ("USB") or an RS 232 port. In some embodiments, various components of medical treatment system 2000 may be located proximate to or remote from other components, and a communication network may be provided for transmitting and receiving information to and from one or more components. In another embodiment the control console/unit 22 physically incorporates the artificial intelligence (A/I) device 27. For the medical treatment system 2000 presented in FIG. 2A, the control console/unit 22 can have its own input/output (I/O) device (control console/unit I/O 2230 from FIG. 2B) for the user to introduce treatment parameters and assess functionality of the control console/unit 22. In another embodiment, the control console/unit 22 can be remotely controlled via a Bluetooth connection 28F from a desktop computer 28A, or a smart phone 28B, or a tablet 28C, or a laptop 28D, or an artificial intelligence (A/I) device 27, devices that also serve as the input/output (I/O) device in this embodiment. If the control console/unit 22 is remotely connected via a Bluetooth connection 28F with a desktop computer 28A, or a smart phone 28B, or a tablet 28C, or a laptop 28D, or an artificial intelligence (A/I) device 27, in one embodiment those devices can also dictate (master-slave electronic relationship) remotely the whole functionality of the control console/unit 22 related to the treatment parameters, security, display of treatment parameters and data, coordination of different subsystems or subcomponents, etc. The control console/unit 22 and/or artificial intelligence (A/I) device 27 may dictate the input and output information that may be displayed on the desktop computer 28A, or a smart phone 28B, or a tablet 28C, or a laptop 28D. For example, in one embodiment, the control console/unit 22 and/or artificial intelligence (A/I) device 27 is a device that can be connected to a desktop computer 28A, or a smart phone 28B, or a tablet 28C, or a laptop 28D and used by a patient or an in-home caregiver. The control console/unit I/O (input/output) element 2230 of the control console/unit 22 and/or the artificial intelligence (A/I) device I/O (input/output) element 2750 of the artificial intelligence (A/I) device 27 may include an on/off mechanism that can be used by user for turning the desktop computer 28A, or a smart phone 28B, or a tablet 28C, or a laptop 28D on and off, respectively.

In other separate embodiments, the control console/unit 22 can function autonomously and at the end of the treatment only transfer the treatment parameters and data via a Bluetooth connection 28F to the remotely connected devices as a desktop computer 28A, or a smart phone 28B, or a tablet 28C, or a laptop 28D, or an artificial intelligence (A/I) device 27. Any transferred parameters and data between control console/unit 22 and a desktop computer 28A, or a smart phone 28B, or a tablet 28C, or a laptop 28D, or an artificial intelligence (A/I) device 27 can be used for the following:

monitoring healing progression over multiple treatments,
providing input data for treatment parameters adjustment from one treatment session to another one based on healing progress,
delivering data for reimbursement or financial payments or insurance assessment,
logging patient personal and medical data, comorbidities, medication, and nutritional facts, in a Health Insurance Portability and Accountability Act (HIPPA) compliant fashion,
recording acoustic shock wave device functional monitoring data, input data, treatment settings and parameters, output data, and treatment duration,
tracking adverse events,
logging the devices or equipment and other ancillary technologies or devices or treatment kits or components used during actual treatment,
recording date and timing of the treatment session, etc.

The above information/data can be transferred via a Wi-Fi connection 28H or any other type of internet connection from the control console/unit 22, or the desktop computer 28A, or the smart phone 28B, or the tablet 28C, or the laptop 28D, or the artificial intelligence (A/I) device 27 towards internet based data storage/cloud database 29A. The data stored into the internet based data storage/cloud database 29A can be further transferred via Wi-Fi connection 28H or any other type of internet connection to an artificial intelligence (AI) server 29B for processing via artificial intelligence (AI) algorithms to extract deep information within the medical treatment data to solve highly complex medical challenges and treatment shortcomings, predict synergetic or non-synergetic interaction between different devices and treatment modalities, advance scientific research, and better predict medical events and patient (human or animal) behavior during treatment, between subsequent treatments, or after the whole therapy sessions are finished. Ultimately, by using the artificial intelligence (AI) data analysis algorithms of the artificial intelligence (AI) server 29B, the following adjustments can be perfected and applied to the medical treatment performed by the medical treatment system 2000:

determine or alter or tune the treatment settings to keep in account patient's medical situation, comorbidities, daily medication regimen, nutritional facts, daily habits (drinking, smoking, etc.), ethnicity, gender, age, genetic make-up, etc., which will make the medical treatment more efficacious and efficient,
assess the treatment targeted tissue location and condition (vascularization, ischemia, perfusion, bacterial load, etc.) that will dictate the treatment selection,
offer treatment options and decision trees based on the healing progress or non-healing progress,
improve treatment outcome based on interactions between different devices or treatment modalities that help or not with the healing,
adjust device settings based on the correlation between treatment settings and treatment targeted region characteristics (type of tissue, area, volume, depth inside the body, etc.), which makes the actual treatment successful or less successful,
propose changes to the device to improve its functionality, to increase its user interface capabilities, and to expand its inter-connectivity with other devices/technologies,
produce spreadsheets for tracking treatments and send information for payment provisioning, insurance coding, security, inventory tracking, or medical treatment setting provisioning, or any combination of these functions,
find new clinical application for the respective technology,
produce customized reports to meet clinical and compliance requirements, etc.

The artificial intelligence (AI) data analysis outcomes are preferably relayed back to the internet based data storage/cloud database 29A from the artificial intelligence (AI) server 29B, to store the actual proposed improvements and also to be able to retrieve this data later when more treatment data is available for further analysis.

According to an embodiment of the invention shown in FIG. 2B, the basic architectural structure of the hardware for the control console/unit 22, the acoustic pressure shock wave applicator/treatment apparatus 10, and the artificial intelligence (A/I) device 27 and their interconnectivity during operation is presented.

The control console/unit 22 includes the control console/unit processor 2200, the control console/unit memory 2210, the control console/unit display 2220, the control console/unit I/O (input/output) device 2230, the control console/unit emission mechanism 2240, the control console/unit timer 2250, and the control console/unit shock wave generator 2260. The control console/unit Bluetooth module 2270, control console/unit Wi-Fi module 2280 and control console/unit RFID module 2290 can be all present individually in some embodiments or in combination with all or some of each other in other embodiments, depending on the specific communication needs.

In one embodiment, the control console/unit 22 processes information received from the control console/unit processor 2200 and transmits the information received to control console/unit shock wave generator 2260 and control console/unit timer 2250. Treatment setting information can be modified by the control console/unit processor 2200, via precise algorithms presented in FIGS. 8A-16D for determining an energy setting used for each treatment. The modification of treatment settings is done using patient data generated during execution of a questionnaire protocol displayed on the control console/unit display 2220 whereby data is introduced by the user (nurse, or physician, and/or medical office dedicated worker) via the control console/unit I/O (input/output) device 2230.

In another embodiment, the optimization of the treatment setting information, e.g. using a precise algorithm, can be done by the artificial intelligence (A/I) device 27, via its artificial intelligence (A/I) device processor 2700. In this embodiment the optimized treatment setting information is transmitted from the artificial intelligence (A/I) device processor 2700 to the control console/unit 22 and specifically to the control console/unit processor 2200, via the control console/unit-artificial intelligence (A/I) device secured data transfer protocol 2790. At that moment the optimized treatment setting information from the control console/unit processor 2200 generates using the control console/unit shock wave generator 2260, the control console/unit timer 2250, and the control console/unit emission mechanism 2240, the necessary number of focused acoustic pressure shock waves 40 or radial acoustic pressure waves 41 or planar acoustic pressure waves 42 or cylindrical acoustic pressure waves 44 at the optimum energy level and frequency, for performing an optimized and efficient treatment. These parameters are then sent to the acoustic pressure shock wave applicator/treatment apparatus 10, via the control console/unit-applicator secured data transfer protocol 1070, in order to perform the actual optimized and efficient treatment session. In another embodiment where the artificial intelligence (A/I) device 27 is an integral part of the control console/unit 22, either the artificial intelligence (A/I) device processor 2700 or the control console/unit processor 2200 can perform the optimization and it is just based on the specific system architecture.

The control console/unit shock wave generator 2260 may include hardware or components for providing, via the acoustic pressure shock wave applicator/treatment apparatus 10, one or more focused acoustic pressure shock waves 40 or radial acoustic pressure waves 41 or planar acoustic pressure waves 42 or cylindrical acoustic pressure waves 44 by electromechanical, electromagnetic, electrohydraulic, or piezoelectric methods (e.g., crystal, thin films or fibers), which are well-known to those skilled in the art and can generate planar, radial, cylindrical, focused or non-focused waves. The control console/unit timer 2250 provides timing sequence for emitting the one or more generated focused acoustic pressure shock waves 40 or radial acoustic pressure waves 41 or planar acoustic pressure waves 42 or cylindrical acoustic pressure waves 44 at a selected frequency as dictated by the one or more treatment settings. The one or more focused acoustic pressure shock waves 40 or radial acoustic pressure waves 41 or planar acoustic pressure waves 42 or cylindrical acoustic pressure waves 44 are emitted in a manner controlled by the control console/unit emission mechanism 2240 towards the acoustic pressure shock wave applicator/treatment apparatus 10, via a control console/unit-applicator secured data transfer protocol 1070. The control console/unit-applicator secured data transfer protocol 1070 provides security via authentication of the control console/unit 22 and of the acoustic pressure shock wave applicator/treatment apparatus 10.

The control console/unit memory 2210 may be any type of memory configured to store downloaded information regarding one or more treatment settings, optimization algorithm, treatment outcomes, errors, warnings, parameters used during the delivered therapy/treatment, patient information, follow-up data, monitoring data, tutorials, troubleshooting, and in general device functionality.

In one embodiment, the control console/unit I/O (input/output) element 2230 receives information indicative of one or more treatment settings, processes the received information to generate a control signal for controlling acoustic pressure shock wave applicator/treatment apparatus 10. The control console/unit I/O (input/output) element 2230 may also transmit the control information to the acoustic pressure shock wave applicator/treatment apparatus 10. Also, the control console/unit I/O (input/output) element 2230 may be configured to receive information such as updated information indicative of new treatment settings resultant from a completed medical treatment. In another embodiment, the control console/unit I/O (input/output) element 2230 may receive information indicating that a treatment has been administered and transmit the information to the control console/unit processor 2200, which may decrement by one a treatment setting indicative of the number of treatments allowed to a patient. The updated treatment setting may then be written on control console/unit memory 2210 for subsequent accessing and use during a next medical treatment or to the artificial intelligence (A/I) device processor 2700 for subsequent metadata analysis.

The control console/unit display 2220 may provide a visual display of graphics and/or text indicative of the one or more treatment settings and selections, patient identity information, patient comorbidities and medication, patient insurance information, ancillary treatment apparatus choice, training materials, troubleshooting, treatment apparatus activation or the like. Additionally, in some embodiments, the control console/unit display 2220 may provide a visual display of navigational treatment setting choices and current treatment parameters. In this embodiment, the control console/unit display 2220 may provide an indicator of the amount of treatment remaining before, during or after a medical treatment, or provide a display of one or more body regions targeted by the treatment.

In another embodiment, the control console/unit display 2220 can substitute completely the artificial intelligence (A/I) device display 2740. For that the control console/unit display 2220 are preferably able to display any pictures, graphs, and outcome information from the artificial intelligence (A/I) device digital/infrared camera 2720 artificial intelligence (A/I) device photo imaging analysis system 2730, which are used to analyze treatment performance and progress. Also, in this embodiment every data display and input/output (I/O) is done by the control console/unit display 2220 and the control console/unit I/O (input/output) element 2230 of the control console/unit 22. In such embodiment, the control console/unit processor 2200 is in a master-slave relationship with the artificial intelligence (A/I) device processor 2700 with the key functions of the medical treatment system 2000 being performed by the control console/unit 22 and its control console/unit processor 2200.

The control console/unit Wi-Fi module 2280 or the control console/unit Bluetooth module 2270 may be used to transmit control info wirelessly to the applicator Wi-Fi module 1040 or to the applicator Bluetooth module 1030, and finally to the applicator processor 1000, in order to make software updates, turn "On" and "Off" internal functions or components incorporated into the acoustic pressure shock wave applicator/treatment apparatus 10. The Wi-Fi and Bluetooth connections can also be used to transmit information regarding the performed treatment, from the acoustic pressure shock wave applicator/treatment apparatus 10 back to the control console/unit 22.

Another way to communicate data between the control console/unit 22 and the acoustic pressure shock wave applicator/treatment apparatus 10 is by using proximity RFID protocol by employing the control console/unit RFID module 2290 and the applicator RFID module 1050. The communication between modules 2290 and 1050 can facilitate the exchange of any data that is processed by the applicator processor 1000 and stored on the applicator memory 1020 with the control console/unit processor 2200 and then stored on the control console/unit memory 2210.

In another embodiment an external information storage device (not shown in any of the figures) can be used in the form of an RFID device that may be used to communicate with either the control console/unit RFID module 2290 or the applicator RFID module 1050. In various embodiments, the RFID external treatment information storage device may be a tag, label, or chip, and may include passive, active or semi-passive technology. In some embodiments, the RFID device may include RFID chip-less technology or electronic product code technology. Chipless RFID devices may allow for discrete identification of RFID tags without an integrated circuit, thereby allowing tags to be printed directly onto the surface of a treatment kit at lower costs than traditional tags. In one embodiment, treatment information RFID storage device may be a passive tag that requires no electrical supply for powering the tag. The tag may be inside of a medical treatment kit or it can be a label placed on the outside of the kit. In another embodiment, the treatment information storage device may be a passive RFID tag incorporating electronic product code technology. In various embodiments, the treatment information storage device may be a polymer tag such as that manufactured by PolyIC (Germany) or by Phillips (Netherlands).

In various embodiments, an RFID device (in the form of applicator RFID module 1050, control console/unit RFID module 2290, or RFID external treatment information storage device) may communicate according to the International Standards Organization ("ISO") 14443 and/or the International Electrotechnical Commission ("IEC") 18000-6 standards. The RFID external treatment information storage device may communicate up to a distance of 10 cm (i.e., 4 inches) from the control console/unit RFID module 2290 or the applicator RFID module 1050, in accordance with ISO 14443. The RFID device may be included in a smart label governed by ISO 15693. In one embodiment, the RFID device is a 13.567 MHz device.

Furthermore, by way of example, but not limitation, external treatment information storage device may be besides an RFID tag, in the form of a label or chip, memory stick, smart card, credit card, barcode, floppy disk, CD-ROM, digital versatile disk ("DVD") or any device configured to store information and from which information may be read.

As seen in FIG. 2B, the acoustic pressure shock wave applicator/treatment apparatus 10 includes the applicator processor 1000, the applicator I/O (input/output) element 1010, and the applicator memory 1020. Depending on the capabilities of the control console/unit 22, the acoustic pressure shock wave applicator/treatment apparatus 10 may also include the applicator Bluetooth module 1030, the applicator Wi-Fi module 1040, and the applicator RFID module 1050 to ensure a proper and rapid communication with the control console/unit 22 via the control console/unit-applicator secured data transfer protocol 1070. In one embodiments only one of these communication modules may be present, in another embodiment two of them, and in yet another embodiment all three of these communication modules may be present.

In one embodiment, the shock wave applicator/treatment apparatus 10 may receive optimized treatment setting control information from the control console/unit 22 and then output optimum focused acoustic pressure shock waves 40 or radial acoustic pressure waves 41 or planar acoustic pressure waves 42 or cylindrical acoustic pressure waves 44 for the treatment. In other situations the shock wave applicator/treatment apparatus 10 may provide other medical treatment according to the control information resultant from processing in control console/unit processor 2200, control console/unit emission mechanism 2240, control console/unit timer 2250 or control console/unit shock wave generator 2260. The acoustic pressure shock wave applicator/treatment apparatus 10 processes the control information from the applicator processor 1000 that received the control information from the control console/unit processor 2200, via the control console/unit-applicator secured data transfer protocol 1070 from the control console/unit 22, for generating a selected/optimized number of focused acoustic pressure shock waves 40 or radial acoustic pressure waves 41 or planar acoustic pressure waves 42 or cylindrical acoustic pressure waves 44, by utilizing a selected/optimized amount of energy, as determined by the one or more treatment settings. The control console/unit-applicator secured data transfer protocol 1070 provides security via authentication of the control console/unit 22 and of the acoustic pressure shock wave applicator/treatment apparatus 10. The applicator processor 1000 will also monitor the treatment parameters for their consistency and repeatability during the actual treatment delivery. The final number of focused acoustic pressure shock waves 40 or radial acoustic pressure waves 41 or planar acoustic pressure waves 42 or cylindrical acoustic pressure waves 44 delivered during treatment, the energy and frequency setting, the type and serial number of acoustic pressure shock wave applicator/treatment apparatus 10, the type and serial number of the control console/unit 22, date and timing are processed by the applicator processor 1000 and then recorded on the applicator memory 1020, at the end of the treatment. The same treatment data and parameters are then send it back to the control console/unit processor 2200, via the control console/unit-applicator secured data transfer protocol 1070 to be recorded on the control console/unit memory 2210. At its turn, the control console/unit 22 can use its control console/unit processor 2200 to transmit the treatment data and parameters to the artificial intelligence (A/I) device 27 for processing by the artificial intelligence (A/I) device processor 2700, or for storage into the artificial intelligence (A/I) device memory 2760, or to be sent via the artificial intelligence (A/I) device Wi-Fi module 2780 towards the internet based data storage/cloud database 29A and its associated artificial intelligence (AI) server 29B (see FIG. 2A). In other embodiment, the treatment data and parameters monitored and recorded inside the applicator processor 1000 that reached the control console/unit processor 2200 can be sent directly from the control console/unit 22 to the internet based data storage/cloud database 29A and its associated artificial intelligence (AI) server 29B, via its control console/unit Wi-Fi module 2280.

In one embodiment, the applicator memory 1020 may be any type of memory configured to store downloaded information regarding one or more treatment settings. In some embodiments, the applicator memory 1020 is any type of memory configured to store control information indicative of the one or more treatment settings or control signals for controlling the shock wave applicator/treatment apparatus 10. The applicator memory 1020 may store downloaded information regarding the actual settings of one or more performed treatments, errors, warnings, and in general the shock wave applicator/treatment apparatus 10 functionality. This data from the applicator memory 1020 can be downloaded for further analysis directly from the shock wave applicator/treatment apparatus 10, via the applicator I/O (input/output) element 1010. Also this treatment data and device functionality can be shared via the control console/unit-applicator secured data transfer protocol 1070 with the control console/unit 22, which at its turn can share it with the artificial intelligence (A/I) device 27, via the control console/unit-artificial intelligence (A/I) device secured data transfer protocol 2790.

In one embodiment, the applicator I/O (input/output) element 1010 receives information indicative of one or more treatment settings, processes the received information to generate a control signal for controlling acoustic pressure shock wave applicator/treatment apparatus 10. Also, the applicator I/O (input/output) element 1010 may also be configured to receive information such as updated information indicative of new treatment settings resultant from a completed medical treatment. In another embodiment, the applicator I/O (input/output) element 1010 may receive information indicating that a treatment has been administered and transmit the information to the control console/unit processor 2200, which may decrement by one a treatment setting indicative of the number of treatments allowed to a patient that was calculated and optimized using the algorithm presented in FIGS. 13A-15G. The updated treatment setting may then be written on control console/unit memory 2210 for subsequent accessing and use during a next medical treatment or to the artificial intelligence (A/I) device processor 2700 for subsequent metadata analysis.

With further reference to FIG. 2B, the acoustic pressure shock wave applicator/treatment apparatus 10 and the control console/unit 22 preferably share a common power supply 21, which can be incorporated inside the control console/unit 22 or can be separate from both the acoustic pressure shock wave applicator/treatment apparatus 10 and the control console/unit 22. The role of the power supply 21 is to convert and provide enough energy/power to activate both the acoustic pressure shock wave applicator/treatment apparatus 10 and the control console/unit 22 and their respective components.

Referring to FIG. 2B, the artificial intelligence (A/I) device 27 is shown. Artificial intelligence (A/I) device 27 includes the artificial intelligence (A/I) device processor 2700, artificial intelligence (A/I) device display 2740, artificial intelligence (A/I) device I/O (input/output) element 2750, artificial intelligence (A/I) device memory 2760, and artificial intelligence (A/I) device power source 2710. The artificial intelligence (A/I) device 27 also includes in embodiments an artificial intelligence (A/I) device digital/infrared camera 2720 and artificial intelligence (A/I) device photo imaging analysis system 2730, which are used for tracking treatment progress and success. These modules can take pictures of the treatment targeted region and calculate/analyze in real time, for example, wound/burn area and volume, perfusion rate, viability of the tissue, oxygenation, vascularization, bioburden, and like parameters. In addition, the artificial intelligence (A/I) device 27 may include the artificial intelligence (A/I) device Bluetooth module 2770 and artificial intelligence (A/I) device Wi-Fi module 2780 to provide proper and rapid communication with the control console/unit 22 via the control console/unit-artificial intelligence (A/I) device secured data transfer protocol 2790.

The artificial intelligence (A/I) device Bluetooth module 2770 and the artificial intelligence (A/I) device Wi-Fi module 2780 are used to wireless communicate with the internet based data storage/cloud database 29A and artificial intelligence (AI) server 29B to provide metadata analysis for extracting deep information within the medical treatment data to solve highly complex medical challenges and treatment shortcomings, predict synergetic or non-synergetic interaction between different devices and treatment modalities, etc. Also, the artificial intelligence (A/I) device Bluetooth module 2770 and the artificial intelligence (A/I) device Wi-Fi module 2780 are used to wireless communicate with control console/unit 22 using the control console/unit Bluetooth module 2270 and control console/unit Wi-Fi module 2280, to exchange any type of information via the control console/unit-artificial intelligence (A/I) device secured data transfer protocol 2790.

In one embodiment, the artificial intelligence (A/I) device 27 processes information received from the artificial intelligence (A/I) device processor 2700 and transmits the information to the control console/unit processor 2200 via the control console/unit-artificial intelligence (A/I) device secured data transfer protocol 2790. This information is used to control the setting and optimized functionality of the acoustic pressure shock wave applicator/treatment apparatus 10 via the control console/unit-applicator secured data transfer protocol 1070. Treatment setting information can be modified by the artificial intelligence (A/I) device processor 2700 or received from the artificial intelligence (AI) server 29B, where the optimization was done, and then stored on the internet based data storage/cloud database 29A, via the Wi-Fi connection 28H (see FIG. 2A). The optimized treatment settings are realized (either by artificial intelligence (A/I) device processor 2700 or by the artificial intelligence (AI) server 29B) via precise algorithms presented in FIGS. 8A-16D for a determined energy setting used for each treatment. The modification of treatment settings is done using patient data generated during execution of a questionnaire protocol provided on the control console/unit display 2220 or artificial intelligence (A/I) device display 2740, whereby data is input by the user (nurse, or physician, and/or medical office dedicated worker) via the control console/unit I/O (input/output) device 2230 or the artificial intelligence (A/I) device I/O (input/output) element 2750.

The artificial intelligence (A/I) device memory 2760 may be any type of memory configured to store downloaded information regarding one or more treatment settings, optimization algorithm, treatment outcomes, errors, warnings, parameters used during the delivered therapy/treatment, patient information, ancillary devices information and their interaction (synergetic or not) with the medical treatment system 2000, follow-up data, monitoring data, tutorials, troubleshooting, general devices functionality and the like.

In one embodiment, the artificial intelligence (A/I) device I/O (input/output) element 2750 receives information indicative of one or more treatment settings, processes the received information to generate a control signal for controlling acoustic pressure shock wave applicator/treatment apparatus 10. The artificial intelligence (A/I) device I/O (input/output) element 2750 may also transmit directly the control information to the acoustic pressure shock wave applicator/treatment apparatus 10. Also, the artificial intelligence (A/I) device I/O (input/output) element 2750 may be configured to receive information such as updated information indicative of new optimized treatment settings resultant from a completed medical treatment. In another embodiment, the artificial intelligence (A/I) device I/O (input/output) element 2750 may receive information indicating that a treatment has been administered and transmit the information to the artificial intelligence (A/I) device processor 2700, which may decrement by one a treatment setting indicative of the number of treatments allowed to a patient based on the algorithm presented in FIGS. 13A-15G. The updated treatment setting may then be written on control console/unit memory 2210 or the artificial intelligence (A/I) device memory 2760 for subsequent accessing and use during a next medical treatment. The updated treatment setting may also be written to the artificial intelligence (A/I) device processor 2700 for subsequent metadata analysis or sent to the artificial intelligence (AI) server 29B.

In another embodiment, the artificial intelligence (A/I) device I/O (input/output) element 2750 may completely take over or replace the control console/unit I/O (input/output) element 2230. In this embodiment the artificial intelligence (A/I) device 27 may ultimately control the functionality of the acoustic pressure shock wave applicator/treatment apparatus 10 and the control console/unit 22 role is minimized to only generate and maintain proper parameters for the focused acoustic pressure shock waves 40 or radial acoustic pressure waves 41 or planar acoustic pressure waves 42 or cylindrical acoustic pressure waves 44 necessary for the treatment.

The artificial intelligence (A/I) device display 2740 may provide a visual display of graphics and/or text indicative of the one or more treatment settings and selections, patient identity information, patient comorbidities and medication, patient insurance information, different algorithm to gather information, ancillary treatment apparatus choice, training materials, troubleshooting, treatment apparatus activation or the like. Additionally, in some embodiments, the artificial intelligence (A/I) device display 2740 may provide a visual display of navigational treatment setting choices and current treatment parameters. In this embodiment, the artificial intelligence (A/I) device display 2740 may provide an indicator of the amount of treatment remaining before, during or after a medical treatment, or provide a display of one or more body regions targeted by the treatment. The artificial intelligence (A/I) device display 2740 are preferably also capable to display pictures, graphs, and outcome information from the artificial intelligence (A/I) device digital/infrared camera 2720 artificial intelligence (A/I) device and photo imaging analysis system 2730.

In another embodiment, the artificial intelligence (A/I) device display 2740 can substitute completely the control console/unit display 2220 of the control console/unit 22. In this embodiment every data display and also input/output (I/O) will be done by the artificial intelligence (A/I) device display 2740 and artificial intelligence (A/I) device I/O (input/output) element 2750 of the artificial intelligence (A/I) device 27. Furthermore, the artificial intelligence (A/I) device processor 2700 will be in a master-slave relationship with the control console/unit processor 2200. That means that the most important functions of the medical treatment system 2000 will be performed by the artificial intelligence (A/I) device 27 and its artificial intelligence (A/I) device processor 2700.

Authentication protocols used by both the control console/unit-applicator secured data transfer protocol 1070 and the control console/unit-artificial intelligence (A/I) device secured data transfer protocol 2790 may reduce the problem of erroneous selection of acoustic pressure shock wave applicator/treatment apparatus 10 or control console/unit 22 and parameters or any other ancillary device in the system. Such authentication may also increase the probability of effective treatment by reducing the probability of selecting primary and supplemental apparatus that reduce the effectiveness of one another. Ancillary treatment apparatus may be disposable and/or consumable. Ancillary treatment apparatus may be any device designed to be used during a medical procedure together with the medical treatment system 2000. In various embodiments, ancillary treatment apparatus may be a device configured to generate and/or emit energy in the form of electric signals, ultrasound, laser, light, heat, cold, vacuum, mechanical pressure etc.

Additionally, determining the identity of a specific devices and ensuring that the proper devices are being used reduces the likelihood of unsafe treatment. For example, the likelihood of unsafe dosages of energy and/or an unsafe number of focused acoustic pressure shock waves 40 or radial acoustic pressure waves 41 or planar acoustic pressure waves 42 or cylindrical acoustic pressure waves 44 being applied to a patient may be reduced because the treatment settings may be programmed into the control console/unit memory 2210 or the artificial intelligence (A/I) device memory 2760.

In other embodiment, the authentication sequence used by the control console/unit-applicator secured data transfer protocol 1070 ensures that the control console/unit 22 and the shock wave applicator/treatment apparatus 10 are not used in regions wherein the government of the region has not authorized the control console/unit 22 and its associated shock wave applicator/treatment apparatus 10 to be used. Accordingly, a control console/unit 22 used in an inappropriate region may not be enabled to operate because the control console/unit-applicator secured data transfer protocol 1070 may only authenticate control console/unit 22 and shock wave applicator/treatment apparatus 10 that are authorized to be used in a certain region. In some embodiments, a Global Positioning System (GPS) receiver, wireless triangulation controller, Internet domain addresses and like location technologies may be used with the controller to determine a geographical region and associated geographical-based setting.

In each embodiment, if the medical treatment system 2000 components are authenticated, then the medical treatment can be performed. If authentication fails, treatment information the applicator processor 1000 or control console/unit processor 2200 or artificial intelligence (A/I) device processor 2700 operate in such a fashion so as to not allow for the medical treatment to be performed by preventing the control console/unit 22 and/or the artificial intelligence (A/I) device 27 from operating.

In one embodiment, authentication is performed using a password that is transmitted from the control console/unit 22 to the acoustic pressure shock wave applicator/treatment apparatus 10 or to the artificial intelligence (A/I) device 27. The password may be encrypted to prevent the password from being pirated and improperly enabling the control console/unit 22 or the acoustic pressure shock wave applicator/treatment apparatus 10 or to the artificial intelligence (A/I) device 27 to be turned on. If the control console/unit 22 matches the correct password send back from the acoustic pressure shock wave applicator/treatment apparatus 10 or to the artificial intelligence (A/I) device 27 then authentication is successful and the medical treatment is allowed. If the password is not matched, then the medical treatment is not allowed and cannot be performed and the control console/unit 22 controller is in an "Off" mode. The control console/unit 22 may be maintained in the "Off" mode, for example, by maintaining a switch in the "Off" mode or by moving an internal switch to the "Off" mode. Accordingly, access to the control console/unit 22 may be denied and/or the control console/unit 22 may be maintained in an off position or in a state otherwise unable to perform a medical treatment if authentication is not successful.

In general the applicator processor 1000 or control console/unit processor 2200 or artificial intelligence (A/I) device processor 2700 may include software, hardware, or a combination of both software and hardware configured to receive and process information from the real-time functionality of the acoustic pressure shock wave applicator/treatment apparatus 10, control console/unit 22, or artificial intelligence (A/I) device 27, respectively. The applicator processor 1000 or control console/unit processor 2200 or artificial intelligence (A/I) device processor 2700 include microprocessor-executable instructions for applying specific medical treatment control parameters to an acoustic pressure shock wave applicator/treatment apparatus 10. In some embodiments, treatment information may be configured with a mechanism or information that may be used to track inventory, perform inventory control functions, reduce theft, facilitate fee provisioning, facilitate insurance coding, facilitate provisioning of payments for medical treatments in advance of receiving the medical treatments, provide security provisioning to enable the control console/unit 22 and or the artificial intelligence (A/I) device 27 to operate or the like, as described above. In this embodiment, the control console/unit processor 2200 and/or the artificial intelligence (A/I) device processor 2700 may be programmed with medical treatment optimized settings and perform the treatment. In response to the treatment ending, the treatment settings used may be recorded in a tabular form into control console/unit 22 and/or the artificial intelligence (A/I) device 27 and then used to calculate the payment for the treatment and to perform insurance coding. The information may also generate data about what was done for the treatment and store the data in the control console/unit 22 and/or the artificial intelligence (A/I) device 27 for a period of time (or for a selected number of future treatments). The tabulated data may also be used to determine whether the control console/unit 22 and/or the artificial intelligence (A/I) device 27 is malfunctioning and reimburse the patient if it is determined that there is malfunctioning or acts of God preventing proper operation of the controller control console/unit 22 and/or the artificial intelligence (A/I) device 27 or acoustic pressure shock wave applicator/treatment apparatus 10. The fee provisioning data can also be used for tracking the treatment of the patient.

The applicator I/O (input/output) element 1010, or control console/unit I/O (input/output) element 2230, or artificial intelligence (A/I) device I/O (input/output) element 2750 includes software, hardware, or a combination of both software and hardware configured to receive inputs initiated by a user and translate the received inputs to signals disposed to be interpreted by one or more of processor, display, or by the acoustic pressure shock wave applicator/treatment apparatus 10, control console/unit 22, or artificial intelligence (A/I) device 27, respectively. In one embodiment, the received inputs are translated into signals configured to cause the applicator processor 1000, or control console/unit processor 2200, or artificial intelligence (A/I) device processor 2700 to read and/or scan the information regarding functionality of the shock wave applicator/treatment apparatus 10, control console/unit 22, or artificial intelligence (A/I) device 27, respectively. In another embodiment, the received inputs are translated into signals configured to cause a mechanism to write the information to the applicator memory 1020, or control console/unit memory 2210, or artificial intelligence (A/I) device memory 2760, respectively. In yet another embodiment, the received inputs are translated into signals configured to control the shock wave applicator/treatment apparatus 10 functionality parameters (energy setting, frequency, and total number of focused acoustic pressure shock waves 40 or radial acoustic pressure waves 41 or planar acoustic pressure waves 42 or cylindrical acoustic pressure waves 44). The applicator I/O (input/output) element 1010, or control console/unit I/O (input/output) element 2230, or artificial intelligence (A/I) device I/O (input/output) element 2750 include, but is not limited to, a keyboard, mouse, human interface device, image or video capture devices, temperature sensors, measuring instruments and the like. The information may be the treatment parameters, a specific body part medical condition, physical and anatomical measurements of a treatment area, pictures of treatment area, information indicative of the type of treatment (e.g., hard tissue, soft tissue), patient anatomic and medical data, and/or the type of treatment (e.g., non-ablative, which does not kill tissue, or ablative, which kills tissue, stimulation, healing or any other type of medical treatment that may be performed using the pressure shock wave applicator/treatment apparatus 10, control console/unit 22, and the artificial intelligence (A/I) device 27). The medical treatment necessary to address the physical and anatomical measurements and/or provide the type of desired treatment may be determined by the control console/unit 22 in some embodiments and by the artificial intelligence (A/I) device 27 in other embodiments. After storing this information in the control console/unit 22 and/or artificial intelligence (A/I) device 27, the control console/unit 22 and/or artificial intelligence (A/I) device 27 may identify a type of ancillary device or devices that are appropriate for the medical treatment. In alternative embodiments, a specific measurement of a desired area or volume of a body targeted region to be treated with focused acoustic pressure shock waves 40 or radial acoustic pressure waves 41 or planar acoustic pressure waves 42 or cylindrical acoustic pressure waves 44 may be the input to the control console/unit 22, via the control console/unit I/O (input/output) element 2230, or to the artificial intelligence (A/I) device 27, via the artificial intelligence (A/I) device I/O (input/output) element 2750, to set appropriate parameters for such area or volume. A density measurement of the targeted body tissue or vascularization or bioburden, etc. may also be input to the control console/unit 22 or to the artificial intelligence (A/I) device 27 for determination of appropriate treatment parameters. Further, in other embodiments, the particular body part and/or tissue condition 19 may be the input to the control console/unit 22 or to the artificial intelligence (A/I) device 27 to set appropriate parameters for treatment of the body part and/or tissue condition 19. Information regarding that status of the condition, such as tissue condition 19 area or volume measurements, healing characteristics, and the like, may be the input to the control console/unit 22 or to the artificial intelligence (A/I) device 27. In one embodiment, the user control console/unit I/O (input/output) element 2230 and/or artificial intelligence (A/I) device I/O (input/output) element 2750 may include an "On/Off" mechanism, a mechanism for receiving treatment settings regarding energy, frequency of shock waves, a preselected dose of shock waves, the number of shocks per area, a position parameter for automatic positioning of the acoustic pressure shock wave applicator/treatment apparatus 10 and/or an editing tool such as an electronic pencil disposed to cooperate with a control console/unit display 2220 and/or artificial intelligence (A/I) device display 2740 configured as a touchscreen for manually editing an image of a treatment area. A wound size may be defined with the editing tool. The editing tool may be used to identify the coordinates of a wound and such coordinates may be sent as electronic signals to the control console/unit processor 2200 and/or artificial intelligence (A/I) device processor 2700, which may automatically calculate the treatment area and/or volume, and tissue characteristics.

The control console/unit display 2220 or artificial intelligence (A/I) device display 2740 includes software, hardware or a combination of both software and hardware configured to receive and format for visual display image information indicative of one or more functional parameters settings, treatment information needed for reimbursement or financial purpose, graphics, data protocols, pictures of the treatment targeted region and measurements for area, volume, perfusion rate, viability of the tissue, oxygenation, vascularization, bioburden, and the like. The visual display may be graphical, pictorial, text or otherwise. In one embodiment, the control console/unit display 2220 or artificial intelligence (A/I) device display 2740 provide a graphical user interface ("GUI"). The GUI may be a touchscreen GUI or a GUI configured to receive signal from inputs received at user input on the control console/unit I/O (input/output) element 2230 or artificial intelligence (A/I) device I/O (input/output) element 2750 for the correct functionality of the pressure shock wave applicator/treatment apparatus 10, control console/unit 22, and the artificial intelligence (A/I) device 27. In one embodiment, the control console/unit display 2220 or artificial intelligence (A/I) device display 2740 shows operational instructions readable by personnel operating the pressure shock wave applicator/treatment apparatus 10, control console/unit 22, and the artificial intelligence (A/I) device 27. In another embodiment, instructions may be provided for performing one or more of: initializing the pressure shock wave applicator/treatment apparatus 10, control console/unit 22, and the artificial intelligence (A/I) device 27; loading optimized operational settings; loading necessary information indicative of the type of setting; or starting procedure for the pressure shock wave applicator/treatment apparatus 10, control console/unit 22, and the artificial intelligence (A/I) device 27.

The applicator memory 1020 or control console/unit memory 2210 or artificial intelligence (A/I) device memory 2760 may be any type of memory configured to store information regarding one or more treatment settings, one or more ancillary treatment apparatus used during a medical treatment administered by the medical treatment system 2000, and/or one or more medical treatments currently or previously performed. Information stored on the applicator memory 1020 and/or control console/unit memory 2210 and/or artificial intelligence (A/I) device memory 2760 may be stored in any manner suitable for facilitating a medical treatment. For example, in various embodiments, the information may be stored as random access memory, read only memory, flash memory or the like. In some embodiments, security information that may be encrypted or unencrypted may be stored on the applicator memory 1020 or control console/unit memory 2210 or artificial intelligence (A/I) device memory 2760. The information may be read to authenticate the pressure shock wave applicator/treatment apparatus 10 and/or the control console/unit 22. The authentication may ensure compatibility between the control console/unit 22 and/or any ancillary devices that may be used during treatment. Additionally, the information may be used to determine whether the pressure shock wave applicator/treatment apparatus 10 and/or the control console/unit 22 are authorized to be used in the geographical region in which the pressure shock wave applicator/treatment apparatus 10 and/or the control console/unit 22 are located. After ending treatment, the log of the treatment may be stored inside the pressure shock wave applicator/treatment apparatus 10, via applicator memory 1020, and/or control console/unit 22, via control console/unit memory 2210, and/or the artificial intelligence (A/I) device 27, via artificial intelligence (A/I) device memory 2760. The way that treatment is ended may be determined and evaluated. When treatment is ended by a shut off of the control console/unit 22 and/or the artificial intelligence (A/I) device 27, a "hard shut off" or a "soft shut off" may occur. As used herein, the term "hard shut off" shall mean a shut off of the control console/unit 22 and/or the artificial intelligence (A/I) device 27 after a power failure, due to a faulty control console/unit 22 and/or the artificial intelligence (A/I) device 27 and/or the pressure shock wave applicator/treatment apparatus, after switching the main switch directly to turn off the control console/unit 22 and/or the artificial intelligence (A/I) device 27 or by unplugging the control console/unit 22 and/or the artificial intelligence (A/I) device 27 from the power source. As used herein, the term "soft shut off" shall mean shut off of the control console/unit 22 and/or the artificial intelligence (A/I) device 27 after a proper shut off by pushing the stand-by button or activating another mechanism for properly stopping the operation of the control console/unit 22 and/or the artificial intelligence (A/I) device 27 and/or the pressure shock wave applicator/treatment apparatus 10 after a medical treatment has ended. When a hard shut off occurs, the patient may be reimbursed for the treatment being performed. In cases wherein the log of the treatment is indicative of the control console/unit 22 and/or the artificial intelligence (A/I) device 27 being shut down in a manner so as to avoid detection that a medical treatment has been performed, the control console/unit 22 and/or the artificial intelligence (A/I) device 27 may be stopped and not started again until authorization by a third-party having the power to authorize the control console/unit 22 and/or the artificial intelligence (A/I) device 27 to be able to be started again. The log of treatment may be indicative of attempts to avoid detection when there have been a selected number of consecutive hard shut offs. For example, after three hard shut offs, the control console/unit 22 and/or the artificial intelligence (A/I) device 27 may be shut down until an authorized third-party starts the control console/unit 22 and/or the artificial intelligence (A/I) device 27 again. The pattern of attempting to avoid detection may differ from that disclosed above.

Figure 3:
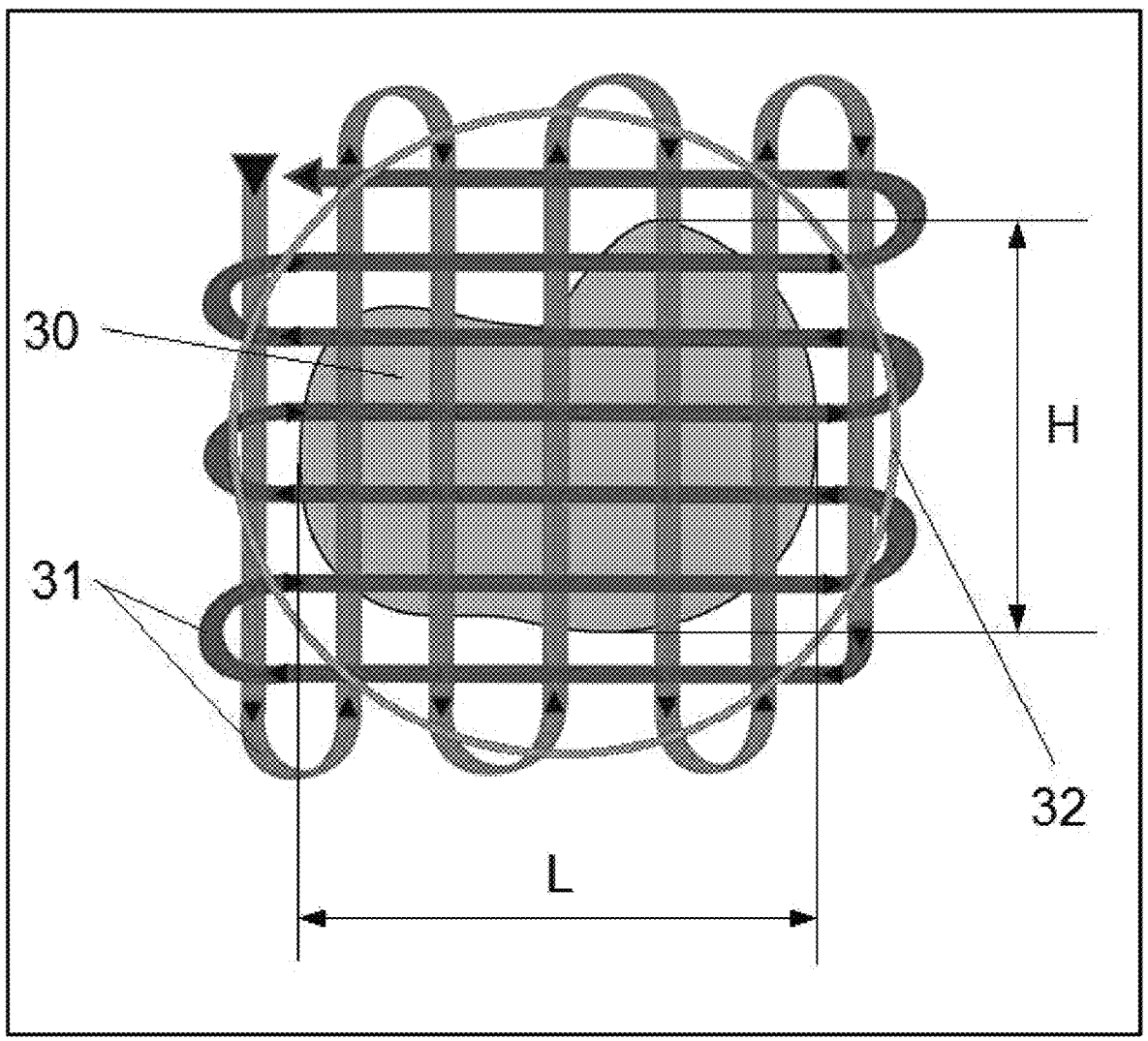
FIG. 3 is a schematic illustration of the way the area of tissue condition is determined and then covered during an acoustic pressure shock wave treatment, according to one embodiment of the present invention.

In practice the physicians or nurses make a judgement on the extent of the treatment with focused acoustic pressure shock waves 40 or radial acoustic pressure waves 41 or planar acoustic pressure waves 42 or cylindrical acoustic pressure waves 44 based on the dimensions of the treatment targeted area 30 of the tissue condition 19, by measuring the treatment area approximate length L and treatment area approximate height H, as shown in FIG. 3. In some situations when ischemia is present around the visible treatment targeted area 30, the physicians or nurses will add 1 or 2 cm in each direction from the edge of the treatment targeted area 30, which will modify the treatment area approximate length L with 2 or 4 cm and treatment area approximate height H in the same manner with 2 or 4 cm, respectively. The same calculation can be done automatically by the control console/unit 22 or the artificial intelligence (A/I) device 27 after the actual perceptible treatment area approximate length L and treatment area approximate height H are measured by the physicians or nurses and introduced via control console/unit I/O (input/output) element 2230 (see FIG. 2B) or artificial intelligence (A/I) device I/O (input/output) element 2750 (see also FIG. 2B) into the control console/unit processor 2200 or artificial intelligence (A/I) device processor 2700. In other situations where tissue ischemia extends beyond 2 cm in each direction of the treatment targeted area 30, larger adjustments can be done manually or automatically, based on measurements on tissue oxygenation and/or perfusion using dedicated ancillary devices or specific modules from the control console/unit 22 or the artificial intelligence (A/I) device 27.

In another embodiment, the treatment area can be determined automatically using pictures of the tissue condition 19 taken by the artificial intelligence (A/I) device digital/infrared camera 2720 and then analyzed and interpreted by the artificial intelligence (A/I) device photo imaging analysis system 2730 from the artificial intelligence (A/I) device 27. The analysis of the pictures taken by the artificial intelligence (A/I) device digital/infrared camera 2720 is done by the artificial intelligence (A/I) device photo imaging system 2730 that identifies the edges of the tissue condition 19 and its depth (thus calculating even a volume of the tissue condition 19). Afterwards the artificial intelligence (A/I) device processor 2700 can adjust the area/volume based on the measurements on tissue oxygenation and/or perfusion done using the artificial intelligence (A/I) device digital/infrared camera 2720 or by a distinct/dedicated ancillary device connected into the medical treatment system 2000 presented in FIGS. 2A and 2B. In another embodiment, a similar photo imaging analysis system as the one from the artificial intelligence (A/I) device 27 can be incorporated directly into the control console/unit 22.

In another embodiment, infrared visualization and optical goggles can be used for wound care treatment to determine the delineation of the poor vascularized tissue from normal tissue and thus be able to treat correctly the tissue condition 19. These goggles can also be interconnected with the control console/unit 22 or the artificial intelligence (A/I) device 27 where the control console/unit display 2220, or artificial intelligence (A/I) device display 2740, or any display of an interconnected device (see FIG. 2A for the medical treatment system 2000) as a desktop computer 28A, or a smart phone 28B, and/or tablet 28C, and/or laptop 28D can be used to show the image of the tissue condition 19. These images then can be loaded in the control console/unit processor 2200 and/or artificial intelligence (A/I) device processor 2700 for further analysis.

In another embodiment, as an alternative to using goggles or the artificial intelligence (A/I) device digital/infrared camera 2720 from the artificial intelligence (A/I) device 27, miniature cameras attached to the pressure shock wave applicator/treatment apparatus 10 can be used to determine the delineation of the poor vascularized tissue from normal tissue and thus to be able to treat correctly the tissue condition 19.

The adjustments made on tissue condition 19 area and/or volume, based on ischemic condition of the targeted region, means that the treatment in reality is performed on an actual treatment circular area 32 surrounding the treatment targeted area 30, as shown in FIG. 3. After the actual treatment circular area 32 is established manually or automatically, then the pressure shock wave applicator/treatment apparatus 10 is preferably passed over the actual treatment circular area 32 using the applicator movement pattern 31, which assures the complete treatment of the tissue condition 19.

In situations where ischemic conditions are not present, then the above mentioned adjustments for ischemia are not necessary and are not done.

Based on the specific status of each tissue condition 19, after tissue condition 19 area and/or volume are determined and possible adjustments for ischemic conditions are done, then the final tissue condition 19 area and/or volume are used to establish a basic/initial number of focused acoustic pressure shock waves 40 or radial acoustic pressure waves 41 or planar acoustic pressure waves 42 or cylindrical acoustic pressure waves 44 that are needed for successful treatment of the tissue condition 19. In general, the basic/initial number of focused acoustic pressure shock waves 40 or radial acoustic pressure waves 41 or planar acoustic pressure waves 42 or cylindrical acoustic pressure waves 44 is called the basic/initial dosage. None of the patient comorbidities, anatomic data, life regimen, etc. are considered in the basic/initial dosage. In order to tailor treatment for a patient's general condition and status of their tissue condition 19, adjustments can be made to the basic/initial dosage or number of treatments or the energy setting based on dedicated algorithms loaded in the control console/unit processor 2200 and/or artificial intelligence (A/I) device processor 2700.

Figure 5:
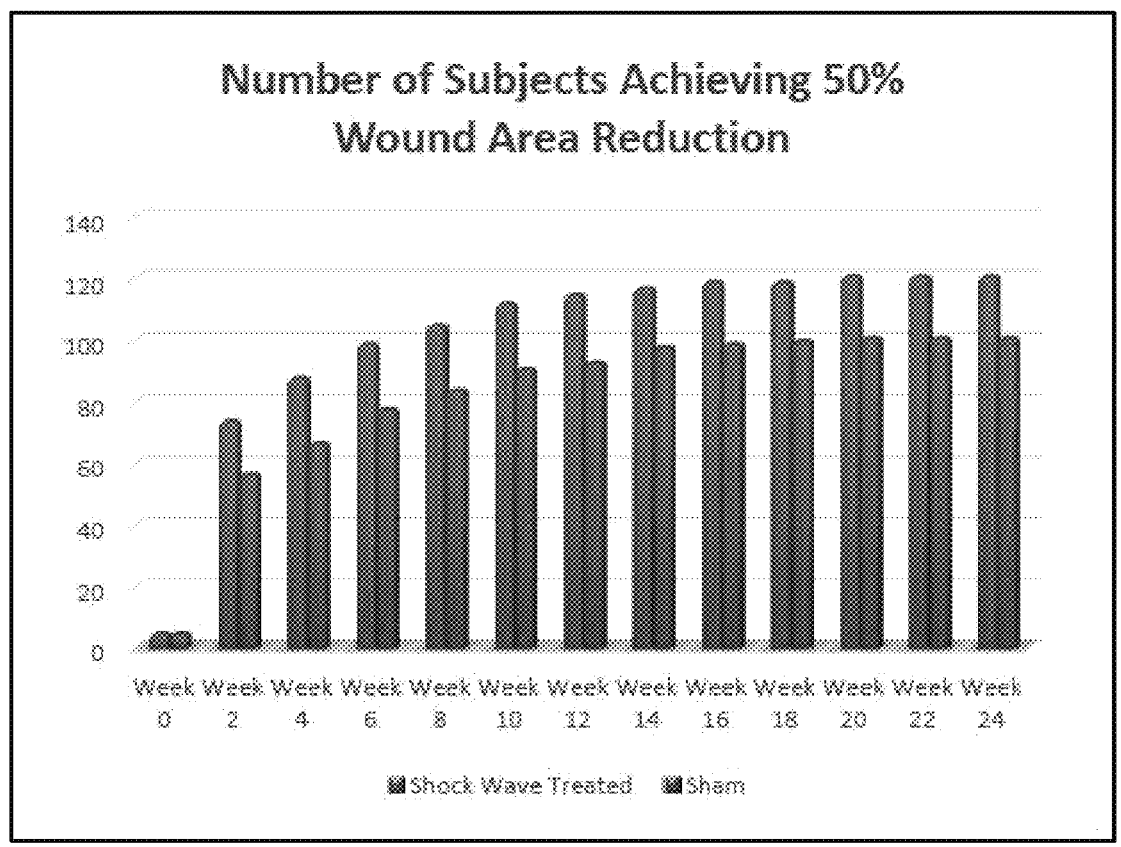
FIG. 5 is a graph of the clinical data from a randomized double-blinded clinical trial for chronic wound care, using acoustic pressure shock waves as active treatment that shows in a graphical form the number of patients with 50% wound area reduction.

In general, about a 50% or more reduction of the area for the tissue condition 19 by week 4 is considered a key parameter in determining if a tissue conditions 19 is responding to treatment and is likely to eventually heal. In a randomized double blind clinical trial with a total of 336 patients, the healing effect of focused acoustic pressure shock waves 40 was assessed for the active group (total 172 patients) against non-treated sham group (total 164 patients) in treating chronic diabetic foot ulcers (DFUs). The results from FIG. 4 show in a tabular form that beginning at 4 weeks, the shock wave treated group has a higher number "n" and respective percentage of subjects with a 50% wound reduction when compared to the control group (statistical significant difference value of $p=0.058$). This advantage for patients subject to shock wave treatment continues throughout the remainder of the trial up to the 24 weeks used for follow-up. These results along the whole duration of the clinical trial (24 weeks) are also presented in a graphical form in FIG. 5.

Figure 6:
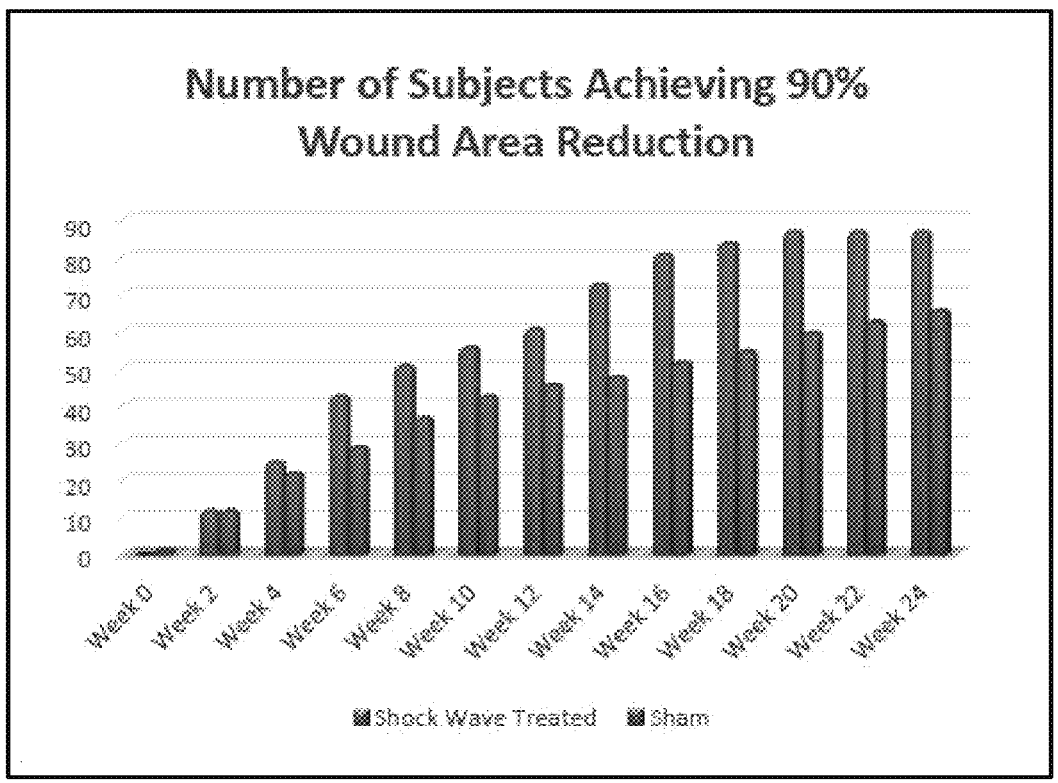
FIG. 6 is a graph of the clinical data from a randomized double-blinded clinical trial for chronic wound care, using acoustic pressure shock waves as active treatment that shows in a graphical form the number of patients with 90% wound area reduction.

FIG. 6 presents in a graphical form the results of the clinical trial as to when 90% or more reduction of the area for the tissue condition 19 has occurred for those in the active group treated with focused acoustic pressure shock waves 40 against those in a non-treated/sham group. The results showed that there was a statistically significant difference between the two cohorts from the 14 week follow-up visit through the end of the study at 24 weeks with a statistical significant difference value of $p=0.055$. Furthermore, the non-invasive, non-pharmacologic, and non-biologic delivery of acoustic energy for the treatment of chronic diabetic foot ulcers (DFUs) shows that there is a good opportunity to reduce the wound area in order to gain benefits of reduced risk of infection and amputations. The active treatment with focused acoustic pressure shock waves 40 allowed the wound to close naturally beyond 12 weeks and the patient's quality of life was improved over the course of the treatment and post-treatment. The shock wave treated-patients demonstrated at 24 weeks superior results in wound closure, reached wound closure at a faster rate, showed superior results in wound reduction in area (cm²), and showed superior results in the prevention of wound expansion over the course of the study.

Finally, the clinical trial results were analyzed for several sub-populations based on age, sex, smoking status, body mass index (BMI), weight, height, wound age, and diabetic status. These results are shown in a tabular form in FIG. 7. At 24 weeks several sub-populations demonstrated a statistically higher percentage of wound closure for the active group treated with focused acoustic pressure shock waves 40 compared to the control subjects. Thus the subjects with age less than 65 years healed faster than the ones that were 65 years or older. The males healed better than the females and also the non-smokers healed better than smokers. When biometrics were taking into account, the subjects with a BMI less than 32, a weight less than 220 pounds/99.8 kg, and a height greater than or equal to 70 inches/177.8 cm healed better. Finally, when presence of diabetes (determined via glycated hemoglobin HbA1c) was analyzed the patients with values higher than 7, which indicates poorer control of blood glucose levels, healed better. These results indicate the possibility to improve treatment with acoustic pressure shock waves by adjusting the treatment dosage, energy setting, and number of treatments based on specific comorbidities, biometrics and personal parameters of a patient, and wounds status. Such adjustments can made to treatment with focused acoustic pressure shock waves 40 or radial acoustic pressure waves 41 or planar acoustic pressure waves 42 or cylindrical acoustic pressure waves 44 more personalized and efficient. These opportunities will be analyzed in detail for diabetic foot ulcers (DFUs), pressure ulcers, arterial ulcers, venous ulcers, burn wounds, and common skin conditions in the following further description of the invention.

Diabetic foot ulcers (DFUs) are one of the leading causes of hospitalization in diabetic patients and lead to billions of dollars in health care expenditures annually. A majority of diabetics presenting with foot ulcers have Type 2 diabetes. Trauma caused by mechanical, surgical, biological, or chemical means can initiate ulceration of the foot in a diabetic patient. In addition, specific diabetic complications such as diabetic neuropathy, ischemia or peripheral vascular disease (PVD), and immune deficiency exacerbate the ulceration. Other contributing risk factors leading to ulcers and poor healing are advanced age, duration of diabetes, poor glycemic control, diabetic neuropathy, age, nutrition, peripheral vascular disease, cigarette smoking, excessive alcohol consumptions, existing comorbidities, previous foot ulcerations or amputations, and ischemia of small and large blood vessels. For diabetic patients only 30-45% of wounds achieve closure using current standard of care. The grade (I, II, or III) of diabetic foot wounds is based on the depth of soft tissue and osseous involvement.

When a DFU does occur, the current standard of care includes medical management of the systemic diabetes, offloading the weight-bearing pressure of the foot (casts, shoes, etc.), debridement of necrotic or non-viable tissue, and wet-to-dry or wet-to-moist wound dressings. When the standard of care does not prove effective, other alternatives such as advanced dressings, biologics, and negative pressure devices are considered before surgical intervention and/or amputation become necessary. Despite the development of advanced wound care products, there is still a need to find the most effective treatment for reducing the time required to close a DFU. Focused acoustic pressure shock waves 40 or radial acoustic pressure waves 41 or planar pressure waves 42 or cylindrical acoustic pressure waves 44 have been shown to promote healing in several wound-healing applications, where they initiate a biological response at the cellular level, stimulating production of angiogenic growth factors, including endothelial nitric oxide synthase, vascular endothelial growth factor, and proliferating cell nuclear antigen, as shown by the results of FIGS. 4-7. These factors are important components of the normal wound healing process. This cellular activation is playing a decisive role in growing of newly formed vessels, increased cellular proliferation, and tissue regeneration needed to heal a wound.

The personalized treatment parameters for diabetic foot ulcers (DFUs) when focused acoustic pressure shock waves 40 or radial acoustic pressure waves 41 or planar acoustic pressure waves 42 or cylindrical acoustic pressure waves 44 are used can be determined using different factors. FIGS. 8A-8E present a novel algorithm that can be used to adjust the number of focused acoustic pressure shock waves 40 or radial acoustic pressure waves 41 or planar acoustic pressure waves 42 or cylindrical acoustic pressure waves 44 used for the treatment of DFUs based on different elements that take into account the characteristics of the DFU, patient's comorbidities, biometrics, personal parameters and lifestyle.

As a starting point for each algorithm in embodiments of the invention, a basic/initial number of focused acoustic pressure shock waves 40 or radial acoustic pressure waves 41 or planar acoustic pressure waves 42 or cylindrical acoustic pressure waves 44 is determined as minimally needed for successful treatment of the tissue condition 19. As previously described, this determination is considered the basic/initial dosage that is calculated after tissue condition 19 area and/or volume are determined and possible adjustments for ischemic conditions are done.

Figure 8A:
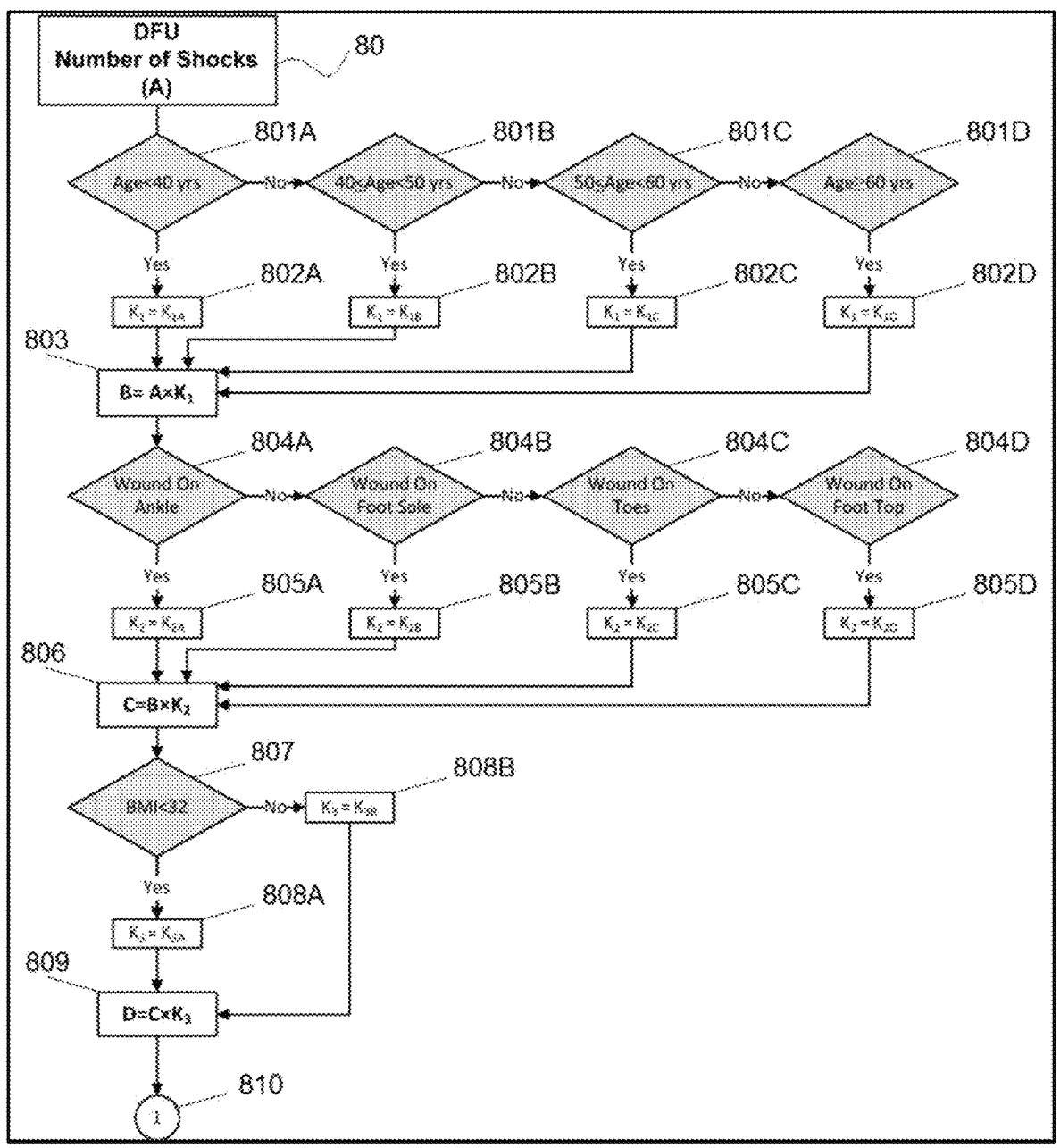
FIG. 8A is a flow diagram of the algorithm used to calculate the number of acoustic pressure shock waves for treatment of diabetic foot ulcers (DFUs) when patient age, location of the wound, and body mass index (BMI) are taken into account, according to one embodiment of the present invention.

Referring to FIG. 8A, the basic/initial number of shocks (A) for diabetic foot ulcer (DFU) 80 represents the starting point of the adjustment/optimization algorithm for number of focused acoustic pressure shock waves 40 or radial acoustic pressure waves 41 or planar acoustic pressure waves 42 or cylindrical acoustic pressure waves 44 for the treatment of diabetic foot ulcers (DFUs). The first element used to alter the basic/initial dosage used for DFUs treatment is the inquiry regarding the age of the patient. Thus on the control console/unit display 2220, or artificial intelligence (A/I) device display 2740, or on the display of an interconnected device (see FIG. 2A for the medical treatment system 2000) as a desktop computer 28A, or a smart phone 28B, and/or tablet 28C, and/or laptop 28D is first displayed the inquiry for age less than 40 years 801A. If the answer is "Yes" then the age modifying coefficient $K_{1A}$ 802A will be used ($K_1=K_{1A}$). If the answer is "No", the inquiry for age between 40 and 50 years 801B is displayed. If the answer is "Yes" then the age modifying coefficient $K_{1B}$ 802B will be used ($K_1=K_{1B}$). If the answer is "No", the inquiry for age between 50 and 60 years 801C is displayed. If the answer is "Yes" then the age modifying coefficient $K_{1C}$ 802C will be used ($K_1=K_{1C}$). If the answer is "No", the inquiry for age older than 60 years 801D is displayed and if the answer is "Yes" then the age modifying coefficient $K_{1D}$ 802D will be used ($K_1=K_{1D}$). Then the basic/initial number of shocks "A" is altered with the determined age modifying coefficient "$K_1$" and thus the new number of shocks becomes "B", which is now the updated number of shocks based on age 803.

The questionnaire from FIG. 8A continues with the inquiry on the location of the wound. Thus the inquiry for wound location on ankle 804A is displayed. If the answer is "Yes" then the wound location modifying coefficient $K_{2A}$ 805A will be used ($K_2=K_{2A}$). If the answer is "No", the inquiry for wound location on foot sole 804B is displayed. If the answer is "Yes" then the wound location modifying coefficient $K_{2B}$ 805B will be used ($K_2=K_{2B}$). If the answer is "No", the inquiry for wound location on toes 804C is displayed. If the answer is "Yes" then the wound location modifying coefficient $K_{2C}$ 805C will be used ($K_2=K_{2C}$). If the answer is "No", the inquiry for wound location on foot top 804D is displayed and if the answer is "Yes" then the wound location modifying coefficient $K_{2D}$ 805D ($K_2=K_{2D}$). Then the number of shocks "B" is altered with the determined wound location modifying coefficient "$K_2$" and thus the new number of shocks becomes "C", which is now the updated number of shocks based on wound location 806.

The questionnaire from FIG. 8A continues with the inquiry on the body mass index (BMI). Thus the inquiry for body mass index (BMI) value 807 is displayed (BMI<32). If the answer is "Yes" then the body mass index (BMI) modifying coefficient $K_{3A}$ 808A will be used ($K_3=K_{3A}$). If the answer is "No" then the body mass index (BMI) modifying coefficient $K_{3B}$ 808B will be used ($K_3=K_{3B}$). Then the number of shocks "C" is altered with the determined body mass index (BMI) modifying coefficient "$K_3$" and thus the new number of shocks becomes "D", which is now the updated number of shocks based on obesity 809.

Figure 8B:
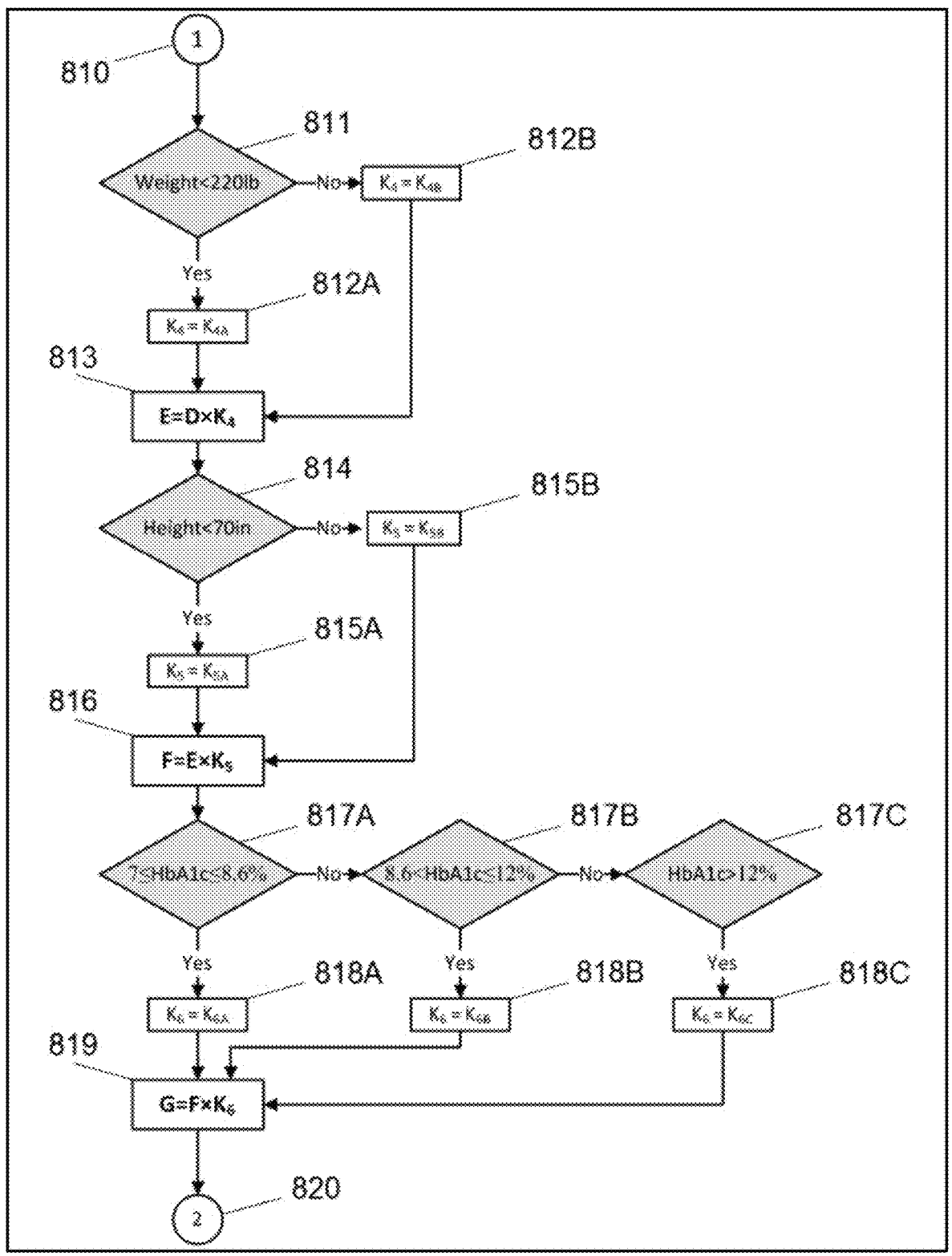
FIG. 8B is a flow diagram of the continuation of the algorithm presented in FIG. 8A used to calculate the number of acoustic pressure shock waves for treatment of diabetic foot ulcers (DFUs), when patient weight, patient height, and glycosylated hemoglobin A1c (HbA1c) are taken into account, according to one embodiment of the present invention.

The optimization continues on FIG. 8B and the continuation of the questionnaire flowchart from FIG. 8A to FIG. 8B is realized by the FIG. 8A to FIG. 8B connector 810, which is seen on both FIG. 8A and FIG. 8B.

The questionnaire from FIG. 8B starts with the inquiry on the patient's weight. Thus the inquiry for weight value 811 is displayed (Weight<220 lb which is 99.8 Kg in metric system). If the answer is "Yes" then the weight modifying coefficient $K_{4A}$ 812A will be used ($K_4=K_{4A}$). If the answer is "No" then the weight modifying coefficient $K_{4B}$ 812B will be used ($K_4=K_{4B}$). Then the number of shocks "D" is altered with the determined weight modifying coefficient "$K_4$" and thus the new number of shocks becomes "E", which is now the updated number of shocks based on weight 813.

The questionnaire from FIG. 8B continues with the inquiry on the patient's height. Thus the inquiry for inquiry for height value 814 is displayed (Height<70 in which is 177.8 cm in metric system). If the answer is "Yes" then the height modifying coefficient $K_{5A}$ 815A will be used ($K_5=K_{5A}$). If the answer is "No" then the height modifying coefficient $K_{5B}$ 815B will be used ($K_5=K_{5B}$). Then the number of shocks "E" is altered with the determined height modifying coefficient "$K_5$" and thus the new number of shocks becomes "F", which is now the updated number of shocks based on height 816.

The questionnaire from FIG. 8B continues with the inquiry on the value for glycated hemoglobin (HbA1c), which is an indication of diabetes presence. Thus the inquiry for glycated hemoglobin (HbA1c) between 7 and 8.6% 817A is displayed. If the answer is "Yes" then the HbA1c modifying coefficient $K_{6A}$ 818A will be used ($K_6=K_{6A}$). If the answer is "No", the inquiry for glycated hemoglobin (HbA1c) between 8.6 and 12% 817B is displayed. If the answer is "Yes" then the HbA1c modifying coefficient $K_{6B}$ 818B will be used ($K_6=K_{6B}$). If the answer is "No", the inquiry for glycated hemoglobin (HbA1c) larger than 12% 817C is displayed. If the answer is "Yes" then the HbA1c modifying coefficient $K_{6C}$ 818C will be used ($K_6=K_{6C}$). Then the number of shocks "F" is altered with the determined HbA1c modifying coefficient "$K_6$" and thus the new number of shocks becomes "G", which is now the updated number of shocks based on diabetes presence 819.

Figure 8C:
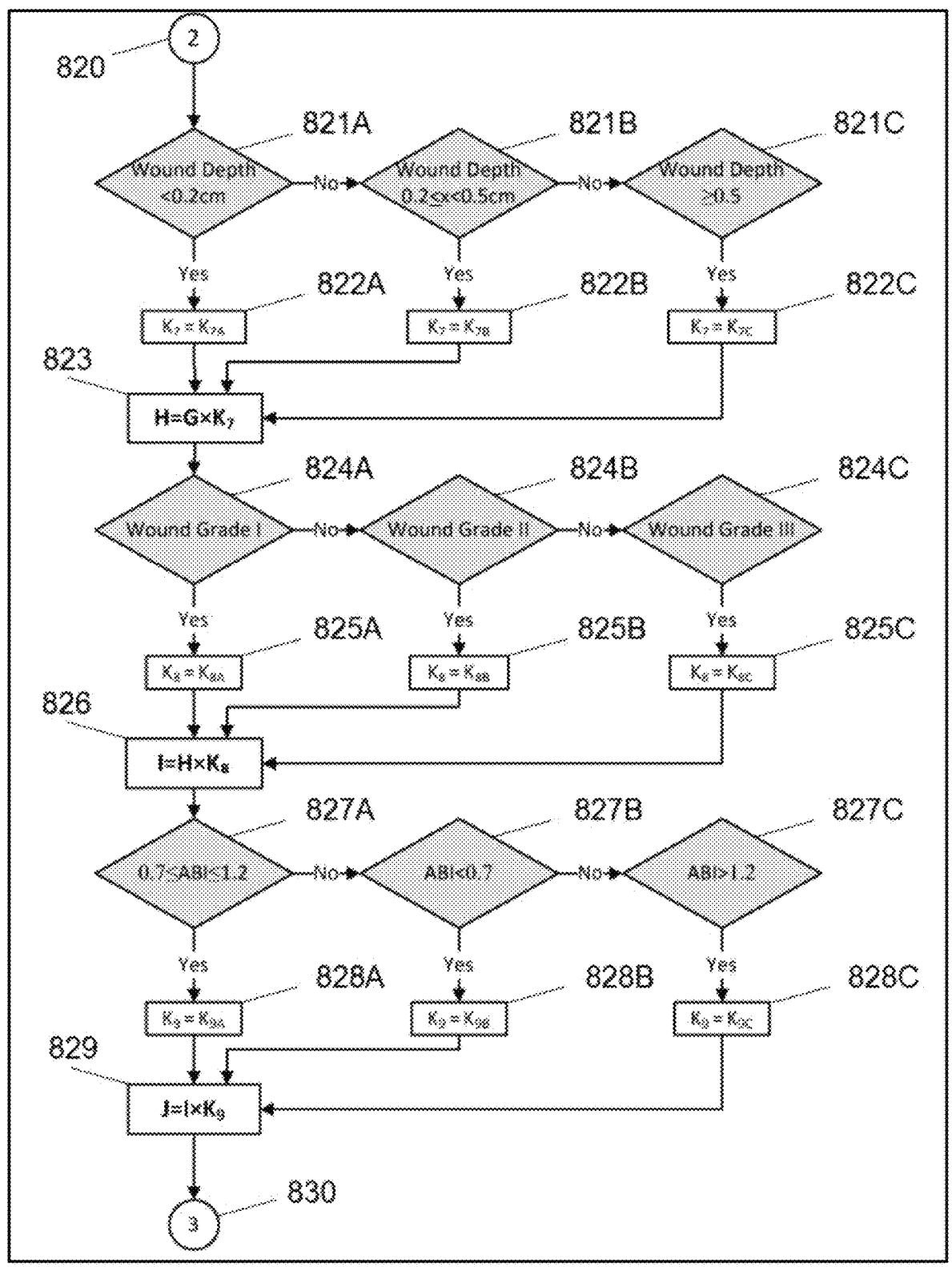
FIG. 8C is a flow diagram of the continuation of the algorithm presented in FIG. 8A and FIG. 8B used to calculate the number of acoustic pressure shock waves for treatment of diabetic foot ulcers (DFUs), when chronic wound depth, DFU grade, and ankle-brachial index (ABI) are taken into account, according to one embodiment of the present invention.

The optimization continues according to the flowchart of FIG. 8C and the continuation of the questionnaire flowchart from FIG. 8B to FIG. 8C is realized by the FIG. 8B to FIG. 8C connector 820, which is seen on both FIG. 8B and FIG. 8C.

The questionnaire according to FIG. 8C starts with the inquiry on wound depth. Thus the inquiry for wound depth less than 0.2 cm 821A is displayed. If the answer is "Yes" then the wound depth modifying coefficient $K_{7A}$ 822A will be used ($K_7=K_{7A}$). If the answer is "No", the inquiry for wound depth between 0.2 and 0.5 cm 821B is displayed. If the answer is "Yes" then the wound depth modifying coefficient $K_{7B}$ 822B will be used ($K_7=K_{7B}$). If the answer is "No", the inquiry for wound depth greater than 0.5 cm 821C is displayed. If the answer is "Yes" then the wound depth modifying coefficient $K_{7C}$ 822C will be used ($K_7=K_{7C}$). Then the number of shocks "G" is altered with the determined wound depth modifying coefficient "$K_7$" and thus the new number of shocks becomes "H", which is now the updated number of shocks based on wound depth 823.

The questionnaire from FIG. 8C continues with the inquiry on wound grade. Thus the inquiry for wound grade I 824A is displayed. If the answer is "Yes" then the wound grade modifying coefficient $K_{8A}$ 825A will be used ($K_8=K_{8A}$). If the answer is "No", the inquiry for wound grade II 824B is displayed. If the answer is "Yes" then the wound grade modifying coefficient $K_{8B}$ 825B will be used ($K_8=K_{8B}$). If the answer is "No", the inquiry for wound grade III 824C is displayed. If the answer is "Yes" then the wound grade modifying coefficient $K_{8C}$ 825C will be used ($K_8=K_{8C}$). Then the number of shocks "H" is altered with the determined wound grade modifying coefficient "$K_8$" and thus the new number of shocks becomes "I", which is now the updated number of shocks based on wound grade 826.

The questionnaire from FIG. 8C continues with the inquiry on ankle-brachial index (ABI), which is an indication on peripheral arterial disease. Thus the inquiry for ankle-brachial index (ABI) between 0.7 and 1.2 827A is displayed. If the answer is "Yes" then the ABI modifying coefficient $K_{9A}$ 828A will be used ($K_9=K_{9A}$). If the answer is "No", the inquiry for ankle-brachial index (ABI) less than 0.7 827B is displayed. If the answer is "Yes" then the ABI modifying coefficient $K_{9B}$ 828B will be used ($K_9=K_{9B}$). If the answer is "No", the inquiry for ankle-brachial index (ABI) greater than 1.2 827C is displayed. If the answer is "Yes" then the ABI modifying coefficient $K_{9C}$ 828C will be used ($K_9=K_{9C}$). Then the number of shocks "I" is altered with the determined ABI modifying coefficient "$K_9$" and thus the new number of shocks becomes "J", which is now the updated number of shocks based on peripheral arterial disease 829.

Figure 8D:
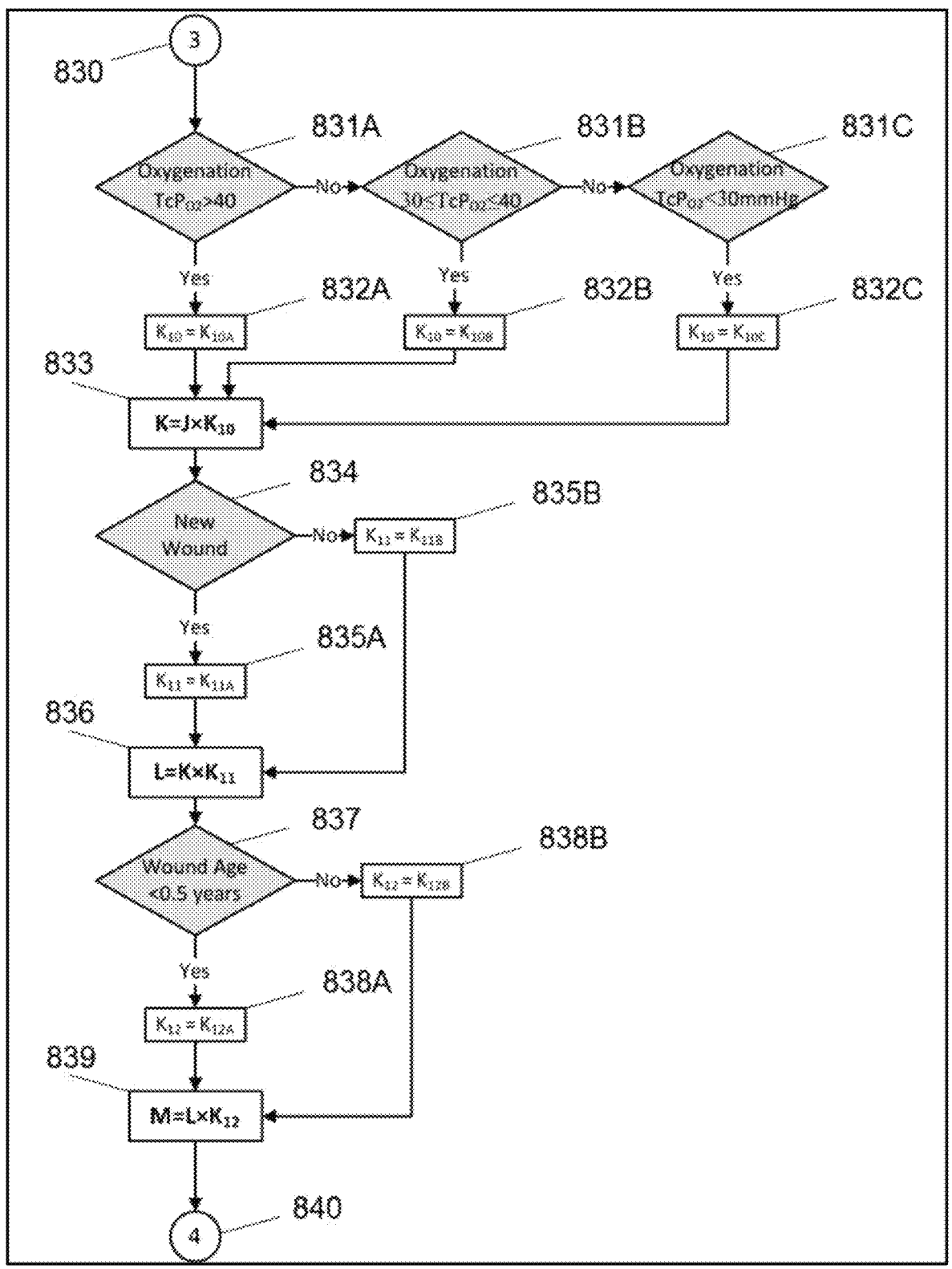
FIG. 8D is a flow diagram of the continuation of the algorithm presented in FIG. 8A, FIG. 8B, and FIG. 8C used to calculate the number of acoustic pressure shock waves for treatment of diabetic foot ulcers (DFUs), when DFU oxygenation ($TcP_{O2}$-Transcutaneous Partial Pressure of Oxygen), wound reoccurrence, and chronic wound age are taken into account, according to one embodiment of the present invention.

The optimization continues on FIG. 8D and the continuation of the questionnaire flowchart from FIG. 8C to FIG. 8D is realized by the FIG. 8C to FIG. 8D connector 830, which is seen on both FIG. 8C and FIG. 8D.

The questionnaire from FIG. 8D starts with the inquiry on transcutaneous monitoring of oxygen ($T_cP_{O2}$), which is an indication on oxygenation of the wound. Thus the inquiry for transcutaneous monitoring of oxygen (TcP$_{O2}$) greater than 40 mmHg 831A is displayed. If the answer is "Yes" then the TcP$_{O2}$ modifying coefficient $K_{10A}$ 832A will be used ($K_{10}=K_{10A}$). If the answer is "No", the inquiry for transcutaneous monitoring of oxygen (TcP$_{O2}$) between 30 and 40 mmHg 831B is displayed. If the answer is "Yes" then the TcP$_{O2}$ modifying coefficient K$_{10B}$ 832B will be used (K$_{10}$=K$_{10B}$). If the answer is "No", the inquiry for transcutaneous monitoring of oxygen (TcP$_{O2}$) less than 30 mmHg 831C is displayed. If the answer is "Yes" then the TcP$_{O2}$ modifying coefficient K$_{10C}$ 832C will be used (K$_{10}$=K$_{10C}$). Then the number of shocks "J" is altered with the determined transcutaneous monitoring of oxygen (TcP$_{O2}$) modifying coefficient "K$_{10}$", and thus the new number of shocks becomes "K", which is now the updated number of shocks based on tissue oxygenation 833.

The questionnaire from FIG. 8D continues with the inquiry on new wound presence, which is an indication of recurrence. Thus the inquiry for new wound 834 is displayed. If the answer is "Yes" then the new wound modifying coefficient K$_{11A}$ 835A will be used (K$_{11}$=K$_{11A}$). If the answer is "No" then the new wound modifying coefficient K$_{11B}$ 835B will be used (K$_{11}$=K$_{11B}$). Then the number of shocks "K" is altered with the determined new wound modifying coefficient "K$_{11}$" and thus the new number of shocks becomes "L", which is now the updated number of shocks based on new wound presence 836.

The questionnaire from FIG. 8D continues with the inquiry on wound age <0.5 years. Thus the inquiry for wound age 837 is displayed. If the answer is "Yes" then the wound age modifying coefficient K$_{12A}$ 838A will be used (K$_{12}$=K$_{12A}$). If the answer is "No" then the wound age modifying coefficient K$_{12B}$ 838B will be used (K$_{12}$=K$_{12B}$). Then the number of shocks "L" is altered with the determined wound age modifying coefficient "K$_{12}$" and thus the new number of shocks becomes "M", which is now the updated number of shocks based on wound age 839.

Figure 8E:
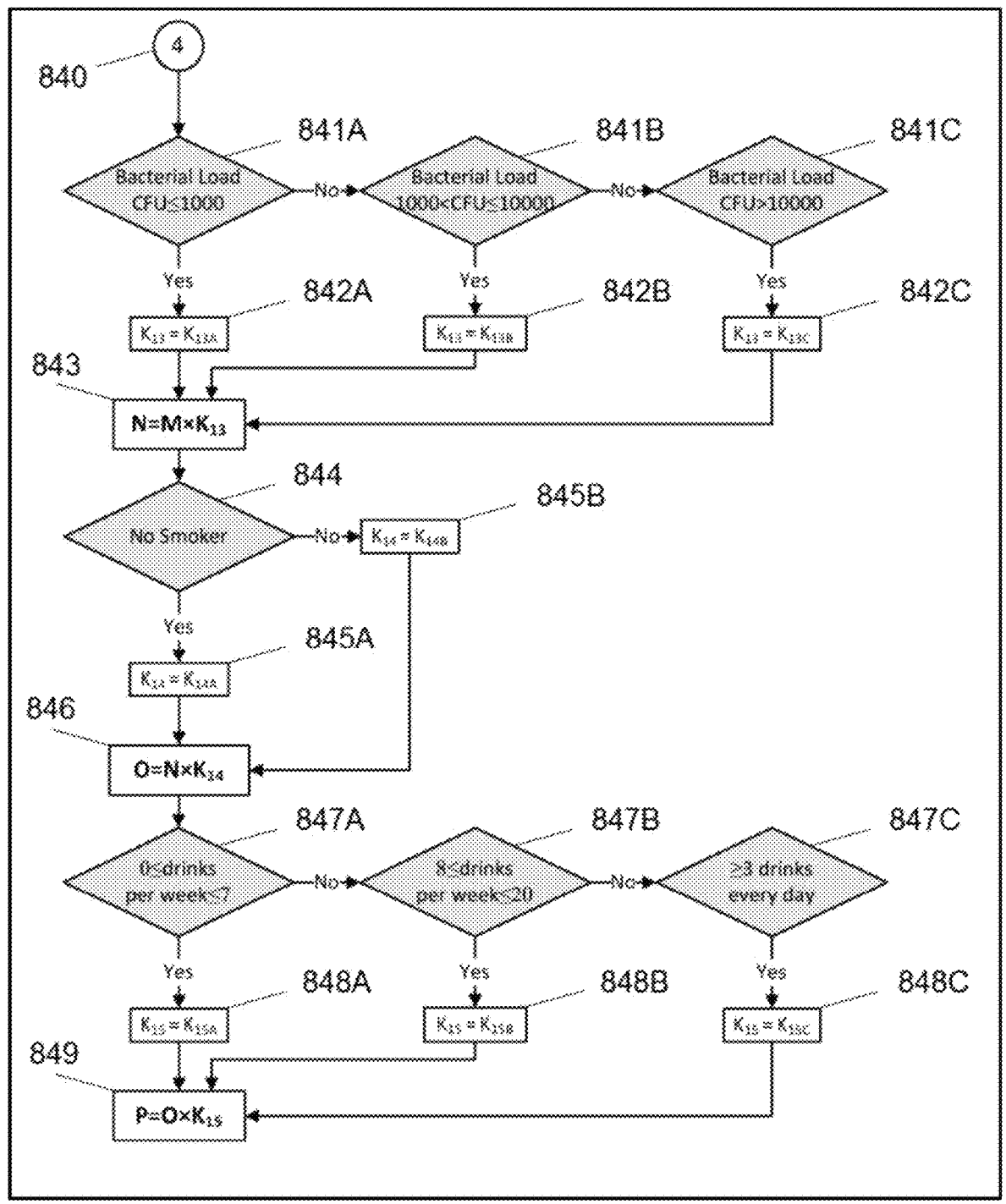
FIG. 8E is a flow diagram the continuation of the algorithm presented in FIG. 8A, FIG. 8B, FIG. 8C, and FIG. 8D used to calculate the number of acoustic pressure shock waves for treatment of diabetic foot ulcers (DFUs), when wound bacterial load, smoker status, and alcohol consumption rate are taken into account, according to one embodiment of the present invention.

The optimization continues on FIG. 8E and the continuation of the questionnaire flowchart from FIG. 8D to FIG. 8E is realized by the FIG. 8D to FIG. 8E connector 840, which is seen on both FIG. 8D and FIG. 8E.

The questionnaire from FIG. 8E starts with the inquiry on bacterial colony forming units (CFU), which is an indication of bacterial load of the wound. Thus the inquiry for bacterial colony forming units (CFU) less than 1000 units 841A is displayed. If the answer is "Yes" then the CFU modifying coefficient K$_{13A}$ 842A will be used (K$_{13}$=K$_{13A}$). If the answer is "No", the inquiry for bacterial colony forming units (CFU) between 1000 and 10000 units 841B is displayed. If the answer is "Yes" then the CFU modifying coefficient K$_{13B}$ 842B will be used (K$_{13}$=K$_{13B}$). If the answer is "No", the inquiry for bacterial colony forming units (CFU) greater than 10000 units 841C is displayed. If the answer is "Yes" then the CFU modifying coefficient K$_{13C}$ 842C will be used (K$_{13}$=K$_{13C}$). Then the number of shocks "M" is altered with the determined CFU modifying coefficient "K$_{13}$" and thus the new number of shocks becomes "N", which is now the updated number of shocks based on bacterial load 843.

The questionnaire from FIG. 8E continues with the inquiry on smoking status. Thus the inquiry for smoking status 844 is displayed. If the answer is "Yes" then the smoking status modifying coefficient K$_{14A}$ 845A will be used (K$_{14}$=K$_{14A}$). If the answer is "No" then the smoking status modifying coefficient K$_{14B}$ 845B will be used (K$_{14}$=K$_{14B}$). Then the number of shocks "N" is altered with the determined smoking status modifying coefficient "K$_{14}$" and thus the new number of shocks becomes "O", which is now the updated number of shocks based on smoking status 846.

The questionnaire from FIG. 8E continues with the inquiry on drinking habit, which is indicated by the number of drinks over a certain period of time. Thus the inquiry for drinks less than 7 per week 847A is displayed. If the answer is "Yes" then the drinking habit modifying coefficient K$_{15A}$ 848A will be used (K$_{15}$=K$_{15A}$). If the answer is "No", the inquiry for drinks between 8 and 20 per week 847B is displayed. If the answer is "Yes" then the drinking habit modifying coefficient K$_{15B}$ 848B will be used (K$_{15}$=K$_{15B}$). If the answer is "No", the inquiry for drinks greater than 3 every day 847C is displayed. If the answer is "Yes" then the drinking habit modifying coefficient K$_{15C}$ 848C will be used (K$_{15}$=K$_{15C}$). Then the number of shocks "O" is altered with the determined drinking habit modifying coefficient "K$_{15}$" and thus the new number of shocks becomes "P", which is now the updated number of shocks based on drinking habit 849.

Coefficients presented for DFU inquiries for patient's comorbidities and habits and wound status from FIGS. 8A-8E are defined with general ranges and also with more preferable ranges and sometimes as a specific number. It will be appreciated, as shown in the Figures that altering with a coefficient means that the applicable number of shocks is multiplied by the applicable respective determined coefficient value.

In FIGS. 8A-8E the values for the coefficients are preferably as follows:

In FIG. 8A, coefficient K$_{1A}$ is preferably 1.00, because patients with age under 40 should have a very good response to the acoustic pressure shock wave treatment.

In FIG. 8A, coefficient K$_{1B}$ may be in the range from about 1.01 to 1.06, and preferably from about 1.02 to 1.04.

In FIG. 8A, coefficient K$_{1C}$ may be in the range from about 1.01 to 1.07, and preferably from about 1.03 to 1.05.

In FIG. 8A, coefficient K$_{1D}$ may be in the range from about 1.01 to 1.08, and preferably from about 1.06 to 1.08.

In FIG. 8A, coefficient K$_{2A}$ may be in the range from about 1.00 to 1.03, and preferably from about 1.02 to 1.03.

In FIG. 8A, coefficient K$_{2B}$ may be in the range from about 1.00 to 1.05, and preferably from about 1.03 to 1.05.

In FIG. 8A, coefficient K$_{2C}$ may be in the range from about 1.00 to 1.04, and preferably from about 1.02 to 1.04.

In FIG. 8A, coefficient K$_{2D}$ may be in the range from about 1.00 to 1.03, and preferably from about 1.01 to 1.02.

In FIG. 8A, coefficient K$_{3A}$ is preferably 1.00, because patients with a body mass index (BMI) below 32 should have a very good response to the acoustic pressure shock wave treatment and do not present any challenges from obesity point of view.

In FIG. 8A, coefficient K$_{3B}$ may be in the range from about 1.02 to 1.10, and preferably from about 1.05 to 1.08.

In FIG. 8B coefficient K$_{4A}$ is preferably 1.00, because patients with a weight below 220 lb/99.8 Kg should have a very good response to the acoustic pressure shock wave treatment and do not present any challenges from obesity point of view.

In FIG. 8B, coefficient K$_{4B}$ may be in the range from about 1.02 to 1.05, and preferably from about 1.03 to 1.05.

In FIG. 8B coefficient K$_{5A}$ is preferably 1.00 for a height below 70 in/177.8 cm.

In FIG. 8B, coefficient K$_{5B}$ may be in the range from about 1.00 to 1.02, and preferably from about 1.01 to 1.02.

In FIG. 8B, coefficient K$_{6A}$ is preferably 1.00, because patients with a HbA1c are controlling their diabetes and should have a very good response to the acoustic pressure shock wave treatment.

In FIG. 8B, coefficient K$_{6B}$ may be in the range from about 1.01 to 1.05, and preferably from about 1.02 to 1.03.

In FIG. 8B, coefficient $K_{6C}$ may be in the range from about 1.02 to 1.08, and preferably from about 1.04 to 1.07.

In FIG. 8C, coefficient $K_{7A}$ is preferably 1.00, because patients with very superficial wounds should have a very good response to the acoustic pressure shock wave treatment.

In FIG. 8C, coefficient $K_{7B}$ may be in the range from about 1.00 to 1.03, and preferably from about 1.01 to 1.02.

In FIG. 8C, coefficient $K_{7C}$ may be in the range from about 1.02 to 1.05, and preferably from about 1.04 to 1.05.

In FIG. 8C, coefficient $K_{8A}$ is preferably 1.00, because patients with Grade I diabetic foot ulcers (DFUs) should have a very good response to the acoustic pressure shock wave treatment.

In FIG. 8C, coefficient $K_{8B}$ may be in the range from about 1.01 to 1.04, and preferably from about 1.01 to 1.02.

In FIG. 8C, coefficient $K_{8C}$ may be in the range from about 1.03 to 1.07, and preferably from about 1.04 to 1.06.

In FIG. 8C, coefficient $K_{9A}$ is preferably 1.00, because patients with an ankle-brachial index (ABI) between 0.7 and 1.2 should have a very good response to the acoustic pressure shock wave treatment.

In FIG. 8C, coefficient $K_{9B}$ may be in the range from about 1.00 to 1.03, and preferably from about 1.01 to 1.02.

In FIG. 8C, coefficient $K_{9C}$ may be in the range from about 1.01 to 1.04, and preferably from about 1.02 to 1.03.

In FIG. 8D, coefficient $K_{10A}$ is preferably 1.00, because patients with a $TcP_{O2}$ value greater than 40 mmHg is normal and the patients should have a very good response to the acoustic pressure shock wave treatment.

In FIG. 8D, coefficient $K_{10B}$ may be in the range from about 1.01 to 1.05, and preferably from about 1.02 to 1.05.

In FIG. 8D, coefficient $K_{10C}$ may be in the range from about 1.02 to 1.07, and preferably from about 1.04 to 1.06.

In FIG. 8D coefficient $K_{11A}$ is preferably 1.00 for a new wound and not a recurrent wound.

In FIG. 8D, coefficient $K_{11B}$ may be in the range from about 1.00 to 1.04, and preferably from about 1.01 to 1.02.

In FIG. 8D coefficient $K_{12A}$ is preferably 1.00 for a wound that is less than 6 month old.

In FIG. 8D, coefficient $K_{12B}$ may be in the range from about 1.00 to 1.05, and preferably from about 1.02 to 1.04.

In FIG. 8E, coefficient $K_{13A}$ is preferably 1.00, because patients with a colony forming units (CFU) of bacteria less than 1000 in the skin lesion should have a very good response to the acoustic pressure shock wave treatment.

In FIG. 8E, coefficient $K_{13B}$ may be in the range from about 1.01 to 1.04, and preferably from about 1.02 to 1.03.

In FIG. 8E, coefficient $K_{13C}$ may be in the range from about 1.04 to 1.08, and preferably from about 1.05 to 1.07.

In FIG. 8E coefficient $K_{14A}$ is preferably 1.00 because a non-smoker should have a very good response to the acoustic pressure shock wave treatment.

In FIG. 8E, coefficient $K_{14B}$ may be in the range from about 1.00 to 1.05, and preferably from about 1.01 to 1.04.

In FIG. 8E, coefficient $K_{15A}$ is preferably 1.00, because occasional drinking patients should have a very good response to the acoustic pressure shock wave treatment.

In FIG. 8E, coefficient $K_{15B}$ may be in the range from about 1.01 to 1.04, and preferably from about 1.02 to 1.03.

In FIG. 8E, coefficient $K_{15C}$ may be in the range from about 1.03 to 1.07, and preferably from about 1.04 to 1.06.

A control console/unit 22 and associated acoustic pressure shock wave applicator/treatment apparatus 10 (see FIG. 2A) used for delivering a treatment for diabetic foot ulcers (DFUs) by means of the proposed adjustment algorithm from FIGS. 8A-8E will use the following formula (where "A" is the initial number of focused acoustic pressure shock waves 40 or radial acoustic pressure waves 41 or planar acoustic pressure waves 42 or cylindrical acoustic pressure waves 44 delivered per treatment and "ATN" is the Adjusted Total Number of focused acoustic pressure shock waves 40 or radial acoustic pressure waves 41 or planar acoustic pressure waves 42 or cylindrical acoustic pressure waves 44 delivered per treatment):

$$ATN = A \cdot K_1 \cdot K_2 \cdot K_3 \cdot K_4 \cdot K_5 \cdot K_6 \cdot K_7 \cdot K_8 \cdot K_9 \cdot K_{10} \cdot K_{11} \cdot K_{12} \cdot K_{13} \cdot K_{14} \cdot K_{15}$$

For the largest values for these coefficients (worst situation) and for example a number of A=500 is used as initial number of focused acoustic pressure shock waves 40 or radial acoustic pressure waves 41 or planar acoustic pressure waves 42 or cylindrical acoustic pressure waves 44 that are minimally needed for successful treatment of the tissue condition 19, then the Adjusted Total Number (ATN) value of focused acoustic pressure shock waves 40 or radial acoustic pressure waves 41 or planar acoustic pressure waves 42 or cylindrical acoustic pressure waves 44 delivered per treatment is the following:

$$ATN = 500 \cdot 1.08 \cdot 1.05 \cdot 1.10 \cdot 1.05 \cdot 1.02 \cdot 1.08 \cdot 1.05$$
$$1.07 \cdot 1.04 \cdot 1.07 \cdot 1.04 \cdot 1.05 \cdot 1.08 \cdot 1.05 \cdot 1.07 = 1195$$
shock waves or pressure waves.

Another important category of chronic wounds are the pressure ulcers. A pressure ulcer is a localized injury to the skin and/or underlying tissue, usually over a bony prominence, as a result of pressure, or pressure in combination with shear and/or friction. The most common sites are the back of the head and ears, the shoulders, the elbows, the lower back and buttocks, the hips, the inner knees, and the heels. The pressure ulcers usually form due to prolonged immobility and they form for the patients that spent long periods of time in bed without moving. A number of contributing or confounding factors are associated with pressure ulcers; the significance of these factors is yet to be determined.

Stage I pressure ulcers appear as intact skin with redness of a localized area, usually over a bony prominence, the area may be painful, firm, soft, and warmer or cooler compared to adjacent tissue. Darkly pigmented skin may not have visible blanching and its color may just be different from the surrounding area.

Stage II pressure ulcers are characterized by partial-thickness loss of dermis presenting as a shallow open ulcer with a red to pink wound bed, presents as a shiny or dry shallow ulcer without slough or bruising. Stage II may also present as an intact or open (ruptured) serum-filled blister.

Stage III pressure ulcers have full-thickness tissue loss. Subcutaneous fat may be visible. However, no visible bone, tendon, or muscle is seen. Slough may be present, which does not obscure the depth of tissue loss. Stage III may include undermining and tunneling. The depth of a Stage III pressure ulcer varies by anatomic location. For example at the buttocks, due to significant adiposity, extremely deep stage III pressure ulcers can be developed, which is in sharp contrast with the ones developed at head, shoulder blade that are shallow.

Stage IV pressure ulcers are characterized by full-thickness tissue loss with exposed bone, tendon, or muscle. Slough or eschar may be present on some parts of the wound bed. Stage IV often includes undermining and tunneling. The depth of a Stage IV pressure ulcer varies by anatomic location and can extend into muscle and/or supporting structures (e.g., fascia, tendon. joint capsule) making osteomyelitis possible. Exposed bone/tendon is visible or directly palpable.

Risk factors implicated in the development of pressure ulcers are immobilization/immobility of the patient, age, existing comorbidities and conditions, diabetic mellitus, peripheral vascular disease, cigarette smoking, excessive alcohol consumption, poor glycemic control, diabetic nephropathy, ischemia of small and large blood vessels, cognitive deficit, poor nutrition, use of steroids, and pressure and/or friction and/or humidity and/or shear force on the skin.

When focused acoustic pressure shock waves 40 or radial acoustic pressure waves 41 or planar acoustic pressure waves 42 or cylindrical acoustic pressure waves 44 are used, the personalized treatment parameters for pressure ulcers can be determined using different factors. In FIGS. 3A-3E is presented a preferable algorithm that can be used to adjust the number of focused acoustic pressure shock waves 40 or radial acoustic pressure waves 41 or planar acoustic pressure waves 42 or cylindrical acoustic pressure waves 44 used for the treatment of pressure ulcers based on different elements that take into account the characteristics of the pressure ulcer, patient's comorbidities and lifestyle.

As a starting point for pressure ulcers algorithm is the basic/initial number of focused acoustic pressure shock waves 40 or radial acoustic pressure waves 41 or planar acoustic pressure waves 42 or cylindrical acoustic pressure waves 44 that are minimally needed for successful treatment of the tissue condition 19. As presented before, this is considered the basic/initial dosage that is calculated after tissue condition 19 area and/or volume were determined and possible adjustments for ischemic conditions were done.

Figure 9A:
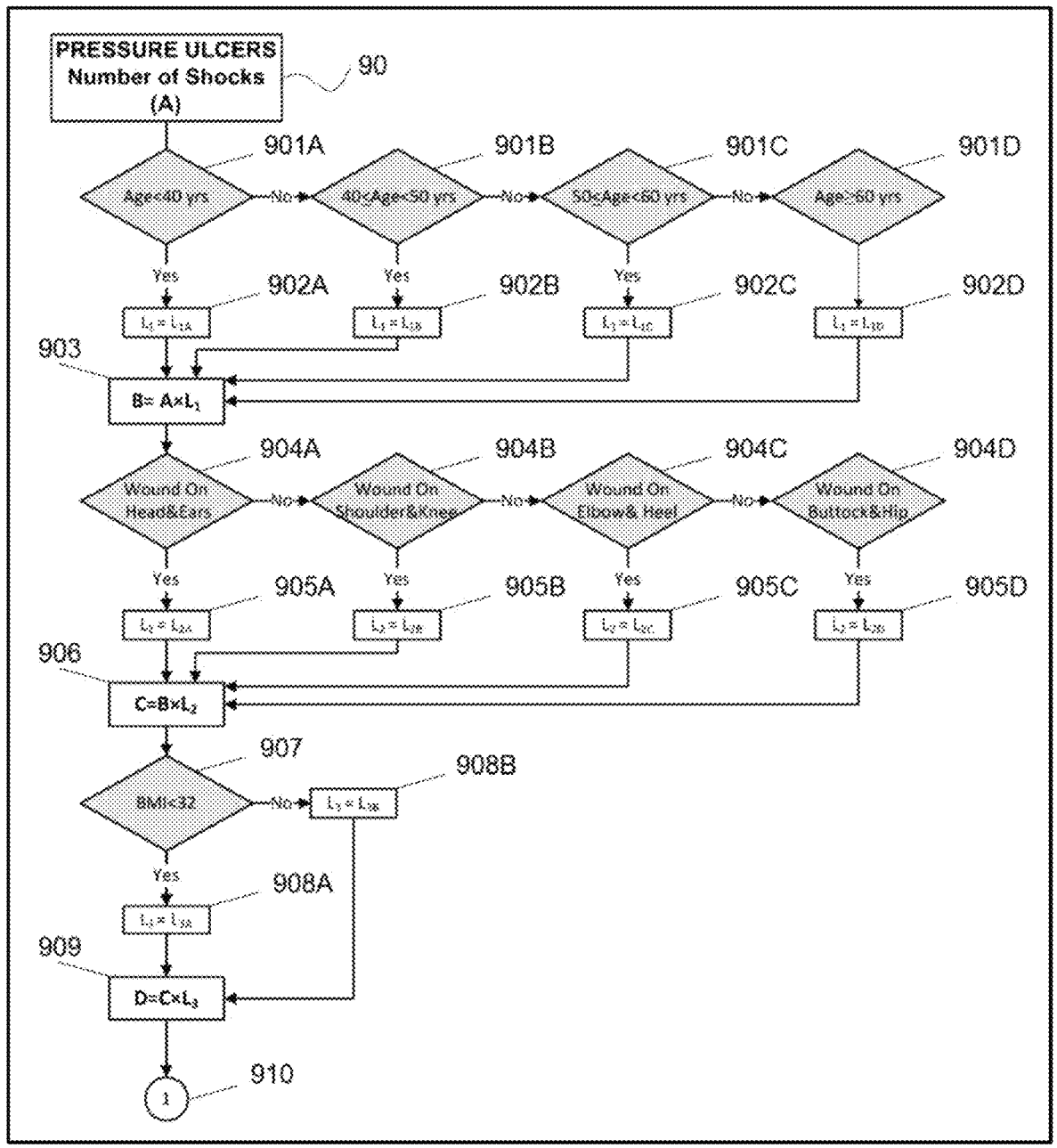
FIG. 9A is a flow diagram of the algorithm used to calculate the number of acoustic pressure shock waves for treatment of pressure ulcers when patient age, location of the wound, and body mass index (BMI) are taken into account, according to one embodiment of the present invention.

In FIG. 9A the basic/initial number of shocks (A) for pressure ulcers 90 represents the starting point of the adjustment/optimization algorithm for number of focused acoustic pressure shock waves 40 or radial acoustic pressure waves 41 or planar acoustic pressure waves 42 or cylindrical acoustic pressure waves 44 for the treatment of pressure ulcers. The first element used to alter the basic/initial dosage used for pressure ulcers treatment is the inquiry regarding the age of the patient. Thus on the control console/unit display 2220, or artificial intelligence (A/I) device display 2740, or on the display of an interconnected device (see FIG. 2A for the medical treatment system 2000) as a desktop computer 28A, or a smart phone 28B, and/or tablet 28C, and/or laptop 28D is first displayed the inquiry for age less than 40 years 901A. If the answer is "Yes" then the age modifying coefficient $L_{1A}$ 902A will be used ($L_1=L_{1A}$). If the answer is "No", the inquiry for age between 40 and 50 years 901B is displayed. If the answer is "Yes" then the age modifying coefficient $L_{1B}$ 902B will be used ($L_1=L_{1B}$). If the answer is "No", the inquiry for age between 50 and 60 years 901C is displayed. If the answer is "Yes" then the age modifying coefficient $L_{1C}$ 902C will be used ($L_1=L_{1C}$). If the answer is "No", the inquiry for age older than 60 years 901D is displayed and if the answer is "Yes" then the age modifying coefficient $L_{1D}$ 902D will be used ($L_1=L_{1D}$). Then the basic/initial number of shocks "A" is altered with the determined age modifying coefficient "$L_1$" and thus the new number of shocks becomes "B", which is now the updated number of shocks based on age 903.

The questionnaire from FIG. 9A continues with the inquiry on the location of the wound. Thus the inquiry for wound location on head and ears 904A is displayed. If the answer is "Yes" then the wound location modifying coefficient $L_{2A}$ 905A will be used ($L_2=L_{2A}$). If the answer is "No", the inquiry for wound location on shoulder and knee 904B is displayed. If the answer is "Yes" then the wound location modifying coefficient $L_{2B}$ 905B will be used ($L_2=L_{2B}$). If the answer is "No", the inquiry for wound location on elbow and heel 904C is displayed. If the answer is "Yes" then the wound location modifying coefficient $L_{2C}$ 905C will be used ($L_2=L_{2C}$). If the answer is "No", the inquiry for wound location on buttock and hip 904D is displayed and if the answer is "Yes" then the wound location modifying coefficient $L_{2D}$ 905D ($L_2=L_{2D}$). Then the number of shocks "B" is altered with the determined wound location modifying coefficient "$L_2$" and thus the new number of shocks becomes "C", which is now the updated number of shocks based on wound location 906.

The questionnaire from FIG. 9A continues with the inquiry on the body mass index (BMI). Thus the inquiry for body mass index (BMI) value 907 is displayed (BMI<32). If the answer is "Yes" then the body mass index (BMI) modifying coefficient $L_{3A}$ 908A will be used ($L_3=L_{3A}$). If the answer is "No" then the body mass index (BMI) modifying coefficient $L_{3B}$ 908B will be used ($L_3=L_{3B}$). Then the number of shocks "C" is altered with the determined body mass index (BMI) modifying coefficient "$L_3$" and thus the new number of shocks becomes "D", which is now the updated number of shocks based on obesity 909.

Figure 9B:
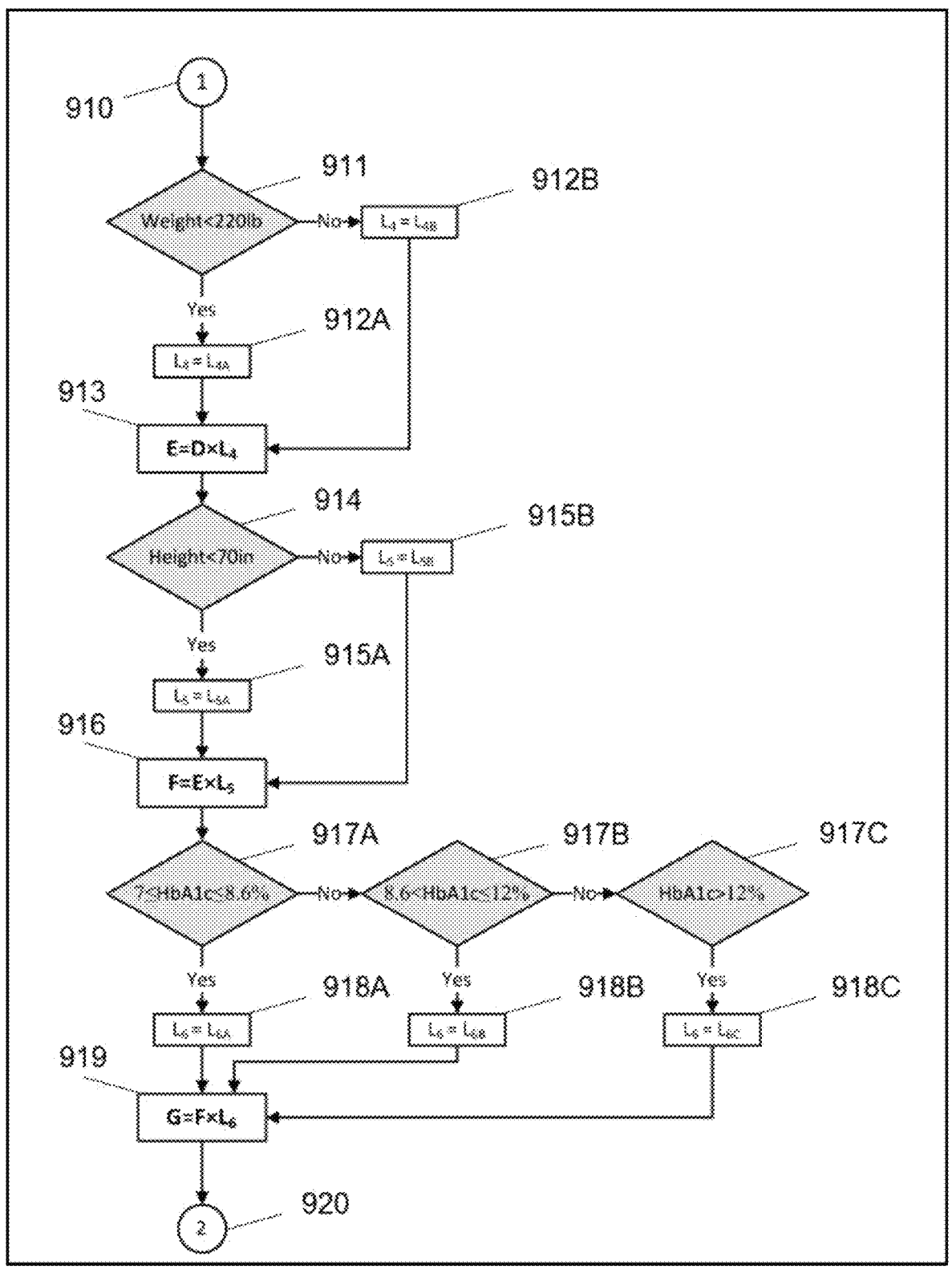
FIG. 9B is a flow diagram of the continuation of the algorithm presented in FIG. 9A used to calculate the number of acoustic pressure shock waves for treatment of pressure ulcers, when patient weight, patient height, and glycosylated hemoglobin A1c (HbA1c) are taken into account, according to one embodiment of the present invention.

The optimization continues on FIG. 9B and the continuation of the questionnaire flowchart from FIG. 9A to FIG. 9B is realized by the FIG. 9A to FIG. 9B connector 910, which is seen on both FIG. 9A and FIG. 9B.

The questionnaire from FIG. 9B starts with the inquiry on the patient's weight. Thus the inquiry for weight value 911 is displayed (Weight<220 lb which is 99.8 Kg in metric system). If the answer is "Yes" then the weight modifying coefficient $L_{4A}$ 912A will be used ($L_4=L_{4A}$). If the answer is "No" then the weight modifying coefficient $L_{4B}$ 912B will be used ($L_4=L_{4B}$). Then the number of shocks "D" is altered with the determined weight modifying coefficient "$L_4$" and thus the new number of shocks becomes "E", which is now the updated number of shocks based on weight 913.

The questionnaire from FIG. 9B continues with the inquiry on the patient's height. Thus the inquiry for inquiry for height value 914 is displayed (Height<70 in which is 177.8 cm in metric system). If the answer is "Yes" then the height modifying coefficient $L_{5A}$ 915A will be used ($L_5=L_{5A}$). If the answer is "No" then the height modifying coefficient $L_{5B}$ 915B will be used ($L_5=L_{5B}$). Then the number of shocks "E" is altered with the determined height modifying coefficient "$L_5$" and thus the new number of shocks becomes "F", which is now the updated number of shocks based on height 916.

The questionnaire from FIG. 9B continues with the inquiry on the value for glycated hemoglobin (HbA1c), which is an indication of diabetes presence. Thus the inquiry for glycated hemoglobin (HbA1c) between 7 and 8.6% 917A is displayed. If the answer is "Yes" then the HbA1c modifying coefficient $L_{6A}$ 918A will be used ($L_6=L_{6A}$). If the answer is "No", the inquiry for glycated hemoglobin (HbA1c) between 8.6 and 12% 917B is displayed. If the answer is "Yes" then the HbA1c modifying coefficient $L_{6B}$ 918B will be used ($L_6=L_{6B}$). If the answer is "No", the inquiry for glycated hemoglobin (HbA1c) larger than 12% 917C is displayed. If the answer is "Yes" then the HbA1c modifying coefficient $L_{6C}$ 918C will be used ($L_6=L_{6C}$). Then the number of shocks "F" is altered with the determined HbA1c modifying coefficient "$L_6$", and thus the new number of shocks becomes "G", which is now the updated number of shocks based on diabetes presence 919.

Figure 9C:
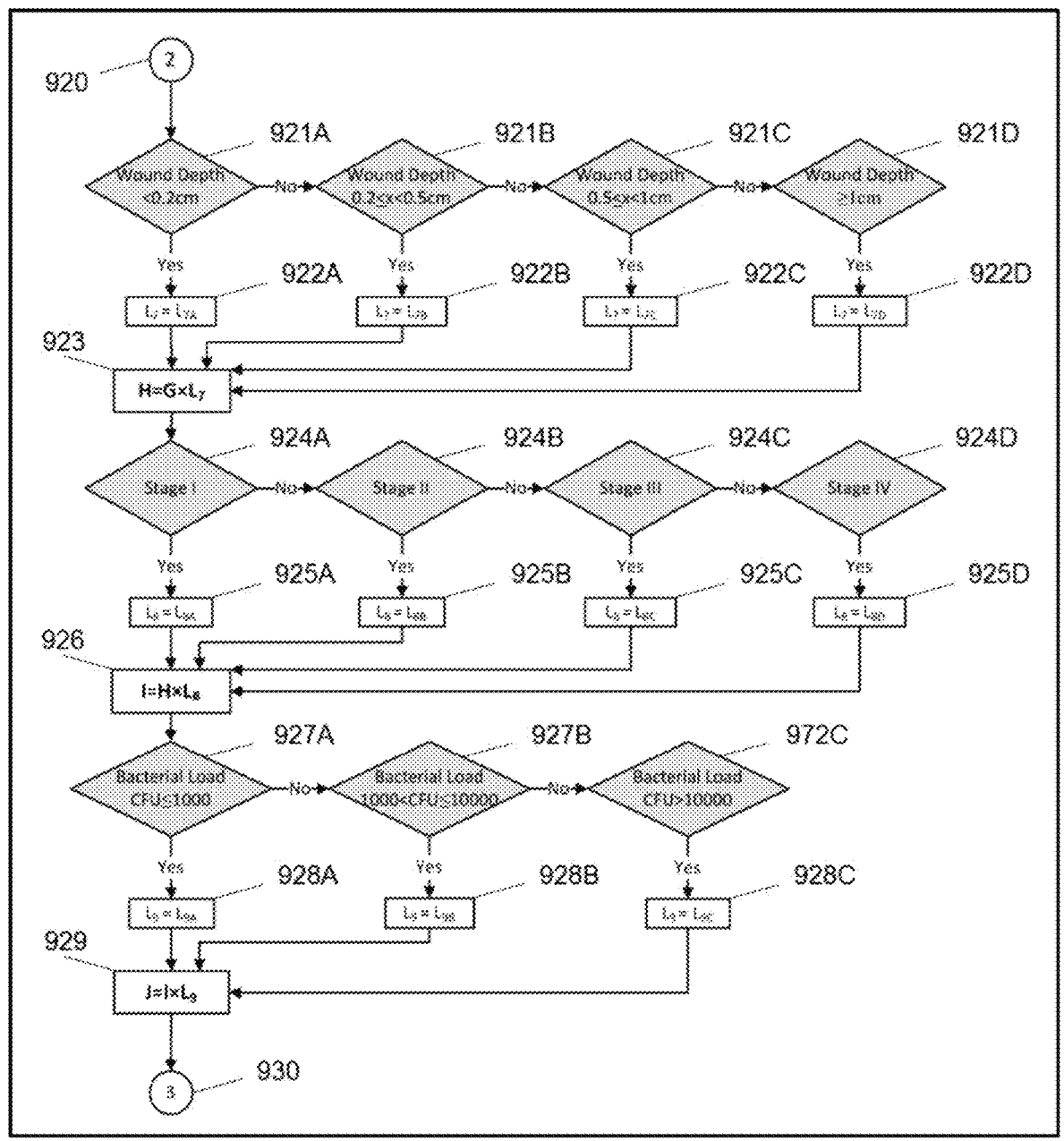
FIG. 9C is a flow diagram of the continuation of the algorithm presented in FIG. 9A and FIG. 9B used to calculate the number of acoustic pressure shock waves for treatment of pressure ulcers, when chronic wound depth, pressure ulcer stage, and bacterial load are taken into account, according to one embodiment of the present invention.

The optimization continues on FIG. 9C and the continuation of the questionnaire flowchart from FIG. 9B to FIG. 9C is realized by the FIG. 9B to FIG. 9C connector 920, which is seen on both FIG. 9B and FIG. 9C.

The questionnaire from FIG. 9C starts with the inquiry on wound depth. Thus the inquiry for wound depth less than 0.2 cm 921A is displayed. If the answer is "Yes" then the wound depth modifying coefficient $L_{7A}$ 922A will be used ($L_7=L_{7A}$). If the answer is "No", the inquiry for wound depth between 0.2 and 0.5 cm 921B is displayed. If the answer is "Yes" then the wound depth modifying coefficient $L_{7B}$ 922B will be used ($L_7=L_{7B}$). If the answer is "No", the inquiry for wound depth between 0.5 cm and 1 cm 921C is displayed. If the answer is "Yes" then the wound depth modifying coefficient $L_{7C}$ 922C will be used ($L_7=L_{7C}$). If the answer is "No", the inquiry for wound depth 1 cm and greater 921D is displayed. If the answer is "Yes" then the wound depth modifying coefficient L7D 922D will be used ($L_7=L_{7D}$). Then the number of shocks "G" is altered with the determined wound depth modifying coefficient "$L_7$" and thus the new number of shocks becomes "H", which is now the updated number of shocks based on wound depth 923.

The questionnaire from FIG. 9C continues with the inquiry on wound stage. Thus the inquiry for wound stage I 924A is displayed. If the answer is "Yes" then the wound stage modifying coefficient $L_{8A}$ 925A will be used ($L_8=L_{8A}$). If the answer is "No", the inquiry for wound stage II 924B is displayed. If the answer is "Yes" then the wound stage modifying coefficient $L_{8B}$ 925B will be used ($L_8=L_{8B}$). If the answer is "No", the inquiry for wound stage III 924C is displayed. If the answer is "Yes" then the wound stage modifying coefficient $L_{8C}$ 925C will be used ($L_8=L_{8C}$). If the answer is "No", the inquiry for wound stage IV 924D is displayed. If the answer is "Yes" then the wound stage modifying coefficient $L_{8D}$ 925D will be used ($L_8=L_{8D}$). Then the number of shocks "H" is altered with the determined wound stage modifying coefficient "$L_8$", and thus the new number of shocks becomes "I", which is now the updated number of shocks based on wound stage 926.

The questionnaire from FIG. 9C continues with the inquiry on bacterial colony forming units (CFU), which is an indication of bacterial load of the wound. Thus the inquiry for bacterial colony forming units (CFU) less than 1000 units 927A is displayed. If the answer is "Yes" then the CFU modifying coefficient $L_{9A}$ 928A will be used ($L_9=L_{9A}$). If the answer is "No", the inquiry for bacterial colony forming units (CFU) between 1000 and 10000 units 927B is displayed. If the answer is "Yes" then the CFU modifying coefficient $L_{9B}$ 928B will be used ($L_9=L_{9B}$). If the answer is "No", the inquiry for bacterial colony forming units (CFU) greater than 10000 units 927C is displayed. If the answer is "Yes" then the CFU modifying coefficient $L_{9C}$ 928C will be used ($L_9=L_{9C}$). Then the number of shocks "I" is altered with the determined CFU modifying coefficient "$L_9$" and thus the new number of shocks becomes "J", which is now the updated number of shocks based on bacterial load 929.

Figure 9D:
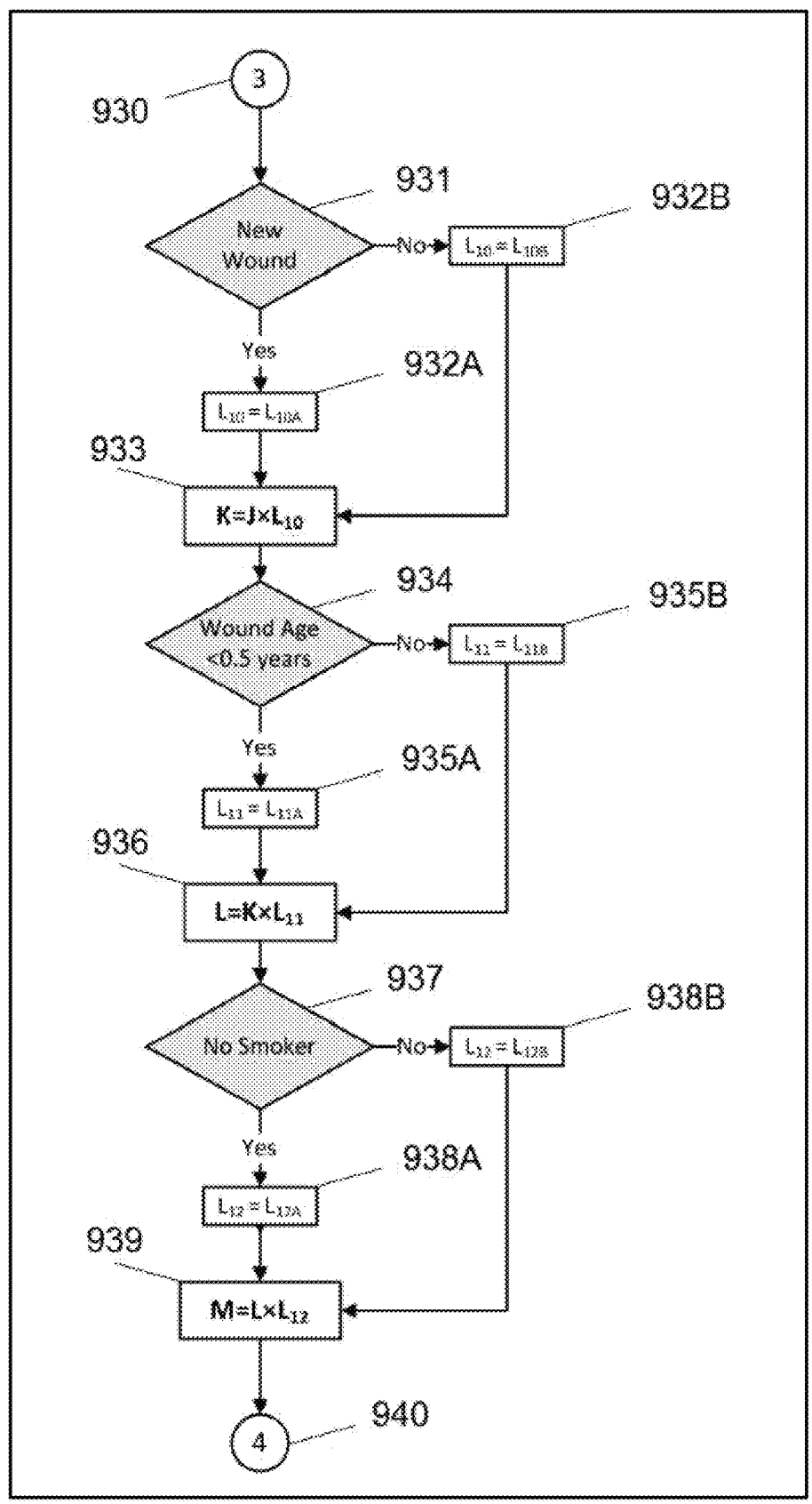
FIG. 9D is a flow diagram of the continuation of the algorithm presented in FIG. 9A, FIG. 9B, and FIG. 9C used to calculate the number of acoustic pressure shock waves for treatment of pressure ulcers, when wound reoccurrence, wound age, and smoker status are taken into account, according to one embodiment of the present invention.

The optimization continues on FIG. 9D and the continuation of the questionnaire flowchart from FIG. 9C to FIG. 9D is realized by the FIG. 9C to FIG. 9D connector 930, which is seen on both FIG. 9C and FIG. 9D.

The questionnaire from FIG. 9D starts with the inquiry on new wound presence, which is an indication of recurrence. Thus the inquiry for new wound 931 is displayed. If the answer is "Yes" then the new wound modifying coefficient $L_{10A}$ 932A will be used ($L_{10}=L_{10A}$). If the answer is "No" then the new wound modifying coefficient $L_{10B}$ 932B will be used ($L_{10}=L_{10B}$). Then the number of shocks "J" is altered with the determined new wound modifying coefficient "$L_{10}$" and thus the new number of shocks becomes "K", which is now the updated number of shocks based on new wound presence 933.

The questionnaire from FIG. 9D continues with the inquiry on wound age <0.5 years. Thus the inquiry for wound age 934 is displayed. If the answer is "Yes" then the wound age modifying coefficient $L_{11A}$ 935A will be used ($L_{11}=L_{11A}$). If the answer is "No" then the wound age modifying coefficient $L_{11B}$ 935B will be used ($L_{11}=L_{11B}$). Then the number of shocks "K" is altered with the determined wound age modifying coefficient "$L_{11}$" and thus the new number of shocks becomes "L", which is now the updated number of shocks based on wound age 936.

The questionnaire from FIG. 9D continues with the inquiry on smoking status. Thus the inquiry for smoking status 937 is displayed. If the answer is "Yes" then the smoking status modifying coefficient $L_{12A}$ 938A will be used ($L_{12}=L_{12A}$). If the answer is "No" then the smoking status modifying coefficient $L_{12B}$ 938B will be used ($L_{12}=L_{12B}$). Then the number of shocks "L" is altered with the determined smoking status modifying coefficient "$L_{12}$" and thus the new number of shocks becomes "M", which is now the updated number of shocks based on smoking status 939.

Figure 9E:
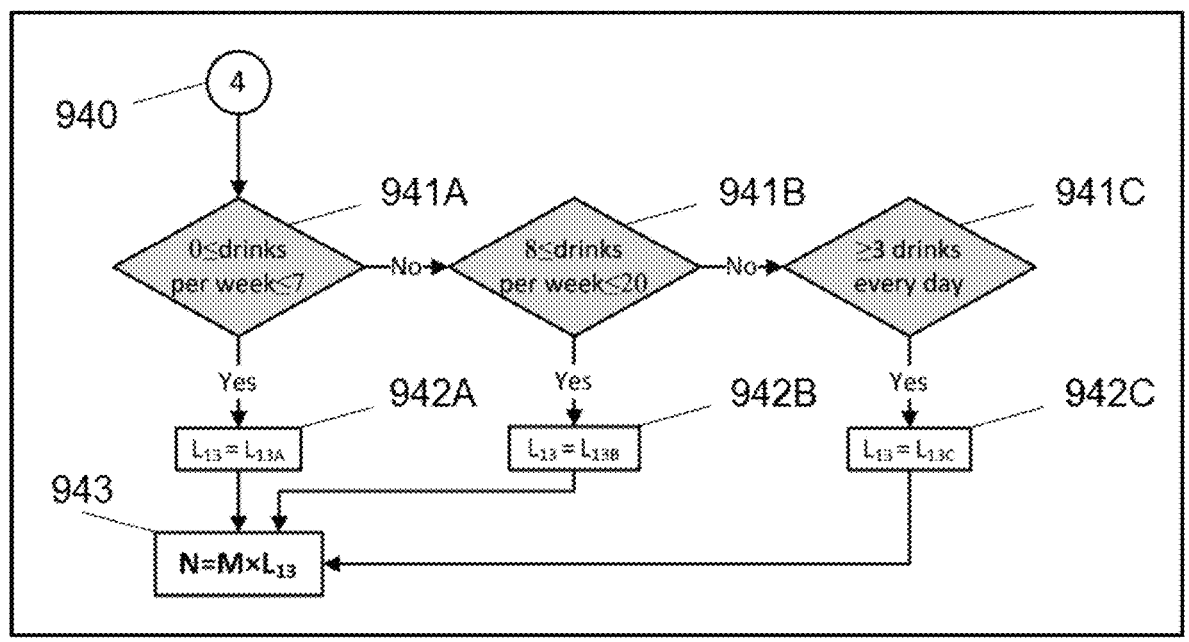
FIG. 9E is a flow diagram of the continuation of the algorithm presented in FIG. 9A, FIG. 9B, FIG. 9C, and FIG. 9D used to calculate the number of acoustic pressure shock waves for treatment of pressure ulcers, when alcohol consumption rate is taken into account, according to one embodiment of the present invention.

The optimization continues on FIG. 9E and the continuation of the questionnaire flowchart from FIG. 9D to FIG. 9E is realized by the FIG. 9D to FIG. 9E connector 940, which is seen on both FIG. 9D and FIG. 9E.

The questionnaire from FIG. 9E starts with the inquiry on drinking habit, which is indicated by the number of drinks over a certain period of time. Thus the inquiry for drinks less than 7 per week 941A is displayed. If the answer is "Yes" then the drinking habit modifying coefficient $L_{13A}$ 942A will be used ($L_{13}=L_{13A}$). If the answer is "No", the inquiry for drinks between 8 and 20 per week 941B is displayed. If the answer is "Yes" then the drinking habit modifying coefficient $L_{13B}$ 942B will be used ($L_{13}=L_{13B}$). If the answer is "No", the inquiry for drinks greater than 3 every day 941C is displayed. If the answer is "Yes" then the drinking habit modifying coefficient $L_{13C}$ 942C will be used ($L_{13}=L_{13C}$). Then the number of shocks "N" is altered with the determined drinking habit modifying coefficient "$L_{13}$" and thus the new number of shocks becomes "M", which is now the updated number of shocks based on drinking habit 943.

Coefficients presented for pressure ulcers inquiries for patient's comorbidities and habits and wound status from FIGS. 9A-9E are defined with general ranges and also with more preferable ranges and sometimes as a specific number.

In FIGS. 9A-9E the values for the coefficients are preferably as follows:

In FIG. 9A, coefficient $L_{1A}$ is preferably 1.00, because patients with age under 40 should have a very good response to the acoustic pressure shock wave treatment.

In FIG. 9A, coefficient $L_{1B}$ may be in the range from about 1.01 to 1.06, and preferably from about 1.02 to 1.04.

In FIG. 9A, coefficient $L_{1C}$ may be in the range from about 1.01 to 1.07, and preferably from about 1.03 to 1.05.

In FIG. 9A, coefficient $L_{1D}$ may be in the range from about 1.01 to 1.08, and preferably from about 1.06 to 1.10.

In FIG. 9A, coefficient $L_{2A}$ may be in the range from about 1.00 to 1.02, and preferably from about 1.01 to 1.02.

In FIG. 9A, coefficient $L_{2B}$ may be in the range from about 1.00 to 1.03, and preferably from about 1.02 to 1.03.

In FIG. 9A, coefficient $L_{2C}$ may be in the range from about 1.01 to 1.03, and preferably from about 1.02 to 1.03.

In FIG. 9A, coefficient $L_{2D}$ may be in the range from about 1.01 to 1.04, and preferably from about 1.02 to 1.04.

In FIG. 9A, coefficient $L_{3A}$ is preferably 1.00, because patients with a body mass index (BMI) below 32 should have a very good response to the acoustic pressure shock wave treatment and do not present any challenges from obesity point of view.

In FIG. 9A, coefficient $L_{3B}$ may be in the range from about 1.02 to 1.07, and preferably from about 1.03 to 1.06.

In FIG. 9B coefficient $L_{4A}$ is preferably 1.00, because patients with a weight below 220 lb should have a very good response to the acoustic pressure shock wave treatment and do not present any challenges from obesity point of view.

In FIG. 9B, coefficient $L_{4B}$ may be in the range from about 1.01 to 1.05, and preferably from about 1.03 to 1.05.

In FIG. 9B coefficient $L_{5A}$ is preferably 1.00 for a height below 70 in.

In FIG. 9B, coefficient $L_{5B}$ may be in the range from about 1.00 to 1.02, and preferably from about 1.01 to 1.02.

In FIG. 9B, coefficient $L_{6A}$ is preferably 1.00, because patients with a HbA1c are controlling their diabetes and should have a very good response to the acoustic pressure shock wave treatment.

In FIG. 9B, coefficient $L_{6B}$ may be in the range from about 1.01 to 1.04, and preferably from about 1.02 to 1.03.

In FIG. 9B, coefficient $L_{6C}$ may be in the range from about 1.02 to 1.06, and preferably from about 1.03 to 1.05.

In FIG. 9C, coefficient $L_{7A}$ is preferably 1.00, because patients with very superficial wounds should have a very good response to the acoustic pressure shock wave treatment.

In FIG. 9C, coefficient $L_{7B}$ may be in the range from about 1.00 to 1.03, and preferably from about 1.01 to 1.02.

In FIG. 9C, coefficient $L_{7C}$ may be in the range from about 1.01 to 1.04, and preferably from about 1.02 to 1.03.

In FIG. 9C, coefficient $L_{7D}$ may be in the range from about 1.02 to 1.06, and preferably from about 1.03 to 1.06.

In FIG. 9C, coefficient $L_{8A}$ is preferably 1.00, because patients with Stage I pressure ulcers should have a very good response to the acoustic pressure shock wave treatment.

In FIG. 9C, coefficient $L_{8B}$ may be in the range from about 1.00 to 1.03, and preferably from about 1.01 to 1.02.

In FIG. 9C, coefficient $L_{8C}$ may be in the range from about 1.01 to 1.04, and preferably from about 1.01 to 1.03.

In FIG. 9C, coefficient $L_{8D}$ may be in the range from about 1.01 to 1.07, and preferably from about 1.03 to 1.06.

In FIG. 9C, coefficient $L_{9A}$ is preferably 1.00, because patients with a colony forming units (CFU) of bacteria less than 1000 in the skin lesion should have a very good response to the acoustic pressure shock wave treatment.

In FIG. 9C, coefficient $L_{9B}$ may be in the range from about 1.00 to 1.03, and preferably from about 1.01 to 1.02.

In FIG. 9C, coefficient $L_{9C}$ may be in the range from about 1.01 to 1.04, and preferably from about 1.02 to 1.03.

In FIG. 9D, coefficient $L_{10A}$ is preferably 1.00, for a new wound and not a recurrent wound.

In FIG. 9D, coefficient $L_{10B}$ may be in the range from about 1.01 to 1.04, and preferably from about 1.02 to 1.04.

In FIG. 9D coefficient $L_{11A}$ is preferably 1.00 for a wound that is less than 6 month old.

In FIG. 9D, coefficient $L_{11B}$ may be in the range from about 1.00 to 1.04, and preferably from about 1.01 to 1.03.

In FIG. 9D coefficient $L_{12A}$ is preferably 1.00 because a non-smoker should have a very good response to the acoustic pressure shock wave treatment.

In FIG. 9D, coefficient $L_{12B}$ may be in the range from about 1.00 to 1.04, and preferably from about 1.02 to 1.03.

In FIG. 9D, coefficient $L_{13A}$ is preferably 1.00, because occasional drinking patients should have a very good response to the acoustic pressure shock wave treatment.

In FIG. 9D, coefficient $L_{13B}$ may be in the range from about 1.01 to 1.04, and preferably from about 1.02 to 1.03.

In FIG. 9D, coefficient $L_{13C}$ may be in the range from about 1.02 to 1.06, and preferably from about 1.04 to 1.06.

A control console/unit 22 and associated acoustic pressure shock wave applicator/treatment apparatus 10 (see FIG. 2A) used for delivering a treatment for pressure ulcers by means of the proposed adjustment algorithm from FIGS. 9A-9D will use the following formula (where "A" is the initial number of focused acoustic pressure shock waves 40 or radial acoustic pressure waves 41 or planar acoustic pressure waves 42 or cylindrical acoustic pressure waves 44 delivered per treatment and "ATN" is the Adjusted Total Number of focused acoustic pressure shock waves 40 or radial acoustic pressure waves 41 or planar acoustic pressure waves 42 or cylindrical acoustic pressure waves 44 delivered per treatment):

$$ATN = A \cdot L_1 \cdot L_2 \cdot L_3 \cdot L_4 \cdot L_5 \cdot L_6 \cdot L_7 \cdot L_8 \cdot L_9 \cdot L_{10} \cdot L_{11} \cdot L_{12} \cdot L_{13}$$

For the largest values for these coefficients (worst situation) and for example a number of A=500 is used as initial number of focused acoustic pressure shock waves 40 or radial acoustic pressure waves 41 or planar acoustic pressure waves 42 or cylindrical acoustic pressure waves 44 that are minimally needed for successful treatment of the tissue condition 19, then the Adjusted Total Number (ATN) value of focused acoustic pressure shock waves 40 or radial acoustic pressure waves 41 or planar acoustic pressure waves 42 or cylindrical acoustic pressure waves 44 delivered per treatment is the following:

$$ATN = 500 \cdot 1.08 \cdot 1.04 \cdot 1.07 \cdot 1.05 \cdot 1.02 \cdot 1.06 \cdot 1.06 \cdot 1.07 \cdot 1.04 \cdot 1.04 \cdot 1.04 \cdot 1.04 \cdot 1.06 = 959.48 \approx 959 \text{ shock waves or pressure waves.}$$

Another important category of chronic wounds are the arterial ulcers. Arterial insufficiency ulcers (ischemic ulcers) are generally found on the lateral surfaces of the ankles or the distal digits. They are the result of insufficient blood flow to the lower extremities commonly caused by peripheral artery disease (PAD).

To assess the grade of ischemia using blood analysis the partial pressure of arterial oxygen (PaO2) and partial pressure of arterial carbon dioxide (PaCO2) can be determined. The normal value for the partial pressure of arterial oxygen (PaO2) irrespective of age is greater than 80 mmHg/10.6 kPa. The normal PaO2 for a given age can be predicted from the following formulas:

Seated PaO2=104 mmHg/13.8 kPa−0.27×age in years

Supine PaO2=104 mmHg/13.8 kPa−0.42×age in years

If PaO2 is <80 mmHg/10.7 kPa, the patient has arterial hypoxemia. When PaO2 is 79-70 mmHg (10.6-9.4 kPa) the patient has mild hypoxemia. If PaO2 is 69-60 (9.3-8.0 kPa) the patient moderate hypoxemia and for values of 59-50 (7.9-6.6 kPa) the patient has severe hypoxemia. Finally, when PaO2 is 50 (6.6 kPa) then the patient has extreme hypoxemia.

A complementary way to measure ischemia to the partial pressure of arterial oxygen (PaO2) is through the value for the partial pressure of arterial carbon dioxide (PaCO2). The normal values for PaCO2 are 35-45 mmHg (4.7-6.0 kPa). These two factors can be used to determine the grade of ischemia (the cause of arterial ulcers), which is also an indication for the chance that the respective arterial ulcer will heal.

Risk factors implicated in the development of arterial ulcers are age, nutrition, peripheral vascular disease, cigarette smoking, excessive alcohol consumptions, existing comorbidities, poor glycemic control, previous foot ulcerations or amputations, and ischemia of small and large blood vessels, hypertension, dyslipidemia, family history, obesity, and sedentary lifestyle.

The personalized treatment parameters for arterial ulcers when focused acoustic pressure shock waves 40 or radial acoustic pressure waves 41 or planar acoustic pressure waves 42 or cylindrical acoustic pressure waves 44 are used can be determined using different factors. In FIGS. 10A-10E is presented a preferable algorithm that can be used to adjust the number of focused acoustic pressure shock waves 40 or radial acoustic pressure waves 41 or planar acoustic pressure waves 42 or cylindrical acoustic pressure waves 44 used for the treatment of arterial ulcers based on different elements that take into account the characteristics of the arterial ulcer, patient's comorbidities and lifestyle.

As a starting point for arterial ulcers algorithm is the basic/initial number of focused acoustic pressure shock waves 40 or radial acoustic pressure waves 41 or planar acoustic pressure waves 42 or cylindrical acoustic pressure waves 44 that are minimally needed for successful treatment of the tissue condition 19. As presented before, this is considered the basic/initial dosage that is calculated after tissue condition 19 area and/or volume were determined.

Figure 10A:
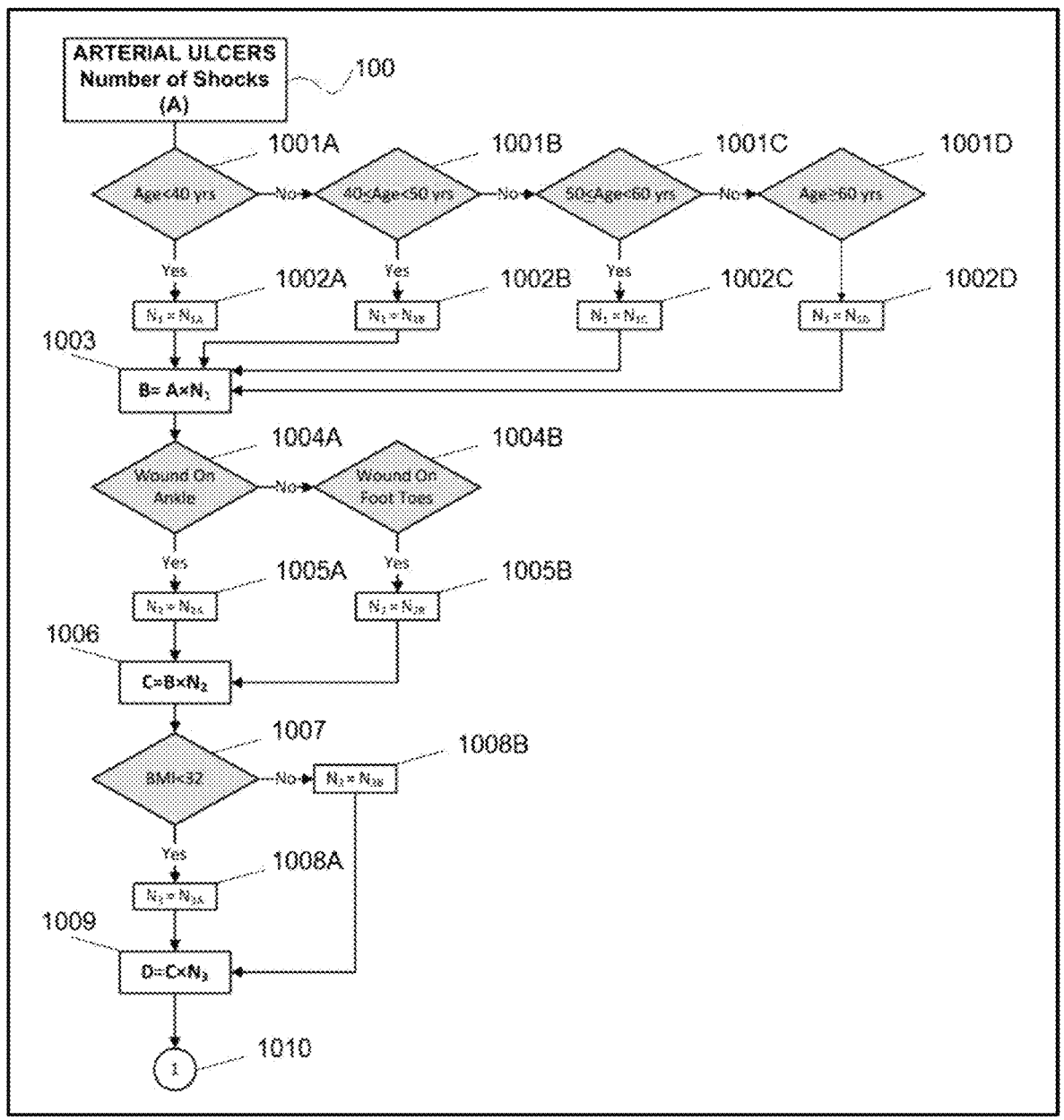
FIG. 10A is a flow diagram of the algorithm used to calculate the number of acoustic pressure shock waves for treatment of arterial ulcers when patient age, location of the wound, and body mass index (BMI) are taken into account, according to one embodiment of the present invention.

In FIG. 10A the basic/initial number of shocks for arterial ulcers 100 represents the starting point of the adjustment/optimization algorithm for number of focused acoustic pressure shock waves 40 or radial acoustic pressure waves 41 or planar acoustic pressure waves 42 or cylindrical acoustic pressure waves 44 for the treatment of arterial ulcers. The first element used to alter the basic/initial dosage used for arterial ulcers treatment is the inquiry regarding the age of the patient. Thus on the control console/unit display 2220, or artificial intelligence (A/I) device display 2740, or on the display of an interconnected device (see FIG. 2A for the medical treatment system 2000) as a desktop computer 28A, or a smart phone 28B, and/or tablet 28C, and/or laptop 28D is first displayed the inquiry for age less than 40 years 1001A. If the answer is "Yes" then the age modifying coefficient $N_{1A}$ 1002A will be used ($N_1=N_{1A}$). If the answer is "No", the inquiry for age between 40 and 50 years 1001B is displayed. If the answer is "Yes" then the age modifying coefficient $N_{1B}$ 1002B will be used ($N_1=N_{1B}$). If the answer is "No", the inquiry for age between 50 and 60 years 1001C is displayed. If the answer is "Yes" then the age modifying coefficient $N_{1C}$ 1002C will be used ($N_1=N_{1C}$). If the answer is "No", the inquiry for age older than 60 years 1001D is displayed and if the answer is "Yes" then the age modifying coefficient $N_{1D}$ 1002D will be used ($N_1=N_{1D}$). Then the basic/initial number of shocks "A" is altered with the determined age modifying coefficient "$N_1$" and thus the new number of shocks becomes "B", which is now the updated number of shocks based on age 1003.

The questionnaire from FIG. 10A continues with the inquiry on the location of the wound. Thus the inquiry for wound location on ankle 1004A is displayed. If the answer is "Yes" then the wound location modifying coefficient $N_{2A}$ 1005A will be used ($N_2=N_{2A}$). If the answer is "No", the inquiry for wound location on foot toes 1004B is displayed. If the answer is "Yes" then the wound location modifying coefficient $N_{2B}$ 1005B will be used ($N_2=N_{2B}$). Then the number of shocks "B" is altered with the determined wound location modifying coefficient "$N_2$" and thus the new number of shocks becomes "C", which is now the updated number of shocks based on wound location 1006.

The questionnaire from FIG. 10A continues with the inquiry on the body mass index (BMI). Thus the inquiry for body mass index (BMI) value 1007 is displayed (BMI<32). If the answer is "Yes" then the body mass index (BMI) modifying coefficient $N_{3A}$ 1008A will be used ($N_3=N_{3A}$). If the answer is "No" then the body mass index (BMI) modifying coefficient $N_{3B}$ 1008B will be used ($N_3=N_{3B}$). Then the number of shocks "C" is altered with the determined body mass index (BMI) modifying coefficient "$N_3$" and thus the new number of shocks becomes "D", which is now the updated number of shocks based on obesity 1009.

Figure 10B:
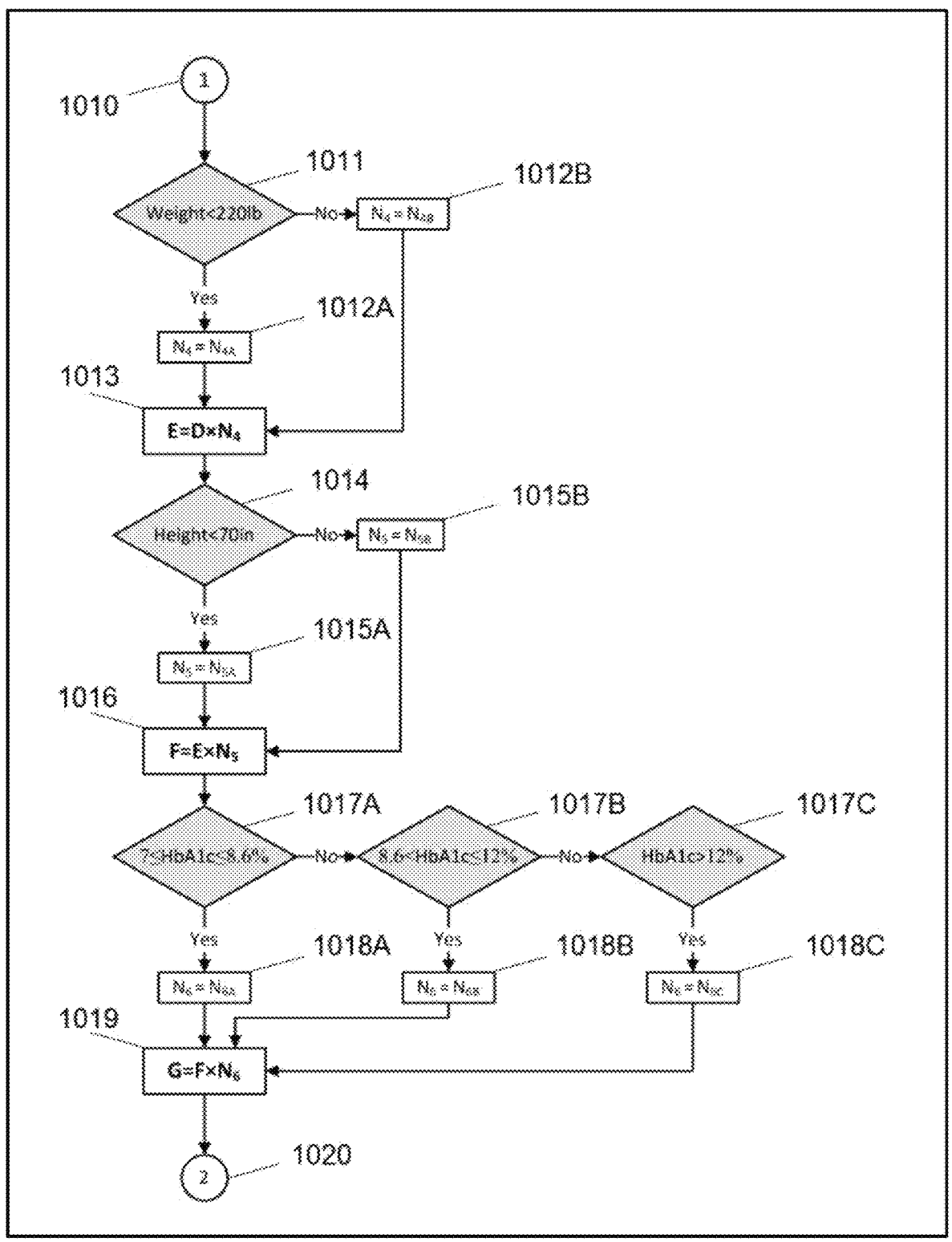
FIG. 10B is a flow diagram of the continuation of the algorithm presented in FIG. 10A used to calculate the number of acoustic pressure shock waves for treatment of arterial ulcers, when patient weight, patient height, and glycosylated hemoglobin A1c (HbA1c) are taken into account, according to one embodiment of the present invention.

The optimization continues on FIG. 10B and the continuation of the questionnaire flowchart from FIG. 10A to FIG. 10B is realized by the FIG. 10A to FIG. 10B connector 1010, which is seen on both FIG. 10A and FIG. 10B.

The questionnaire from FIG. 10B starts with the inquiry on the patient's weight. Thus the inquiry for weight value 1011 is displayed (Weight<220 lb which is 99.8 Kg in metric system). If the answer is "Yes" then the weight modifying coefficient $N_{4A}$ 1012A will be used ($N_4=N_{4A}$). If the answer is "No" then the weight modifying coefficient $N_{4B}$ 1012B will be used ($N_4=N_{4B}$). Then the number of shocks "D" is altered with the determined weight modifying coefficient "$N_4$" and thus the new number of shocks becomes "E", which is now the updated number of shocks based on weight 1013.

The questionnaire from FIG. 10B continues with the inquiry on the patient's height. Thus the inquiry for inquiry for height value 1014 is displayed (Height<70 in which is 177.8 cm in metric system). If the answer is "Yes" then the height modifying coefficient $N_{5A}$ 1015A will be used ($N_5=N_{5A}$). If the answer is "No" then the height modifying coefficient $N_{5B}$ 1015B will be used ($N_5=N_{5B}$). Then the number of shocks "E" is altered with the determined height modifying coefficient "$N_5$" and thus the new number of shocks becomes "F", which is now the updated number of shocks based on height 1016.

The questionnaire from FIG. 10B continues with the inquiry on the value for glycated hemoglobin (HbA1c), which is an indication of diabetes presence. Thus the inquiry for glycated hemoglobin (HbA1c) between 7 and 8.6% 1017A is displayed. If the answer is "Yes" then the HbA1c modifying coefficient $N_{6A}$ 1018A will be used ($N_6=N_{6A}$). If the answer is "No", the inquiry for glycated hemoglobin (HbA1c) between 8.6 and 12% 1017B is displayed. If the answer is "Yes" then the HbA1c modifying coefficient $N_{6B}$ 1018B will be used ($N_6=N_{6B}$). If the answer is "No", the inquiry for glycated hemoglobin (HbA1c) larger than 12% 1017C is displayed. If the answer is "Yes" then the HbA1c modifying coefficient $N_{6C}$ 1018C will be used ($N_6=N_{6C}$). Then the number of shocks "F" is altered with the determined HbA1c modifying coefficient "$N_6$", and thus the new number of shocks becomes "G", which is now the updated number of shocks based on diabetes presence 1019.

Figure 10C:
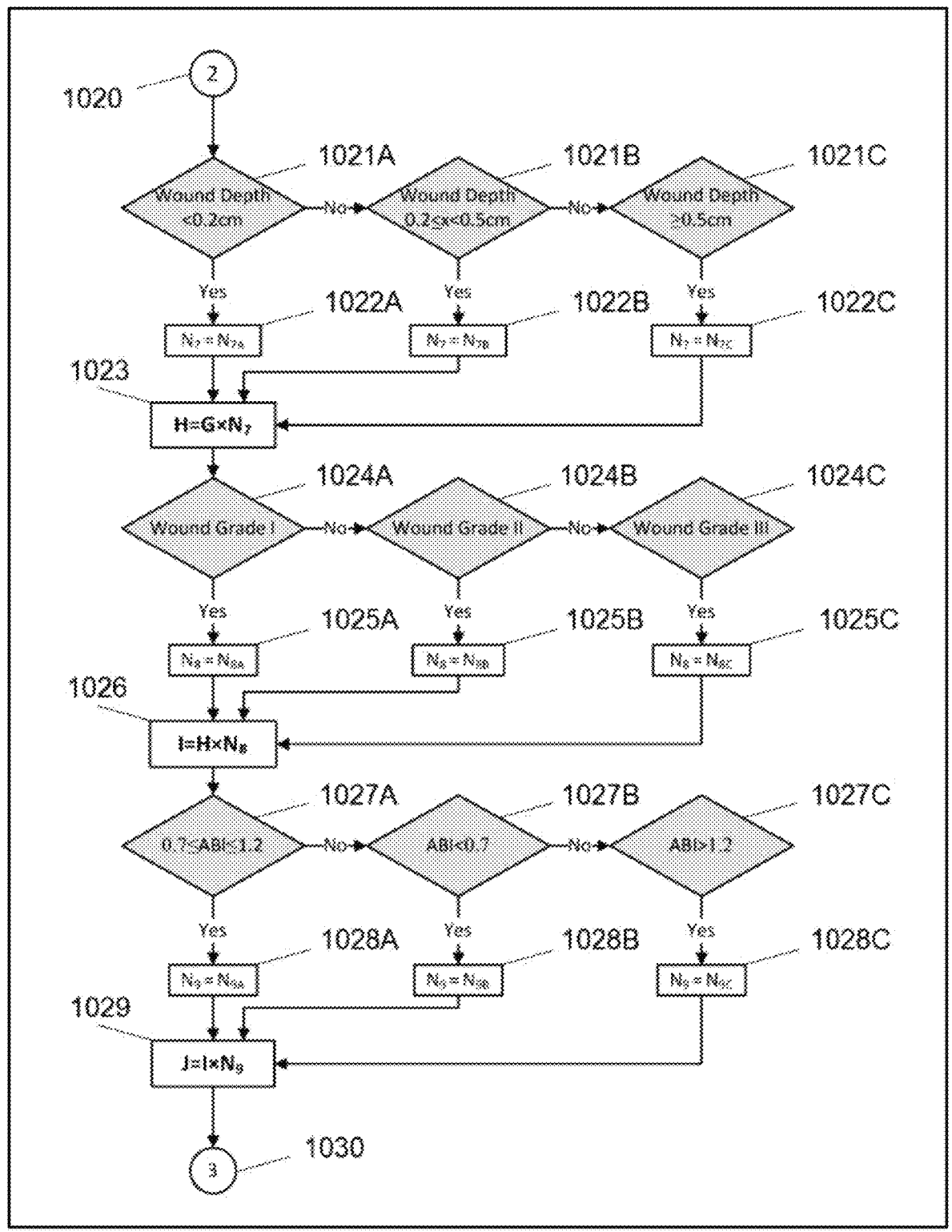
FIG. 10C is a flow diagram of the continuation of the algorithm presented in FIG. 10A and FIG. 10B used to calculate the number of acoustic pressure shock waves for treatment of arterial ulcers, when chronic wound depth, wound grade, and ankle-brachial index (ABI) are taken into account, according to one embodiment of the present invention.

The optimization continues on FIG. 10C and the continuation of the questionnaire flowchart from FIG. 10B to FIG. 10C is realized by the FIG. 10B to FIG. 10C connector 1020, which is seen on both FIG. 10B and FIG. 10C.

The questionnaire from FIG. 10C starts with the inquiry on wound depth. Thus the inquiry for wound depth less than 0.2 cm 1021A is displayed. If the answer is "Yes" then the wound depth modifying coefficient $N_{7A}$ 1022A will be used ($N_7=N_{7A}$). If the answer is "No", the inquiry for wound depth between 0.2 and 0.5 cm 1021B is displayed. If the answer is "Yes" then the wound depth modifying coefficient $N_{7B}$ 1022B will be used ($N_7=N_{7B}$). If the answer is "No", the inquiry for wound depth greater than 0.5 cm 1021C is displayed. If the answer is "Yes" then the wound depth modifying coefficient $N_{7C}$ 1022C will be used ($N_7=N_{7C}$). Then the number of shocks "G" is altered with the determined wound depth modifying coefficient "$N_7$", and thus the new number of shocks becomes "H", which is now the updated number of shocks based on wound depth 1023.

The questionnaire from FIG. 10C continues with the inquiry on wound grade. Thus the inquiry for wound grade I 1024A is displayed. If the answer is "Yes" then the wound grade modifying coefficient $N_{8A}$ 1025A will be used ($N_8=N_{8A}$). If the answer is "No", the inquiry for wound grade II 1024B is displayed. If the answer is "Yes" then the wound grade modifying coefficient $N_{8B}$ 1025B will be used ($N_8=N_{8B}$). If the answer is "No", the inquiry for wound grade III 1024C is displayed. If the answer is "Yes" then the wound grade modifying coefficient $N_{8C}$ 1025C will be used ($N_8=N_{8C}$). Then the number of shocks "H" is altered with the determined wound grade modifying coefficient "$N_8$", and thus the new number of shocks becomes "I", which is now the updated number of shocks based on wound grade 1026.

The questionnaire from FIG. 10C continues with the inquiry on ankle-brachial index (ABI), which is an indication on peripheral arterial disease. Thus the inquiry for ankle-brachial index (ABI) between 0.7 and 1.2 1027A is displayed. If the answer is "Yes" then the ABI modifying coefficient $N_{9A}$ 1028A will be used ($N_9=N_{9A}$). If the answer is "No", the inquiry for ankle-brachial index (ABI) less than 0.7 1027B is displayed. If the answer is "Yes" then the ABI modifying coefficient $N_{9B}$ 1028B will be used ($N_9=N_{9B}$). If the answer is "No", the inquiry for ankle-brachial index (ABI) greater 1.2 1027C is displayed. If the answer is "Yes" then the ABI modifying coefficient $N_{9C}$ 1028C will be used ($N_9=N_{9C}$). Then the number of shocks "I" is altered with the determined ABI modifying coefficient "$N_9$", and thus the new number of shocks becomes "J", which is now the updated number of shocks based on peripheral arterial disease 1029.

Figure 10D:
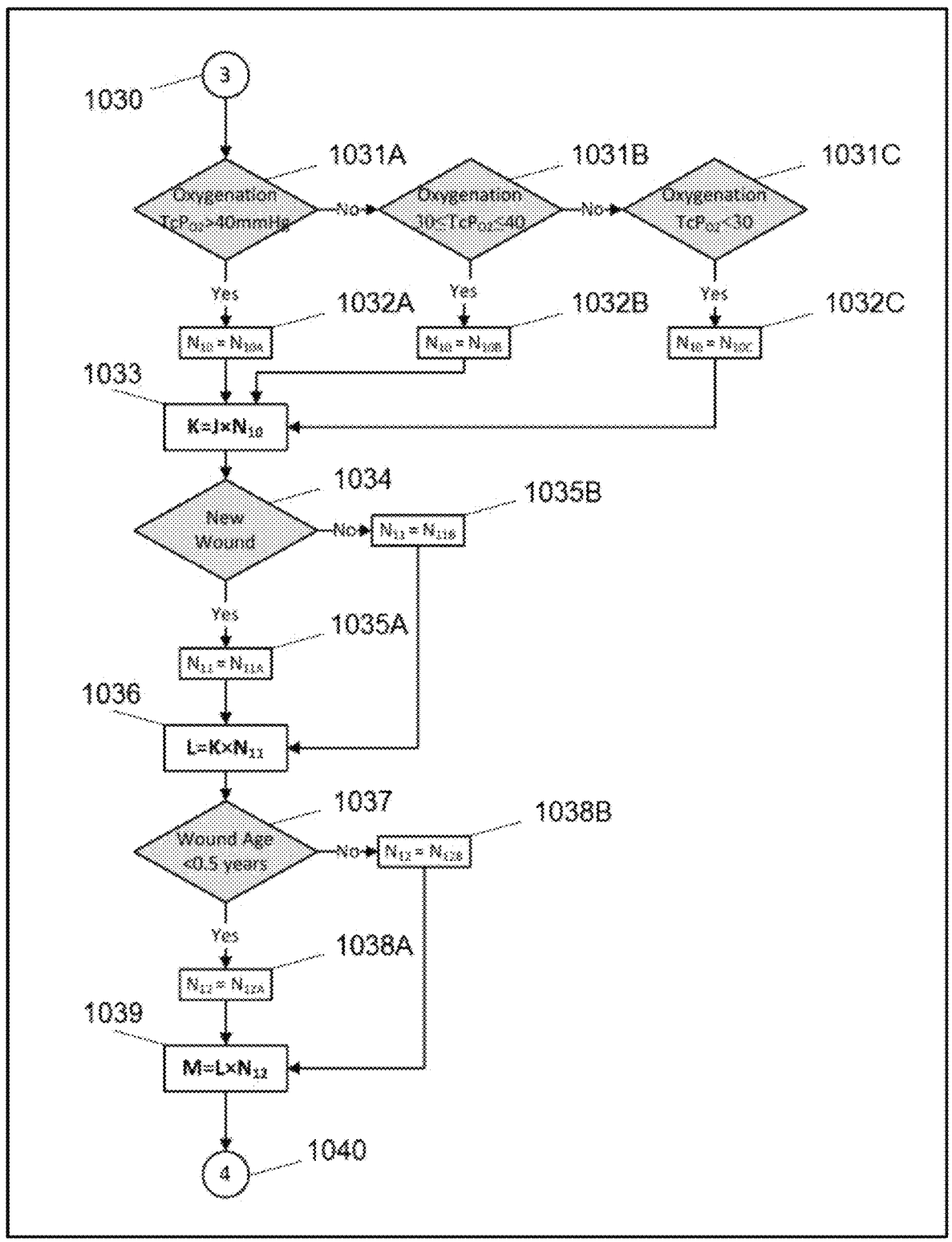
FIG. 10D is a flow diagram of the continuation of the algorithm presented in FIG. 10A, FIG. 10B, and FIG. 10C used to calculate the number of acoustic pressure shock waves for treatment of arterial ulcers, when arterial wound oxygenation ($T_cP_{O2}$-Transcutaneous Partial Pressure of Oxygen), wound reoccurrence, and chronic wound age are taken into account, according to one embodiment of the present invention.

The optimization continues on FIG. 10D and the continuation of the questionnaire flowchart from FIG. 10C to FIG. 10D is realized by the FIG. 10C to FIG. 10D connector 1030, which is seen on both FIG. 10C and FIG. 10D.

The questionnaire from FIG. 10D starts with the inquiry on transcutaneous monitoring of oxygen ($T_cP_{O2}$), which is an indication on oxygenation of the wound. Thus the inquiry for transcutaneous monitoring of oxygen (TcP$_{O2}$) greater than 40 mmHg 1031A is displayed. If the answer is "Yes" then the TcP$_{O2}$ modifying coefficient $N_{10A}$ 1032A will be used ($N_{10}=N_{10A}$). If the answer is "No", the inquiry for transcutaneous monitoring of oxygen (TcP$_{O2}$) between 30 and 40 mmHg 1031B is displayed. If the answer is "Yes" then the TcP$_{O2}$ modifying coefficient $N_{10B}$ 1032B will be used ($N_{10}=N_{10B}$). If the answer is "No", the inquiry for transcutaneous monitoring of oxygen (TcP$_{O2}$) less than 30 mmHg 1031C is displayed. If the answer is "Yes" then the TcP$_{O2}$ modifying coefficient $N_{10C}$ 1032C will be used ($N_{10}=N_{10C}$). Then the number of shocks "J" is altered with the determined transcutaneous monitoring of oxygen (TcP$_{O2}$) modifying coefficient "$N_{10}$", and thus the new number of shocks becomes "K", which is now the updated number of shocks based on tissue oxygenation 1033.

The questionnaire from FIG. 10D continues with the inquiry on new wound presence, which is an indication of recurrence. Thus the inquiry for new wound 1034 is displayed. If the answer is "Yes" then the new wound modifying coefficient $N_{11A}$ 1035A will be used ($N_{11}=N_{11A}$). If the answer is "No" then the new wound modifying coefficient $N_{11B}$ 1035B will be used ($N_{11}=N_{11B}$). Then the number of shocks "K" is altered with the determined new wound modifying coefficient "$N_{11}$", and thus the new number of shocks becomes "L", which is now the updated number of shocks based on new wound presence 1036.

The questionnaire from FIG. 10D continues with the inquiry on wound age <0.5 years. Thus the inquiry for wound age 1037 is displayed. If the answer is "Yes" then the wound age modifying coefficient $N_{12A}$ 1038A will be used ($N_{12}=N_{12A}$). If the answer is "No" then the wound age modifying coefficient $N_{12B}$ 1038B will be used ($N_{12}=N_{12B}$). Then the number of shocks "L" is altered with the determined wound age modifying coefficient "$N_{12}$", and thus the new number of shocks becomes "M", which is now the updated number of shocks based on wound age 1039.

Figure 10E:
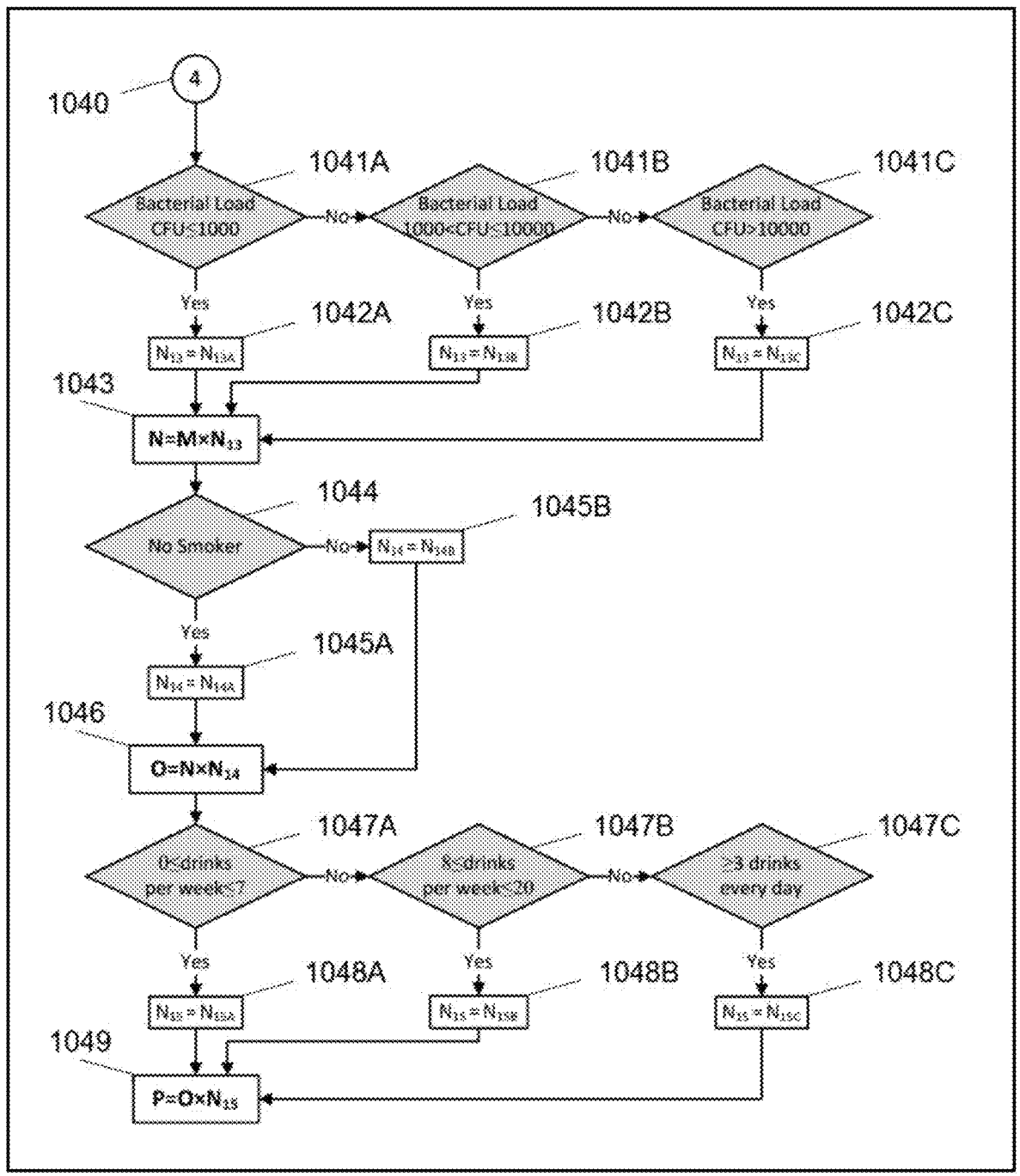
FIG. 10E is a flow diagram of the continuation of the algorithm presented in FIG. 10A, FIG. 10B, FIG. 10C, and FIG. 10D used to calculate the number of acoustic pressure shock waves for treatment of arterial ulcers, when wound bacterial load, smoker status, and alcohol consumption rate are taken into account, according to one embodiment of the present invention.

The optimization continues on FIG. 10E and the continuation of the questionnaire flowchart from FIG. 10D to FIG. 10E is realized by the FIG. 10D to FIG. 10E connector 1040, which is seen on both FIG. 10D and FIG. 10E.

The questionnaire from FIG. 10E starts with the inquiry on bacterial colony forming units (CFU), which is an indication of bacterial load of the wound. Thus the inquiry for bacterial colony forming units (CFU) less than 1000 units 1041A is displayed. If the answer is "Yes" then the CFU modifying coefficient $N_{13A}$ 1042A will be used ($N_{13}=N_{13A}$). If the answer is "No", the inquiry for bacterial colony forming units (CFU) between 1000 and 10000 units 1041B is displayed. If the answer is "Yes" then the CFU modifying coefficient $N_{13B}$ 1042B will be used ($N_{13}=N_{13B}$). If the answer is "No", the inquiry for bacterial colony forming units (CFU) greater than 10000 units 1041C is displayed. If the answer is "Yes" then the CFU modifying coefficient $N_{13C}$ 1042C will be used ($N_{13}=N_{13C}$). Then the number of shocks "M" is altered with the determined CFU modifying coefficient "$N_{13}$", and thus the new number of shocks becomes "N", which is now the updated number of shocks based on bacterial load 1043.

The questionnaire from FIG. 10E continues with the inquiry on smoking status. Thus the inquiry for smoking status 1044 is displayed. If the answer is "Yes" then the smoking status modifying coefficient $N_{14A}$ 1045A will be used ($N_{14}=N_{14A}$). If the answer is "No" then the smoking status modifying coefficient $N_{14B}$ 1045B will be used ($N_{14}=N_{14B}$). Then the number of shocks "N" is altered with the determined smoking status modifying coefficient "$N_{14}$", and thus the new number of shocks becomes "O", which is now the updated number of shocks based on smoking status 1046.

The questionnaire from FIG. 10E continues with the inquiry on drinking habit, which is indicated by the number of drinks over a certain period of time. Thus the inquiry for drinks less than 7 per week 1047A is displayed. If the answer is "Yes" then the drinking habit modifying coefficient $N_{15A}$ 1048A will be used ($N_{15}=N_{15A}$). If the answer is "No", the inquiry for drinks between 8 and 20 per week 1047B is displayed. If the answer is "Yes" then the drinking habit modifying coefficient $N_{13B}$ 1048B will be used ($N_{15}=N_{15B}$). If the answer is "No", the inquiry for drinks greater than 3 every day 1047C is displayed. If the answer is "Yes" then the drinking habit modifying coefficient $N_{15C}$ 1048C will be used ($N_{15}=N_{15C}$). Then the number of shocks "O" is altered with the determined drinking habit modifying coefficient "$N_{15}$" and thus the new number of shocks becomes "P", which is now the updated number of shocks based on drinking habit 1049.

Coefficients presented for arterial ulcers inquiries for patient's comorbidities and habits and wound status from FIGS. 10A-10E are defined with general ranges and also with more preferable ranges and sometimes as a specific number.

In FIGS. 10A-10E the values for the coefficients are preferably as follows:

In FIG. 10A, coefficient $N_{1A}$ is preferably 1.00, because patients with age under 40 should have a very good response to the acoustic pressure shock wave treatment.

In FIG. 10A, coefficient $N_{1B}$ may be in the range from about 1.01 to 1.04, and preferably from about 1.02 to 1.04.

In FIG. 10A, coefficient $N_{1C}$ may be in the range from about 1.01 to 1.05, and preferably from about 1.03 to 1.05.

In FIG. 10A, coefficient $N_{1D}$ may be in the range from about 1.01 to 1.06, and preferably from about 1.04 to 1.06.

In FIG. 10A, coefficient $N_{2A}$ may be in the range from about 1.00 to 1.03, and preferably from about 1.02 to 1.03.

In FIG. 10A, coefficient $N_{2B}$ may be in the range from about 1.00 to 1.04, and preferably from about 1.03 to 1.04.

In FIG. 10A, coefficient $N_{3A}$ is preferably 1.00, because patients with a body mass index (BMI) below 32 should have a very good response to the acoustic pressure shock wave treatment and do not present any challenges from obesity point of view.

In FIG. 10A, coefficient $N_{3B}$ may be in the range from about 1.02 to 1.08, and preferably from about 1.05 to 1.08.

In FIG. 10B coefficient $N_{4A}$ is preferably 1.00, because patients with a weight below 220 lb should have a very good response to the acoustic pressure shock wave treatment and do not present any challenges from obesity point of view.

In FIG. 10B, coefficient $N_{4B}$ may be in the range from about 1.02 to 1.05, and preferably from about 1.03 to 1.05.

In FIG. 10B coefficient $N_{5A}$ is preferably 1.00 for a height below 70 in.

In FIG. 10B, coefficient $N_{5B}$ may be in the range from about 1.00 to 1.02, and preferably from about 1.01 to 1.02.

In FIG. 10B, coefficient $N_{6A}$ is preferably 1.00, because patients with a HbA1c are controlling their diabetes and should have a very good response to the acoustic pressure shock wave treatment.

In FIG. 10B, coefficient $N_{6B}$ may be in the range from about 1.01 to 1.05, and preferably from about 1.02 to 1.04.

In FIG. 10B, coefficient $N_{6C}$ may be in the range from about 1.02 to 1.07, and preferably from about 1.04 to 1.07.

In FIG. 10C, coefficient $N_{7A}$ is preferably 1.00, because patients with very superficial wounds should have a very good response to the acoustic pressure shock wave treatment.

In FIG. 10C, coefficient $N_{7B}$ may be in the range from about 1.00 to 1.03, and preferably from about 1.01 to 1.02.

In FIG. 10C, coefficient $N_{7C}$ may be in the range from about 1.02 to 1.06, and preferably from about 1.03 to 1.05.

In FIG. 10C, coefficient $N_{8A}$ is preferably 1.00, because patients with Grade I arterial ulcers should have a very good response to the acoustic pressure shock wave treatment.

In FIG. 10C, coefficient $N_{8B}$ may be in the range from about 1.01 to 1.04, and preferably from about 1.01 to 1.03.

In FIG. 10C, coefficient $N_{8C}$ may be in the range from about 1.03 to 1.06, and preferably from about 1.04 to 1.06.

In FIG. 10C, coefficient $N_{9A}$ is preferably 1.00, because patients with an ankle-brachial index (ABI) between 0.7 and 1.2 should have a very good response to the acoustic pressure shock wave treatment.

In FIG. 10C, coefficient $N_{9B}$ may be in the range from about 1.00 to 1.03, and preferably from about 1.01 to 1.02.

In FIG. 10C, coefficient $N_{9C}$ may be in the range from about 1.01 to 1.04, and preferably from about 1.02 to 1.03.

In FIG. 10D, coefficient $N_{10A}$ is preferably 1.00, because patients with a $TcP_{O2}$ value greater than 40 mmHg is normal and the patients should have a very good response to the acoustic pressure shock wave treatment.

In FIG. 10D, coefficient $N_{10B}$ may be in the range from about 1.01 to 1.05, and preferably from about 1.02 to 1.05.

In FIG. 10D, coefficient $N_{10C}$ may be in the range from about 1.02 to 1.07, and preferably from about 1.04 to 1.06.

In FIG. 10D coefficient $N_{11A}$ is preferably 1.00 for a new wound and not a recurrent wound.

In FIG. 10D, coefficient $N_{11B}$ may be in the range from about 1.00 to 1.05, and preferably from about 1.01 to 1.04.

In FIG. 10D coefficient $N_{12A}$ is preferably 1.00 for a wound that is less than 6 month old.

In FIG. 10D, coefficient $N_{12B}$ may be in the range from about 1.00 to 1.05, and preferably from about 1.02 to 1.04.

In FIG. 10E, coefficient $N_{13A}$ is preferably 1.00, because patients with a colony forming units (CFU) of bacteria less than 1000 in the skin lesion should have a very good response to the acoustic pressure shock wave treatment.

In FIG. 10E, coefficient $N_{13B}$ may be in the range from about 1.01 to 1.04, and preferably from about 1.02 to 1.03.

In FIG. 10E, coefficient $N_{13C}$ may be in the range from about 1.04 to 1.08, and preferably from about 1.05 to 1.07.

In FIG. 10E coefficient $N_{14A}$ is preferably 1.00 because a non-smoker should have a very good response to the acoustic pressure shock wave treatment.

In FIG. 10E, coefficient $N_{14B}$ may be in the range from about 1.01 to 1.04, and preferably from about 1.02 to 1.04.

In FIG. 10E, coefficient $N_{15A}$ is preferably 1.00, because occasional drinking patients should have a very good response to the acoustic pressure shock wave treatment.

In FIG. 10E, coefficient $N_{15B}$ may be in the range from about 1.01 to 1.04, and preferably from about 1.02 to 1.04.

In FIG. 10E, coefficient $N_{15C}$ may be in the range from about 1.03 to 1.07, and preferably from about 1.04 to 1.06.

A control console/unit 22 and associated acoustic pressure shock wave applicator/treatment apparatus 10 (see FIG. 2A) used for delivering a treatment for arterial ulcers by means of the proposed adjustment algorithm from FIGS. 10A-10E will use the following formula (where "A" is the initial number of focused acoustic pressure shock waves 40 or radial acoustic pressure waves 41 or planar acoustic pressure waves 42 or cylindrical acoustic pressure waves 44 delivered per treatment and "ATN" is the Adjusted Total Number of focused acoustic pressure shock waves 40 or radial acoustic pressure waves 41 or planar acoustic pressure waves 42 or cylindrical acoustic pressure waves 44 delivered per treatment):

$$ATN = A \cdot N_1 \cdot N_2 \cdot N_3 \cdot N_4 \cdot N_5 \cdot N_6 \cdot N_7 \cdot N_8 \cdot N_9 \cdot N_{10} \cdot N_{11} \cdot N_{12} \cdot N_{13} \cdot N_{14} \cdot N_{15}$$

For the largest values for these coefficients (worst situation) and for example a number of A=500 is used as initial number of focused acoustic pressure shock waves 40 or radial acoustic pressure waves 41 or planar acoustic pressure waves 42 or cylindrical acoustic pressure waves 44 that are minimally needed for successful treatment of the tissue condition 19, then the Adjusted Total Number (ATN) value of focused acoustic pressure shock waves 40 or radial acoustic pressure waves 41 or planar acoustic pressure waves 42 or cylindrical acoustic pressure waves 44 delivered per treatment is the following:

$$ATN = 500 \cdot 1.06 \cdot 1.04 \cdot 1.1 \cdot 1.05 \cdot 1.02 \cdot 1.07 \cdot 1.06 \cdot 1.04 \cdot 1.07 \cdot 1.05 \cdot 1.05 \cdot 1.08 \cdot 1.04 \cdot 1.07 = 1130.20 \approx 1130 \text{ shock waves or pressure waves.}$$

Another important category of chronic wounds are the venous ulcers. Venous ulcers are wounds that occur due to improper functioning of venous valves, usually of the legs causing the pressure in veins to increase. The body needs the pressure gradient between arteries and veins in order for the heart to pump blood forward through arteries and into veins. When venous hypertension exists, arteries no longer have significantly higher pressure than veins, and blood is not pumped as effectively into or out of the area. Venous hypertension may also stretch veins and allow blood proteins to leak into the extravascular space, isolating extracellular matrix (ECM) molecules and growth factors, preventing them from helping to heal the wound.

Risk factors implicated in the development of venous ulcers are age, obesity, existing comorbidities and conditions, diabetic neuropathy, peripheral vascular disease, venous insufficiency/stasis, cigarette smoking, excessive alcohol consumption, poor glycemic control, diabetic nephropathy, ischemia of small and large blood vessels, previous leg injuries, deep venous thrombosis, and phlebitis.

The personalized treatment parameters for venous ulcers when focused acoustic pressure shock waves 40 or radial acoustic pressure waves 41 or planar acoustic pressure waves 42 or cylindrical acoustic pressure waves 44 are used can be determined using different factors. In FIGS. 11A-11E is presented a preferable algorithm that can be used to adjust the number of focused acoustic pressure shock waves 40 or radial acoustic pressure waves 41 or planar acoustic pressure waves 42 or cylindrical acoustic pressure waves 44 used for the treatment of venous ulcers based on different elements that take into account the characteristics of the venous ulcer, patient's comorbidities and lifestyle.

As a starting point for venous ulcers algorithm is the basic/initial number of focused acoustic pressure shock waves 40 or radial acoustic pressure waves 41 or planar acoustic pressure waves 42 or cylindrical acoustic pressure waves 44 that are minimally needed for successful treatment of the tissue condition 19. As presented before, this is considered the basic/initial dosage that is calculated after tissue condition 19 area and/or volume were determined.

Figure 11A:
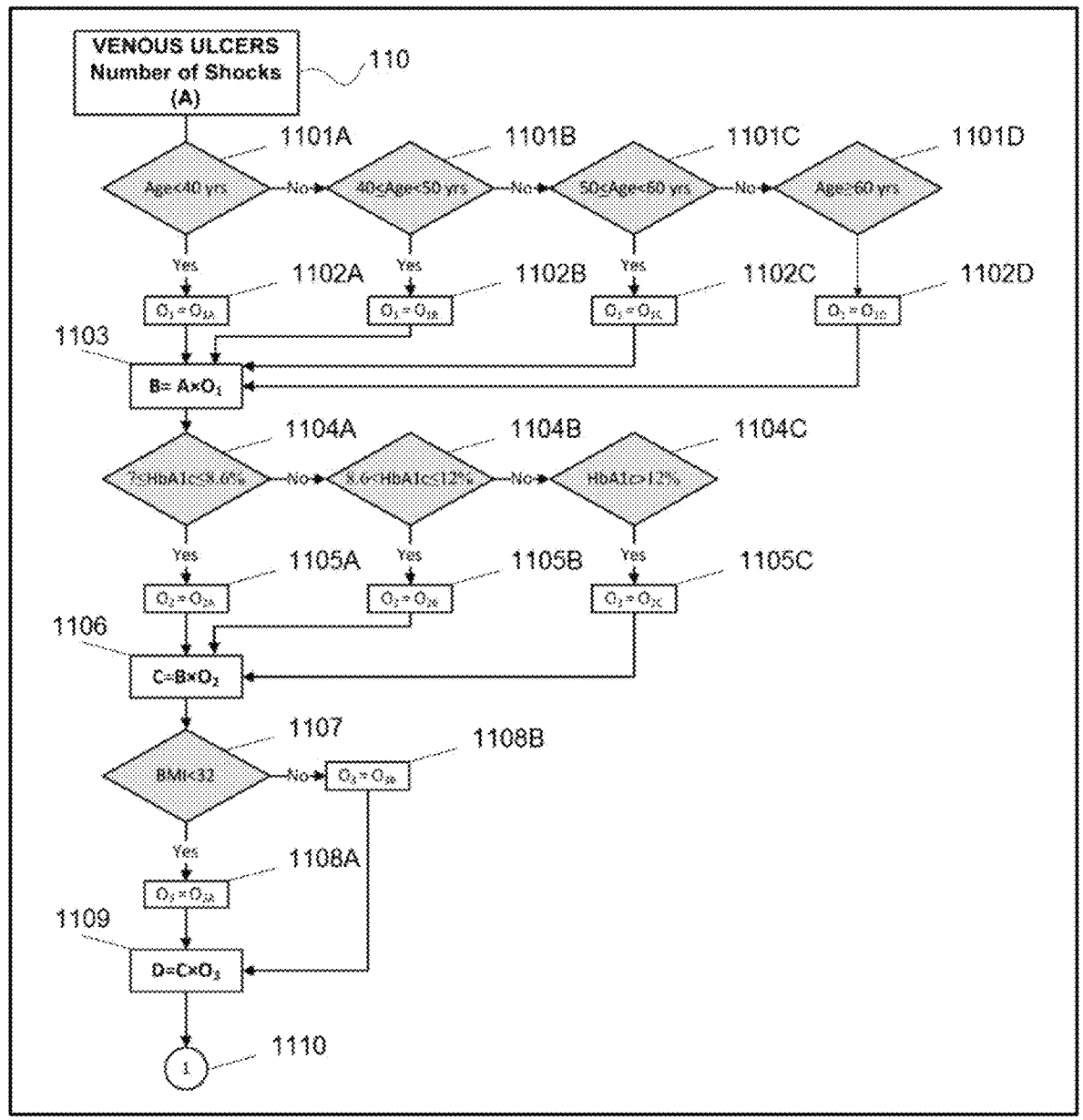
FIG. 11A is a flow diagram of the algorithm used to calculate the number of acoustic pressure shock waves for treatment of venous ulcers when patient age, glycosylated hemoglobin A1c (HbA1c), and body mass index (BMI) are taken into account, according to one embodiment of the present invention.

In FIG. 11A the basic/initial number of shocks for venous ulcers 110 represents the starting point of the adjustment/optimization algorithm for number of focused acoustic pressure shock waves 40 or radial acoustic pressure waves 41 or planar acoustic pressure waves 42 or cylindrical acoustic pressure waves 44 for the treatment of venous ulcers. The first element used to alter the basic/initial dosage used for venous ulcers treatment is the inquiry regarding the age of the patient. Thus on the control console/unit display 2220, or artificial intelligence (A/I) device display 2740, or on the display of an interconnected device (see FIG. 2A for the medical treatment system 2000) as a desktop computer 28A, or a smart phone 28B, and/or tablet 28C, and/or laptop 28D is first displayed the inquiry for age less than 40 years 1101A. If the answer is "Yes" then the age modifying coefficient $O_{1A}$ 1102A will be used ($O_1=O_{1A}$). If the answer is "No", the inquiry for age between 40 and 50 years 1101B is displayed. If the answer is "Yes" then the age modifying coefficient $O_{1B}$ 1102B will be used ($O_1=O_{1B}$). If the answer is "No", the inquiry for age between 50 and 60 years 1101C is displayed. If the answer is "Yes" then the age modifying coefficient $O_{1C}$ 1102C will be used ($O_1=O_{1C}$). If the answer is "No", the inquiry for age older than 60 years 1101D is displayed and if the answer is "Yes" then the age modifying coefficient $O_{1D}$ 1102D will be used ($O_1=O_{1D}$). Then the basic/initial number of shocks "A" is altered with the determined age modifying coefficient "$O_1$", and thus the new number of shocks becomes "B", which is now the updated number of shocks based on age 1103.

The questionnaire from FIG. 11A continues with the inquiry on the value for glycated hemoglobin (HbA1c), which is an indication of diabetes presence. Thus the inquiry for glycated hemoglobin (HbA1c) between 7 and 8.6% 1104A is displayed. If the answer is "Yes" then the HbA1c modifying coefficient $O_{2A}$ 1105A will be used ($O_2=O_{2A}$). If the answer is "No", the inquiry for glycated hemoglobin (HbA1c) between 8.6 and 12% 1104B is displayed. If the answer is "Yes" then the HbA1c modifying coefficient $O_{2B}$ 1105B will be used ($O_2=O_{2B}$). If the answer is "No", the inquiry for glycated hemoglobin (HbA1c) larger than 12% 1104C is displayed. If the answer is "Yes" then the HbA1c modifying coefficient $O_{2C}$ 1105C will be used ($O_2=O_{2C}$). Then the number of shocks "B" is altered with the determined HbA1c modifying coefficient "$O_2$" and thus the new number of shocks becomes "C", which is now the updated number of shocks based on diabetes presence 1106.

The questionnaire from FIG. 11A continues with the inquiry on the body mass index (BMI). Thus the inquiry for body mass index (BMI) value 1107 is displayed (BMI<32). If the answer is "Yes" then the body mass index (BMI) modifying coefficient $O_{3A}$ 1108A will be used ($O_3=O_{3A}$). If the answer is "No" then the body mass index (BMI) modifying coefficient $N_{3B}$ 1108B will be used ($O_3=O_{3B}$). Then the number of shocks "C" is altered with the determined body mass index (BMI) modifying coefficient "$O_3$", and thus the new number of shocks becomes "D", which is now the updated number of shocks based on obesity 1109.

Figure 11B:
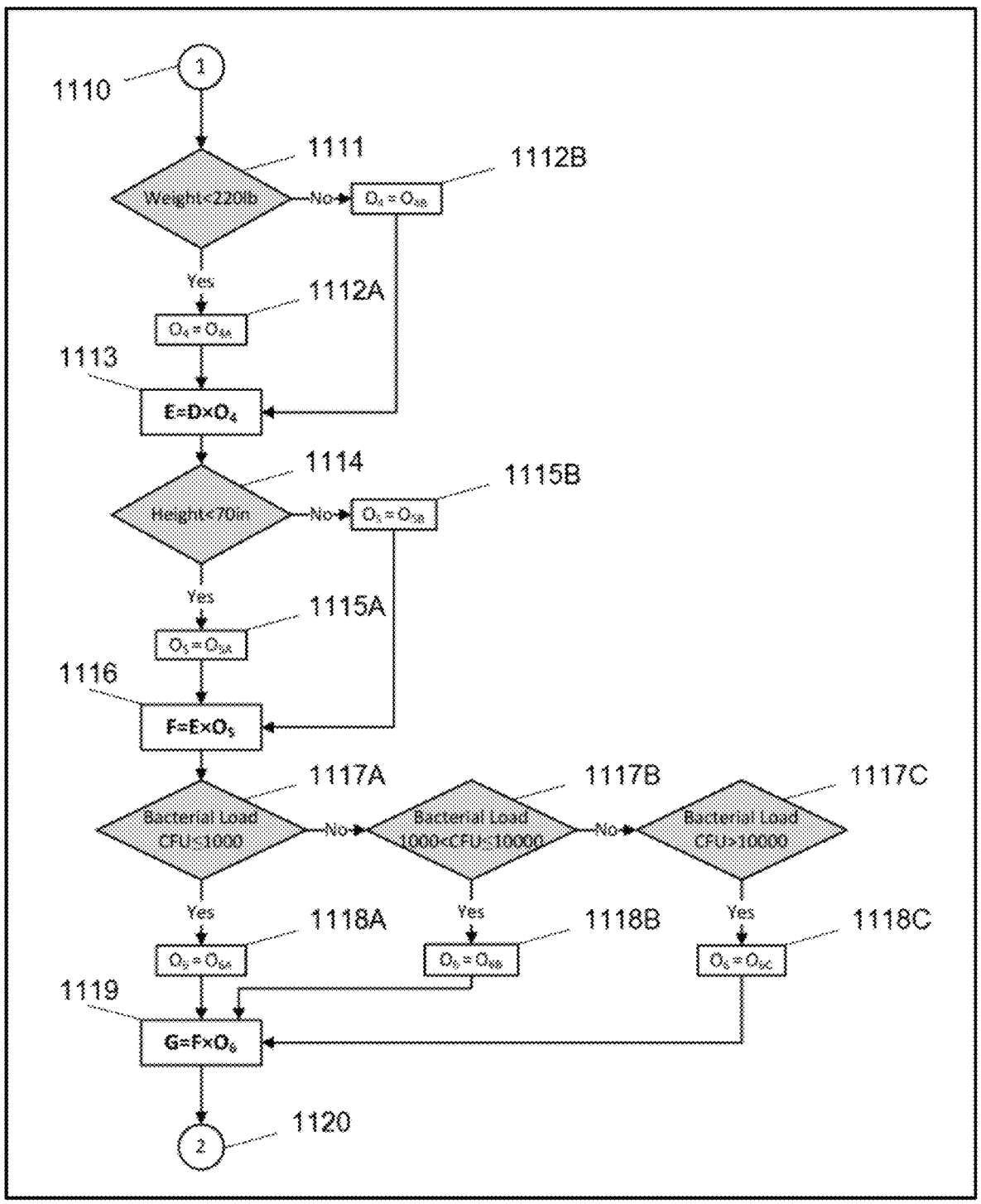
FIG. 11B is a flow diagram of the continuation of the algorithm presented in FIG. 11A used to calculate the number of acoustic pressure shock waves for treatment of venous ulcers, when patient weight, patient height, and wound bacterial load are taken into account, according to one embodiment of the present invention.

The optimization continues on FIG. 11B and the continuation of the questionnaire flowchart from FIG. 11A to FIG. 11B is realized by the FIG. 11A to FIG. 11B connector 1110, which is seen on both FIG. 11A and FIG. 11B.

The questionnaire from FIG. 11B starts with the inquiry on the patient's weight. Thus the inquiry for weight value 1111 is displayed (Weight<220 lb which is 99.8 Kg in metric system). If the answer is "Yes" then the weight modifying coefficient $O_{4A}$ 1112A will be used $O_4=O_{4A}$). If the answer is "No" then the weight modifying coefficient $O_{4B}$ 1112B will be used ($O_4=O_{4B}$). Then the number of shocks "D" is altered with the determined weight modifying coefficient "$O_4$", and thus the new number of shocks becomes "E", which is now the updated number of shocks based on weight 1113.

The questionnaire from FIG. 11B continues with the inquiry on the patient's height. Thus the inquiry for inquiry for height value 1114 is displayed (Height<70 in which is 177.8 cm in metric system). If the answer is "Yes" then the height modifying coefficient $O_{5A}$ 1115A will be used ($O_5=O_{5A}$). If the answer is "No" then the height modifying coefficient $N_{5B}$ 1115B will be used ($O_5=O_{5B}$). Then the number of shocks "E" is altered with the determined height modifying coefficient "$O_5$", and thus the new number of shocks becomes "F", which is now the updated number of shocks based on height 1116.

The questionnaire from FIG. 11B continues with the inquiry on bacterial colony forming units (CFU), which is an indication of bacterial load of the wound. Thus the inquiry for bacterial colony forming units (CFU) less than 1000 units 1117A is displayed. If the answer is "Yes" then the CFU modifying coefficient $O_{6A}$ 1118A will be used ($O_6=O_{6A}$). If the answer is "No", the inquiry for bacterial colony forming units (CFU) between 1000 and 10000 units 1117B is displayed. If the answer is "Yes" then the CFU modifying coefficient $O_{6B}$ 1118B will be used ($O_6=O_{6B}$). If the answer is "No", the inquiry for bacterial colony forming units (CFU) greater than 10000 units 1117C is displayed. If the answer is "Yes" then the CFU modifying coefficient $O_{6C}$ 1118C will be used ($O_6=O_{6C}$). Then the number of shocks "F" is altered with the determined CFU modifying coefficient "$O_6$", and thus the new number of shocks becomes "G", which is now the updated number of shocks based on bacterial load 1119.

Figure 11C:
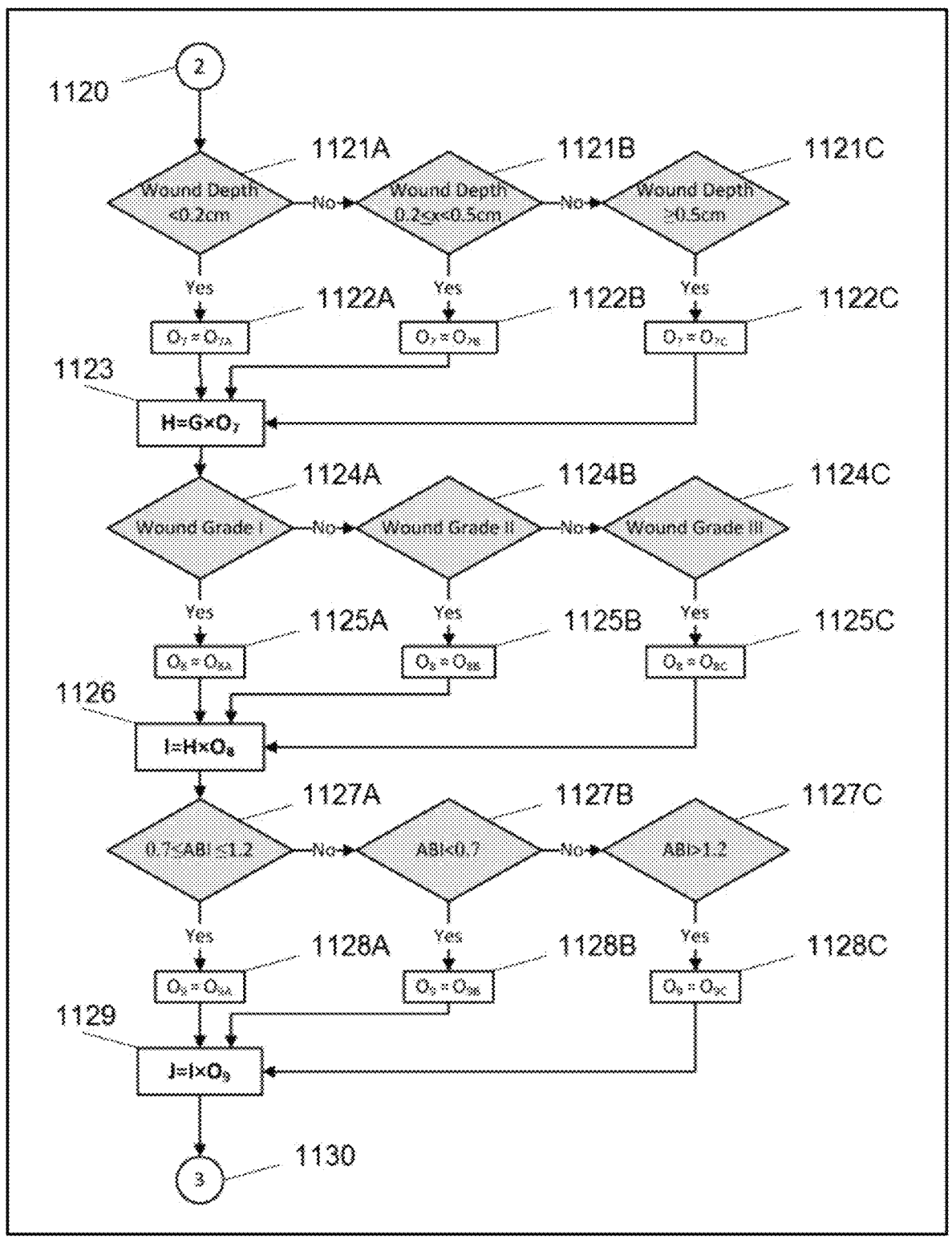
FIG. 11C is a flow diagram of the continuation of the algorithm presented in FIG. 11A and FIG. 11B used to calculate the number of acoustic pressure shock waves for treatment of venous ulcers, when chronic wound depth, wound grade, and ankle-brachial index (ABI) are taken into account, according to one embodiment of the present invention.

The optimization continues on FIG. 11C and the continuation of the questionnaire flowchart from FIG. 11B to FIG. 11C is realized by the FIG. 11B to FIG. 11C connector 1120, which is seen on both FIG. 11B and FIG. 11C.

The questionnaire from FIG. 11C starts with the inquiry on wound depth. Thus the inquiry for wound depth less than 0.2 cm 1121A is displayed. If the answer is "Yes" then the wound depth modifying coefficient $O_{7A}$ 1122A will be used ($O_7=O_{7A}$). If the answer is "No", the inquiry for wound depth between 0.2 and 0.5 cm 1121B is displayed. If the answer is "Yes" then the wound depth modifying coefficient $O_{7B}$ 1122B will be used ($O_7=O_{7B}$). If the answer is "No", the inquiry for wound depth greater than 0.5 cm 1121C is displayed. If the answer is "Yes" then the wound depth modifying coefficient $O_{7C}$ 1122C will be used ($O_7=O_{7C}$). Then the number of shocks "G" is altered with the determined wound depth modifying coefficient "$O_7$", and thus the new number of shocks becomes "H", which is now the updated number of shocks based on wound depth 1123.

The questionnaire from FIG. 11C continues with the inquiry on wound grade. Thus the inquiry for wound grade I 1124A is displayed. If the answer is "Yes" then the wound grade modifying coefficient $O_{8A}$ 1125A will be used ($O_8=O_{8A}$). If the answer is "No", the inquiry for wound grade II 1124B is displayed. If the answer is "Yes" then the wound grade modifying coefficient $N_{8B}$ 1125B will be used ($O_8=O_{8B}$). If the answer is "No", the inquiry for wound grade III 1124C is displayed. If the answer is "Yes" then the wound grade modifying coefficient $N_{8C}$ 1125C will be used ($O_8=O_{8C}$). Then the number of shocks "H" is altered with the determined wound grade modifying coefficient "$O_8$", and thus the new number of shocks becomes "I", which is now the updated number of shocks based on wound grade 1126.

The questionnaire from FIG. 11C continues with the inquiry on ankle-brachial index (ABI), which is an indication on peripheral arterial disease. Thus the inquiry for ankle-brachial index (ABI) between 0.7 and 1.2 1127A is displayed. If the answer is "Yes" then the ABI modifying coefficient $O_{9A}$ 1128A will be used ($O_9=O_{9A}$). If the answer is "No", the inquiry for ankle-brachial index (ABI) less than 0.7 1127B is displayed. If the answer is "Yes" then the ABI modifying coefficient $O_{9B}$ 1128B will be used ($O_9=O_{9B}$). If the answer is "No", the inquiry for ankle-brachial index (ABI) greater than 1.2 1127C is displayed. If the answer is "Yes" then the ABI modifying coefficient $O_{9C}$ 1128C will be used ($O_9=O_{9C}$). Then the number of shocks "I" is altered with the determined ABI modifying coefficient "$O_9$", and thus the new number of shocks becomes "J", which is now the updated number of shocks based on peripheral arterial disease 1129.

Figure 11D:
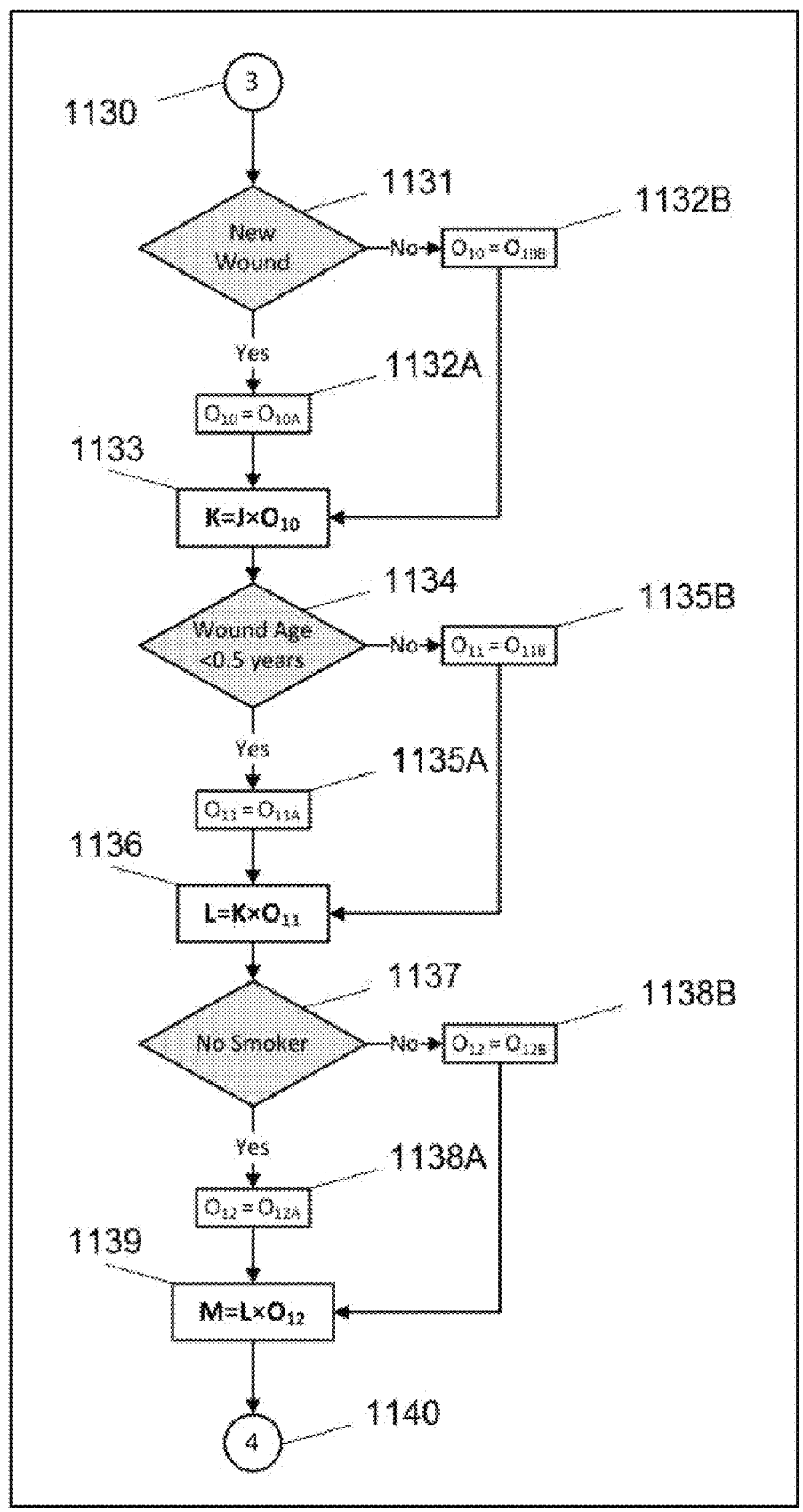
FIG. 11D is a flow diagram of the continuation of the algorithm presented in FIG. 11A, FIG. 11B, and FIG. 11C used to calculate the number of acoustic pressure shock waves for treatment of venous ulcers, when wound reoccurrence, chronic wound age, and smoker status are taken into account, according to one embodiment of the present invention.

The optimization continues on FIG. 11D and the continuation of the questionnaire flowchart from FIG. 11C to FIG. 11D is realized by the FIG. 11C to FIG. 11D connector 1130, which is seen on both FIG. 11C and FIG. 11D.

The questionnaire from FIG. 11D starts with the inquiry on new wound presence, which is an indication of recurrence. Thus the inquiry for new wound 1131 is displayed. If the answer is "Yes" then the new wound modifying coefficient $O_{10A}$ 1132A will be used ($O_{10}=O_{10A}$). If the answer is "No" then the new wound modifying coefficient $O_{10B}$ 1132B will be used ($O_{10}=O_{10B}$). Then the number of shocks "J" is altered with the determined new wound modifying coefficient "$O_{10}$", and thus the new number of shocks becomes "K", which is now the updated number of shocks based on new wound presence 1133.

The questionnaire from FIG. 11D continues with the inquiry on wound age <0.5 years. Thus the inquiry for wound age 1135 is displayed. If the answer is "Yes" then the wound age modifying coefficient $O_{11A}$ 1136A will be used ($O_{11}=O_{11A}$). If the answer is "No" then the wound age modifying coefficient $O_{11B}$ 1136B will be used ($O_{11}=O_{11B}$). Then the number of shocks "K" is altered with the determined wound age modifying coefficient "$O_{11}$", and thus the new number of shocks becomes "L", which is now the updated number of shocks based on wound age 1136.

The questionnaire from FIG. 11D continues with the inquiry on smoking status. Thus the inquiry for smoking status 1137 is displayed. If the answer is "Yes" then the smoking status modifying coefficient $O_{12A}$ 1138A will be used ($O_{12}=O_{12A}$). If the answer is "No" then the smoking status modifying coefficient $O_{12B}$ 1138B will be used ($O_{12}=O_{12B}$). Then the number of shocks "L" is altered with the determined smoking status modifying coefficient "$O_{12}$", and thus the new number of shocks becomes "M", which is now the updated number of shocks based on smoking status 1139.

Figure 11E:
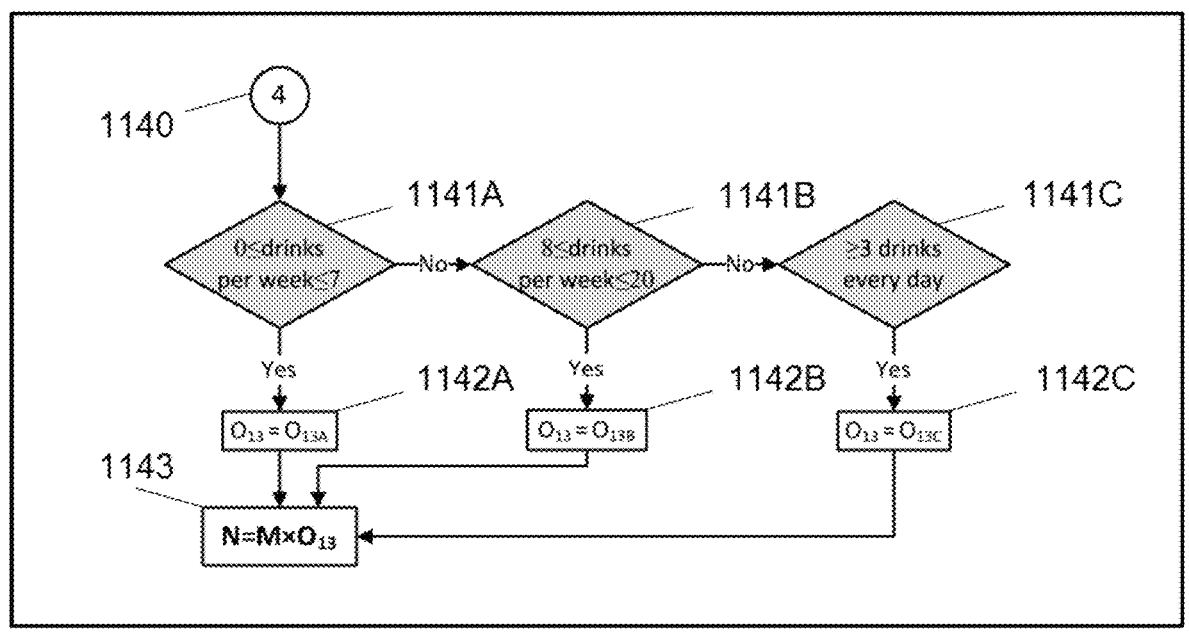
FIG. 11E is a flow diagram of the continuation of the algorithm presented in FIG. 11A, FIG. 11B, FIG. 11C, and FIG. 11D used to calculate the number of acoustic pressure shock waves for treatment of venous ulcers, when alcohol consumption rate is taken into account, according to one embodiment of the present invention.

The optimization continues on FIG. 11E and the continuation of the questionnaire flowchart from FIG. 11D to FIG. 11E is realized by the FIG. 11D to FIG. 11E connector 1140, which is seen on both FIG. 11D and FIG. 11E.

The questionnaire from FIG. 11E starts with the inquiry on drinking habit, which is indicated by the number of drinks over a certain period of time. Thus the inquiry for drinks less than 7 per week 1141A is displayed. If the answer is "Yes" then the drinking habit modifying coefficient $O_{13A}$ 1142A will be used ($O_{13}=O_{13A}$). If the answer is "No", the inquiry for drinks between 8 and 20 per week 1141B is displayed. If the answer is "Yes" then the drinking habit modifying coefficient $O_{13B}$ 1142B will be used ($O_{13}=O_{13B}$). If the answer is "No", the inquiry for drinks greater than 3 every day 1141C is displayed. If the answer is "Yes" then the drinking habit modifying coefficient $O_{13C}$ 1142C will be used ($O_{13}=O_{13C}$). Then the number of shocks "M" is altered with the determined drinking habit modifying coefficient "$O_{13}$", and thus the new number of shocks becomes "N", which is now the updated number of shocks based on drinking habit 1143.

Coefficients presented for venous ulcers inquiries for patient's comorbidities and habits and wound status from FIGS. 11A-11E are defined with general ranges and also with more preferable ranges and sometimes as a specific number.

In FIGS. 11A-11E the values for the coefficients are preferably as follows:

In FIG. 11A, coefficient $O_{1A}$ is preferably 1.00, because patients with age under 40 should have a very good response to the acoustic pressure shock wave treatment.

In FIG. 11A, coefficient $O_{1B}$ may be in the range from about 1.01 to 1.04, and preferably from about 1.02 to 1.04.

In FIG. 11A, coefficient $O_{1C}$ may be in the range from about 1.01 to 1.05, and preferably from about 1.03 to 1.05.

In FIG. 11A, coefficient $O_{1D}$ may be in the range from about 1.01 to 1.06, and preferably from about 1.04 to 1.06.

In FIG. 11A, coefficient $O_{2A}$ is preferably 1.00, because patients with a HbA1c are controlling their diabetes and should have a very good response to the acoustic pressure shock wave treatment.

In FIG. 11A, coefficient $O_{2B}$ may be in the range from about 1.01 to 1.04, and preferably from about 1.02 to 1.03.

In FIG. 11A, coefficient $O_{2C}$ may be in the range from about 1.02 to 1.06, and preferably from about 1.04 to 1.06.

In FIG. 11A, coefficient $O_{3A}$ is preferably 1.00, because patients with a body mass index (BMI) below 32 should have a very good response to the acoustic pressure shock wave treatment and do not present any challenges from obesity point of view.

In FIG. 11A, coefficient $O_{3B}$ may be in the range from about 1.02 to 1.08, and preferably from about 1.05 to 1.08.

In FIG. 11B coefficient $O_{4A}$ is preferably 1.00, because patients with a weight below 220 lb should have a very good response to the acoustic pressure shock wave treatment and do not present any challenges from obesity point of view.

In FIG. 11B, coefficient $O_{4B}$ may be in the range from about 1.02 to 1.04, and preferably from about 1.03 to 1.04.

In FIG. 11B coefficient $O_{5A}$ is preferably 1.00 for a height below 70 in.

In FIG. 11B, coefficient $O_{5B}$ may be in the range from about 1.00 to 1.02, and preferably from about 1.01 to 1.02.

In FIG. 11B, coefficient $O_{6A}$ is preferably 1.00, because patients with a colony forming units (CFU) of bacteria less than 1000 in the skin lesion should have a very good response to the acoustic pressure shock wave treatment.

In FIG. 11B, coefficient $O_{6B}$ may be in the range from about 1.01 to 1.04, and preferably from about 1.02 to 1.03.

In FIG. 11B, coefficient $O_{6C}$ may be in the range from about 1.04 to 1.07, and preferably from about 1.03 to 1.05.

In FIG. 11C, coefficient $O_{7A}$ is preferably 1.00, because patients with very superficial wounds should have a very good response to the acoustic pressure shock wave treatment.

In FIG. 11C, coefficient $O_{7B}$ may be in the range from about 1.00 to 1.03, and preferably from about 1.01 to 1.02.

In FIG. 11C, coefficient $O_{7C}$ may be in the range from about 1.01 to 1.04, and preferably from about 1.02 to 1.04.

In FIG. 11C, coefficient $O_{8A}$ is preferably 1.00, because patients with Grade I venous ulcers should have a very good response to the acoustic pressure shock wave treatment.

In FIG. 11C, coefficient $O_{8B}$ may be in the range from about 1.01 to 1.04, and preferably from about 1.01 to 1.03.

In FIG. 11C, coefficient $O_{8C}$ may be in the range from about 1.02 to 1.06, and preferably from about 1.03 to 1.06.

In FIG. 11C, coefficient $O_{9A}$ is preferably 1.00, because patients with an ankle-brachial index (ABI) between 0.7 and 1.2 should have a very good response to the acoustic pressure shock wave treatment.

In FIG. 11C, coefficient $O_{9B}$ may be in the range from about 1.00 to 1.03, and preferably from about 1.01 to 1.02.

In FIG. 11C, coefficient $O_{9C}$ may be in the range from about 1.01 to 1.04, and preferably from about 1.02 to 1.03.

In FIG. 11D coefficient $O_{10A}$ is preferably 1.00 for a new wound and not a recurrent wound.

In FIG. 1D, coefficient $O_{10B}$ may be in the range from about 1.01 to 1.04, and preferably from about 1.01 to 1.03.

In FIG. 11D coefficient $O_{11A}$ is preferably 1.00 for a wound that is less than 6 month old.

In FIG. 11D, coefficient $O_{11B}$ may be in the range from about 1.01 to 1.05, and preferably from about 1.02 to 1.04.

In FIG. 11D coefficient $O_{12A}$ is preferably 1.00 because a non-smoker should have a very good response to the acoustic pressure shock wave treatment.

In FIG. 11D, coefficient $O_{12B}$ may be in the range from about 1.01 to 1.04, and preferably from about 1.02 to 1.04.

In FIG. 11E, coefficient $O_{13A}$ is preferably 1.00, because occasional drinking patients should have a very good response to the acoustic pressure shock wave treatment.

In FIG. 11E, coefficient $O_{13B}$ may be in the range from about 1.01 to 1.04, and preferably from about 1.02 to 1.03.

A control console/unit 22 and associated acoustic pressure shock wave applicator/treatment apparatus 10 (see FIG. 2A) used for delivering a treatment for venous ulcers by means of the proposed adjustment algorithm from FIGS. 11A-11E will use the following formula (where "A" is the initial number of focused acoustic pressure shock waves 40 or radial acoustic pressure waves 41 or planar acoustic pressure waves 42 or cylindrical acoustic pressure waves 44 delivered per treatment and "ATN" is the Adjusted Total Number of focused acoustic pressure shock waves 40 or radial acoustic pressure waves 41 or planar acoustic pressure waves 42 or cylindrical acoustic pressure waves 44 delivered per treatment):

$$\text{ATN} = A \cdot O_1 \cdot O_2 \cdot O_3 \cdot O_4 \cdot O_5 \cdot O_6 \cdot O_7 \cdot O_8 \cdot O_9 \cdot O_{10} \cdot O_{11} \cdot O_{12} \cdot O_{13}.$$

For the largest values for these coefficients (worst situation) and for example a number of A=500 is used as initial number of focused acoustic pressure shock waves 40 or radial acoustic pressure waves 41 or planar acoustic pressure waves 42 or cylindrical acoustic pressure waves 44 that are minimally needed for successful treatment of the tissue condition 19, then the Adjusted Total Number (ATN) value of focused acoustic pressure shock waves 40 or radial acoustic pressure waves 41 or planar acoustic pressure waves 42 or cylindrical acoustic pressure waves 44 delivered per treatment is the following:

$$\text{ATN} = 500 \cdot 1.06 \cdot 1.04 \cdot 1.08 \cdot 1.04 \cdot 1.02 \cdot 1.07 \cdot 1.04 \cdot 1.06 \cdot 1.04 \cdot 1.04 \cdot 1.05 \cdot 1.04 \cdot 1.04 = 932.58 \approx 933 \text{ shock waves or pressure waves.}$$

Another important category of wounds are the burn wounds. Burns are an acute tissue condition that is characterized by severe skin damage that causes the affected skin cells to die. Burns are caused by a variety of external sources classified as thermal (heat-related), chemical, electrical, and radiation. There are three primary types of burns: first-, second-, and third-degree. Each degree is based on the severity of damage to the skin, with first-degree being the most minor and third-degree being the most severe. There are also fourth-degree burns. This type of burn includes all of the symptoms of a third-degree burn and also extends beyond the skin into tendons and bones.

First-degree burns cause minimal skin damage. They are also called "superficial burns" because they affect the outermost layer of skin. Signs of a first-degree burn include redness, minor inflammation, or swelling, pain, dry, peeling skin occurs as the burn heals. Since this burn affects the top layer of skin, the signs and symptoms disappear once the skin cells shed. First-degree burns usually heal within 7 to 10 days without scarring.

Second-degree burns are more serious because the damage extends beyond the top layer of skin. This type burn causes the skin to blister and become extremely red and sore. Some blisters pop open, giving the burn a wet or weeping appearance. Over time, thick, soft, scab-like tissue called fibrinous exudate may develop over the wound. Some second-degree burns take longer than three weeks to heal, but most heal within two to three weeks without scarring, but often with pigment changes to the skin.

Excluding fourth-degree burns, third-degree burns are the most severe. They cause the most damage, extending through every layer of skin. There is a misconception that third-degree burns are the most painful. However, with this type of burn the damage is so extensive that there may not be any pain because of nerve damage. Depending on the cause, the symptoms third-degree burns can exhibit include waxy and white color, char, dark brown color, raised and leathery texture, blisters that do not develop. Without surgery, these wounds heal with severe scarring and contracture. There is no set timeline for complete spontaneous healing for third-degree burns.

Risk factors implicated in the development of burns are infection, age, existing comorbidities and conditions, diabetic neuropathy, peripheral vascular disease, cigarette smoking, excessive alcohol consumption, physical and mental illness, poor glycemic control, diabetic nephropathy, and ischemia of small and large blood vessels.

The personalized treatment parameters for burn wounds when focused acoustic pressure shock waves 40 or radial acoustic pressure waves 41 or planar acoustic pressure waves 42 or cylindrical acoustic pressure waves 44 are used can be determined using different factors. FIGS. 12A-12D present a preferable algorithm that can be used to adjust the number of focused acoustic pressure shock waves 40 or radial acoustic pressure waves 41 or planar acoustic pressure waves 42 or cylindrical acoustic pressure waves 44 used for the treatment of burn wounds based on different elements that take into account the characteristics of the burn wound, patient's comorbidities and lifestyle.

As a starting point for burn wounds algorithm is the basic/initial number of focused acoustic pressure shock waves 40 or radial acoustic pressure waves 41 or planar acoustic pressure waves 42 or cylindrical acoustic pressure waves 44 that are minimally needed for successful treatment of the tissue condition 19. As presented before, this is considered the basic/initial dosage that is calculated after tissue condition 19 area and/or volume were determined.

Figure 12A:
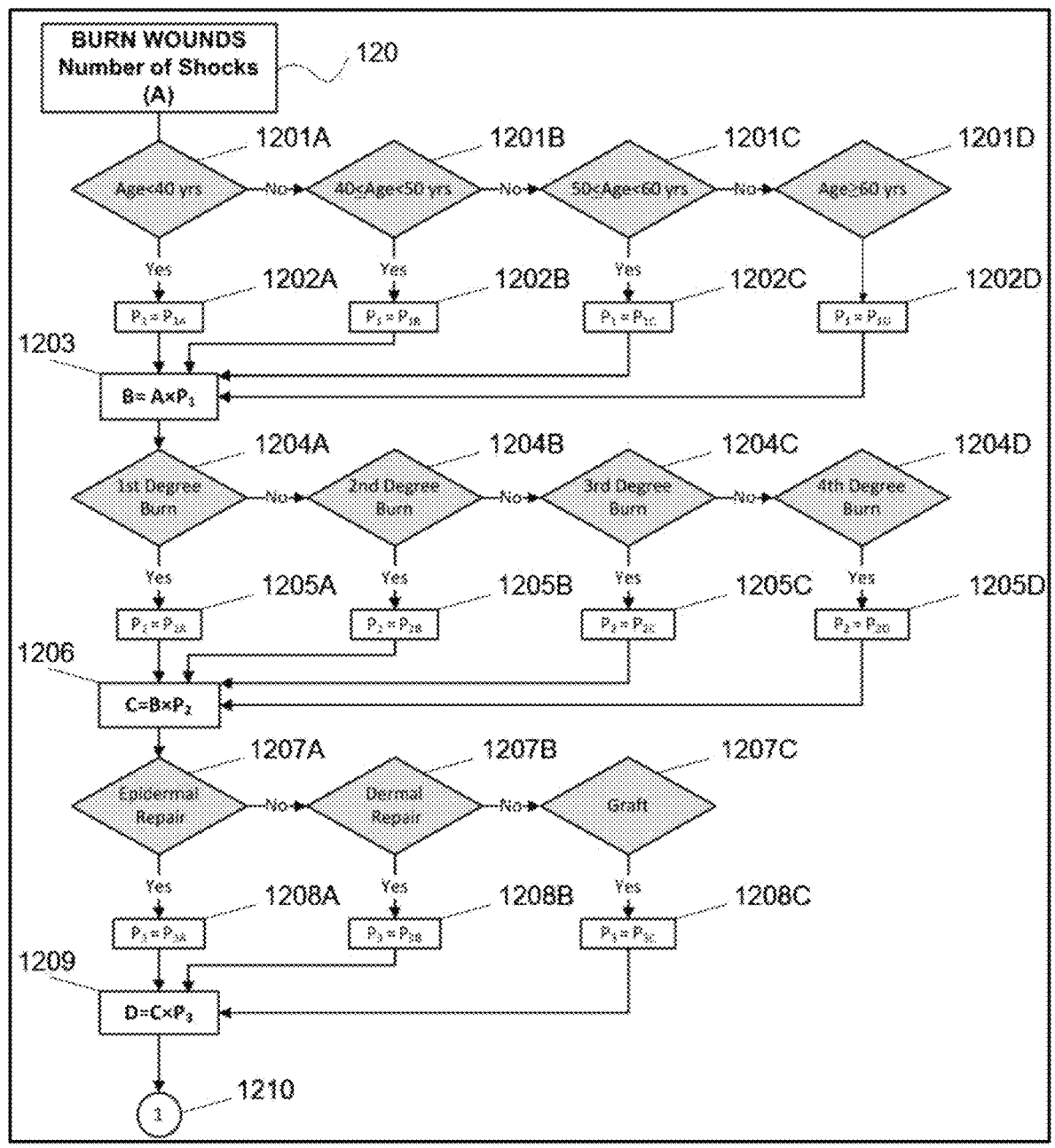
FIG. 12A is a flow diagram of the algorithm used to calculate the number of acoustic pressure shock waves for treatment of burns when patient age, degree of burn, and type of repair treatment approach are taken into account, according to one embodiment of the present invention.

In FIG. 12A the basic/initial number of shocks for burn wounds 120 represents the starting point of the adjustment/optimization algorithm for number of focused acoustic pressure shock waves 40 or radial acoustic pressure waves 41 or planar acoustic pressure waves 42 or cylindrical acoustic pressure waves 44 for the treatment of burn wounds. The first element used to alter the basic/initial dosage used for burn wounds treatment is the inquiry regarding the age of the patient. Thus on the control console/unit display 2220, or artificial intelligence (A/I) device display 2740, or on the display of an interconnected device (see FIG. 2A for the medical treatment system 2000) as a desktop computer 28A, or a smart phone 28B, and/or tablet 28C, and/or laptop 28D is first displayed the inquiry for age less than 40 years 1201A. If the answer is "Yes" then the age modifying coefficient $P_{1A}$ 1202A will be used ($P_1=P_{1A}$). If the answer is "No", the inquiry for age between 40 and 50 years 1201B is displayed. If the answer is "Yes" then the age modifying coefficient $P_{1B}$ 1202B will be used ($P_1=P_{1B}$). If the answer is "No", the inquiry for age between 50 and 60 years 1201C is displayed. If the answer is "Yes" then the age modifying coefficient $P_{1C}$ 1202C will be used ($P_1=P_{1C}$). If the answer is "No", the inquiry for age older than 60 years 1201D is displayed and if the answer is "Yes" then the age modifying coefficient $P_{1D}$ 1202D will be used ($P_1=P_{1D}$). Then the basic/initial number of shocks "A" is altered with the determined age modifying coefficient "$P_1$", and thus the new number of shocks becomes "B", which is now the updated number of shocks based on age 1203.

The questionnaire from FIG. 12A continues with the inquiry on the degree of burn. Thus the inquiry for first degree burn 1204A is displayed. If the answer is "Yes" then the degree of burn modifying coefficient $P_{2A}$ 1205A will be used ($P_2=P_{2A}$). If the answer is "No", the inquiry for second degree burn 1204B is displayed. If the answer is "Yes" then the degree of burn modifying coefficient $P_{2B}$ 1205B will be used ($P_2=P_{2B}$). If the answer is "No", the inquiry for third degree burn 1204C is displayed. If the answer is "Yes" then the degree of burn modifying coefficient $P_{2C}$ 1205C will be used ($P_2=P_{2C}$). If the answer is "No", the inquiry for fourth degree burn 1204D is displayed and if the answer is "Yes" then the degree of burn modifying coefficient $P_{2D}$ 1205D will be used ($P_2=P_{2D}$). Then the number of shocks "B" is altered with the determined degree of burn modifying coefficient "$P_2$", and thus the new number of shocks becomes "C", which is now the updated number of shocks based on degree of burn 1206.

The questionnaire from FIG. 12A continues with the inquiry on the tissue repair needed after burn injury. Thus the inquiry for epidermal repair needed 1207A is displayed. If the answer is "Yes" then the extend of tissue repair modifying coefficient $P_{3A}$ 1208A will be used ($P_3=P_{3A}$). If the answer is "No", the inquiry for dermal repair needed 1207B is displayed. If the answer is "Yes" then the extend of tissue repair modifying coefficient $P_{3B}$ 1208B will be used ($P_3=P_{3B}$). If the answer is "No", the inquiry for graft needed 1207C is displayed. If the answer is "Yes" then the extend of tissue repair modifying coefficient $P_{3C}$ 1208C will be used ($P_3=P_{3C}$). Then the number of shocks "C" is altered with the determined tissue repair modifying coefficient "$P_3$", and thus the new number of shocks becomes "D", which is now the updated number of shocks based on tissue repair needed 1206.

Figure 12B:
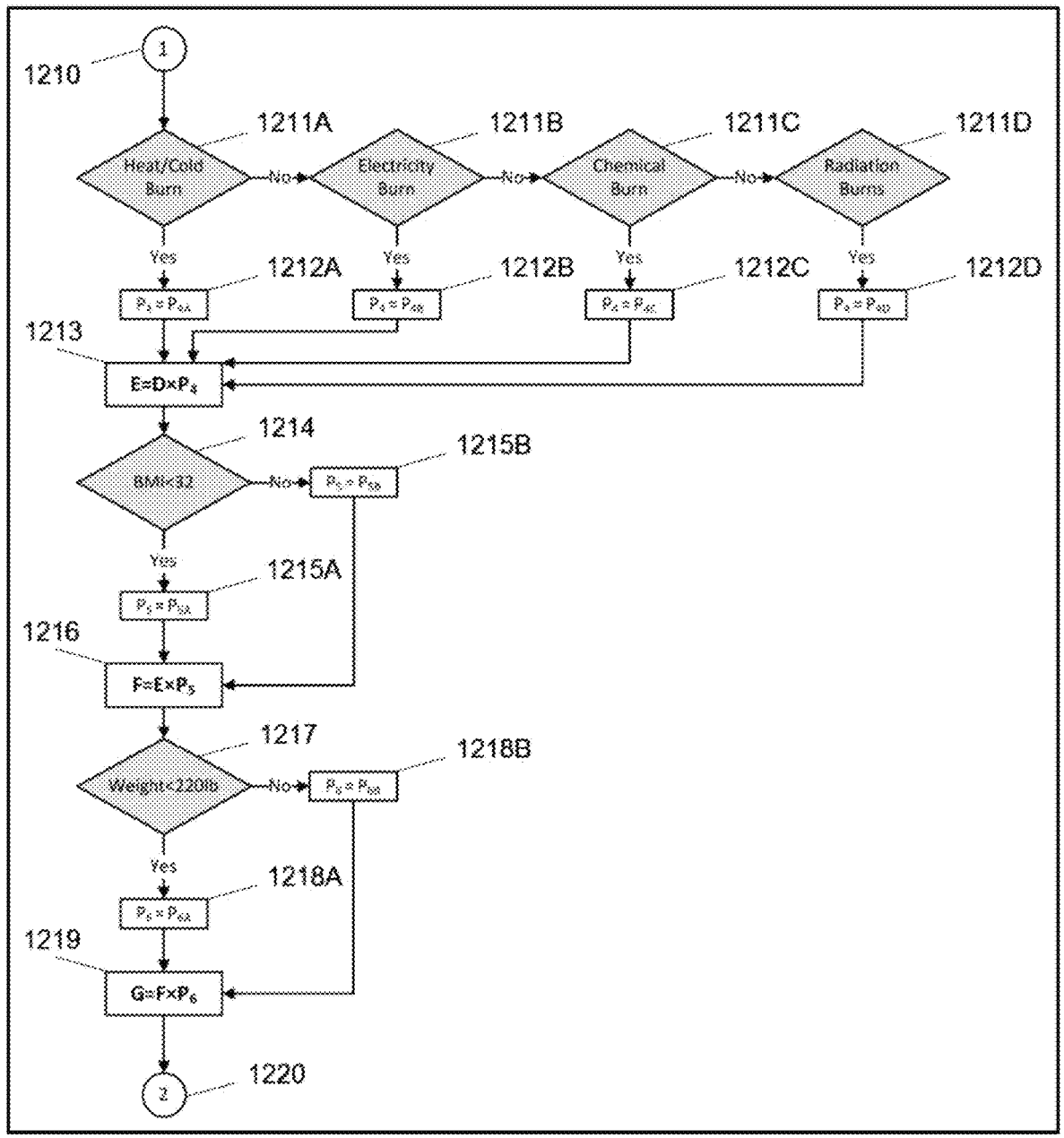
FIG. 12B is a flow diagram of the continuation of the algorithm presented in FIG. 12A used to calculate the number of acoustic pressure shock waves for treatment of burns, when type of burn, body mass index (BMI), and patient weight are taken into account, according to one embodiment of the present invention.

The optimization continues on FIG. 12B and the continuation of the questionnaire flowchart from FIG. 12A to FIG. 12B is realized by the FIG. 12A to FIG. 12B connector 1210, which is seen on both FIG. 12A and FIG. 12B.

The questionnaire from FIG. 12B starts with the inquiry on the cause of burn. Thus the inquiry for heat/cold burn 1211A is displayed. If the answer is "Yes" then the cause of burn modifying coefficient $P_{4A}$ 1212A will be used ($P_4=P_{4A}$). If the answer is "No", the inquiry for electricity burn 1211B is displayed. If the answer is "Yes" then the cause of burn modifying coefficient $P_{4B}$ 1212B will be used ($P_4=P_{4B}$). If the answer is "No", the inquiry for chemical burn 1211C is displayed. If the answer is "Yes" then the cause of burn modifying coefficient $P_{4C}$ 1212C will be used ($P_4=P_{4C}$). If the answer is "No", the inquiry for radiation burn 1211D is displayed and if the answer is "Yes" then the cause of burn modifying coefficient $P_{4D}$ 1212D will be used ($P_4=P_{4D}$). Then the number of shocks "D" is altered with the determined cause of burn modifying coefficient "$P_4$", and thus the new number of shocks becomes "E", which is now the updated number of shocks based on cause of burn 1213.

The questionnaire from FIG. 12B continues with the inquiry on the body mass index (BMI). Thus the inquiry for body mass index (BMI) value 1214 is displayed (BMI<32). If the answer is "Yes" then the body mass index (BMI) modifying coefficient $P_{5A}$ 1215A will be used ($P_5=P_{5A}$). If the answer is "No" then the body mass index (BMI) modifying coefficient $P_{5B}$ 1215B will be used ($P_5=P_{5B}$). Then the number of shocks "E" is altered with the determined body mass index (BMI) modifying coefficient "$P_5$", and thus the new number of shocks becomes "F", which is now the updated number of shocks based on obesity 1216.

The questionnaire from FIG. 12B continues with the inquiry on the patient's weight. Thus the inquiry for weight value 1217 is displayed (Weight<220 lb which is 99.8 Kg in metric system). If the answer is "Yes" then the weight modifying coefficient $P_{6A}$ 1218A will be used ($P_6=P_{6A}$). If the answer is "No" then the weight modifying coefficient $P_{6B}$ 1218B will be used ($P_6=P_{6B}$). Then the number of shocks "F" is altered with the determined weight modifying coefficient "$P_6$", and thus the new number of shocks becomes "G", which is now the updated number of shocks based on weight 1219.

Figure 12C:
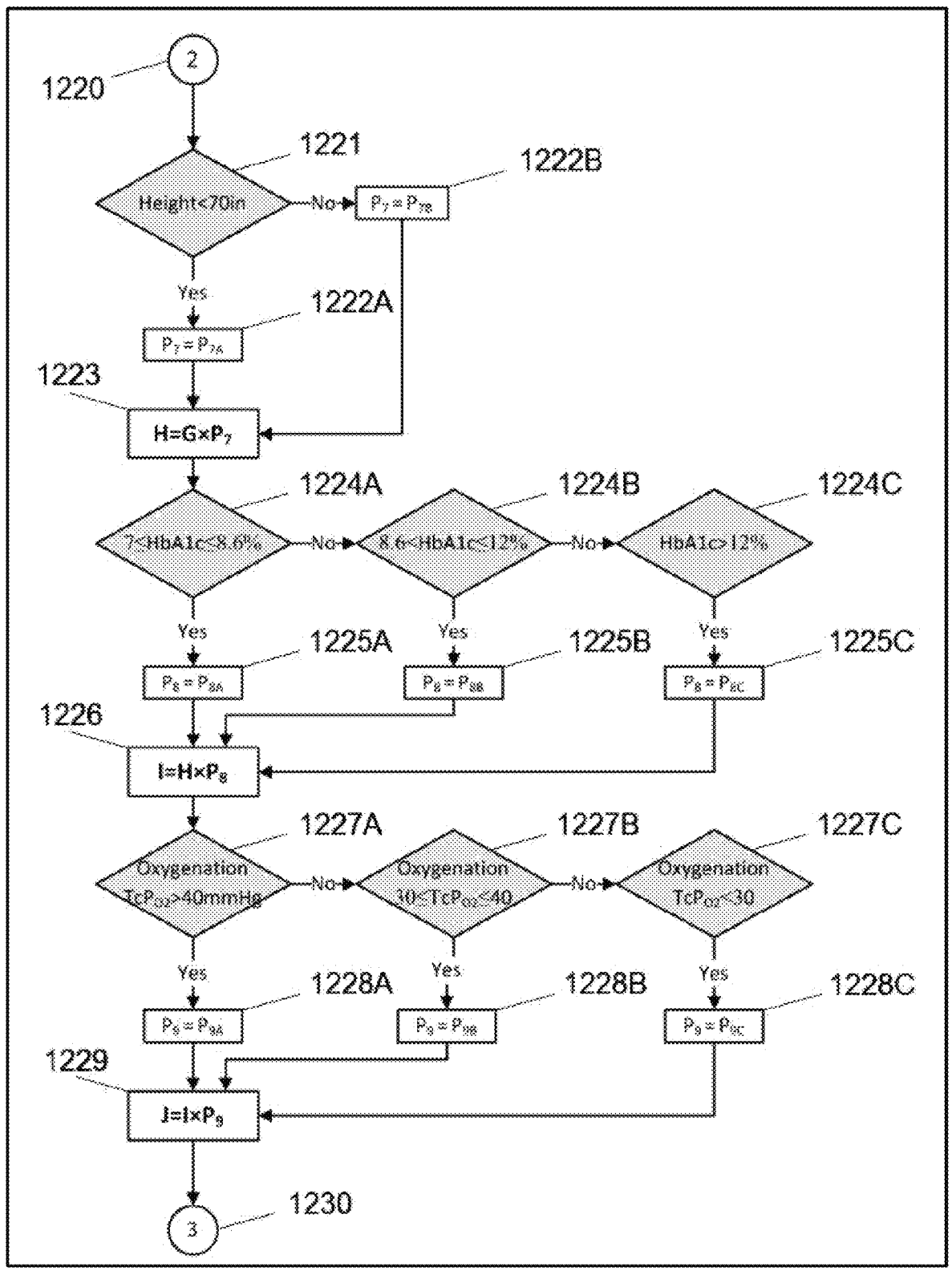
FIG. 12C is a flow diagram of the continuation of the algorithm presented in FIG. 12A and FIG. 12B used to calculate the number of acoustic pressure shock waves for treatment of burns, when patient height, glycosylated hemoglobin A1c (HbA1c), and arterial wound oxygenation ($T_cP_{O2}$—Transcutaneous Partial Pressure of Oxygen) are taken into account, according to one embodiment of the present invention.

The optimization continues on FIG. 12C and the continuation of the questionnaire flowchart from FIG. 12B to FIG. 12C is realized by the FIG. 12B to FIG. 12C connector 1220, which is seen on both FIG. 12B and FIG. 12C.

The questionnaire from FIG. 12C starts with the inquiry on the patient's height. Thus the inquiry for inquiry for height value 1221 is displayed (Height<70 in which is 177.8 cm in metric system). If the answer is "Yes" then the height modifying coefficient $P_{7A}$ 1222A will be used ($P_7=P_{7A}$). If the answer is "No" then the height modifying coefficient $P_{7B}$ 1222B will be used ($P_7=P_{7B}$). Then the number of shocks "G" is altered with the determined height modifying coefficient "$P_7$", and thus the new number of shocks becomes "H", which is now the updated number of shocks based on height 1223.

The questionnaire from FIG. 12C continues with the inquiry on the value for glycated hemoglobin (HbA1c), which is an indication of diabetes presence. Thus the inquiry for glycated hemoglobin (HbA1c) between 7 and 8.6% 1224A is displayed. If the answer is "Yes" then the HbA1c modifying coefficient $P_{8A}$ 1225A will be used ($P_8=P_{8A}$). If the answer is "No", the inquiry for glycated hemoglobin (HbA1c) between 8.6 and 12% 1224B is displayed. If the answer is "Yes" then the HbA1c modifying coefficient $P_{8B}$ 1225B will be used ($P_8=P_{8B}$). If the answer is "No", the inquiry for glycated hemoglobin (HbA1c) larger than 12% 1224C is displayed. If the answer is "Yes" then the HbA1c modifying coefficient $P_{8C}$ 1225C will be used ($P_8=P_{8C}$). Then the number of shocks "H" is altered with the determined HbA1c modifying coefficient "$P_8$", and thus the new number of shocks becomes "I", which is now the updated number of shocks based on diabetes presence 1226.

The questionnaire from FIG. 12C continues with the inquiry on transcutaneous monitoring of oxygen ($T_cP_{O2}$), which is an indication on oxygenation of the wound. Thus the inquiry for transcutaneous monitoring of oxygen (TcP$_{O2}$) greater than 40 mmHg 1227A is displayed. If the answer is "Yes" then the TcP$_{O2}$ modifying coefficient $P_{9A}$ 1228A will be used ($P_9=P_{9A}$). If the answer is "No", the inquiry for transcutaneous monitoring of oxygen (TcP$_{O2}$) between 30 and 40 mmHg 1227B is displayed. If the answer is "Yes" then the TcP$_{O2}$ modifying coefficient $P_{9B}$ 1228B will be used ($P_9=P_{9B}$). If the answer is "No", the inquiry for transcutaneous monitoring of oxygen (TcP$_{O2}$) less than 30 mmHg 1227C is displayed. If the answer is "Yes" then the TcP$_{O2}$ modifying coefficient $P_{9C}$ 1228C will be used ($P_9=P_{9C}$). Then the number of shocks "I" is altered with the determined transcutaneous monitoring of oxygen (TcP$_{O2}$) modifying coefficient "$P_9$", and thus the new number of shocks becomes "J", which is now the updated number of shocks based on tissue oxygenation 1229.

Figure 12D:
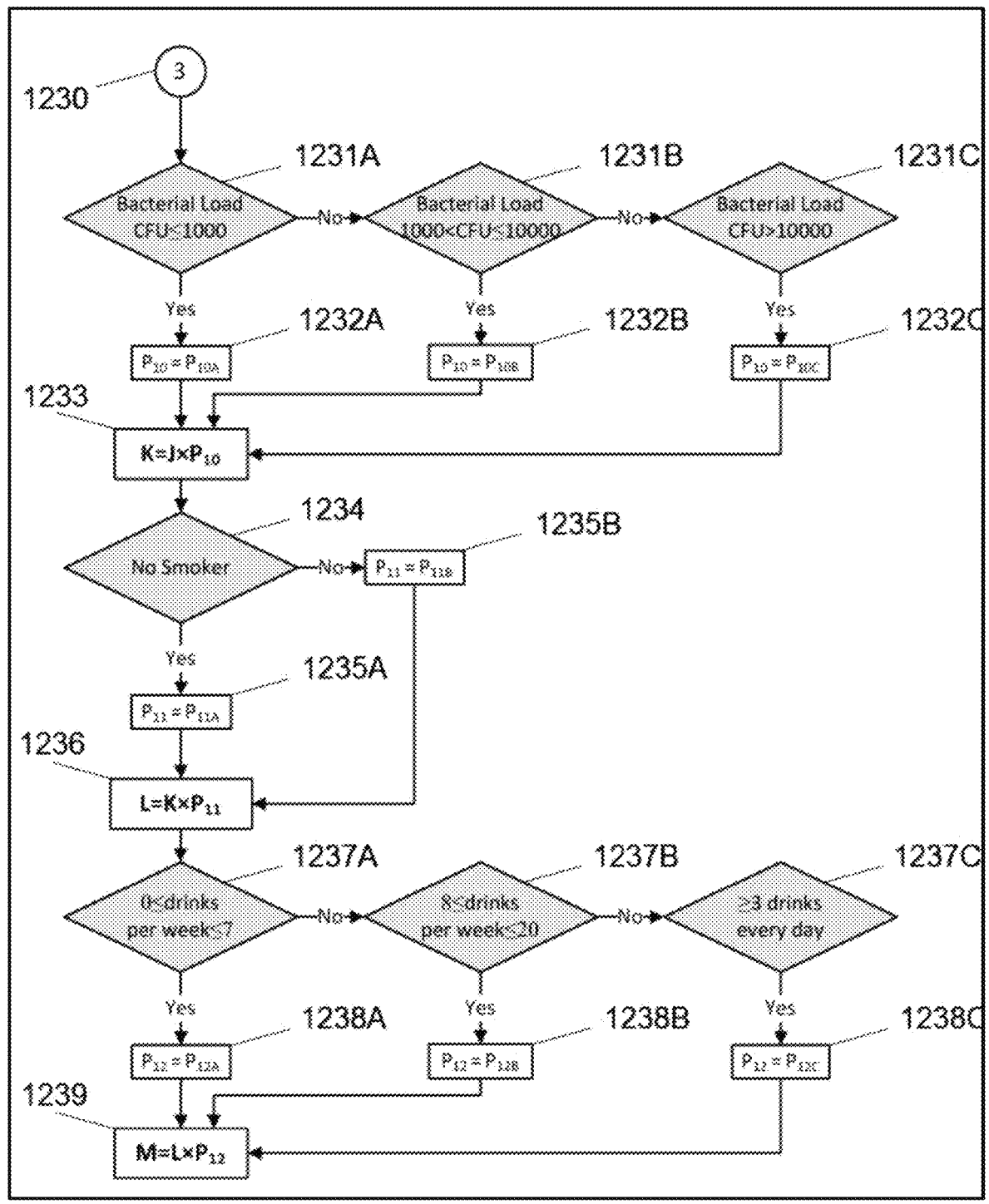
FIG. 12D is a flow diagram of the continuation of the algorithm presented in FIG. 12A, FIG. 12B, and FIG. 12C used to calculate the number of acoustic pressure shock waves for treatment of burns, when burn bacterial load, smoker status, and alcohol consumption rate are taken into account, according to one embodiment of the present invention.

The optimization continues on FIG. 12D and the continuation of the questionnaire flowchart from FIG. 12C to FIG. 12D is realized by the FIG. 12C to FIG. 12D connector 1230, which is seen on both FIG. 12C and FIG. 12D.

The questionnaire from FIG. 12D starts with the inquiry on bacterial colony forming units (CFU), which is an indication of bacterial load of the wound. Thus the inquiry for bacterial colony forming units (CFU) less than 1000 units 1231A is displayed. If the answer is "Yes" then the CFU modifying coefficient $P_{10A}$ 1232A will be used ($P_{10}=P_{10A}$). If the answer is "No", the inquiry for bacterial colony forming units (CFU) between 1000 and 10000 units 1231B is displayed. If the answer is "Yes" then the CFU modifying coefficient $P_{10B}$ 1232B will be used ($P_{10}=P_{10B}$). If the answer is "No", the inquiry for bacterial colony forming units (CFU) greater than 10000 units 1231C is displayed. If the answer is "Yes" then the CFU modifying coefficient $P_{10C}$ 1232C will be used ($P_{10}=P_{10C}$). Then the number of shocks "J" is altered with the determined CFU modifying coefficient "$P_{10}$", and thus the new number of shocks becomes "K", which is now the updated number of shocks based on bacterial load 1233.

The questionnaire from FIG. 12D continues with the inquiry on smoking status. Thus the inquiry for smoking status 1234 is displayed. If the answer is "Yes" then the smoking status modifying coefficient $P_{11A}$ 1235A will be used ($P_{11}=P_{11A}$). If the answer is "No" then the smoking status modifying coefficient $P_{11B}$ 1235B will be used ($P_{11}=P_{11B}$). Then the number of shocks "K" is altered with the determined smoking status modifying coefficient "$P_{11}$", and thus the new number of shocks becomes "L", which is now the updated number of shocks based on smoking status 1236.

The questionnaire from FIG. 12D continues with the inquiry on drinking habit, which is indicated by the number of drinks over a certain period of time. Thus the inquiry for drinks less than 7 per week 1237A is displayed. If the answer is "Yes" then the drinking habit modifying coefficient $P_{12A}$ 1238A will be used ($P_{12}=P_{12A}$). If the answer is "No", the inquiry for drinks between 8 and 20 per week 1237B is displayed. If the answer is "Yes" then the drinking habit modifying coefficient $P_{12B}$ 1238B will be used ($P_{12}=P_{12B}$). If the answer is "No", the inquiry for drinks greater than 3 every day 1237C is displayed. If the answer is "Yes" then the drinking habit modifying coefficient $P_{12C}$ 1238C will be used ($P_{12}=P_{12C}$). Then the number of shocks "L" is altered with the determined drinking habit modifying coefficient "$P_{12}$", and thus the new number of shocks becomes "M", which is now the updated number of shocks based on drinking habit 1239.

Coefficients presented for burn wounds inquiries for patient's comorbidities and habits and wound status from FIGS. 12A-12D are defined with general ranges and also with more preferable ranges and sometimes as a specific number.

In FIGS. 12A-12D the values for the coefficients are preferably as follows:

In FIG. 12A, coefficient $P_{1A}$ is preferably 1.00, because patients with age under 40 should have a very good response to the acoustic pressure shock wave treatment.

In FIG. 12A, coefficient $P_{1B}$ may be in the range from about 1.01 to 1.04, and preferably from about 1.02 to 1.04.

In FIG. 12A, coefficient $P_{1C}$ may be in the range from about 1.01 to 1.05, and preferably from about 1.03 to 1.05.

In FIG. 12A, coefficient $P_{1D}$ may be in the range from about 1.01 to 1.06, and preferably from about 1.04 to 1.06.

In FIG. 12A, coefficient $P_{2A}$ may be in the range from about 1.00 to 1.03, and preferably from about 1.02 to 1.03.

In FIG. 12A, coefficient $P_{2B}$ may be in the range from about 1.01 to 1.04, and preferably from about 1.03 to 1.04.

In FIG. 12A, coefficient $P_{2C}$ may be in the range from about 1.02 to 1.06, and preferably from about 1.03 to 1.06.

In FIG. 12A, coefficient $P_{2D}$ may be in the range from about 1.03 to 1.08, and preferably from about 1.05 to 1.08.

In FIG. 12A, coefficient $P_{3A}$ may be in the range from about 1.00 to 1.02, and preferably from about 1.01 to 1.02.

In FIG. 12A, coefficient $P_{3B}$ may be in the range from about 1.01 to 1.04, and preferably from about 1.03 to 1.04.

In FIG. 12A, coefficient $P_{3C}$ may be in the range from about 1.02 to 1.08, and preferably from about 1.05 to 1.08.

In FIG. 12B, coefficient $P_{4A}$ may be in the range from about 1.00 to 1.04, and preferably from about 1.01 to 1.04.

In FIG. 12B, coefficient $P_{4B}$ may be in the range from about 1.01 to 1.04, and preferably from about 1.02 to 1.04.

In FIG. 12B, coefficient $P_{4C}$ may be in the range from about 1.02 to 1.05, and preferably from about 1.03 to 1.05.

In FIG. 12B, coefficient $P_{4D}$ may be in the range from about 1.03 to 1.08, and preferably from about 1.05 to 1.08.

In FIG. 12B, coefficient $P_{5A}$ is preferably 1.00, because patients with a body mass index (BMI) below 32 should have a very good response to the acoustic pressure shock wave treatment and do not present any challenges from obesity point of view.

In FIG. 12B, coefficient $P_{5B}$ may be in the range from about 1.02 to 1.07, and preferably from about 1.03 to 1.06.

In FIG. 12B coefficient $P_{6A}$ is preferably 1.00, because patients with a weight below 220 lb/99.8 Kg should have a very good response to the acoustic pressure shock wave treatment and do not present any challenges from obesity point of view.

In FIG. 12B, coefficient $P_{6B}$ may be in the range from about 1.01 to 1.04, and preferably from about 1.02 to 1.04.

In FIG. 12C coefficient $P_{7A}$ is preferably 1.00 for a height below 70 in/177.8 cm.

In FIG. 12C, coefficient $P_{7B}$ may be in the range from about 1.00 to 1.02, and preferably from about 1.01 to 1.02.

In FIG. 12C, coefficient $P_{8A}$ is preferably 1.00, because patients with a HbA1c are controlling their diabetes and should have a very good response to the acoustic pressure shock wave treatment.

In FIG. 12C, coefficient $P_{8B}$ may be in the range from about 1.01 to 1.04, and preferably from about 1.02 to 1.03.

In FIG. 12C, coefficient $P_{8C}$ may be in the range from about 1.02 to 1.06, and preferably from about 1.03 to 1.06.

In FIG. 12C, coefficient $P_{9A}$ is preferably 1.00, because patients with a TcP$_{O2}$ value greater than 40 mmHg is normal and the patients should have a very good response to the acoustic pressure shock wave treatment.

In FIG. 12C, coefficient $P_{9B}$ may be in the range from about 1.01 to 1.05, and preferably from about 1.02 to 1.05.

In FIG. 12C, coefficient $P_{9C}$ may be in the range from about 1.02 to 1.07, and preferably from about 1.04 to 1.06.

In FIG. 12D, coefficient $P_{10A}$ may be in the range from about 1.01 to 1.03, and preferably from about 1.02 to 1.03.

In FIG. 12D, coefficient $P_{10B}$ may be in the range from about 1.01 to 1.06, and preferably from about 1.03 to 1.05.

In FIG. 12D, coefficient $P_{10C}$ may be in the range from about 1.04 to 1.10, and preferably from about 1.05 to 1.09.

In FIG. 12D coefficient $P_{11A}$ is preferably 1.00 because a non-smoker should have a very good response to the acoustic pressure shock wave treatment.

In FIG. 12D, coefficient $P_{11B}$ may be in the range from about 1.00 to 1.04, and preferably from about 1.02 to 1.04.

In FIG. 12D, coefficient $P_{12A}$ is preferably 1.00, because occasional drinking patients should have a very good response to the acoustic pressure shock wave treatment.

In FIG. 12D, coefficient $P_{12B}$ may be in the range from about 1.01 to 1.04, and preferably from about 1.02 to 1.03.

In FIG. 12D, coefficient $P_{12C}$ may be in the range from about 1.02 to 1.06, and preferably from about 1.04 to 1.06.

A control console/unit 22 and associated acoustic pressure shock wave applicator/treatment apparatus 10 (see FIG. 2A) used for delivering a treatment for burn wounds by means of the proposed adjustment algorithm from FIGS. 12A-12D will use the following formula (where "A" is the initial number of focused acoustic pressure shock waves 40 or radial acoustic pressure waves 41 or planar acoustic pressure waves 42 or cylindrical acoustic pressure waves 44 delivered per treatment and "ATN" is the Adjusted Total Number of focused acoustic pressure shock waves 40 or radial acoustic pressure waves 41 or planar acoustic pressure waves 42 or cylindrical acoustic pressure waves 44 delivered per treatment):

$$ATN = A \cdot P_1 \cdot P_2 \cdot P_3 \cdot P_4 \cdot P_5 \cdot P_6 \cdot P_7 \cdot P_8 \cdot P_9 \cdot P_{10} \cdot P_{11} \cdot P_{12}.$$

For the largest values for these coefficients (worst situation) and for example a number of A=500 is used as initial number of focused acoustic pressure shock waves 40 or radial acoustic pressure waves 41 or planar acoustic pressure waves 42 or cylindrical acoustic pressure waves 44 that are minimally needed for successful treatment of the tissue condition 19, then the Adjusted Total Number (ATN) value of focused acoustic pressure shock waves 40 or radial acoustic pressure waves 41 or planar acoustic pressure waves 42 or cylindrical acoustic pressure waves 44 delivered per treatment is the following:

$$ATN = 500 \cdot 1.06 \cdot 1.08 \cdot 1.08 \cdot 1.08 \cdot 1.07 \cdot 1.04 \cdot 1.02 \cdot 1.06 \cdot 1.07 \cdot 1.10 \cdot 1.04 \cdot 1.06 = 1042.29 \approx 1042 \text{ shock waves or pressure waves.}$$

Using similar set of questions regarding the patient's comorbidities, existing therapies, and lifestyle, an algorithm can be also developed for adjusting the number of treatments that use focused acoustic pressure shock waves 40 or radial acoustic pressure waves 41 or planar acoustic pressure waves 42 or cylindrical acoustic pressure waves 44 for the successful treatment of tissue condition 19.

The personalized number of treatments for diabetic foot ulcers (DFUs), arterial ulcers, or venous ulcers when focused acoustic pressure shock waves 40 or radial acoustic pressure waves 41 or planar acoustic pressure waves 42 or cylindrical acoustic pressure waves 44 are used can be determined using different factors. FIGS. 13A-13G present a preferable algorithm that can be used to adjust the number of treatments used for diabetic foot ulcers (DFUs), arterial ulcers, or venous ulcers based on different elements that take into account the characteristics/status of the diabetic foot ulcers (DFUs), arterial ulcers, or venous ulcers, and patient's comorbidities, existing therapies, and habits/lifestyle.

As a starting point for the algorithm used to personalize/adjust the number of treatments using focused acoustic pressure shock waves 40 or radial acoustic pressure waves 41 or planar acoustic pressure waves 42 or cylindrical acoustic pressure waves 44 for diabetic foot ulcers (DFUs), arterial ulcers, or venous ulcers is the basic/initial number of treatments that are minimally needed for successful treatment of the tissue condition 19.

Figure 13A:
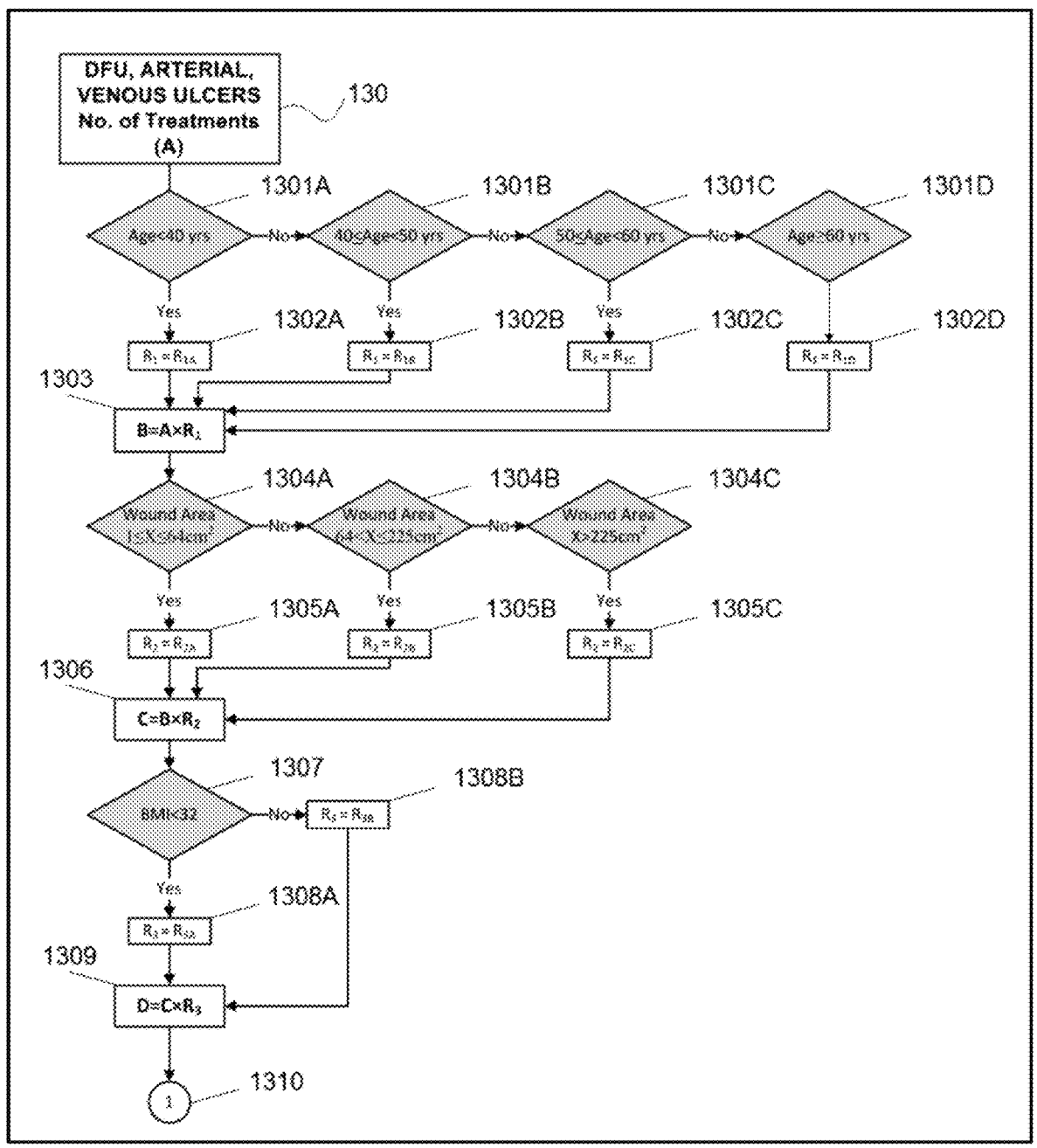
FIG. 13A is a flow diagram of the algorithm used to calculate the number of treatments with acoustic pressure shock waves for diabetic foot ulcers (DFUs), arterial ulcers, or venous ulcers when patient age, wound area, and body mass index (BMI) are taken into account, according to one embodiment of the present invention.

In FIG. 13A the basic/initial number of treatments for diabetic foot ulcers (DFUs), arterial ulcers, or venous ulcers 130 represents the starting point of the adjustment/optimization algorithm for number of treatments using focused acoustic pressure shock waves 40 or radial acoustic pressure waves 41 or planar acoustic pressure waves 42 or cylindrical acoustic pressure waves 44 for the treatment of diabetic foot ulcers (DFUs), arterial ulcers, or venous ulcers. The first element used to alter the basic/initial number of treatments used for diabetic foot ulcers (DFUs), arterial ulcers, or venous ulcers treatment is the inquiry regarding the age of the patient. Thus on the control console/unit display 2220, or artificial intelligence (A/I) device display 2740, or on the display of an interconnected device (see FIG. 2A for the medical treatment system 2000) as a desktop computer 28A, or a smart phone 28B, and/or tablet 28C, and/or laptop 28D is first displayed the inquiry for age less than 40 years 1301A. If the answer is "Yes" then the age modifying coefficient $R_{1A}$ 1302A will be used ($R_1=R_{1A}$). If the answer is "No", the inquiry for age between 40 and 50 years 1301B is displayed. If the answer is "Yes" then the age modifying coefficient $R_{1B}$ 1302B will be used ($R_1=R_{1B}$). If the answer is "No", the inquiry for age between 50 and 60 years 1301C is displayed. If the answer is "Yes" then the age modifying coefficient $R_{1C}$ 1302C will be used ($R_1=R_{1C}$). If the answer is "No", the inquiry for age older than 60 years 1301D is displayed and if the answer is "Yes" then the age modifying coefficient $R_{1D}$ 1302D will be used ($R_1=R_{1D}$). Then the basic/initial number of treatments "A" is altered with the determined age modifying coefficient "$R_1$" and thus the new number of treatments becomes "B", which is now the updated number of treatments based on age 1303.

The questionnaire from FIG. 13A continues with the inquiry on the value for wound area. Thus the inquiry for wound area between 1 and 64 cm² 1304A is displayed. If the answer is "Yes" then the wound area modifying coefficient $R_{2A}$ 1305A will be used ($R_2=R_{2A}$). If the answer is "No", the inquiry for wound area between 64 and 225 cm² 1304B is displayed. If the answer is "Yes" then the wound area modifying coefficient $R_{2B}$ 1305B will be used ($R_2=R_{2B}$). If the answer is "No", the inquiry for wound area larger than 225 cm² 1304C is displayed. If the answer is "Yes" then the wound area modifying coefficient $R_{2C}$ 1305C will be used ($R_2=R_{2C}$). Then the number of treatments "B" is altered with the determined value for wound area modifying coefficient "$R_2$" and thus the new number of treatments becomes "C", which is now the updated number of treatments based on wound area 1306.

The questionnaire from FIG. 13A continues with the inquiry on the body mass index (BMI). Thus the inquiry for body mass index (BMI) value 1307 is displayed (BMI<32). If the answer is "Yes" then the body mass index (BMI) modifying coefficient $R_{3A}$ 1308A will be used ($R_3=R_{3A}$). If the answer is "No" then the body mass index (BMI) modifying coefficient $R_{3B}$ 1308B will be used ($R_3=R_{3B}$). Then the number of treatments "C" is altered with the determined body mass index (BMI) modifying coefficient "$R_3$", and thus the new number of treatments becomes "D", which is now the updated number of treatments based on obesity 1309.

Figure 13B:
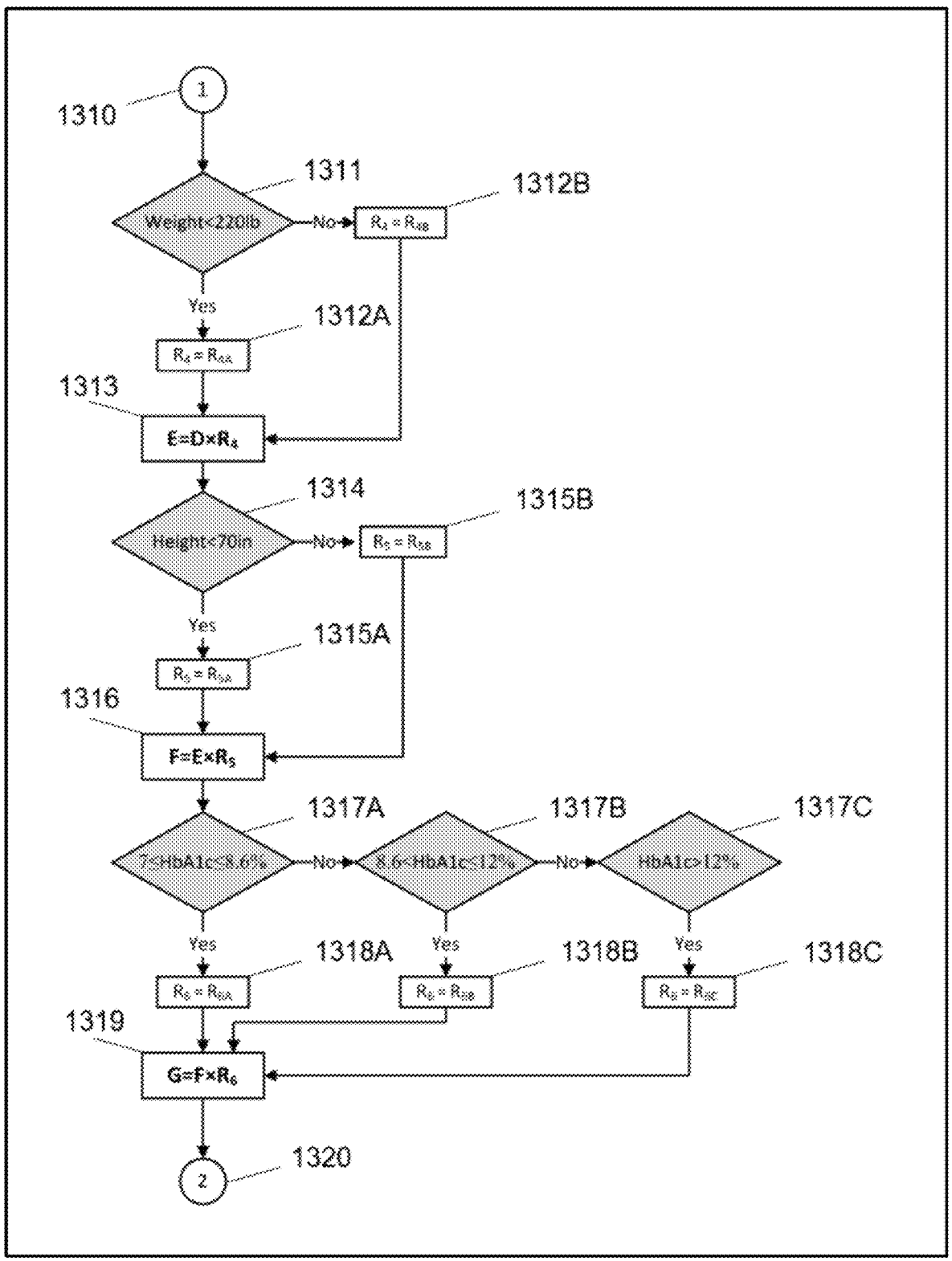
FIG. 13B is a flow diagram of the continuation of the algorithm presented in FIG. 13A used to calculate the number of treatments with acoustic pressure shock waves for diabetic foot ulcers (DFUs), arterial ulcers, or venous ulcers, when patient weight, patient height, and glycosylated hemoglobin A1c (HbA1c) are taken into account, according to one embodiment of the present invention.

The optimization continues on FIG. 13B and the continuation of the questionnaire flowchart from FIG. 13A to FIG. 13B is realized by the FIG. 13A to FIG. 13B connector 1310, which is seen on both FIG. 13A and FIG. 13B.

The questionnaire from FIG. 13B starts with the inquiry on the patient's weight. Thus the inquiry for weight value 1311 is displayed (Weight<220 lb which is 99.8 Kg in metric system). If the answer is "Yes" then the weight modifying coefficient $R_{4A}$ 1312A will be used ($R_4=R_{4A}$). If the answer is "No" then the weight modifying coefficient $R_{4B}$ 1312B will be used ($R_4=R_{4B}$). Then the number of treatments "D" is altered with the determined weight modifying coefficient "$R_4$", and thus the new number of treatments becomes "E", which is now the updated number of treatments based on weight 1313.

The questionnaire from FIG. 13B continues with the inquiry on the patient's height. Thus the inquiry for inquiry for height value 1314 is displayed (Height<70 in which is 177.8 cm in metric system). If the answer is "Yes" then the height modifying coefficient $R_{5A}$ 1315A will be used ($R_5=R_{5A}$). If the answer is "No" then the height modifying coefficient $R_{5B}$ 1315B will be used ($R_5=R_{5B}$). Then the number of treatments "E" is altered with the determined height modifying coefficient "$R_5$", and thus the new number of treatments becomes "F", which is now the updated number of treatments based on height 1316.

The questionnaire from FIG. 13B continues with the inquiry on the value for glycated hemoglobin (HbA1c), which is an indication of diabetes presence. Thus the inquiry for glycated hemoglobin (HbA1c) between 7 and 8.6% 1317A is displayed. If the answer is "Yes" then the HbA1c modifying coefficient $R_{6A}$ 1318A will be used ($R_6=R_{6A}$). If the answer is "No", the inquiry for glycated hemoglobin (HbA1c) between 8.6 and 12% 1317B is displayed. If the answer is "Yes" then the HbA1c modifying coefficient $R_{6B}$ 1318B will be used ($R_6=R_{6B}$). If the answer is "No", the inquiry for glycated hemoglobin (HbA1c) larger than 12% 1317C is displayed. If the answer is "Yes" then the HbA1c modifying coefficient $R_{6C}$ 1318C will be used ($R_6=R_{6C}$). Then the number of treatments "F" is altered with the determined HbA1c modifying coefficient "$R_6$", and thus the new number of treatments becomes "G", which is now the updated number of treatments based on diabetes presence 1319.

Figure 13C:
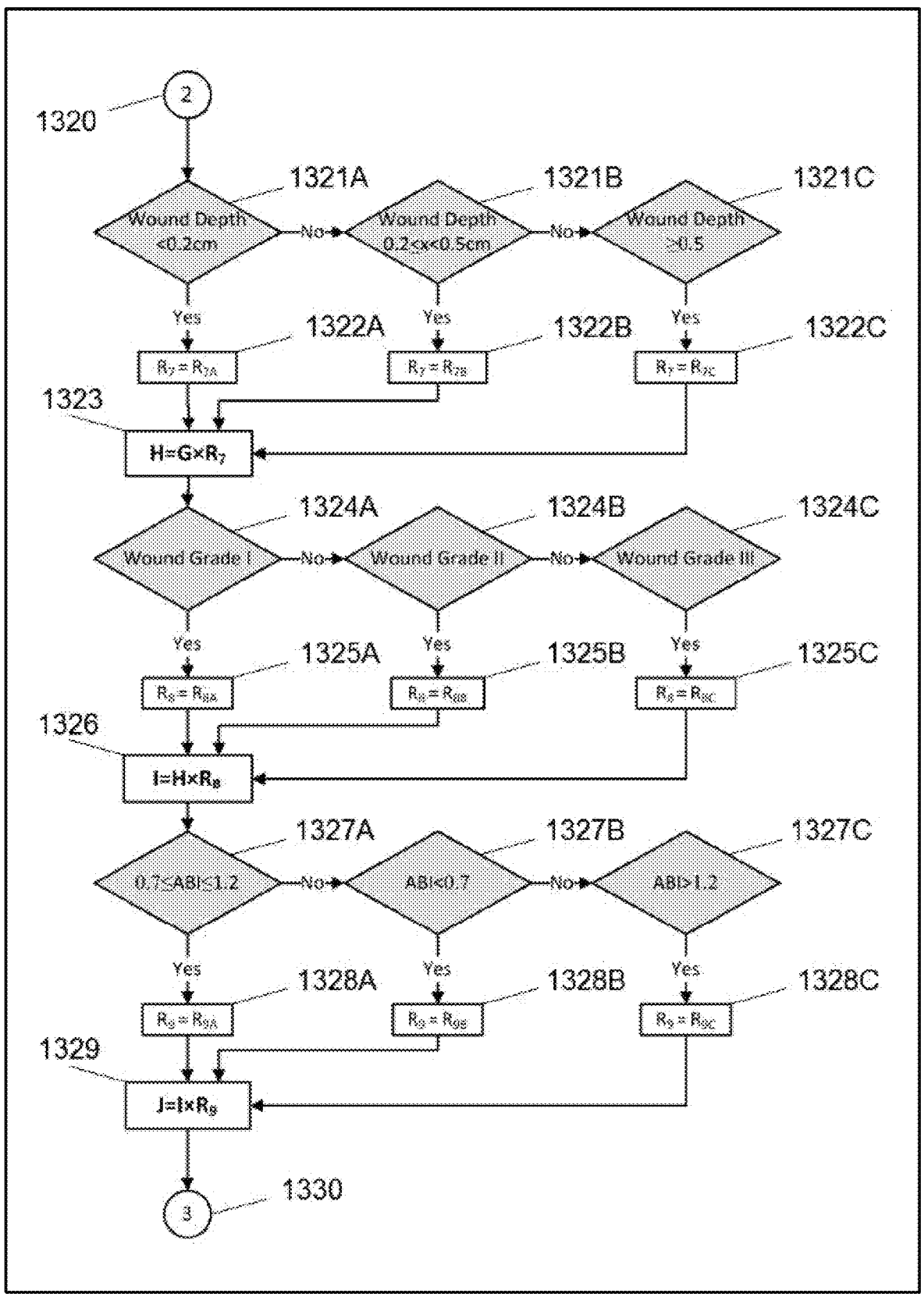
FIG. 13C is a flow diagram of the continuation of the algorithm presented in FIG. 13A and FIG. 13B used to calculate the number of treatments with acoustic pressure shock waves for diabetic foot ulcers (DFUs), arterial ulcers, or venous ulcers, when chronic wound depth, DFU or arterial ulcers grade (not applicable for venous ulcers), and ankle-brachial index (ABI) are taken into account, according to one embodiment of the present invention.

The optimization continues on FIG. 13C and the continuation of the questionnaire flowchart from FIG. 13B to FIG. 13C is realized by the FIG. 13B to FIG. 13C connector 1320, which is seen on both FIG. 13B and FIG. 13C.

The questionnaire from FIG. 13C starts with the inquiry on wound depth. Thus the inquiry for wound depth less than 0.2 cm 1321A is displayed. If the answer is "Yes" then the wound depth modifying coefficient $R_{7A}$ 1322A will be used ($R_7=R_{7A}$). If the answer is "No", the inquiry for wound depth between 0.2 and 0.5 cm 1321B is displayed. If the answer is "Yes" then the wound depth modifying coefficient $R_{7B}$ 1322B will be used ($R_7=R_{7B}$). If the answer is "No", the inquiry for wound depth greater than 0.5 cm 1321C is displayed. If the answer is "Yes" then the wound depth modifying coefficient $R_{7C}$ 1322C will be used ($R_7=R_{7C}$). Then the number of treatments "G" is altered with the determined wound depth modifying coefficient "$N_7$", and thus the new number of treatments becomes "H", which is now the updated number of treatments based on wound depth 1323.

The questionnaire from FIG. 13C continues with the inquiry on wound grade. Thus the inquiry for wound grade I 1324A is displayed. If the answer is "Yes" then the wound grade modifying coefficient $R_{8A}$ 1325A will be used ($R_8=R_{8A}$). If the answer is "No", the inquiry for wound grade II 1324B is displayed. If the answer is "Yes" then the wound grade modifying coefficient $R_{8B}$ 1325B will be used ($R_8=R_{8B}$). If the answer is "No", the inquiry for wound grade III 1324C is displayed. If the answer is "Yes" then the wound grade modifying coefficient $R_{8C}$ 1325C will be used ($R_8=R_{8C}$). Then the number of treatments "H" is altered with the determined wound grade modifying coefficient "$R_8$", and thus the new number of treatments becomes "I", which is now the updated number of treatments based on wound grade 1326.

The questionnaire from FIG. 13C continues with the inquiry on ankle-brachial index (ABI), which is an indication on peripheral arterial disease. Thus the inquiry for ankle-brachial index (ABI) between 0.7 and 1.2 1327A is displayed. If the answer is "Yes" then the ABI modifying coefficient $R_{9A}$ 1328A will be used ($R_9=R_{9A}$). If the answer is "No", the inquiry for ankle-brachial index (ABI) less than 0.7 1327B is displayed. If the answer is "Yes" then the ABI modifying coefficient $R_{9B}$ 1328B will be used ($R_9=R_{9B}$). If the answer is "No", the inquiry for ankle-brachial index (ABI) greater than 1.2 1327C is displayed. If the answer is "Yes" then the ABI modifying coefficient $N_{9C}$ 1328C will be used ($R_9=R_{9C}$). Then the number of treatments "I" is altered with the determined ABI modifying coefficient "$R_9$", and thus the new number of treatments becomes "J", which is now the updated number of treatments based on peripheral arterial disease 1329.

Figure 13D:
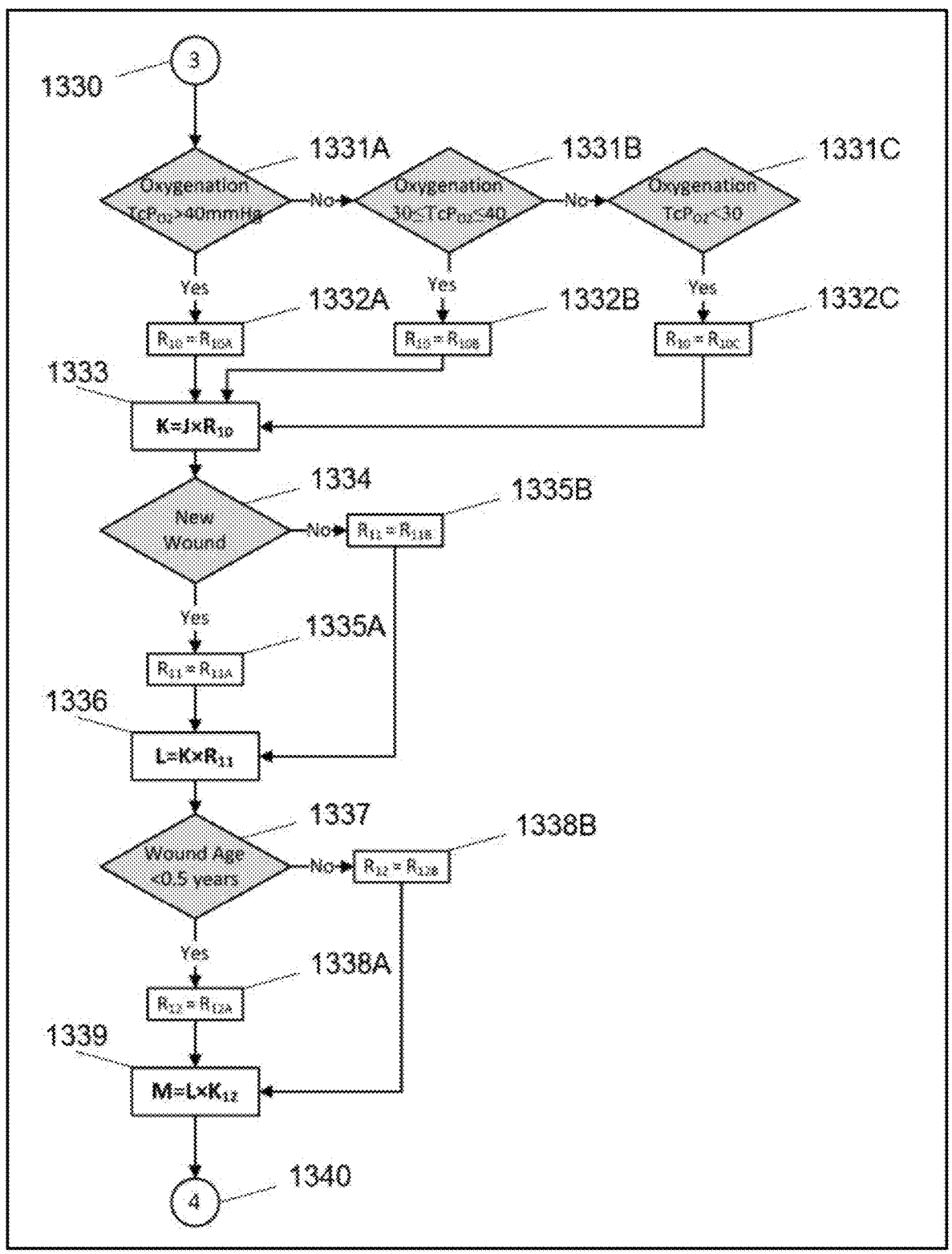
FIG. 13D is a flow diagram of the continuation of the algorithm presented in FIG. 13A, FIG. 13B, and FIG. 13C used to calculate the number of treatments with acoustic pressure shock waves for diabetic foot ulcers (DFUs), arterial ulcers, or venous ulcers, when ulcer area oxygenation ($T_cP_{O2}$-Transcutaneous Partial Pressure of Oxygen), wound reoccurrence, and chronic wound age are taken into account, according to one embodiment of the present invention.

The optimization continues on FIG. 13D and the continuation of the questionnaire flowchart from FIG. 13C to FIG. 13D is realized by the FIG. 13C to FIG. 13D connector 1330, which is seen on both FIG. 13C and FIG. 13D.

The questionnaire from FIG. 13D starts with the inquiry on transcutaneous monitoring of oxygen ($T_cP_{O2}$), which is an indication on oxygenation of the wound. Thus the inquiry for transcutaneous monitoring of oxygen (TcP$_{O2}$) greater than 40 mmHg 1331A is displayed. If the answer is "Yes" then the TcP$_{O2}$ modifying coefficient $R_{10A}$ 1332A will be used ($R_{10}=R_{10A}$). If the answer is "No", the inquiry for transcutaneous monitoring of oxygen (TcP$_{O2}$) between 30 and 40 mmHg 1331B is displayed. If the answer is "Yes" then the TcP$_{O2}$ modifying coefficient $R_{10B}$ 1332B will be used ($R_{10}=R_{10B}$). If the answer is "No", the inquiry for transcutaneous monitoring of oxygen (TcP$_{O2}$) less than 30 mmHg 1331C is displayed. If the answer is "Yes" then the TcP$_{O2}$ modifying coefficient $R_{10C}$ 1332C will be used ($R_{10}=R_{10C}$). Then the number of treatments "J" is altered with the determined transcutaneous monitoring of oxygen (TcP$_{O2}$) modifying coefficient "$R_{10}$", and thus the new number of treatments becomes "K", which is now the updated number of treatments based on tissue oxygenation 1333.

The questionnaire from FIG. 13D continues with the inquiry on new wound presence, which is an indication of recurrence. Thus the inquiry for new wound 1334 is displayed. If the answer is "Yes" then the new wound modifying coefficient $R_{11A}$ 1335A will be used ($R_{11}=R_{11A}$). If the answer is "No" then the new wound modifying coefficient $R_{11B}$ 1335B will be used ($R_{11}=R_{11B}$). Then the number of treatments "K" is altered with the determined new wound modifying coefficient "$R_{11}$", and thus the new number of treatments becomes "L", which is now the updated number of treatments based on new wound presence 1336.

The questionnaire from FIG. 13D continues with the inquiry on wound age <0.5 years. Thus the inquiry for wound age 1337 is displayed. If the answer is "Yes" then the wound age modifying coefficient $R_{12A}$ 1338A will be used ($R_{12}=R_{12A}$). If the answer is "No" then the wound age modifying coefficient $R_{12B}$ 1338B will be used ($R_{12}=R_{12B}$). Then the number of treatments "L" is altered with the determined wound age modifying coefficient "$R_{12}$", and thus the new number of treatments becomes "M", which is now the updated number of treatments based on wound age 1339.

Figure 13E:
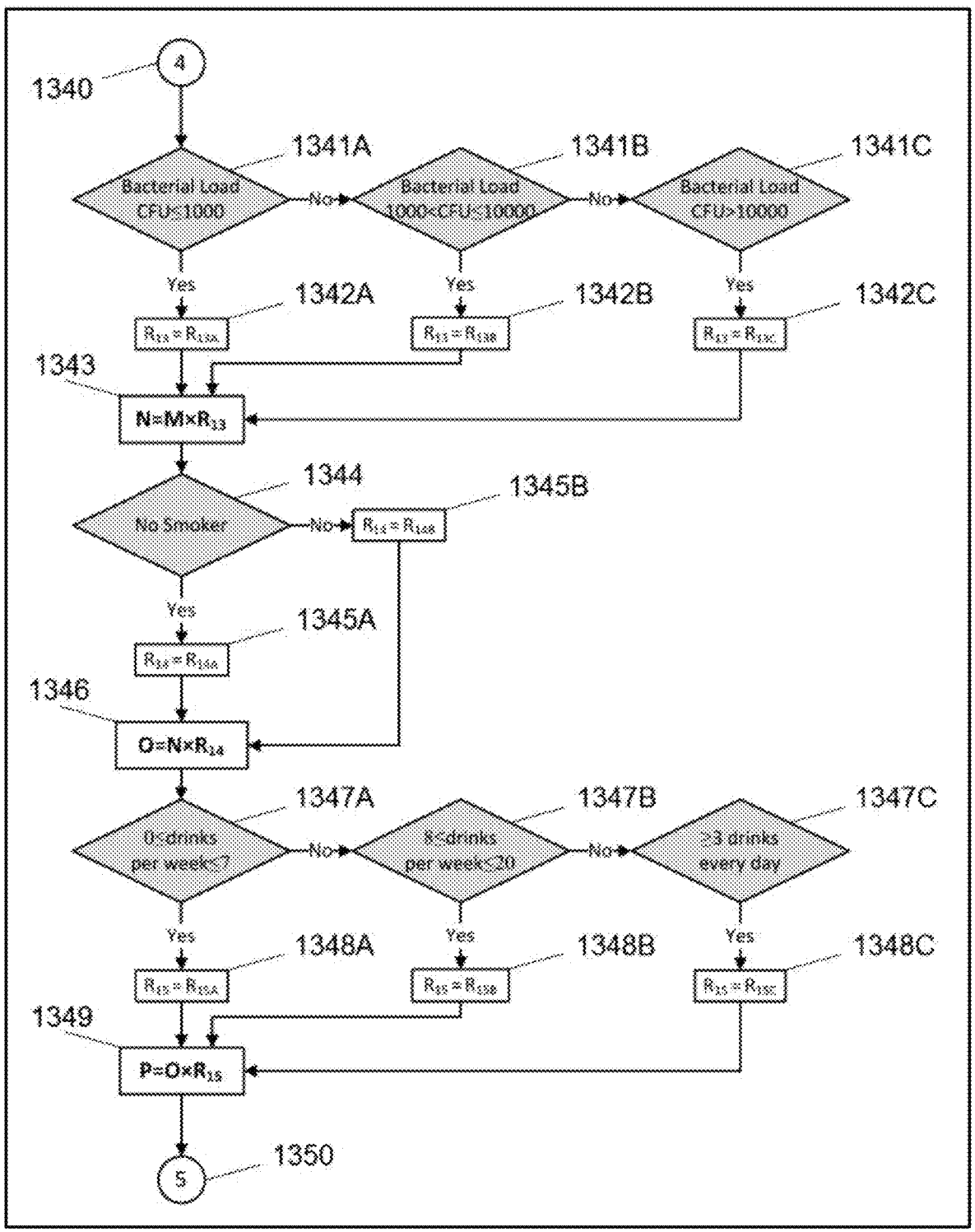
FIG. 13E is a flow diagram of the continuation of the algorithm presented in FIG. 13A, FIG. 13B, FIG. 13C, and FIG. 13D used to calculate the number of treatments with acoustic pressure shock waves for diabetic foot ulcers (DFUs), arterial ulcers, or venous ulcers, when wound bacterial load, smoker status, and alcohol consumption rate are taken into account, according to one embodiment of the present invention.

The optimization continues on FIG. 13E and the continuation of the questionnaire flowchart from FIG. 13D to FIG. 13E is realized by the FIG. 13D to FIG. 13E connector 1340, which is seen on both FIG. 13D and FIG. 13E.

The questionnaire from FIG. 13E starts with the inquiry on bacterial colony forming units (CFU), which is an indication of bacterial load of the wound. Thus the inquiry for bacterial colony forming units (CFU) less than 1000 units 1341A is displayed. If the answer is "Yes" then the CFU modifying coefficient $R_{13A}$ 1342A will be used ($R_{13}=R_{13A}$). If the answer is "No", the inquiry for bacterial colony forming units (CFU) between 1000 and 10000 units 1341B is displayed. If the answer is "Yes" then the CFU modifying coefficient $R_{13B}$ 1342B will be used ($R_{13}=R_{13B}$).

If the answer is "No", the inquiry for bacterial colony forming units (CFU) greater than 10000 units 1341C is displayed. If the answer is "Yes" then the CFU modifying coefficient $R_{13C}$ 1342C will be used ($R_{13}=R_{13C}$). Then the number of treatments "M" is altered with the determined CFU modifying coefficient "$R_{13}$", and thus the new number of treatments becomes "N", which is now the updated number of treatments based on bacterial load 1343.

The questionnaire from FIG. 13E continues with the inquiry on smoking status. Thus the inquiry for smoking status 1344 is displayed. If the answer is "Yes" then the smoking status modifying coefficient $R_{14A}$ 1345A will be used ($R_{14}=R_{14A}$). If the answer is "No" then the smoking status modifying coefficient $R_{14B}$ 1345B will be used ($R_{14}=R_{14B}$). Then the number of treatments "N" is altered with the determined smoking status modifying coefficient "$R_{14}$", and thus the new number of treatments becomes "O", which is now the updated number of treatments based on smoking status 1346.

The questionnaire from FIG. 13E continues with the inquiry on drinking habit, which is indicated by the number of drinks over a certain period of time. Thus the inquiry for drinks less than 7 per week 1347A is displayed. If the answer is "Yes" then the drinking habit modifying coefficient $R_{15A}$ 1348A will be used ($R_{15}=R_{15A}$). If the answer is "No", the inquiry for drinks between 8 and 20 per week 1347B is displayed. If the answer is "Yes" then the drinking habit modifying coefficient $R_{15B}$ 1348B will be used ($R_{15}=R_{15B}$). If the answer is "No", the inquiry for drinks greater than 3 every day 1347C is displayed. If the answer is "Yes" then the drinking habit modifying coefficient $R_{15C}$ 1348C will be used ($R_{15}=R_{15C}$). Then the number of treatments "O" is altered with the determined drinking habit modifying coefficient "$R_{15}$", and thus the new number of treatments becomes "P", which is now the updated number of treatments based on drinking habit 1349.

Figure 13F:
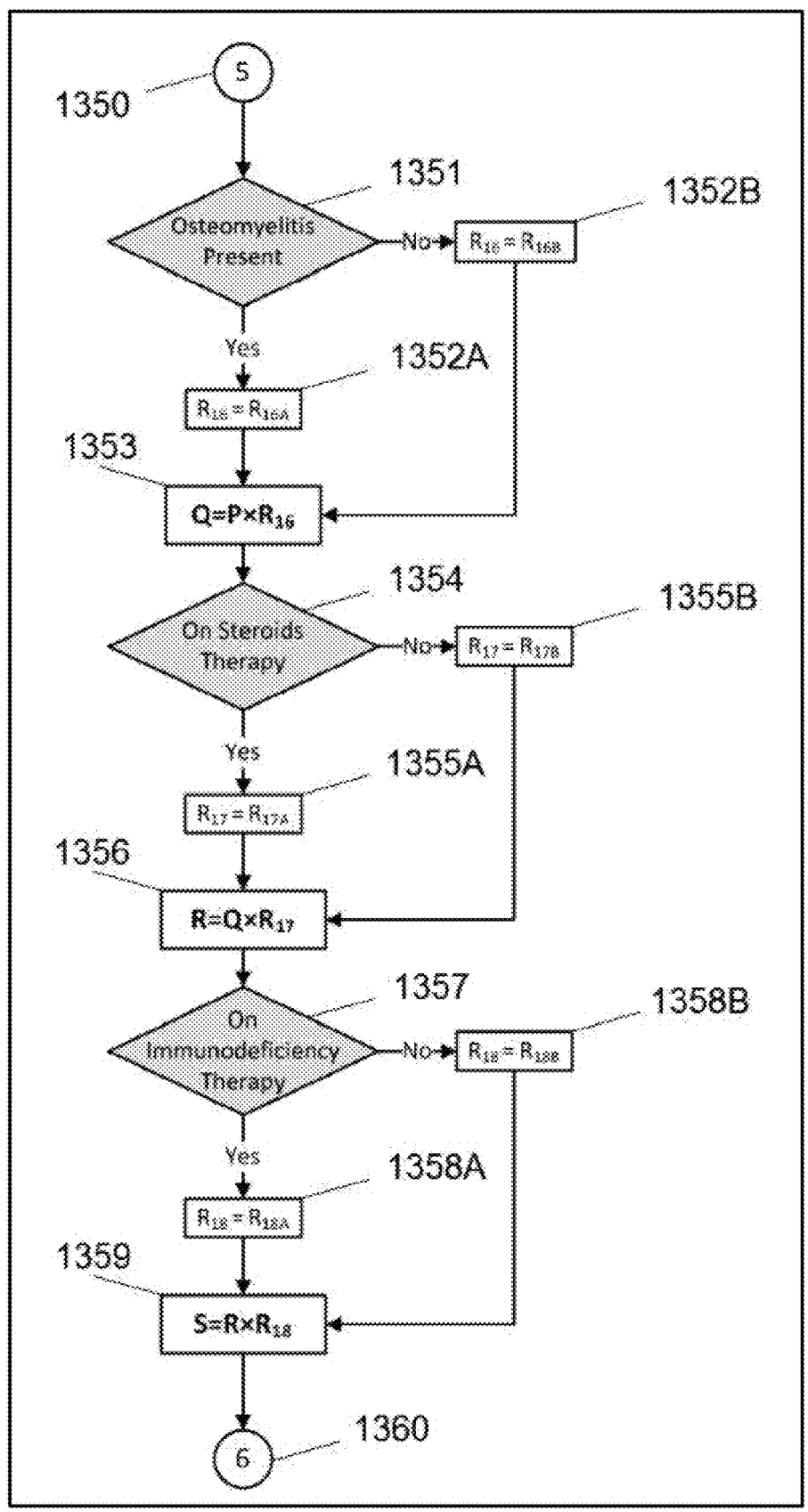
FIG. 13F is a flow diagram of the continuation of the algorithm presented in FIG. 13A, FIG. 13B, FIG. 13C, FIG. 13D, and FIG. 13E used to calculate the number of treatments with acoustic pressure shock waves for diabetic foot ulcers (DFUs), arterial ulcers, or venous ulcers, when presence of bone osteomyelitis, patient possible steroids therapy, and possible patient immunodeficiency therapy are taken into account, according to one embodiment of the present invention.

The optimization continues on FIG. 13F and the continuation of the questionnaire flowchart from FIG. 13E to FIG. 13F is realized by the FIG. 13E to FIG. 13F connector 1350, which is seen on both FIG. 13E and FIG. 13F.

The questionnaire from FIG. 13F continues with the inquiry on comorbidities as osteomyelitis. Thus the inquiry for presence of osteomyelitis 1351 is displayed. If the answer is "Yes" then the osteomyelitis presence modifying coefficient $R_{16A}$ 1352A will be used ($R_{16}=R_{16A}$). If the answer is "No" then the osteomyelitis presence modifying coefficient $R_{16B}$ 1352B will be used ($R_{16}=R_{16B}$). Then the number of treatments "P" is altered with the determined osteomyelitis presence modifying coefficient "$R_{16}$", and thus the new number of treatments becomes "Q", which is now the updated number of treatments based on presence of osteomyelitis 1353.

The questionnaire from FIG. 13F continues with the inquiry on steroids therapy. Thus the inquiry for steroids therapy 1354 is displayed. If the answer is "Yes" then the steroids therapy modifying coefficient $R_{17A}$ 1355A will be used ($R_{17}=R_{17A}$). If the answer is "No" then the steroids therapy modifying coefficient $R_{17B}$ 1355B will be used ($R_{17}=R_{17B}$). Then the number of treatments "Q" is altered with the determined steroids therapy modifying coefficient "$R_{17}$", and thus the new number of treatments becomes "R", which is now the updated number of treatments based on steroids therapy 1356.

The questionnaire from FIG. 13F continues with the inquiry on immunodeficiency therapy. Thus the inquiry for immunodeficiency therapy 1357 is displayed. If the answer is "Yes" then the immunodeficiency therapy modifying coefficient $R_{18A}$ 1358A will be used ($R_{18}=R_{18A}$). If the answer is "No" then the immunodeficiency therapy modifying coefficient $R_{18B}$ 1358B will be used ($R_8=R_{18B}$). Then the number of treatments "R" is altered with the determined immunodeficiency therapy modifying coefficient "$R_{18}$", and thus the new number of treatments becomes "S", which is now the updated number of treatments based on immunodeficiency therapy 1359.

Figure 13G:
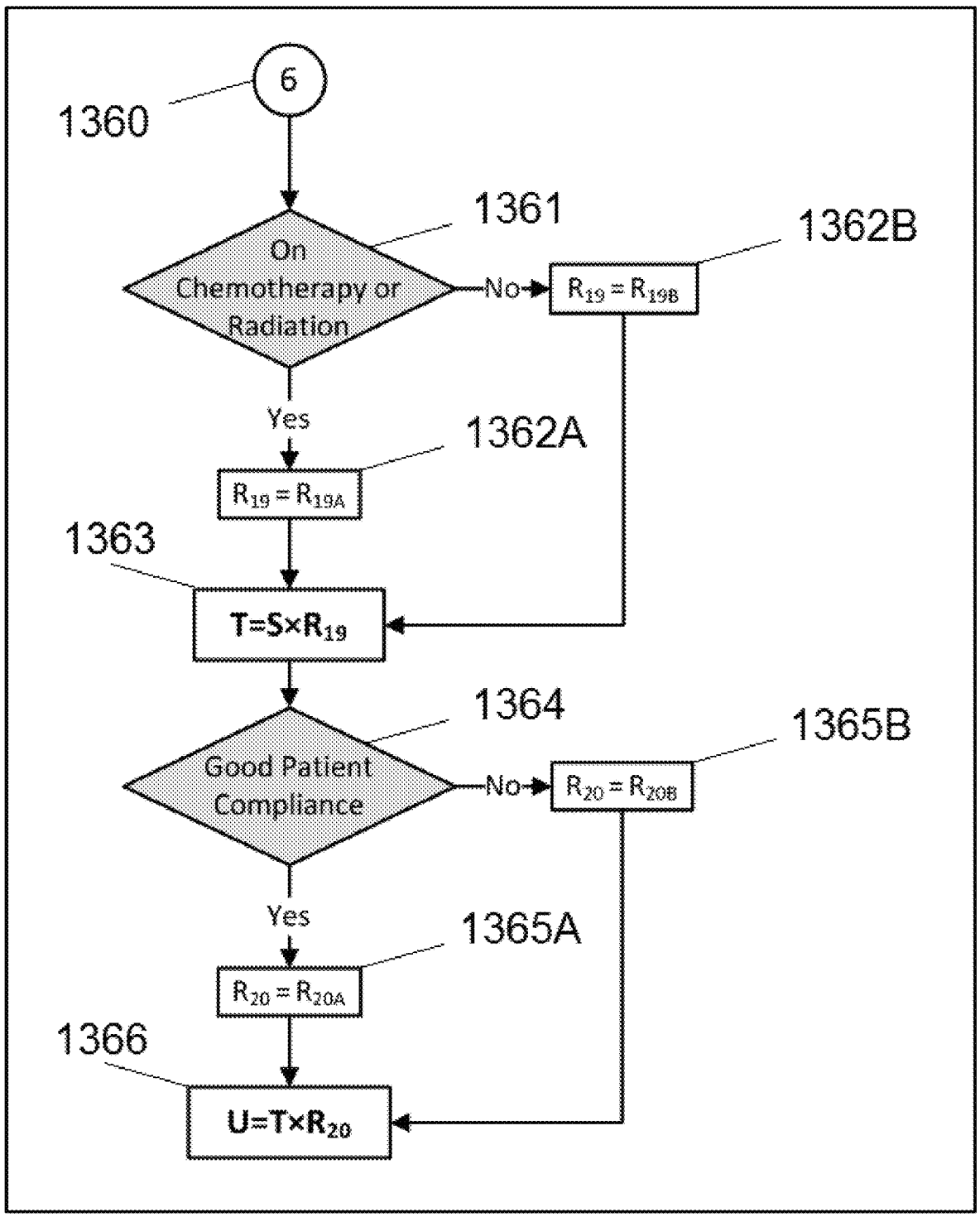
FIG. 13G is a flow diagram of the continuation of the algorithm presented in FIG. 13A, FIG. 13B, FIG. 13C, FIG. 13D, FIG. 13E, and FIG. 13F used to calculate the number of treatments with acoustic pressure shock waves for diabetic foot ulcers (DFUs), arterial ulcers, or venous ulcers, when possible chemotherapy or radiation therapy and patient history of compliance to the treatment are taken into account, according to one embodiment of the present invention.

The optimization continues on FIG. 13G and the continuation of the questionnaire flowchart from FIG. 13F to FIG. 13G is realized by the FIG. 13F to FIG. 13G connector 1360, which is seen on both FIG. 13F and FIG. 13G.

The questionnaire from FIG. 13G starts with the inquiry on chemotherapy or radiation therapy. Thus the inquiry for chemotherapy or radiation therapy 1361 is displayed. If the answer is "Yes" then the chemotherapy or radiation therapy modifying coefficient $R_{19A}$ 1362A will be used ($R_{19}=R_{19A}$). If the answer is "No" then the chemotherapy or radiation therapy modifying coefficient $R_{19B}$ 1362B will be used ($R_{19}=R_{19B}$). Then the number of treatments "S" is altered with the determined chemotherapy or radiation therapy modifying coefficient "$R_{19}$", and thus the new number of treatments becomes "T", which is now the updated number of treatments based on chemotherapy and radiation therapy 1363.

The questionnaire from FIG. 13G continues with the inquiry on good patient compliance. Thus the inquiry for good patient compliance 1364 is displayed. If the answer is "Yes" then the patient compliance modifying coefficient $R_{20A}$ 1365A will be used ($R_{20}=R_{20A}$). If the answer is "No" then the patient compliance modifying coefficient $R_{20B}$ 1365B will be used ($R_{20}=R_{20B}$). Then the number of treatments "T" is altered with the determined patient compliance modifying coefficient "$R_{20}$", and thus the new number of treatments becomes "U", which is now the updated number of treatments based on patient compliance 1366.

In FIGS. 13A-13G the coefficients presented for diabetic foot ulcers (DFUs), arterial ulcers, and venous ulcers that can be used to adjust the number of treatments based on inquiries for patient's comorbidities, existing therapies, habits/lifestyle and wound status are defined with general ranges and also with more preferable ranges and sometimes as a specific number.

In FIGS. 13A-13G the values for the coefficients are preferably as follows:

In FIG. 13A, coefficient $R_{1A}$ is preferably 1.00, because patients with age under 40 should have a very good response to the acoustic pressure shock wave treatment.

In FIG. 13A, coefficient $R_{1B}$ may be in the range from about 1.00 to 1.02, and preferably from about 1.01 to 1.02.

In FIG. 13A, coefficient $R_{1C}$ may be in the range from about 1.00 to 1.03, and preferably from about 1.02 to 1.03.

In FIG. 13A, coefficient $R_{1D}$ may be in the range from about 1.00 to 1.04, and preferably from about 1.03 to 1.04.

In FIG. 13A, coefficient $R_{2A}$ is preferably 1.00, because patients with wound area less than 64 cm² have a very good response to the acoustic pressure shock wave treatment.

In FIG. 13A, coefficient $R_{2B}$ may be in the range from about 1.00 to 1.02, and preferably from about 1.01 to 1.02.

In FIG. 13A, coefficient $R_{2C}$ may be in the range from about 1.00 to 1.03, and preferably from about 1.02 to 1.03.

In FIG. 13A, coefficient $R_{3A}$ is preferably 1.00, because patients with a body mass index (BMI) below 32 should have a very good response to the acoustic pressure shock wave treatment and do not present any challenges from obesity point of view.

In FIG. 13A, coefficient $R_{3B}$ may be in the range from about 1.01 to 1.03, and preferably from about 1.02 to 1.03.

In FIG. 13B coefficient $R_{4A}$ is preferably 1.00, because patients with a weight below 220 lb/99.8 Kg should have a very good response to the acoustic pressure shock wave treatment and do not present any challenges from obesity point of view.

In FIG. 13B, coefficient $R_{4B}$ may be in the range from about 1.00 to 1.03, and preferably from about 1.01 to 1.02.

In FIG. 13B coefficient $R_{5A}$ is preferably 1.00 for a height below 70 in/177.8 cm.

In FIG. 13B, coefficient $R_{5B}$ may be in the range from about 1.00 to 1.02, and preferably from about 1.01 to 1.02.

In FIG. 13B, coefficient $R_{6A}$ is preferably 1.00, because patients with a HbA1c are controlling their diabetes and should have a very good response to the acoustic pressure shock wave treatment.

In FIG. 13B, coefficient $R_{6B}$ may be in the range from about 1.01 to 1.03, and preferably from about 1.02 to 1.03.

In FIG. 13B, coefficient $R_{6C}$ may be in the range from about 1.01 to 1.04, and preferably from about 1.03 to 1.04.

In FIG. 13C, coefficient $R_{7A}$ is preferably 1.00, because patients with very superficial wounds should have a very good response to the acoustic pressure shock wave treatment.

In FIG. 13C, coefficient $R_{7B}$ may be in the range from about 1.00 to 1.02, and preferably from about 1.01 to 1.02.

In FIG. 13C, coefficient $R_{7C}$ may be in the range from about 1.01 to 1.03, and preferably from about 1.02 to 1.03.

In FIG. 13C, coefficient $R_{8A}$ is preferably 1.00, because patients with Grade I diabetic foot ulcers (DFUs) or arterial ulcers (this coefficient does not apply for venous ulcers) should have a very good response to the acoustic pressure shock wave treatment.

In FIG. 13C, coefficient $R_{8B}$ for diabetic foot ulcers (DFUs) or arterial ulcers (this coefficient does not apply for venous ulcers) may be in the range from about 1.01 to 1.03, and preferably from about 1.02 to 1.03.

In FIG. 13C, coefficient $R_{8C}$ for diabetic foot ulcers (DFUs) or arterial ulcers (this coefficient does not apply for venous ulcers) may be in the range from about 1.02 to 1.04, and preferably from about 1.03 to 1.04.

In FIG. 13C, coefficient $R_{9A}$ is preferably 1.00, because patients with an ankle-brachial index (ABI) between 0.7 and 1.2 should have a very good response to the acoustic pressure shock wave treatment.

In FIG. 13C, coefficient $R_{9B}$ may be in the range from about 1.00 to 1.03, and preferably from about 1.01 to 1.02.

In FIG. 13C, coefficient $R_{9C}$ may be in the range from about 1.01 to 1.04, and preferably from about 1.02 to 1.03.

In FIG. 13D, coefficient $R_{10A}$ is preferably 1.00, because patients with a TcP$_{O2}$ value greater than 40 mmHg is normal and the patients should have a very good response to the acoustic pressure shock wave treatment.

In FIG. 13D, coefficient $R_{10B}$ may be in the range from about 1.01 to 1.03, and preferably from about 1.02 to 1.03.

In FIG. 13D, coefficient $R_{10C}$ may be in the range from about 1.02 to 1.04, and preferably from about 1.03 to 1.04.

In FIG. 13D coefficient $R_{11A}$ is preferably 1.00 for a new wound and not a recurrent wound.

In FIG. 13D, coefficient $R_{11B}$ may be in the range from about 1.00 to 1.03, and preferably from about 1.01 to 1.02.

In FIG. 13D coefficient $R_{12A}$ is preferably 1.00 for a wound that is less than 6 month old.

In FIG. 13D, coefficient $R_{12B}$ may be in the range from about 1.00 to 1.04, and preferably from about 1.02 to 1.03.

In FIG. 13E, coefficient $R_{13A}$ is preferably 1.00, because patients with a colony forming units (CFU) of bacteria less than 1000 in the skin lesion should have a very good response to the acoustic pressure shock wave treatment.

In FIG. 13E, coefficient $R_{13B}$ may be in the range from about 1.01 to 1.03, and preferably from about 1.02 to 1.03.

In FIG. 13E, coefficient $R_{13C}$ may be in the range from about 1.02 to 1.04, and preferably from about 1.03 to 1.04.

In FIG. 13E coefficient $R_{14A}$ is preferably 1.00 because a non-smoker should have a very good response to the acoustic pressure shock wave treatment.

In FIG. 13E, coefficient $R_{14B}$ may be in the range from about 1.00 to 1.03, and preferably from about 1.01 to 1.02.

In FIG. 13E, coefficient $R_{15A}$ is preferably 1.00, because occasional drinking patients should have a very good response to the acoustic pressure shock wave treatment.

In FIG. 13E, coefficient $R_{15B}$ may be in the range from about 1.01 to 1.03, and preferably from about 1.02 to 1.03.

In FIG. 13E, coefficient $R_{15C}$ may be in the range from about 1.02 to 1.04, and preferably from about 1.03 to 1.04.

In FIG. 13F, coefficient $R_{16A}$ may be in the range from about 1.00 to 1.03, and preferably from about 1.01 to 1.02.

In FIG. 13F coefficient $R_{16B}$ is preferably 1.00 because a patient without osteomyelitis should have a very good response to the acoustic pressure shock wave treatment.

In FIG. 13F, coefficient $R_{17A}$ may be in the range from about 1.00 to 1.03, and preferably from about 1.01 to 1.02.

In FIG. 13F coefficient $R_{17B}$ is preferably 1.00 because a patient that is not on steroids therapy should have a very good response to the acoustic pressure shock wave treatment.

In FIG. 13F, coefficient $R_{18A}$ may be in the range from about 1.00 to 1.03, and preferably from about 1.01 to 1.02.

In FIG. 13F coefficient $R_{18B}$ is preferably 1.00 because a patient that is not on immunodeficiency therapy should have a very good response to the acoustic pressure shock wave treatment.

In FIG. 13G, coefficient $R_{19A}$ may be in the range from about 1.00 to 1.04, and preferably from about 1.02 to 1.04.

In FIG. 13G coefficient $R_{19B}$ is preferably 1.00 because a patient that is not on chemotherapy or radiation therapy should have a very good response to the acoustic pressure shock wave treatment.

In FIG. 13G coefficient $R_{20A}$ is preferably 1.00 because a patient with a history of compliance to treatments should have a very good response to the acoustic pressure shock wave treatment.

In FIG. 13G, coefficient $R_{20B}$ may be in the range from about 1.00 to 1.03, and preferably from about 1.01 to 1.02.

A control console/unit 22 and associated acoustic pressure shock wave applicator/treatment apparatus 10 (see FIG. 2A) used for delivering a treatment for diabetic foot ulcers (DFUs) or arterial ulcers by means of the proposed adjustment algorithm for number of treatments from FIGS. 13A-13G will use the following formula (where A is the initial number of treatments with focused acoustic pressure shock waves 40 or radial acoustic pressure waves 41 or planar acoustic pressure waves 42 or cylindrical acoustic pressure waves 44 and ANTT is the Adjusted Number of Total Treatments):

$$ANTT = A \cdot R_1 \cdot R_2 \cdot R_3 \cdot R_4 \cdot R_5 \cdot R_6 \cdot R_7 \cdot R_8 \cdot R_9 \cdot R_{10} \cdot R_{11} \cdot R_{12} \cdot R_{13} \cdot R_{14} \cdot R_{15} \cdot R_{16} \cdot R_{17} \cdot R_{18} i \cdot R_{19} \cdot R_{20}.$$

For the largest values for these coefficients (worst situation) and for example a number of A=8 treatments is used as the initial number of treatments with focused acoustic pressure shock waves 40 or radial acoustic pressure waves 41 or planar acoustic pressure waves 42 or cylindrical acoustic pressure waves 44 that are minimally needed for successful treatment of the tissue condition 19, then the Adjusted Number of Total Treatments (ANTT) value is the following:

ANTT=8·1.04·1.03·1.03·1.03·1.02·1.04·1.03·1.04·1.04·1.04·1.03·1.04·1.04·1.03·1.04·1.03·1.03·1.03·1.04·1.03=15.61≈16 treatments for DFU or arterial ulcers.

A control console/unit 22 and associated acoustic pressure shock wave applicator/treatment apparatus 10 (see FIG. 2A) used for delivering a treatment for venous ulcers (where coefficient $R_8$ for wound grade does not apply) by means of the proposed adjustment algorithm for number of treatments from FIGS. 13A-13G will use the following formula (where A is the initial number of treatments with focused acoustic pressure shock waves 40 or radial acoustic pressure waves 41 or planar acoustic pressure waves 42 or cylindrical acoustic pressure waves 44 and ANTT is the Adjusted Number of Total Treatments):

$$ANTT = A \cdot R_1 \cdot R_2 \cdot R_3 \cdot R_4 \cdot R_5 \cdot R_6 \cdot R_7 \cdot R_9 \cdot R_{10} \cdot R_{11} \cdot R_{12} \cdot R_{13} \cdot R_{14} \cdot R_{15} \cdot R_{16} \cdot R_{17} \cdot R_{18} \cdot R_{19} \cdot R_{20}.$$

For venous ulcers (where coefficient $R_8$ for wound grade does not apply) and the largest values for these coefficients (worst situation) and for example a number of A=8 treatments is used as the initial number of treatments with focused acoustic pressure shock waves 40 or radial acoustic pressure waves 41 or planar acoustic pressure waves 42 or cylindrical acoustic pressure waves 44 that are minimally needed for successful treatment of the tissue condition 19, then the Adjusted Number of Total Treatments (ANTT) value is the following:

ANTT=8·1.04·1.03·1.03·1.03·1.02·1.04·1.03·1.04·1.04·1.03·1.04·1.04·1.03·1.04·1.03·1.03·1.03·1.04·1.03=15.01≈15 treatments for venous ulcers.

The personalized number of treatments for pressure ulcers when focused acoustic pressure shock waves 40 or radial acoustic pressure waves 41 or planar acoustic pressure waves 42 or cylindrical acoustic pressure waves 44 are used can be determined using different factors. FIGS. 14A-14G present a preferable algorithm that can be used to adjust the number of treatments used for pressure ulcers based on different elements that take into account the characteristics/status of the pressure ulcers, and patient's comorbidities, existing therapies, and habits/lifestyle.

As a starting point for the algorithm used to personalize/adjust the number of treatments using focused acoustic pressure shock waves 40 or radial acoustic pressure waves 41 or planar acoustic pressure waves 42 or cylindrical acoustic pressure waves 44 for pressure ulcers is the basic/initial number of treatments that are minimally needed for successful treatment of the tissue condition 19.

Figure 14A:
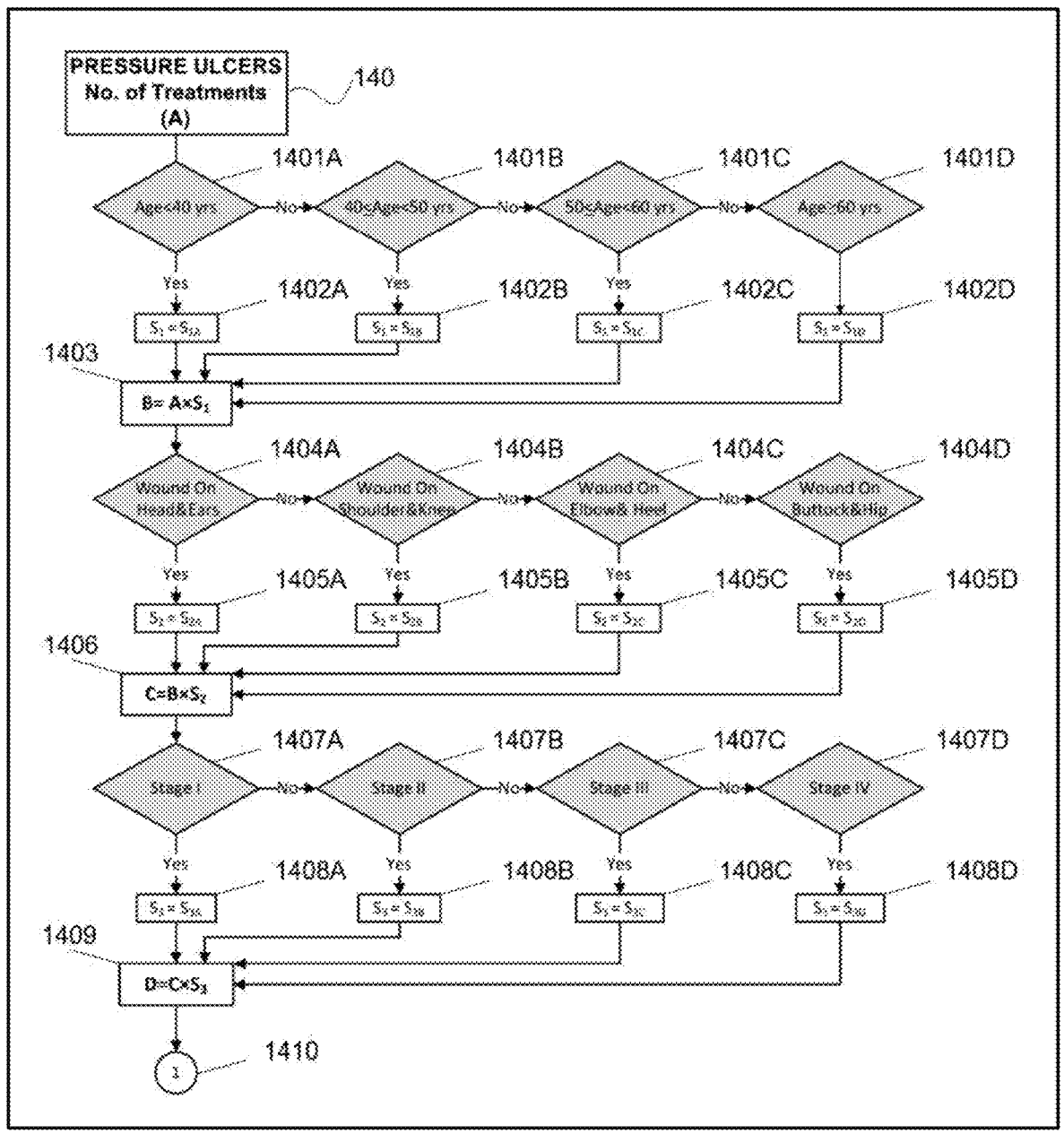
FIG. 14A is a flow diagram of the algorithm used to calculate the number of treatments with acoustic pressure shock waves for pressure ulcers when patient age, wound location, and wound stage are taken into account, according to one embodiment of the present invention.

In FIG. 14A the basic/initial number of treatments for pressure ulcers 140 represents the starting point of the adjustment/optimization algorithm for number of treatments using focused acoustic pressure shock waves 40 or radial acoustic pressure waves 41 or planar acoustic pressure waves 42 or cylindrical acoustic pressure waves 44 for the treatment of pressure ulcers. The first element used to alter the basic/initial number of treatments used for pressure ulcers treatment is the inquiry regarding the age of the patient. Thus on the control console/unit display 2220, or artificial intelligence (A/I) device display 2740, or on the display of an interconnected device (see FIG. 2A for the medical treatment system 2000) as a desktop computer 28A, or a smart phone 28B, and/or tablet 28C, and/or laptop 28D is first displayed the inquiry for age less than 40 years 1401A. If the answer is "Yes" then the age modifying coefficient $S_{1A}$ 1402A will be used ($S_1 = S_{1A}$). If the answer is "No", the inquiry for age between 40 and 50 years 1401B is displayed. If the answer is "Yes" then the age modifying coefficient $S_{1B}$ 1402B will be used ($S_1=S_{1B}$). If the answer is "No", the inquiry for age between 50 and 60 years 1401C is displayed. If the answer is "Yes" then the age modifying coefficient $S_{1C}$ 1402C will be used ($S_1=S_{1C}$). If the answer is "No", the inquiry for age older than 60 years 1401D is displayed and if the answer is "Yes" then the age modifying coefficient $S_{1D}$ 1402D will be used ($S_1=S_{1D}$). Then the basic/initial number of treatments "A" is altered with the determined age modifying coefficient "$S_1$", and thus the new number of treatments becomes "B", which is now the updated number of treatments based on age 1403.

The questionnaire from FIG. 14A continues with the inquiry on the location of the wound. Thus the inquiry for wound location on head and ears 1404A is displayed. If the answer is "Yes" then the wound location modifying coefficient $S_{2A}$ 1405A will be used ($S_2=S_{2A}$). If the answer is "No", the inquiry for wound location on shoulder and knee 1404B is displayed. If the answer is "Yes" then the wound location modifying coefficient $S_{2B}$ 1405B will be used ($S_2=S_{2B}$). If the answer is "No", the inquiry for wound location on elbow and heel 1404C is displayed. If the answer is "Yes" then the wound location modifying coefficient $S_{2C}$ 1405C will be used ($S_2=S_{2C}$). If the answer is "No", the inquiry for wound location on buttock and hip 1404D is displayed and if the answer is "Yes" then the wound location modifying coefficient $S_{2D}$ 1405D ($S_2=S_{2D}$). Then the number of treatments "B" is altered with the determined wound location modifying coefficient "$S_2$", and thus the new number of treatments becomes "C", which is now the updated number of treatments based on wound location 1406.

The questionnaire from FIG. 14A continues with the inquiry on wound stage. Thus the inquiry for wound stage I 1407A is displayed. If the answer is "Yes" then the wound grade modifying coefficient $S_{3A}$ 1408A will be used ($S_3=S_{3A}$). If the answer is "No", the inquiry for wound stage II 1407B is displayed. If the answer is "Yes" then the wound stage modifying coefficient $S_{3B}$ 1408B will be used ($S_3=S_{3B}$). If the answer is "No", the inquiry for wound stage III 1407C is displayed. If the answer is "Yes" then the wound stage modifying coefficient $S_{3C}$ 1408C will be used ($S_3=S_{3C}$). If the answer is "No", the inquiry for wound stage IV 1407D is displayed. If the answer is "Yes" then the wound stage modifying coefficient $S_{3D}$ 1408D will be used ($S_3=S_{3D}$). Then the number of treatments "C" is altered with the determined wound stage modifying coefficient "$S_3$", and thus the new number of treatments becomes "D", which is now the updated number of shocks based on wound stage 1409.

Figure 14B:
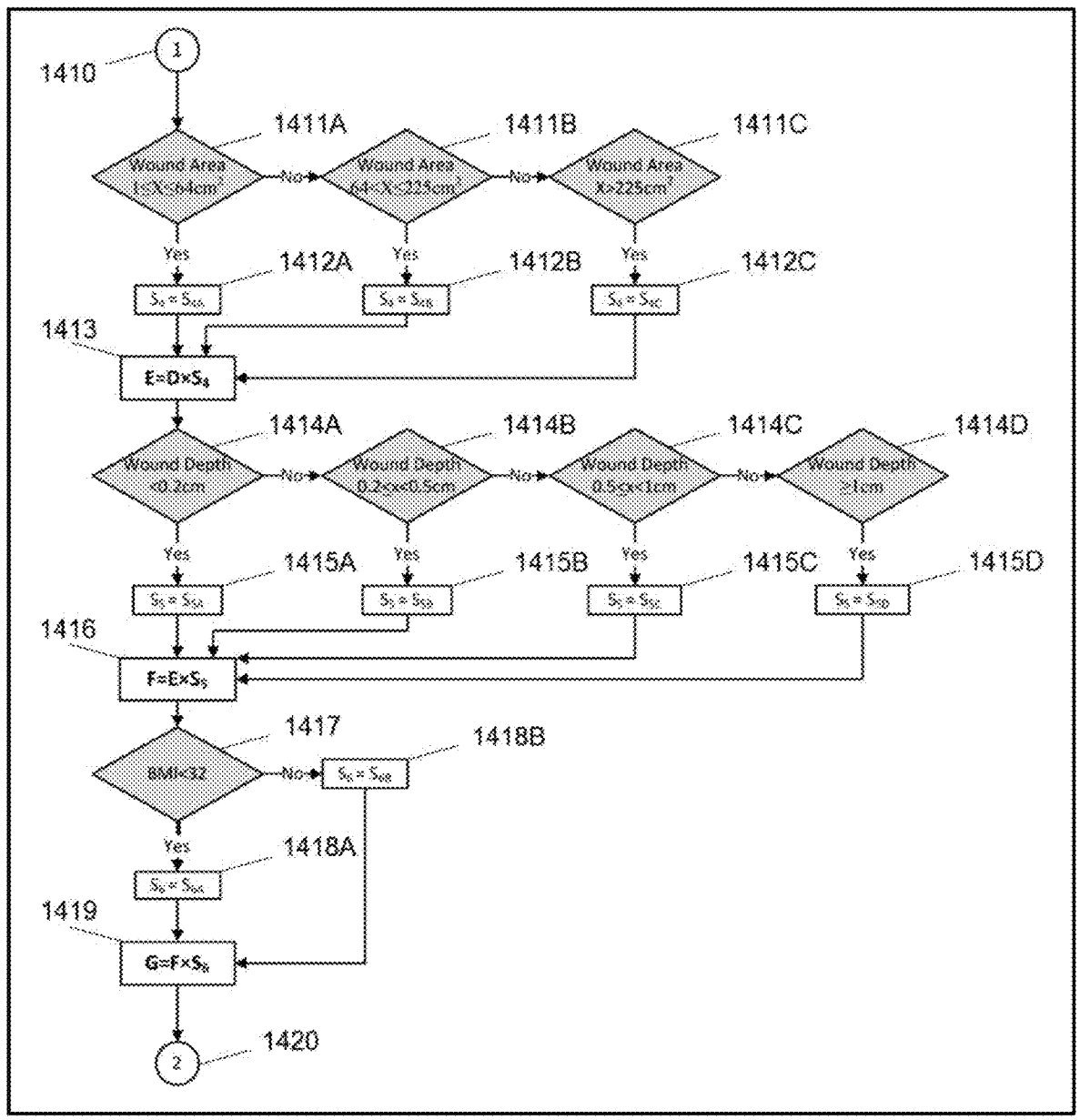
FIG. 14B is a flow diagram of the continuation of the algorithm presented in FIG. 14A used to calculate the number of treatments with acoustic pressure shock waves for pressure ulcers, when wound area, wound depth, and body mass index (BMI) are taken into account, according to one embodiment of the present invention.

The optimization continues on FIG. 14B and the continuation of the questionnaire flowchart from FIG. 14A to FIG. 14B is realized by the FIG. 14A to FIG. 14B connector 1410, which is seen on both FIG. 14A and FIG. 14B.

The questionnaire from FIG. 14B starts with the inquiry on the value for wound area. Thus the inquiry for wound area between 1 and 64 cm² 1411A is displayed. If the answer is "Yes" then the wound area modifying coefficient $S_{4A}$ 1412A will be used ($S_4=S_{4A}$). If the answer is "No", the inquiry for wound area between 64 and 225 cm² 1411B is displayed. If the answer is "Yes" then the wound area modifying coefficient $S_{4B}$ 1412B will be used ($S_4=S_{4B}$). If the answer is "No", the inquiry for wound area larger than 225 cm² 1411C is displayed. If the answer is "Yes" then the wound area modifying coefficient $S_{4C}$ 1412C will be used ($S_4=S_{4C}$). Then the number of treatments "D" is altered with the determined value for wound area modifying coefficient "$S_4$", and thus the new number of treatments becomes "E", which is now the updated number of treatments based on wound area 1413.

The questionnaire from FIG. 14B continues with the inquiry on wound depth. Thus the inquiry for wound depth less than 0.2 cm 1414A is displayed. If the answer is "Yes" then the wound depth modifying coefficient $S_{5A}$ 1415A will be used ($S_5=S_{5A}$). If the answer is "No", the inquiry for wound depth between 0.2 and 0.5 cm 1414B is displayed. If the answer is "Yes" then the wound depth modifying coefficient $S_{5B}$ 1415B will be used ($S_5=S_{5B}$). If the answer is "No", the inquiry for wound depth between 0.5 and 1 cm 1414C is displayed. If the answer is "Yes" then the wound depth modifying coefficient $S_{5C}$ 1415C will be used ($S_5=S_{5C}$). If the answer is "No", the inquiry for wound depth greater than 1 cm 1414D is displayed. If the answer is "Yes" then the wound depth modifying coefficient $S_{5D}$ 1415D will be used ($S_5=S_{5D}$). Then the number of treatments "E" is altered with the determined wound depth modifying coefficient "$S_5$", and thus the new number of treatments becomes "F", which is now the updated number of treatments based on wound depth 1416.

The questionnaire from FIG. 14B continues with the inquiry on the body mass index (BMI). Thus the inquiry for body mass index (BMI) value 1417 is displayed (BMI<32). If the answer is "Yes" then the body mass index (BMI) modifying coefficient $S_{6A}$ 1418A will be used ($S_6=S_{6A}$). If the answer is "No" then the body mass index (BMI) modifying coefficient $S_{6B}$ 1418B will be used ($S_6=S_{6B}$). Then the number of treatments "F" is altered with the determined body mass index (BMI) modifying coefficient "$S_6$", and thus the new number of treatments becomes "G", which is now the updated number of treatments based on obesity 1419.

Figure 14C:
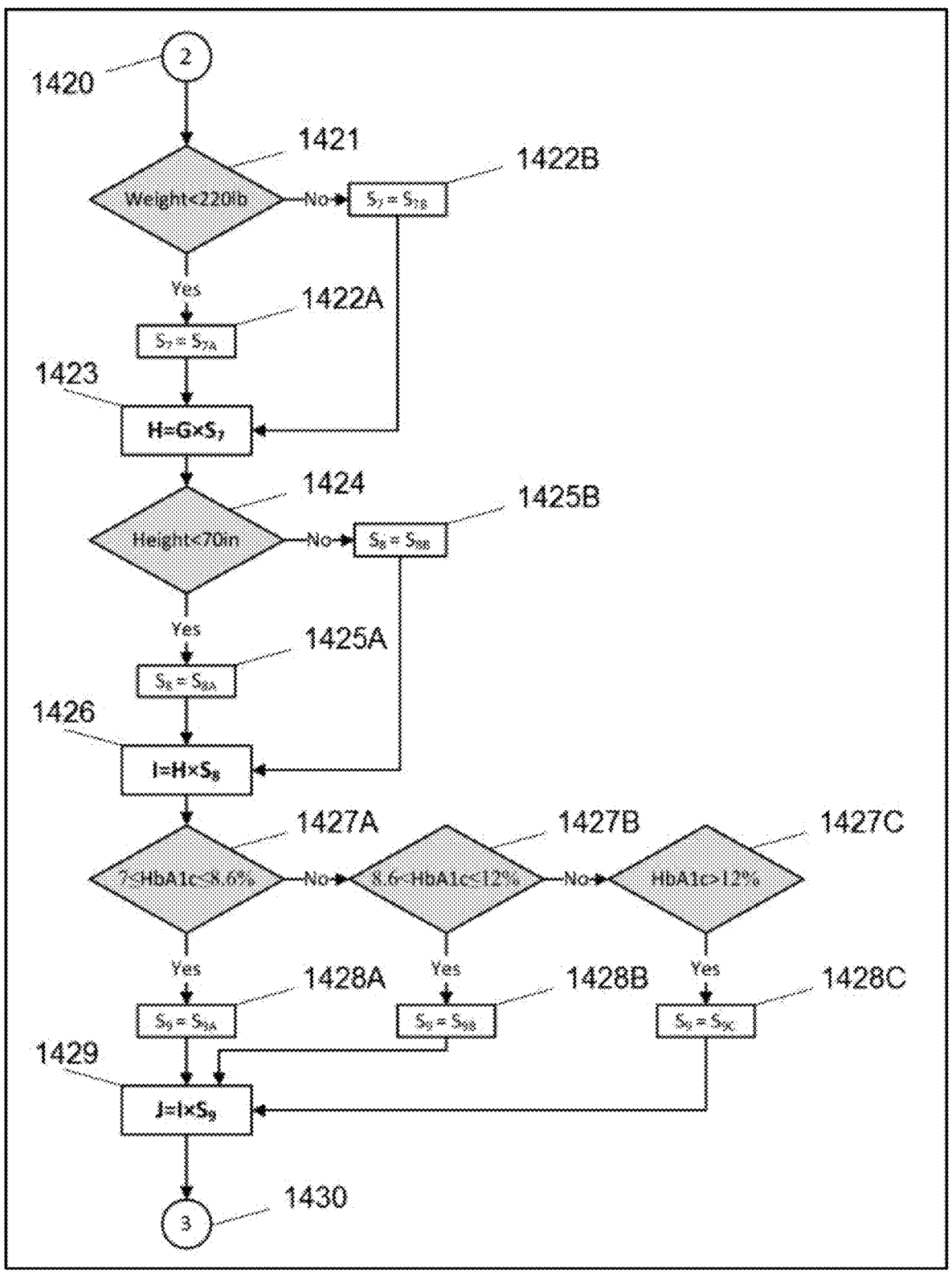
FIG. 14C is a flow diagram of the continuation of the algorithm presented in FIG. 14A and FIG. 14B used to calculate the number of treatments with acoustic pressure shock waves for pressure ulcers, when patient weight, patient height, and glycosylated hemoglobin A1c (HbA1c) are taken into account, according to one embodiment of the present invention.

The optimization continues on FIG. 14C and the continuation of the questionnaire flowchart from FIG. 14B to FIG. 14C is realized by the FIG. 14B to FIG. 14C connector 1420, which is seen on both FIG. 14B and FIG. 14C.

The questionnaire from FIG. 14C starts with the inquiry on the patient's weight. Thus the inquiry for weight value 1421 is displayed (Weight<220 lb which is 99.8 Kg in metric system). If the answer is "Yes" then the weight modifying coefficient $S_{7A}$ 1422A will be used ($S_7=S_{7A}$). If the answer is "No" then the weight modifying coefficient $S_{7B}$ 1422B will be used ($S_7=S_{7B}$). Then the number of treatments "G" is altered with the determined weight modifying coefficient "$S_7$", and thus the new number of treatments becomes "H", which is now the updated number of treatments based on weight 1423.

The questionnaire from FIG. 14C continues with the inquiry on the patient's height. Thus the inquiry for inquiry for height value 1424 is displayed (Height<70 in which is 177.8 cm in metric system). If the answer is "Yes" then the height modifying coefficient $S_{8A}$ 1425A will be used ($S_8=S_{8A}$). If the answer is "No" then the height modifying coefficient $S_{8B}$ 1425B will be used ($S_8=S_{8B}$). Then the number of treatments "H" is altered with the determined height modifying coefficient "$S_8$", and thus the new number of treatments becomes "I", which is now the updated number of treatments based on height 1426.

The questionnaire from FIG. 14C continues with the inquiry on the value for glycated hemoglobin (HbA1c), which is an indication of diabetes presence. Thus the inquiry for glycated hemoglobin (HbA1c) between 7 and 8.6% 1427A is displayed. If the answer is "Yes" then the HbA1c modifying coefficient $S_{9A}$ 1428A will be used ($S_9=S_{9A}$). If the answer is "No", the inquiry for glycated hemoglobin (HbA1c) between 8.6 and 12% 1427B is displayed. If the answer is "Yes" then the HbA1c modifying coefficient $S_{9B}$ 1428B will be used ($S_9=S_{9B}$). If the answer is "No", the inquiry for glycated hemoglobin (HbA1c) larger than 12% 1427C is displayed. If the answer is "Yes" then the HbA1c modifying coefficient $S_{9C}$ 1428C will be used ($S_9=S_{9C}$). Then the number of treatments "I" is altered with the determined HbA1c modifying coefficient "$S_9$", and thus the new number of treatments becomes "J", which is now the updated number of treatments based on diabetes presence 1429.

Figure 14D:
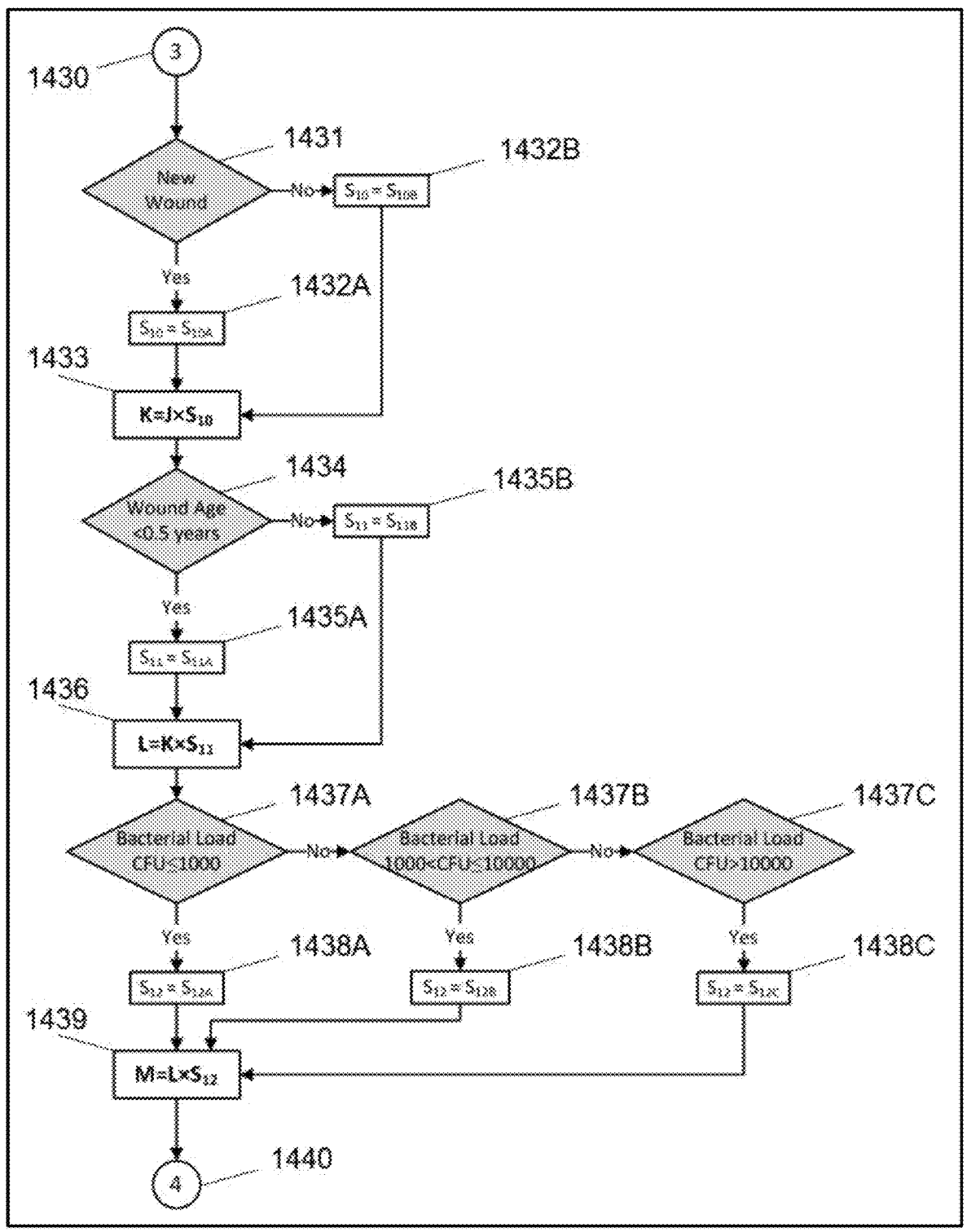
FIG. 14D is a flow diagram of the continuation of the algorithm presented in FIG. 14A, FIG. 14B, and FIG. 14C used to calculate the number of treatments with acoustic pressure shock waves for pressure ulcers, when wound reoccurrence, wound age, wound bacterial load are taken into account, according to one embodiment of the present invention.

The optimization continues on FIG. 14D and the continuation of the questionnaire flowchart from FIG. 14C to FIG. 14D is realized by the FIG. 14C to FIG. 14D connector 1430, which is seen on both FIG. 14C and FIG. 14D.

The questionnaire from FIG. 14D starts with the inquiry on new wound presence, which is an indication of recurrence. Thus the inquiry for new wound 1431 is displayed. If the answer is "Yes" then the new wound modifying coefficient $S_{10A}$ 1432A will be used ($S_{10}=S_{10A}$). If the answer is "No" then the new wound modifying coefficient $S_{10B}$ 1432B will be used ($S_{10}=S_{10B}$). Then the number of treatments "J" is altered with the determined new wound modifying coefficient "$S_{10}$", and thus the new number of treatments becomes "K", which is now the updated number of treatments based on new wound presence 1433.

The questionnaire from FIG. 14D continues with the inquiry on wound age <0.5 years. Thus the inquiry for wound age 1434 is displayed. If the answer is "Yes" then the wound age modifying coefficient $S_{11A}$ 1435A will be used ($S_{11}=S_{11A}$). If the answer is "No" then the wound age modifying coefficient $S_{11B}$ 1435B will be used ($S_{11}=S_{11B}$). Then the number of treatments "K" is altered with the determined wound age modifying coefficient "$S_{11}$", and thus the new number of treatments becomes "L", which is now the updated number of treatments based on wound age 1436.

The questionnaire from FIG. 14D continues with the inquiry on bacterial colony forming units (CFU), which is an indication of bacterial load of the wound. Thus the inquiry for bacterial colony forming units (CFU) less than 1000 units 1437A is displayed. If the answer is "Yes" then the CFU modifying coefficient $S_{12A}$ 1438A will be used ($S_{12}=S_{12A}$). If the answer is "No", the inquiry for bacterial colony forming units (CFU) between 1000 and 10000 units 1437B is displayed. If the answer is "Yes" then the CFU modifying coefficient $S_{12B}$ 1438B will be used ($S_{12}=S_{12B}$). If the answer is "No", the inquiry for bacterial colony forming units (CFU) greater than 10000 units 1437C is displayed. If the answer is "Yes" then the CFU modifying coefficient $S_{12C}$ 1438C will be used ($S_{12}=S_{12C}$). Then the number of treatments "L" is altered with the determined CFU modifying coefficient "$S_{12}$", and thus the new number of treatments becomes "M", which is now the updated number of treatments based on bacterial load 1439.

Figure 14E:
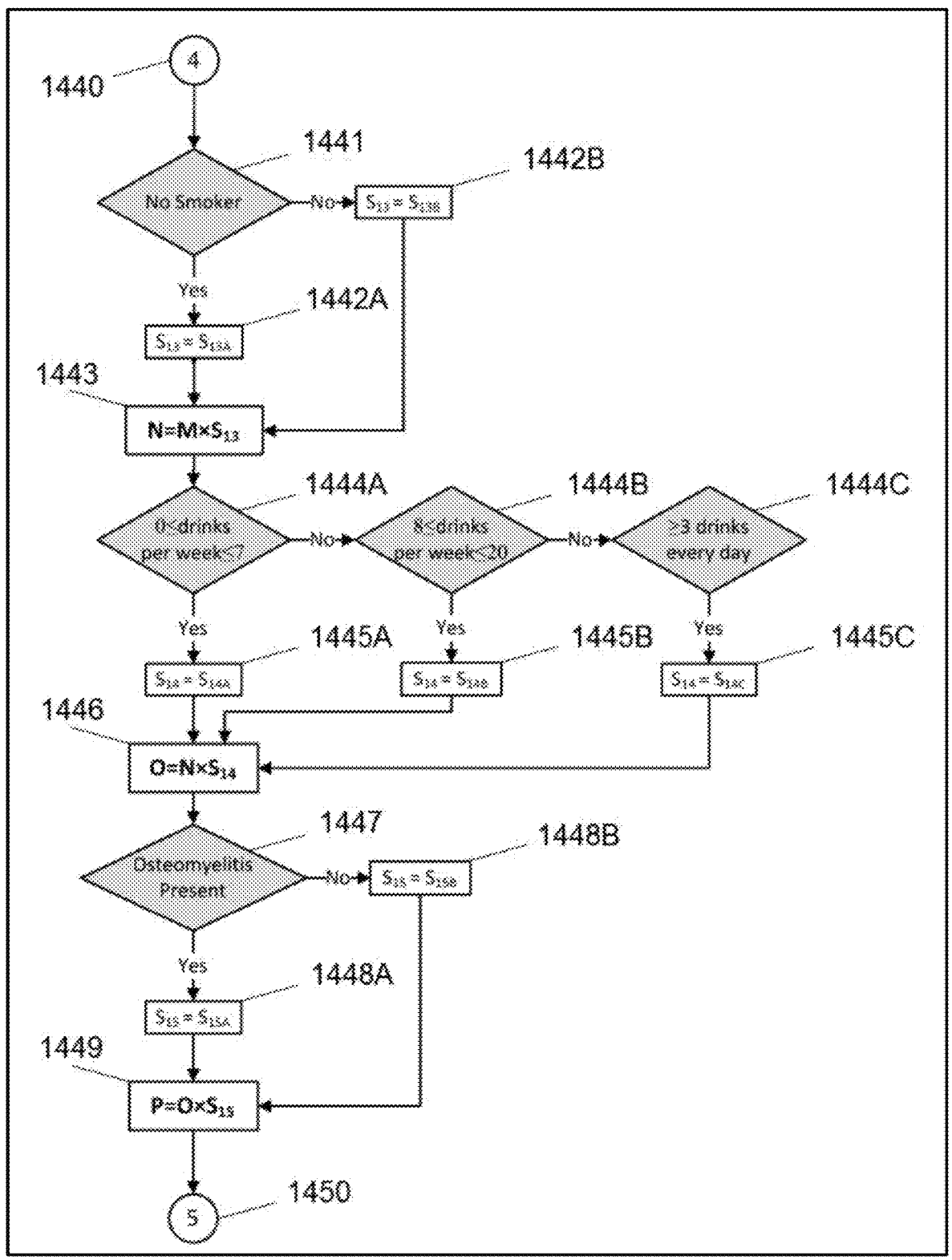
FIG. 14E is a flow diagram of the continuation of the algorithm presented in FIG. 14A, FIG. 14B, FIG. 14C, and FIG. 14D used to calculate the number of treatments with acoustic pressure shock waves for pressure ulcers, when smoker status, alcohol consumption rate, and presence of bone osteomyelitis are taken into account, according to one embodiment of the present invention.

The optimization continues on FIG. 14E and the continuation of the questionnaire flowchart from FIG. 14D to FIG. 14E is realized by the FIG. 14D to FIG. 14E connector 1440, which is seen on both FIG. 14D and FIG. 14E.

The questionnaire from FIG. 14E starts with the inquiry on smoking status. Thus the inquiry for smoking status 1441 is displayed. If the answer is "Yes" then the smoking status modifying coefficient $S_{13A}$ 1442A will be used ($S_{13}=S_{13A}$). If the answer is "No" then the smoking status modifying coefficient $S_{13B}$ 1442B will be used ($S_{13}=S_{13B}$). Then the number of treatments "M" is altered with the determined smoking status modifying coefficient "$S_{13}$", and thus the new number of treatments becomes "N", which is now the updated number of treatments based on smoking status 1443.

The questionnaire from FIG. 14E continues with the inquiry on drinking habit, which is indicated by the number of drinks over a certain period of time. Thus the inquiry for drinks less than 7 per week 1444A is displayed. If the answer is "Yes" then the drinking habit modifying coefficient $S_{14A}$ 1445A will be used ($S_{14}=S_{14A}$). If the answer is "No", the inquiry for drinks between 8 and 20 per week 1444B is displayed. If the answer is "Yes" then the drinking habit modifying coefficient $S_{14B}$ 1445B will be used ($S_{14}=S_{14B}$). If the answer is "No", the inquiry for drinks greater than 3 every day 1444C is displayed. If the answer is "Yes" then the drinking habit modifying coefficient $S_{14C}$ 1445C will be used ($S_{14}=S_{14}c$). Then the number of treatments "N" is altered with the determined drinking habit modifying coefficient "$S_{14}$", and thus the new number of treatments becomes "O", which is now the updated number of treatments based on drinking habit 1446.

The questionnaire from FIG. 14E continues with the inquiry on comorbidities as osteomyelitis. Thus the inquiry for presence of osteomyelitis 1447 is displayed. If the answer is "Yes" then the osteomyelitis presence modifying coefficient $S_{15A}$ 1448A will be used ($S_{15}=S_{15A}$). If the answer is "No" then the osteomyelitis presence modifying coefficient $S_{15B}$ 1448B will be used ($S_{15}=S_{15B}$). Then the number of treatments "O" is altered with the determined osteomyelitis presence modifying coefficient "$S_{15}$", and thus the new number of treatments becomes "P", which is now the updated number of treatments based on presence of osteomyelitis 1449.

Figure 14F:
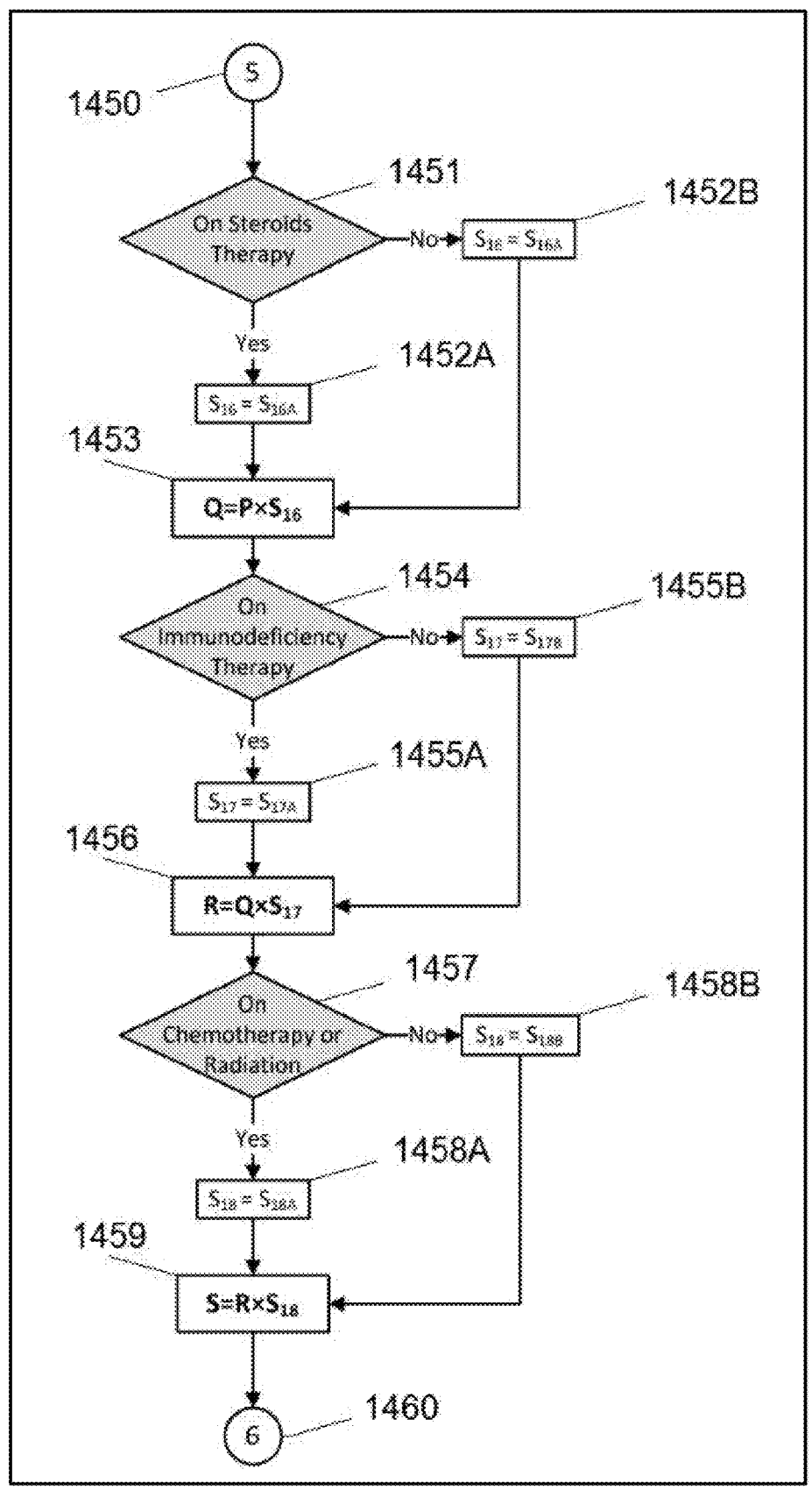
FIG. 14F is a flow diagram of the continuation of the algorithm presented in FIG. 14A, FIG. 14B, FIG. 14C, FIG. 14D, and FIG. 14E used to calculate the number of treatments with acoustic pressure shock waves for pressure ulcers, when patient possible steroids therapy, possible patient immunodeficiency therapy, and possible chemotherapy or radiation therapy are taken into account, according to one embodiment of the present invention.

The optimization continues on FIG. 14F and the continuation of the questionnaire flowchart from FIG. 14E to FIG. 14F is realized by the FIG. 14E to FIG. 14F connector 1450, which is seen on both FIG. 14E and FIG. 14F.

The questionnaire from FIG. 14F starts with the inquiry on steroids therapy. Thus the inquiry for steroids therapy 1451 is displayed. If the answer is "Yes" then the steroids therapy modifying coefficient $S_{16A}$ 1452A will be used ($S_{16}=S_{16A}$). If the answer is "No" then the steroids therapy modifying coefficient $S_{16B}$ 1452B will be used ($S_{16}=S_{16B}$). Then the number of treatments "P" is altered with the determined steroids therapy modifying coefficient "$S_{16}$", and thus the new number of treatments becomes "Q", which is now the updated number of treatments based on steroids therapy 1453.

The questionnaire from FIG. 14F continues with the inquiry on immunodeficiency therapy. Thus the inquiry for immunodeficiency therapy 1454 is displayed. If the answer is "Yes" then the immunodeficiency therapy modifying coefficient $S_{17A}$ 1455A will be used ($S_{17}=S_{17A}$). If the answer is "No" then the immunodeficiency therapy modifying coefficient $S_{17B}$ 1455B will be used ($S_{17}=S_{17B}$). Then the number of treatments "Q" is altered with the determined immunodeficiency therapy modifying coefficient "$S_{17}$", and thus the new number of treatments becomes "R", which is now the updated number of treatments based on immunodeficiency therapy 1456.

The questionnaire from FIG. 14F continues with the inquiry on chemotherapy or radiation therapy. Thus the inquiry for chemotherapy or radiation therapy 1457 is displayed. If the answer is "Yes" then the chemotherapy or radiation therapy modifying coefficient $S_{18A}$ 1458A will be used ($S_{18}=S_{18A}$). If the answer is "No" then the chemotherapy or radiation therapy modifying coefficient $S_{18B}$ 1458B will be used ($S_{18}=S_{18B}$). Then the number of treatments "R" is altered with the determined chemotherapy or radiation therapy modifying coefficient "$S_{18}$", and thus the new number of treatments becomes "S", which is now the updated number of treatments based on chemotherapy and radiation therapy 1459.

Figure 14G:
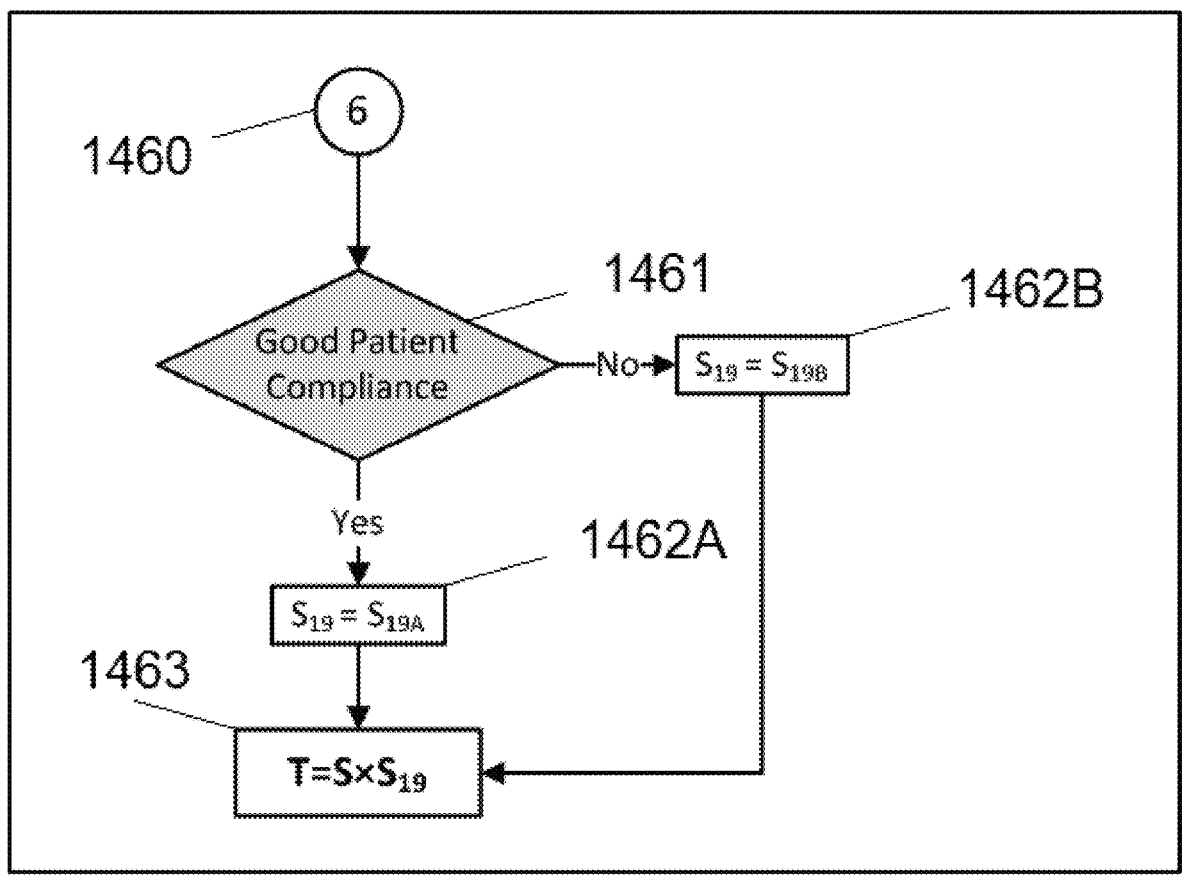
FIG. 14G is a flow diagram of the continuation of the algorithm presented in FIG. 14A, FIG. 14B, FIG. 14C, FIG. 14D, FIG. 14E, and FIG. 14F used to calculate the number of treatments with acoustic pressure shock waves for pressure ulcers, when the patient history of compliance to the treatment is taken into account, according to one embodiment of the present invention.

The optimization continues on FIG. 14G and the continuation of the questionnaire flowchart from FIG. 14F to FIG. 14G is realized by the FIG. 14F to FIG. 14G connector 1460, which is seen on both FIG. 14F and FIG. 14G.

The questionnaire from FIG. 14G starts with the inquiry on good patient compliance. Thus the inquiry for good patient compliance 1461 is displayed. If the answer is "Yes" then the patient compliance modifying coefficient $S_{19A}$ 1462A will be used ($S_{19}=S_{19A}$). If the answer is "No" then the patient compliance modifying coefficient $S_{19B}$ 1462B will be used ($S_{19}=S_{19B}$). Then the number of treatments "S" is altered with the determined patient compliance modifying coefficient "$S_{19}$", and thus the new number of treatments becomes "T", which is now the updated number of treatments based on patient compliance 1463.

In FIGS. 14A-14G the coefficients presented for pressure ulcers that can be used to adjust the number of treatments based on inquiries for patient's comorbidities, existing therapies, habits/lifestyle and wound status are defined with general ranges and also with more preferable ranges and sometimes as a specific number.

In FIGS. 14A-14G the values for the coefficients are preferably as follows:

In FIG. 14A, coefficient $S_{1A}$ is preferably 1.00, because patients with age under 40 should have a very good response to the acoustic pressure shock wave treatment.

In FIG. 14A, coefficient $S_{1B}$ may be in the range from about 1.00 to 1.02, and preferably from about 1.01 to 1.02.

In FIG. 14A, coefficient Sic may be in the range from about 1.00 to 1.03, and preferably from about 1.02 to 1.03.

In FIG. 14A, coefficient $S_{1D}$ may be in the range from about 1.00 to 1.04, and preferably from about 1.03 to 1.04.

In FIG. 14A, coefficient $S_{2A}$ may be in the range from about 1.00 to 1.02, and preferably from about 1.01 to 1.02.

In FIG. 14A, coefficient $S_{2B}$ may be in the range from about 1.00 to 1.03, and preferably from about 1.02 to 1.03.

In FIG. 14A, coefficient $S_{2C}$ may be in the range from about 1.01 to 1.03, and preferably from about 1.02 to 1.03.

In FIG. 14A, coefficient $S_{2D}$ may be in the range from about 1.01 to 1.04, and preferably from about 1.02 to 1.04.

In FIG. 14A, coefficient $S_{3A}$ is preferably 1.00, because patients with Stage I pressure ulcers should have a very good response to the acoustic pressure shock wave treatment.

In FIG. 14A, coefficient $S_{3B}$ for pressure ulcers may be in the range from about 1.01 to 1.03, and preferably from about 1.02 to 1.03.

In FIG. 14A, coefficient $S_{3C}$ for pressure ulcers may be in the range from about 1.02 to 1.04, and preferably from about 1.03 to 1.04.

In FIG. 14A, coefficient $S_{3D}$ for pressure ulcers may be in the range from about 1.03 to 1.05, and preferably from about 1.04 to 1.05.

In FIG. 14B, coefficient $S_{4A}$ is preferably 1.00, because patients with wound area less than 64 cm² have a very good response to the acoustic pressure shock wave treatment.

In FIG. 14B, coefficient $S_{4B}$ may be in the range from about 1.00 to 1.03, and preferably from about 1.01 to 1.02.

In FIG. 14B, coefficient $S_{4C}$ may be in the range from about 1.00 to 1.04, and preferably from about 1.02 to 1.03.

In FIG. 14B, coefficient $S_{5A}$ is preferably 1.00, because patients with very superficial wounds should have a very good response to the acoustic pressure shock wave treatment.

In FIG. 14B, coefficient $S_{5B}$ may be in the range from about 1.00 to 1.02, and preferably from about 1.01 to 1.02.

In FIG. 14B, coefficient $S_{5C}$ may be in the range from about 1.01 to 1.03, and preferably from about 1.02 to 1.03.

In FIG. 14B, coefficient $S_{5D}$ may be in the range from about 1.01 to 1.04, and preferably from about 1.03 to 1.04.

In FIG. 14B, coefficient $S_{6A}$ is preferably 1.00, because patients with a body mass index (BMI) below 32 should have a very good response to the acoustic pressure shock wave treatment and do not present any challenges from obesity point of view.

In FIG. 14B, coefficient $S_{6B}$ may be in the range from about 1.01 to 1.04, and preferably from about 1.02 to 1.04.

In FIG. 14C coefficient $S_{7A}$ is preferably 1.00, because patients with a weight below 220 lb/99.8 Kg should have a very good response to the acoustic pressure shock wave treatment and do not present any challenges from obesity point of view.

In FIG. 14C, coefficient $S_{7B}$ may be in the range from about 1.00 to 1.03, and preferably from about 1.01 to 1.02.

In FIG. 14C coefficient $S_{8A}$ is preferably 1.00 for a height below 70 in/177.8 cm.

In FIG. 14C, coefficient $S_{8B}$ may be in the range from about 1.00 to 1.02, and preferably from about 1.01 to 1.02.

In FIG. 14C, coefficient $S_{9A}$ is preferably 1.00, because patients with a HbA1c are controlling their diabetes and should have a very good response to the acoustic pressure shock wave treatment.

In FIG. 14C, coefficient $S_{9B}$ may be in the range from about 1.01 to 1.03, and preferably from about 1.02 to 1.03.

In FIG. 14C, coefficient $S_{9C}$ may be in the range from about 1.01 to 1.04, and preferably from about 1.03 to 1.04.

In FIG. 14D coefficient $S_{10A}$ is preferably 1.00 for a new wound and not a recurrent wound.

In FIG. 14D, coefficient $S_{10B}$ may be in the range from about 1.00 to 1.03, and preferably from about 1.01 to 1.02.

In FIG. 14D coefficient $S_{11A}$ is preferably 1.00 for a wound that is less than 6 month old.

In FIG. 14D, coefficient $S_{11B}$ may be in the range from about 1.00 to 1.04, and preferably from about 1.02 to 1.04.

In FIG. 14D, coefficient $S_{12A}$ is preferably 1.00, because patients with a colony forming units (CFU) of bacteria less than 1000 in the skin lesion should have a very good response to the acoustic pressure shock wave treatment.

In FIG. 14D, coefficient $S_{12B}$ may be in the range from about 1.01 to 1.04, and preferably from about 1.02 to 1.03.

In FIG. 14D, coefficient $S_{12C}$ may be in the range from about 1.02 to 1.05, and preferably from about 1.03 to 1.04.

In FIG. 14E coefficient $S_{13A}$ is preferably 1.00 because a non-smoker should have a very good response to the acoustic pressure shock wave treatment.

In FIG. 14E, coefficient $S_{13B}$ may be in the range from about 1.00 to 1.03, and preferably from about 1.01 to 1.02.

In FIG. 14E, coefficient $S_{14A}$ is preferably 1.00, because occasional drinking patients should have a very good response to the acoustic pressure shock wave treatment.

In FIG. 14E, coefficient $S_{14B}$ may be in the range from about 1.01 to 1.03, and preferably from about 1.02 to 1.03.

In FIG. 14E, coefficient $S_{14C}$ may be in the range from about 1.02 to 1.04, and preferably from about 1.02 to 1.04.

In FIG. 14E, coefficient $S_{15A}$ may be in the range from about 1.00 to 1.04, and preferably from about 1.01 to 1.03.

In FIG. 14E coefficient $S_{15B}$ is preferably 1.00 because a patient without osteomyelitis should have a very good response to the acoustic pressure shock wave treatment.

In FIG. 14F, coefficient $S_{16A}$ may be in the range from about 1.00 to 1.03, and preferably from about 1.01 to 1.02.

In FIG. 14F coefficient $S_{16B}$ is preferably 1.00 because a patient that is not on steroids therapy should have a very good response to the acoustic pressure shock wave treatment.

In FIG. 14F, coefficient $S_{17A}$ may be in the range from about 1.00 to 1.03, and preferably from about 1.01 to 1.02.

In FIG. 14F coefficient $S_{17B}$ is preferably 1.00 because a patient that is not on immunodeficiency therapy should have a very good response to the acoustic pressure shock wave treatment.

In FIG. 14F, coefficient $S_{18A}$ may be in the range from about 1.01 to 1.04, and preferably from about 1.02 to 1.04.

In FIG. 14F coefficient $S_{18B}$ is preferably 1.00 because a patient that is not on chemotherapy or radiation therapy should have a very good response to the acoustic pressure shock wave treatment.

In FIG. 14G coefficient $S_{19A}$ is preferably 1.00 because a patient with a history of compliance to treatments should have a very good response to the acoustic pressure shock wave treatment.

In FIG. 14G, coefficient $S_{19B}$ may be in the range from about 1.00 to 1.03, and preferably from about 1.01 to 1.02.

A control console/unit 22 and associated acoustic pressure shock wave applicator/treatment apparatus 10 (see FIG. 2A) used for delivering a treatment for pressure ulcers by means of the proposed adjustment algorithm for number of treatments from FIGS. 14A-14G will use the following formula (where A is the initial number of treatments with focused acoustic pressure shock waves 40 or radial acoustic pressure waves 41 or planar acoustic pressure waves 42 or cylindrical acoustic pressure waves 44 and ANTT is the Adjusted Number of Total Treatments):

$$ANTT = A \cdot S_1 \cdot S_2 \cdot S_3 \cdot S_4 \cdot S_5 \cdot S_6 \cdot S_7 \cdot S_8 \cdot S_9 \cdot S_{10} \cdot S_{11} \cdot S_{12} \cdot S_{13} \cdot S_{14} \cdot S_{15} \cdot S_{16} \cdot S_{17} \cdot S_{18} \cdot S_{19}.$$

For the largest values for these coefficients (worst situation) and for example a number of A=8 treatments is used as the initial number of treatments with focused acoustic pressure shock waves 40 or radial acoustic pressure waves 41 or planar acoustic pressure waves 42 or cylindrical acoustic pressure waves 44 that are minimally needed for successful treatment of the tissue condition 19, then the Adjusted Number of Total Treatments (ANTT) value is the following:

$$ANTT = 8 \cdot 1.03 \cdot 1.04 \cdot 1.05 \cdot 1.04 \cdot 1.03 \cdot 1.04 \cdot 1.03 \cdot 1.02 \cdot 1.04 \cdot 1.03 \cdot 1.04 \cdot 1.05 \cdot 1.03 \cdot 1.04 \cdot 1.04 \cdot 1.03 \cdot 1.03 \cdot 1.04 \cdot 1.03 = 15.60 = 16$$
treatments for pressure ulcers.

The personalized number of treatments for burn wounds when focused acoustic pressure shock waves 40 or radial acoustic pressure waves 41 or planar acoustic pressure waves 42 or cylindrical acoustic pressure waves 44 are used can be determined using different factors in other embodiments of the invention. FIGS. 15A-15G present another embodiment of the invention that uses a preferable algorithm that can be used to adjust the number of treatments used for burn wounds based on different elements that take into account the characteristics/status of the burn wounds, and patient's comorbidities, existing therapies, and habits/lifestyle.

As a starting point for the algorithm used to personalize/adjust the number of treatments using focused acoustic pressure shock waves 40 or radial acoustic pressure waves 41 or planar acoustic pressure waves 42 or cylindrical acoustic pressure waves 44 for burn wounds is the basic/initial number of treatments that are minimally needed for successful treatment of the tissue condition 19.

Figure 15A:
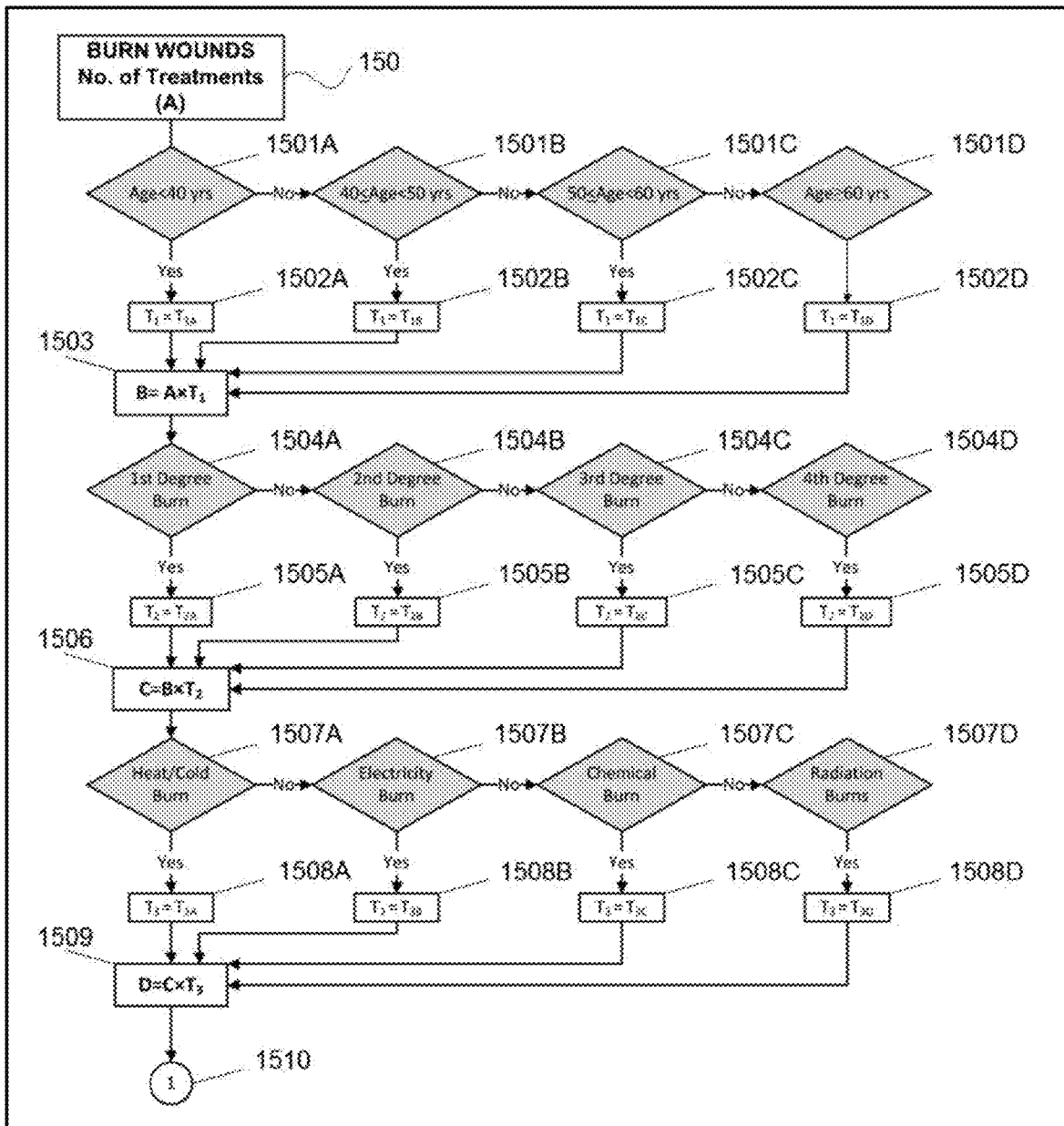
FIG. 15A is a flow diagram of the algorithm used to calculate the number of treatments with acoustic pressure shock waves for burns when patient age, degree of burn, and type of burn are taken into account, according to one embodiment of the present invention.

In FIG. 15A the basic/initial number of treatments for burn wounds 150 represents the starting point of the adjustment/optimization algorithm for number of treatments using focused acoustic pressure shock waves 40 or radial acoustic pressure waves 41 or planar acoustic pressure waves 42 or cylindrical acoustic pressure waves 44 for the treatment of burn wounds. The first element used to alter the basic/initial number of treatments used for burn wounds treatment is the inquiry regarding the age of the patient. Thus on the control console/unit display 2220, or artificial intelligence (A/I) device display 2740, or on the display of an interconnected device (see FIG. 2A for the medical treatment system 2000) as a desktop computer 28A, or a smart phone 28B, and/or tablet 28C, and/or laptop 28D is first displayed the inquiry for age less than 40 years 1501A. If the answer is "Yes" then the age modifying coefficient $T_{1A}$ 1502A will be used ($T_1 = T_{1A}$). If the answer is "No", the inquiry for age between 40 and 50 years 1501B is displayed. If the answer is "Yes" then the age modifying coefficient $T_{1B}$ 1502B will be used ($T_1 = T_{1B}$). If the answer is "No", the inquiry for age between 50 and 60 years 1501C is displayed. If the answer is "Yes" then the age modifying coefficient $T_{1C}$ 1502C will be used ($T_1 = T_{1C}$). If the answer is "No", the inquiry for age older than 60 years 1501D is displayed and if the answer is "Yes" then the age modifying coefficient $T_{1D}$ 1502D will be used ($T_1 = T_{1D}$). Then the basic/initial number of treatments "A" is altered with the determined age modifying coefficient "$T_1$", and thus the new number of treatments becomes "B", which is now the updated number of treatments based on age 1503.

The questionnaire from FIG. 15A continues with the inquiry on the degree of burn. Thus the inquiry for first degree burn 1504A is displayed. If the answer is "Yes" then the degree of burn modifying coefficient $T_{2A}$ 1505A will be used ($T_2 = T_{2A}$). If the answer is "No", the inquiry for second degree burn 1504B is displayed. If the answer is "Yes" then the degree of burn modifying coefficient $T_{2B}$ 1505B will be used ($T_2 = T_{2B}$). If the answer is "No", the inquiry for third degree burn 1504C is displayed. If the answer is "Yes" then the degree of burn modifying coefficient $T_{2C}$ 1505C will be used ($T_2 = T_{2C}$). If the answer is "No", the inquiry for fourth degree burn 1504D is displayed and if the answer is "Yes" then the degree of burn modifying coefficient $T_{2D}$ 1505D will be used ($T_2 = T_{2D}$). Then the number of treatments "B" is altered with the determined degree of burn modifying coefficient "$T_2$", and thus the new number of treatments becomes "C", which is now the updated number of treatments based on degree of burn 1506.

The questionnaire from FIG. 15A continues with the inquiry on the cause of burn. Thus the inquiry for heat/cold burn 1507A is displayed. If the answer is "Yes" then the cause of burn modifying coefficient $T_{3A}$ 1508A will be used ($T_3 = T_{3A}$). If the answer is "No", the inquiry for electricity burn 1507B is displayed. If the answer is "Yes" then the cause of burn modifying coefficient $T_{3B}$ 1508B will be used ($T_3 = T_{3B}$). If the answer is "No", the inquiry for chemical burn 1507C is displayed. If the answer is "Yes" then the cause of burn modifying coefficient $T_{3C}$ 1508C will be used ($T_3 = T_{3C}$). If the answer is "No", the inquiry for radiation burn 1507D is displayed and if the answer is "Yes" then the cause of burn modifying coefficient $T_{3D}$ 1508D will be used ($T_3 = T_{3D}$). Then the number of treatments "C" is altered with the determined cause of burn modifying coefficient "$T_3$", and thus the new number of treatments becomes "D", which is now the updated number of treatments based on cause of burn 1509.

Figure 15B:
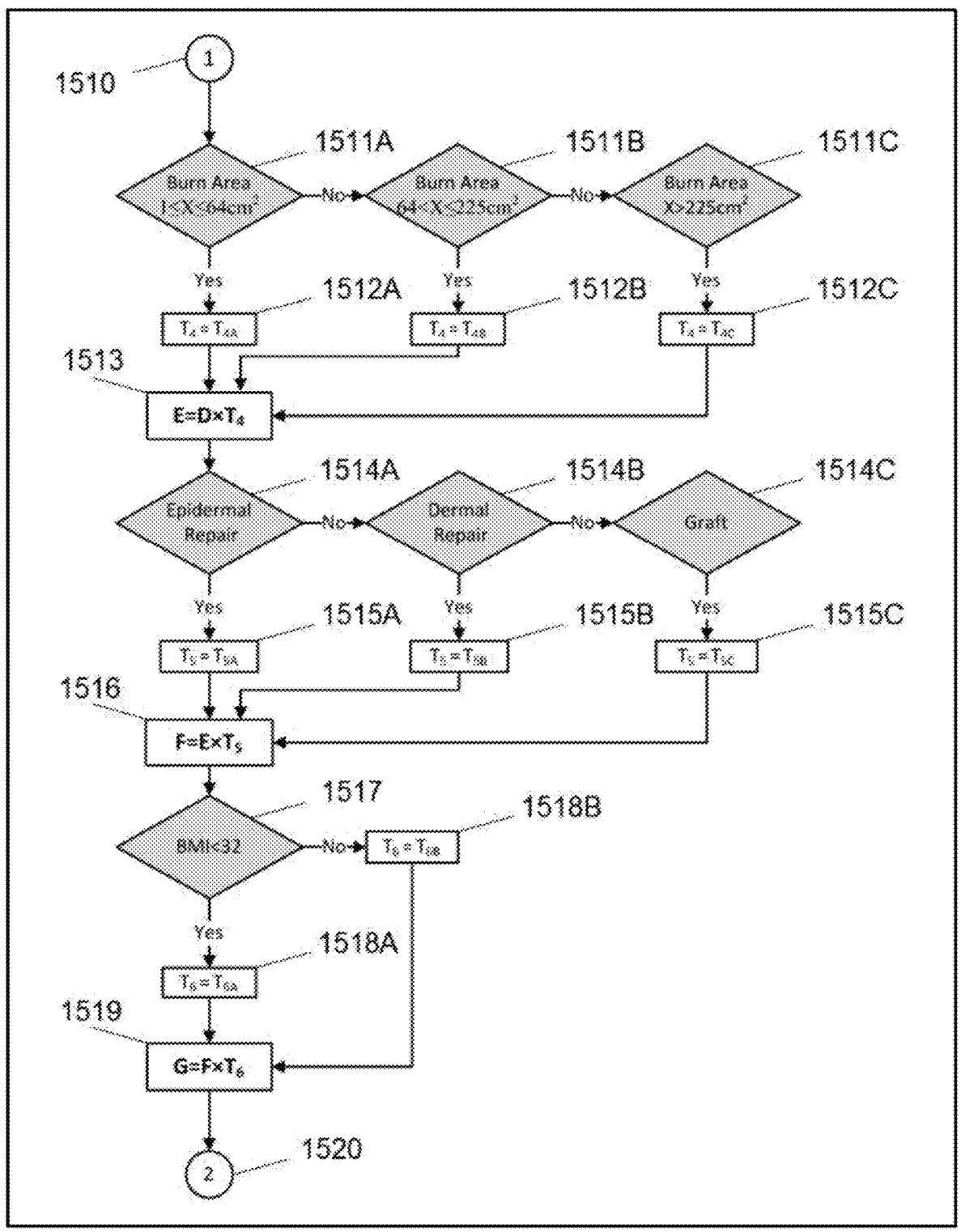
FIG. 15B is a flow diagram of the continuation of the algorithm presented in FIG. 15A used to calculate the number of treatments with acoustic pressure shock waves for burns, when burn area, type of repair treatment approach, and body mass index (BMI) are taken into account, according to one embodiment of the present invention.

The optimization continues on FIG. 15B and the continuation of the questionnaire flowchart from FIG. 15A to FIG. 15B is realized by the FIG. 15A to FIG. 15B connector 1510, which is seen on both FIG. 15A and FIG. 15B.

The questionnaire from FIG. 15B starts with the inquiry on the value for burn wound area. Thus the inquiry for burn area between 1 and 64 cm² 1511A is displayed. If the answer is "Yes" then the wound area modifying coefficient $T_{4A}$ 1512A will be used ($T_4=T_{4A}$). If the answer is "No", the inquiry for wound area between 64 and 225 cm² 1511B is displayed. If the answer is "Yes" then the wound area modifying coefficient $T_{4B}$ 1512B will be used ($T_4=T_{4B}$). If the answer is "No", the inquiry for wound area larger than 225 cm² 1511C is displayed. If the answer is "Yes" then the wound area modifying coefficient $T_{4C}$ 1512C will be used ($T_4=T_{4C}$). Then the number of treatments "D" is altered with the determined value for wound area modifying coefficient "$T_4$", and thus the new number of treatments becomes "E", which is now the updated number of treatments based on wound area 1513.

The questionnaire from FIG. 15B continues with the inquiry on the tissue repair needed after burn injury. Thus the inquiry for epidermal repair needed 1514A is displayed. If the answer is "Yes" then the extend of tissue repair modifying coefficient $T_{5A}$ 1515A will be used ($T_5=T_{5A}$). If the answer is "No", the inquiry for dermal repair needed 1514B is displayed. If the answer is "Yes" then the extend of tissue repair modifying coefficient $T_{5B}$ 1515B will be used ($T_5=T_{5B}$). If the answer is "No", the inquiry for graft needed 1514C is displayed. If the answer is "Yes" then the extend of tissue repair modifying coefficient $T_{8C}$ 1515C will be used ($T_5=T_{5C}$). Then the number of treatments "E" is altered with the determined tissue repair modifying coefficient "$T_5$", and thus the new number of treatments becomes "F", which is now the updated number of treatments based on tissue repair needed 1516.

The questionnaire from FIG. 15B continues with the inquiry on the body mass index (BMI). Thus the inquiry for body mass index (BMI) value 1517 is displayed (BMI<32). If the answer is "Yes" then the body mass index (BMI) modifying coefficient $T_{6A}$ 1518A will be used ($T_6=T_{6A}$). If the answer is "No" then the body mass index (BMI) modifying coefficient $T_{6B}$ 1518B will be used ($T_6=T_{6B}$). Then the number of treatments "F" is altered with the determined body mass index (BMI) modifying coefficient "$T_6$", and thus the new number of treatments becomes "G", which is now the updated number of treatments based on obesity 1519.

Figure 15C:
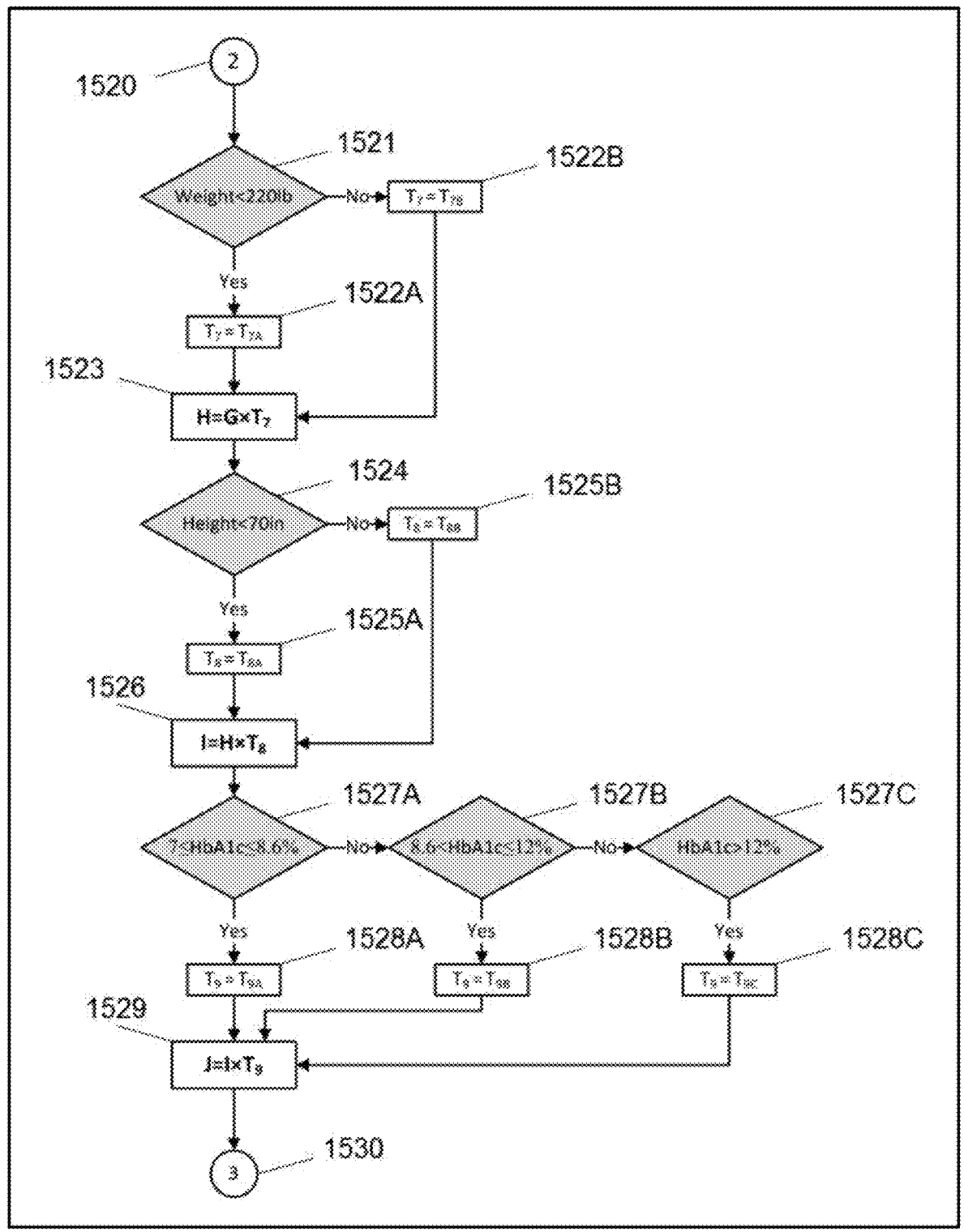
FIG. 15C is a flow diagram of the continuation of the algorithm presented in FIG. 15A and FIG. 15B used to calculate the number of treatments with acoustic pressure shock waves for burns, when patient weight, patient height, and glycosylated hemoglobin A1c (HbA1c) are taken into account, according to one embodiment of the present invention.

The optimization continues on FIG. 15C and the continuation of the questionnaire flowchart from FIG. 15B to FIG. 15C is realized by the FIG. 15B to FIG. 15C connector 1520, which is seen on both FIG. 15B and FIG. 15C.

The questionnaire from FIG. 15C starts with the inquiry on the patient's weight. Thus the inquiry for weight value 1521 is displayed (Weight<220 lb which is 99.8 Kg in metric system). If the answer is "Yes" then the weight modifying coefficient $T_{7A}$ 1522A will be used ($T_7=T_{7A}$). If the answer is "No" then the weight modifying coefficient $T_{7B}$ 1522B will be used ($T_7=T_{7B}$). Then the number of treatments "G" is altered with the determined weight modifying coefficient "$T_7$", and thus the new number of treatments becomes "H", which is now the updated number of treatments based on weight 1523.

The questionnaire from FIG. 15C continues with the inquiry on the patient's height. Thus the inquiry for inquiry for height value 1524 is displayed (Height<70 in which is 177.8 cm in metric system). If the answer is "Yes" then the height modifying coefficient $T_{8A}$ 1525A will be used ($T_8=T_{8A}$). If the answer is "No" then the height modifying coefficient $T_{8B}$ 1525B will be used ($T_8=T_{8B}$). Then the number of treatments "H" is altered with the determined height modifying coefficient "$T_8$", and thus the new number of treatments becomes "I", which is now the updated number of treatments based on height 1526.

The questionnaire from FIG. 15C continues with the inquiry on the value for glycated hemoglobin (HbA1c), which is an indication of diabetes presence. Thus the inquiry for glycated hemoglobin (HbA1c) between 7 and 8.6% 1527A is displayed. If the answer is "Yes" then the HbA1c modifying coefficient $T_{9A}$ 1528A will be used ($T_9=T_{9A}$). If the answer is "No", the inquiry for glycated hemoglobin (HbA1c) between 8.6 and 12% 1527B is displayed. If the answer is "Yes" then the HbA1c modifying coefficient $T_{9B}$ 1528B will be used ($T_9=T_{9B}$). If the answer is "No", the inquiry for glycated hemoglobin (HbA1c) larger than 12% 1527C is displayed. If the answer is "Yes" then the HbA1c modifying coefficient $T_{9C}$ 1528C will be used ($T_9=T_{9C}$). Then the number of treatments "I" is altered with the determined HbA1c modifying coefficient "$T_9$", and thus the new number of treatments becomes "J", which is now the updated number of treatments based on diabetes presence 1529.

Figure 15D:
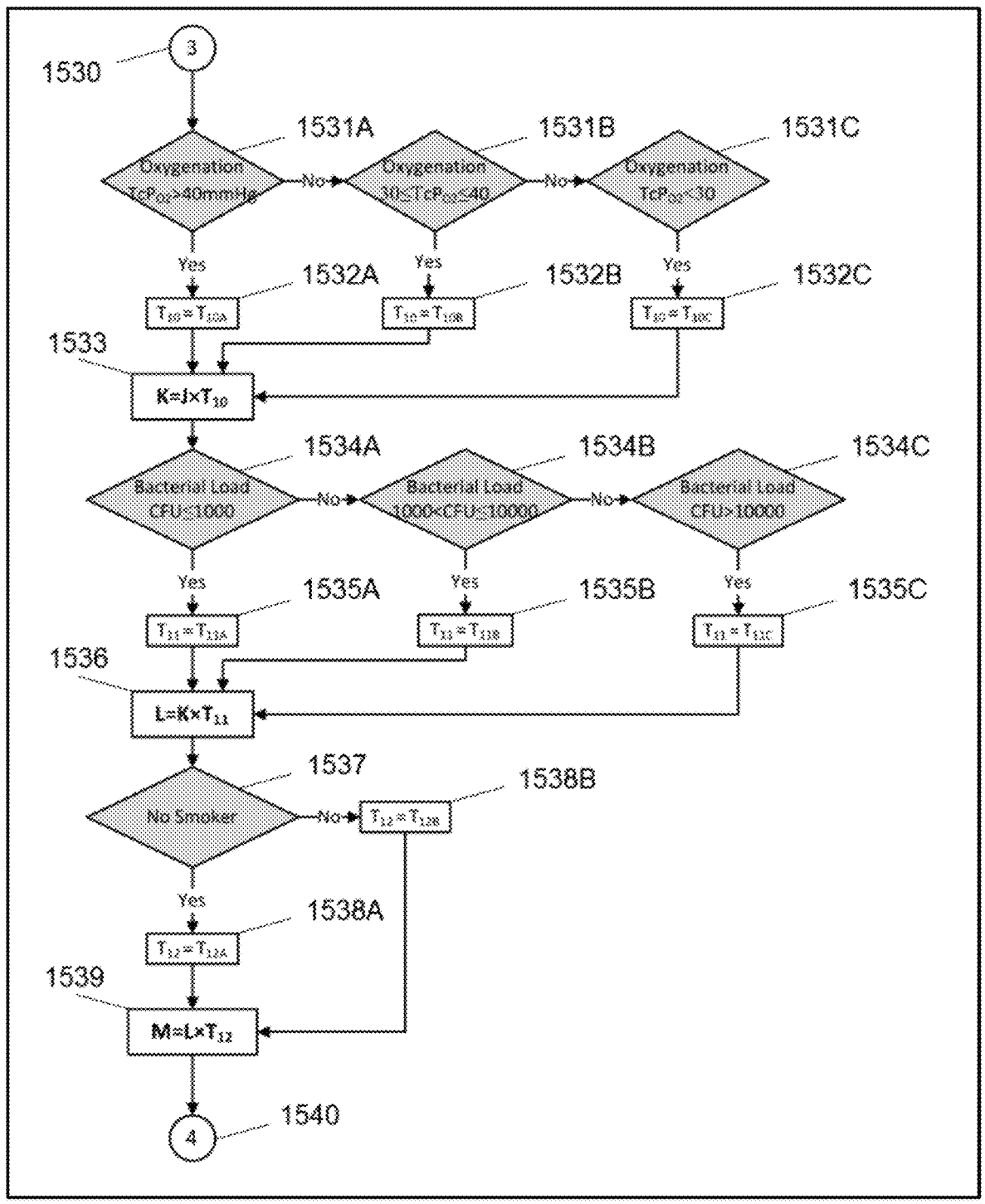
FIG. 15D presents the continuation of the algorithm presented in FIG. 15A, FIG. 15B, and FIG. 15C used to calculate the number of treatments with acoustic pressure shock waves for burns, when burn area oxygenation ($T_cP_{O2}$-Transcutaneous Partial Pressure of Oxygen), bacterial load, and smoker status are taken into account, according to one embodiment of the present invention.

The optimization continues on FIG. 15D and the continuation of the questionnaire flowchart from FIG. 15C to FIG. 15D is realized by the FIG. 15C to FIG. 15D connector 1530, which is seen on both FIG. 15C and FIG. 15D.

The questionnaire from FIG. 15D starts with the inquiry on transcutaneous monitoring of oxygen ($T_cP_{O2}$), which is an indication on oxygenation of the wound. Thus the inquiry for transcutaneous monitoring of oxygen ($TcP_{O2}$) greater than 40 mmHg 1531A is displayed. If the answer is "Yes" then the $TcP_{O2}$ modifying coefficient $T_{10A}$ 1532A will be used ($T_{10}=T_{10A}$). If the answer is "No", the inquiry for transcutaneous monitoring of oxygen ($TcP_{O2}$) between 30 and 40 mmHg 1531B is displayed. If the answer is "Yes" then the $TcP_{O2}$ modifying coefficient $T_{10B}$ 1532B will be used ($T_{10}=T_{10B}$). If the answer is "No", the inquiry for transcutaneous monitoring of oxygen ($TcP_{O2}$) less than 30 mmHg 1531C is displayed. If the answer is "Yes" then the $TcP_{O2}$ modifying coefficient $T_{10C}$ 1532C will be used ($T_{10}=T_{10C}$). Then the number of treatments "J" is altered with the determined transcutaneous monitoring of oxygen ($TcP_{O2}$) modifying coefficient "$T_{10}$", and thus the new number of treatments becomes "K", which is now the updated number of treatments based on tissue oxygenation 1533.

The questionnaire from FIG. 15D continues with the inquiry on bacterial colony forming units (CFU), which is an indication of bacterial load of the wound. Thus the inquiry for bacterial colony forming units (CFU) less than 1000 units 1534A is displayed. If the answer is "Yes" then the CFU modifying coefficient $T_{11A}$ 1535A will be used ($T_{11}=T_{11A}$). If the answer is "No", the inquiry for bacterial colony forming units (CFU) between 1000 and 10000 units 1534B is displayed. If the answer is "Yes" then the CFU modifying coefficient $T_{11B}$ 1535B will be used ($T_{11}=T_{11B}$). If the answer is "No", the inquiry for bacterial colony forming units (CFU) greater than 10000 units 1534C is displayed. If the answer is "Yes" then the CFU modifying coefficient $T_{11C}$ 1535C will be used ($T_{11}=T_{11C}$). Then the number of treatments "K" is altered with the determined CFU modifying coefficient "$T_{11}$", and thus the new number of treatments becomes "L", which is now the updated number of treatments based on bacterial load 1536.

The questionnaire from FIG. 15D continues with the inquiry on smoking status. Thus the inquiry for smoking status 1537 is displayed. If the answer is "Yes" then the smoking status modifying coefficient $T_{12A}$ 1538A will be used ($T_{12}=T_{12A}$). If the answer is "No" then the smoking status modifying coefficient $T_{12B}$ 1538B will be used ($T_{12}=T_{12B}$). Then the number of treatments "L" is altered with the determined smoking status modifying coefficient "$T_{12}$", and thus the new number of treatments becomes "M", which is now the updated number of treatments based on smoking status 1539.

Figure 15E:
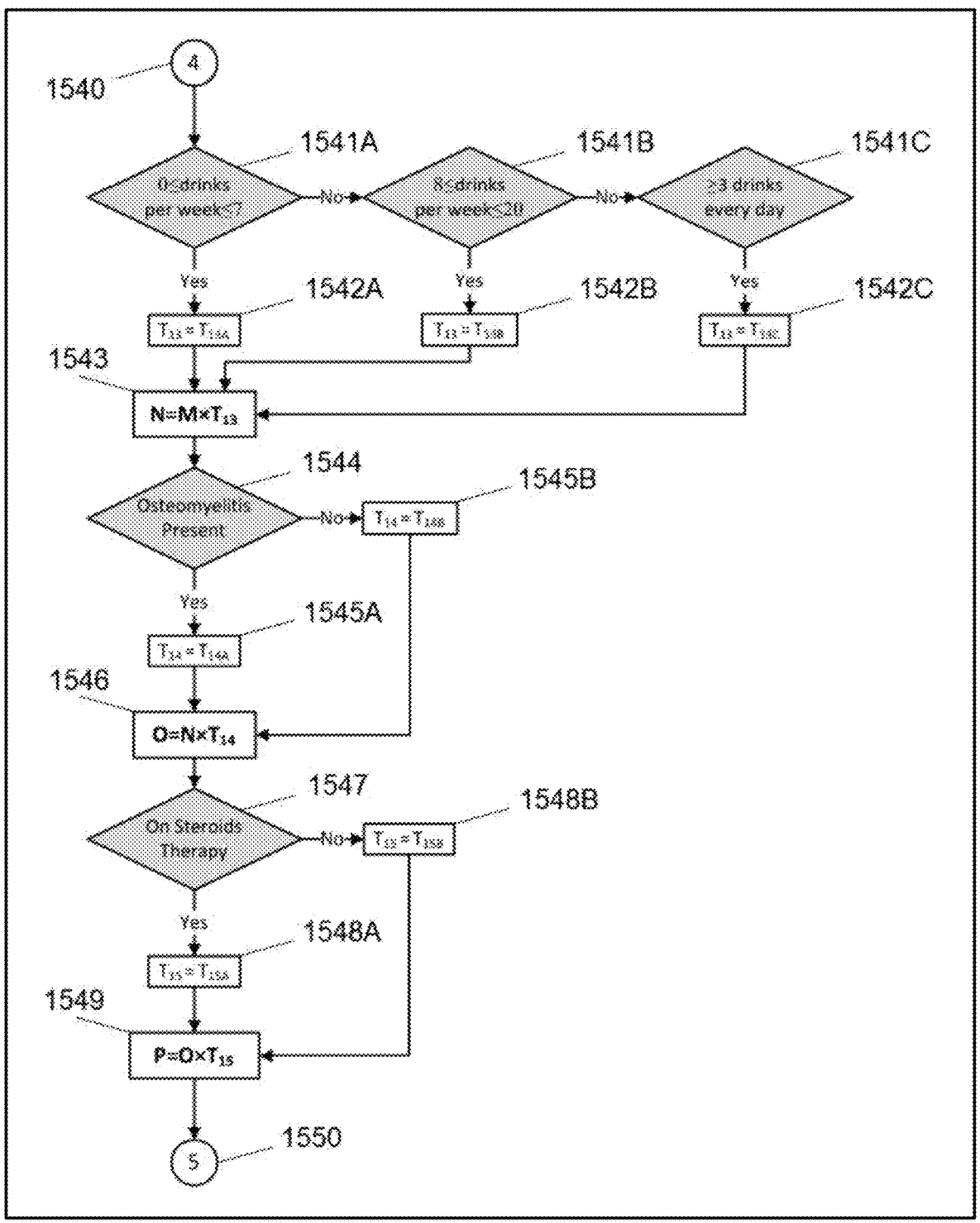
FIG. 15E is a flow diagram of the continuation of the algorithm presented in FIG. 15A, FIG. 15B, FIG. 15C, and FIG. 15D used to calculate the number of treatments with acoustic pressure shock waves for burns, when alcohol consumption rate, presence of bone osteomyelitis, and patient possible steroids therapy are taken into account, according to one embodiment of the present invention.

The optimization continues on FIG. 15E and the continuation of the questionnaire flowchart from FIG. 15D to FIG. 15E is realized by the FIG. 15D to FIG. 15E connector 1540, which is seen on both FIG. 15D and FIG. 15E.

The questionnaire from FIG. 15E starts with the inquiry on drinking habit, which is indicated by the number of drinks over a certain period of time. Thus the inquiry for drinks less than 7 per week 1541A is displayed. If the answer is "Yes" then the drinking habit modifying coefficient $T_{13A}$ 1542A will be used ($T_{13}=T_{13A}$). If the answer is "No", the inquiry for drinks between 8 and 20 per week 1541B is displayed. If the answer is "Yes" then the drinking habit modifying coefficient $T_{13B}$ 1542B will be used ($T_{13}=T_{13B}$). If the answer is "No", the inquiry for drinks greater than 3 every day 1541C is displayed. If the answer is "Yes" then the drinking habit modifying coefficient $T_{13C}$ 1542C will be used ($T_{13}=T_{13C}$). Then the number of treatments "M" is altered with the determined drinking habit modifying coefficient "$T_{13}$", and thus the new number of treatments becomes "N", which is now the updated number of treatments based on drinking habit 1543.

The questionnaire from FIG. 15E continues with the inquiry on comorbidities as osteomyelitis. Thus the inquiry for presence of osteomyelitis 1544 is displayed. If the answer is "Yes" then the osteomyelitis presence modifying coefficient $T_{14A}$ 1545A will be used ($T_{14}=T_{14A}$). If the answer is "No" then the osteomyelitis presence modifying coefficient $T_{14B}$ 1545B will be used ($T_{14}=T_{14B}$). Then the number of treatments "N" is altered with the determined osteomyelitis presence modifying coefficient "$T_{14}$", and thus the new number of treatments becomes "O", which is now the updated number of treatments based on presence of osteomyelitis 1546.

The questionnaire from FIG. 15E continues with the inquiry on steroids therapy. Thus the inquiry for steroids therapy 1547 is displayed. If the answer is "Yes" then the steroids therapy modifying coefficient $T_{15A}$ 1548A will be used ($T_{15}=T_{15A}$). If the answer is "No" then the steroids therapy modifying coefficient $T_{15B}$ 1548B will be used ($T_{15}=T_{15B}$). Then the number of treatments "O" is altered with the determined steroids therapy modifying coefficient "$T_{15}$", and thus the new number of treatments becomes "P", which is now the updated number of treatments based on steroids therapy 1549.

Figure 15F:
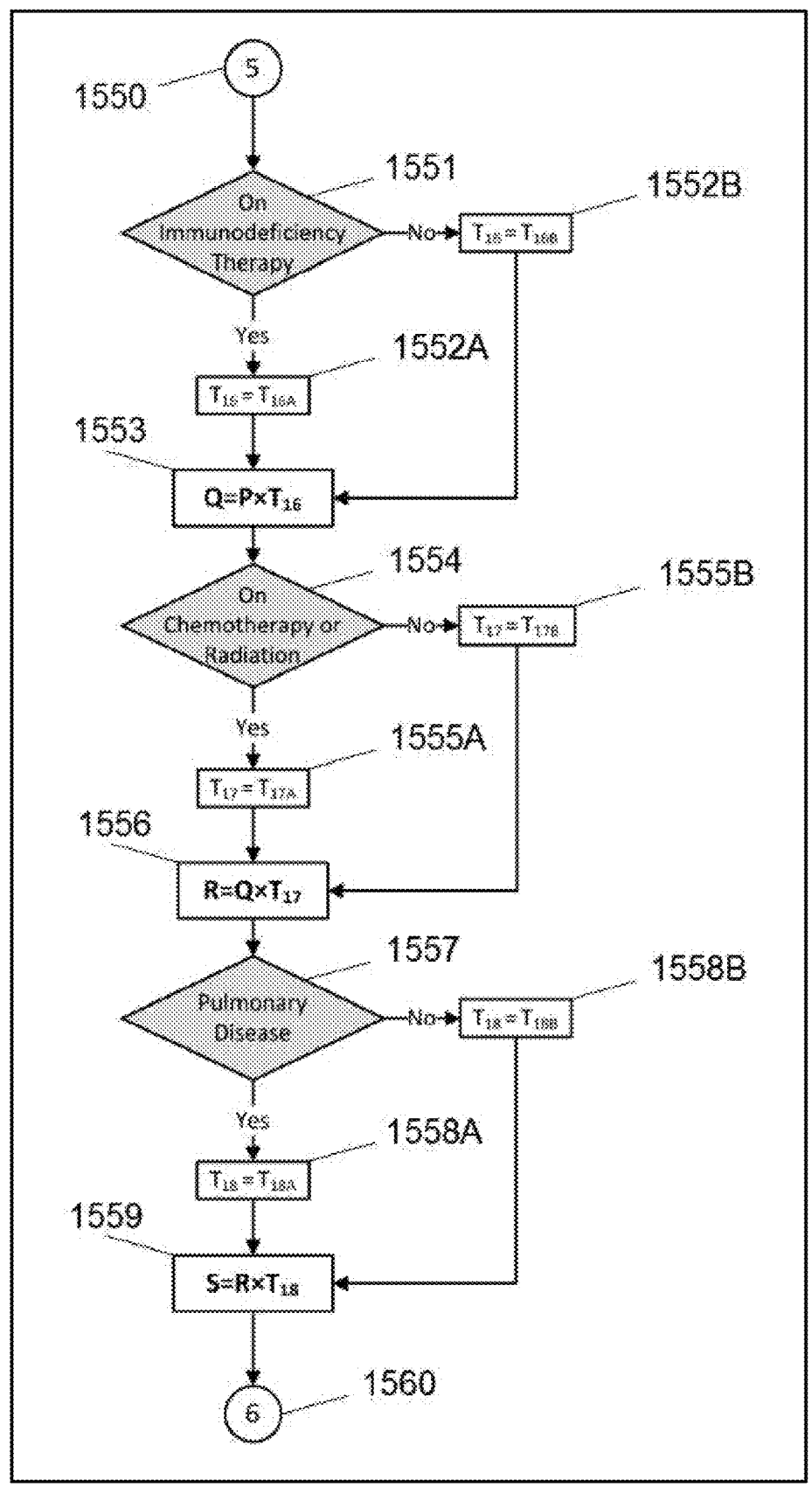
FIG. 15F is a flow diagram of the continuation of the algorithm presented in FIG. 15A, FIG. 15B, FIG. 15C, FIG. 15D, and FIG. 15E used to calculate the number of treatments with acoustic pressure shock waves for burns, when possible patient immunodeficiency therapy, possible chemotherapy or radiation therapy, and patient's possible pulmonary disease are taken into account, according to one embodiment of the present invention.

The optimization continues on FIG. 15F and the continuation of the questionnaire flowchart from FIG. 15E to FIG. 15F is realized by the FIG. 15E to FIG. 15F connector 1550, which is seen on both FIG. 15E and FIG. 15F.

The questionnaire from FIG. 15F starts with the inquiry on immunodeficiency therapy. Thus the inquiry for immunodeficiency therapy 1551 is displayed. If the answer is "Yes" then the immunodeficiency therapy modifying coefficient $T_{16A}$ 1552A will be used ($T_{16}=T_{16A}$). If the answer is "No" then the immunodeficiency therapy modifying coefficient $T_{16B}$ 1552B will be used ($T_{16}=T_{16B}$). Then the number of treatments "P" is altered with the determined immunodeficiency therapy modifying coefficient "$T_{16}$", and thus the new number of treatments becomes "Q", which is now the updated number of treatments based on immunodeficiency therapy 1553.

The questionnaire from FIG. 15F continues with the inquiry on chemotherapy or radiation therapy. Thus the inquiry for chemotherapy or radiation therapy 1554 is displayed. If the answer is "Yes" then the chemotherapy or radiation therapy modifying coefficient $T_{17A}$ 1555A will be used ($T_{17}=T_{17A}$). If the answer is "No" then the chemotherapy or radiation therapy modifying coefficient $T_{17B}$ 1555B will be used ($T_{17}=T_{17B}$). Then the number of treatments "Q" is altered with the determined chemotherapy or radiation therapy modifying coefficient "$T_{17}$", and thus the new number of treatments becomes "R", which is now the updated number of treatments based on chemotherapy and radiation therapy 1556.

The questionnaire from FIG. 15F continues with the inquiry on pulmonary disease. Thus the inquiry for pulmonary disease 1557 is displayed. If the answer is "Yes" then the pulmonary disease modifying coefficient $T_{18A}$ 1558A will be used ($T_{18}=T_{18A}$). If the answer is "No" then the pulmonary disease modifying coefficient $T_{18B}$ 1558B will be used ($T_{18}=T_{18B}$). Then the number of treatments "R" is altered with the determined pulmonary disease modifying coefficient "$T_{18}$", and thus the new number of treatments becomes "S", which is now the updated number of treatments based on pulmonary disease 1559.

Figure 15G:
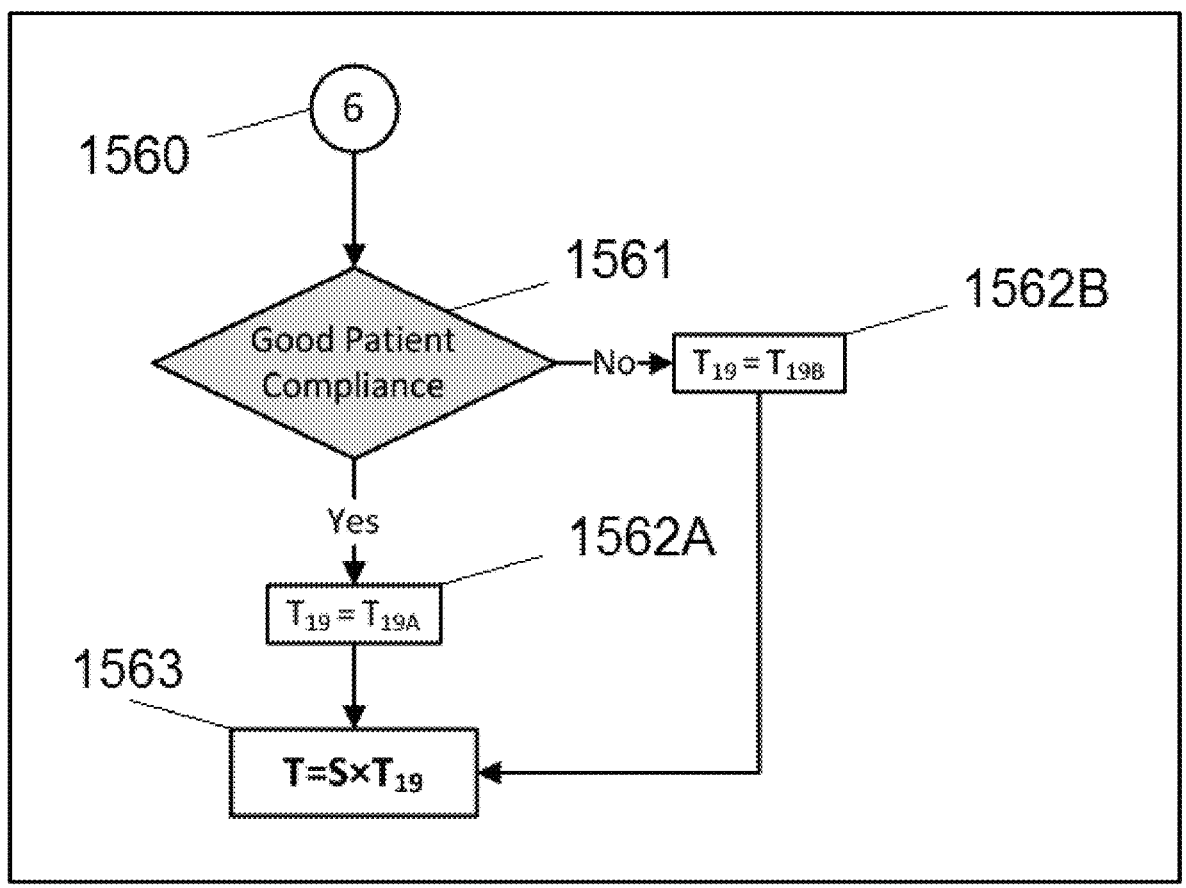
FIG. 15G is a flow diagram of the continuation of the algorithm presented in FIG. 15A, FIG. 15B, FIG. 15C, FIG. 15D, FIG. 15E, and FIG. 15F used to calculate the number of treatments with acoustic pressure shock waves for burns, when patient history of compliance to the treatment is taken into account, according to one embodiment of the present invention.

The optimization continues on FIG. 15G and the continuation of the questionnaire flowchart from FIG. 15F to FIG. 15G is realized by the FIG. 15F to FIG. 15G connector 1560, which is seen on both FIG. 15F and FIG. 15G.

The questionnaire from FIG. 15G starts with the inquiry on good patient compliance. Thus the inquiry for good patient compliance 1561 is displayed. If the answer is "Yes" then the patient compliance modifying coefficient $T_{19A}$ 1562A will be used ($T_{19}=T_{19A}$). If the answer is "No" then the patient compliance modifying coefficient $T_{19B}$ 1562B will be used ($T_{19}=T_{19B}$). Then the number of treatments "S" is altered with the determined patient compliance modifying coefficient "$T_{19}$", and thus the new number of treatments becomes "T", which is now the updated number of treatments based on patient compliance 1563.

In FIGS. 15A-15G the coefficients presented for burn wounds that can be used to adjust the number of treatments based on inquiries for patient's comorbidities, existing therapies, habits/lifestyle and wound status are defined with general ranges and also with more preferable ranges and sometimes as a specific number.

In FIGS. 15A-15G the values for the coefficients are preferably as follows:

In FIG. 15A, coefficient $T_{1A}$ is preferably 1.00, because patients with age under 40 should have a very good response to the acoustic pressure shock wave treatment.

In FIG. 15A, coefficient $T_{1B}$ may be in the range from about 1.00 to 1.02, and preferably from about 1.01 to 1.02.

In FIG. 15A, coefficient $T_{1C}$ may be in the range from about 1.00 to 1.03, and preferably from about 1.02 to 1.03.

In FIG. 15A, coefficient $T_{1D}$ may be in the range from about 1.00 to 1.04, and preferably from about 1.03 to 1.04.

In FIG. 15A, coefficient $T_{2A}$ may be in the range from about 1.00 to 1.03, and preferably from about 1.02 to 1.03.

In FIG. 15A, coefficient $T_{2B}$ may be in the range from about 1.01 to 1.04, and preferably from about 1.03 to 1.04.

In FIG. 15A, coefficient $T_{2C}$ may be in the range from about 1.02 to 1.05, and preferably from about 1.03 to 1.06.

In FIG. 15A, coefficient $T_{2D}$ may be in the range from about 1.02 to 1.06, and preferably from about 1.03 to 1.05.

In FIG. 15A, coefficient $T_{3A}$ may be in the range from about 1.00 to 1.03, and preferably from about 1.01 to 1.02.

In FIG. 15A, coefficient $T_{3B}$ may be in the range from about 1.01 to 1.03, and preferably from about 1.02 to 1.03.

In FIG. 15A, coefficient $T_{3C}$ may be in the range from about 1.02 to 1.04, and preferably from about 1.03 to 1.04.

In FIG. 15A, coefficient $T_{3D}$ may be in the range from about 1.03 to 1.06, and preferably from about 1.04 to 1.06.

In FIG. 15B, coefficient $T_{4A}$ may be in the range from about 1.00 to 1.02, and preferably from about 1.01 to 1.02.

In FIG. 15B, coefficient $T_{4B}$ may be in the range from about 1.01 to 1.03, and preferably from about 1.02 to 1.03.

In FIG. 15B, coefficient $T_{4C}$ may be in the range from about 1.02 to 1.04, and preferably from about 1.03 to 1.04.

In FIG. 15B, coefficient $T_{5A}$ may be in the range from about 1.00 to 1.02, and preferably from about 1.01 to 1.02.

In FIG. 15B, coefficient $T_{5B}$ may be in the range from about 1.01 to 1.03, and preferably from about 1.02 to 1.03.

In FIG. 15B, coefficient $T_{5C}$ may be in the range from about 1.02 to 1.05, and preferably from about 1.03 to 1.05.

In FIG. 15B, coefficient $T_{6A}$ is preferably 1.00, because patients with a body mass index (BMI) below 32 should have a very good response to the acoustic pressure shock wave treatment and do not present any challenges from obesity point of view.

In FIG. 15B, coefficient $T_{6B}$ may be in the range from about 1.01 to 1.03, and preferably from about 1.02 to 1.03.

In FIG. 15C coefficient $T_{7A}$ is preferably 1.00, because patients with a weight below 220 lb/99.8 Kg should have a very good response to the acoustic pressure shock wave treatment and do not present any challenges from obesity point of view.

In FIG. 15C, coefficient $T_{7B}$ may be in the range from about 1.00 to 1.03, and preferably from about 1.01 to 1.02.

In FIG. 15C coefficient $T_{8A}$ is preferably 1.00 for a height below 70 in/177.8 cm.

In FIG. 15C, coefficient $T_{8B}$ may be in the range from about 1.00 to 1.02, and preferably from about 1.01 to 1.02.

In FIG. 15C, coefficient $T_{9A}$ is preferably 1.00, because patients with a HbA1c are controlling their diabetes and should have a very good response to the acoustic pressure shock wave treatment.

In FIG. 15C, coefficient $T_{9B}$ may be in the range from about 1.01 to 1.03, and preferably from about 1.02 to 1.03.

In FIG. 15C coefficient $T_{9C}$ may be in the range from about 1.01 to 1.04, and preferably from about 1.03 to 1.04.

In FIG. 15D, coefficient $T_{10A}$ is preferably 1.00, because patients with a $T_cP_{O2}$ value greater than 40 mmHg is normal and the patients should have a very good response to the acoustic pressure shock wave treatment.

In FIG. 15D, coefficient $T_{10B}$ may be in the range from about 1.01 to 1.03, and preferably from about 1.02 to 1.03.

In FIG. 15D, coefficient $T_{10C}$ may be in the range from about 1.02 to 1.04, and preferably from about 1.03 to 1.04.

In FIG. 15D, coefficient $T_{11A}$ may be in the range from about 1.00 to 1.02, and preferably from about 1.01 to 1.02.

In FIG. 15D, coefficient $T_{11B}$ may be in the range from about 1.01 to 1.03, and preferably from about 1.02 to 1.03.

In FIG. 15D, coefficient $T_{11C}$ may be in the range from about 1.02 to 1.04, and preferably from about 1.03 to 1.04.

In FIG. 15D coefficient $T_{12A}$ is preferably 1.00 because a non-smoker should have a very good response to the acoustic pressure shock wave treatment.

In FIG. 15D, coefficient $T_{12B}$ may be in the range from about 1.00 to 1.03, and preferably from about 1.01 to 1.02.

In FIG. 15E, coefficient $T_{13A}$ is preferably 1.00, because occasional drinking patients should have a very good response to the acoustic pressure shock wave treatment.

In FIG. 15E, coefficient $T_{13B}$ may be in the range from about 1.01 to 1.03, and preferably from about 1.02 to 1.03.

In FIG. 15E, coefficient $T_{13C}$ may be in the range from about 1.02 to 1.04, and preferably from about 1.03 to 1.04.

In FIG. 15E, coefficient $T_{14A}$ may be in the range from about 1.00 to 1.03, and preferably from about 1.01 to 1.02.

In FIG. 15E coefficient $T_{14B}$ is preferably 1.00 because a patient without osteomyelitis should have a very good response to the acoustic pressure shock wave treatment.

In FIG. 15E, coefficient $T_{15A}$ may be in the range from about 1.00 to 1.03, and preferably from about 1.01 to 1.02.

In FIG. 15E coefficient $T_{15B}$ is preferably 1.00 because a patient that is not on steroids therapy should have a very good response to the acoustic pressure shock wave treatment.

In FIG. 15F, coefficient $T_{16A}$ may be in the range from about 1.00 to 1.03, and preferably from about 1.01 to 1.02.

In FIG. 15F coefficient $T_{16B}$ is preferably 1.00 because a patient that is not on immunodeficiency therapy should have a very good response to the acoustic pressure shock wave treatment.

In FIG. 15F, coefficient $T_{17A}$ may be in the range from about 1.00 to 1.04, and preferably from about 1.02 to 1.04.

In FIG. 15F coefficient $T_{17B}$ is preferably 1.00 because a patient that is not on chemotherapy or radiation therapy should have a very good response to the acoustic pressure shock wave treatment.

In FIG. 15F, coefficient $T_{18A}$ may be in the range from about 1.00 to 1.03, and preferably from about 1.01 to 1.02.

In FIG. 15F coefficient $T_{18B}$ is preferably 1.00 because a patient without a pulmonary disease should have a very good response to the acoustic pressure shock wave treatment.

In FIG. 15G coefficient $T_{18A}$ is preferably 1.00 because a patient with a history of compliance to treatments should have a very good response to the acoustic pressure shock wave treatment.

In FIG. 15G, coefficient $T_{18B}$ may be in the range from about 1.00 to 1.03, and preferably from about 1.01 to 1.02.

A control console/unit 22 and associated acoustic pressure shock wave applicator/treatment apparatus 10 (see FIG. 2A) used for delivering a treatment for burn wounds by means of the proposed adjustment algorithm for number of treatments from FIGS. 15A-15G will use the following formula (where A is the initial number of treatments with focused acoustic pressure shock waves 40 or radial acoustic pressure waves 41 or planar acoustic pressure waves 42 or cylindrical acoustic pressure waves 44 and ANTT is the Adjusted Number of Total Treatments):

$$ANTT = A \cdot T_1 \cdot T_2 \cdot T_3 \cdot T_4 \cdot T_5 \cdot T_6 \cdot T_7 \cdot T_8 \cdot T_9 \cdot T_{10} \cdot T_{11} \cdot T_{12} \cdot T_{13} \cdot T_{14} \cdot T_{15} \cdot T_{16} \cdot T_{17} \cdot T_{18} \cdot T_{19}.$$

For the largest values for these coefficients (worst situation) and for example a number of A=8 treatments is used as the initial number of treatments with focused acoustic pressure shock waves 40 or radial acoustic pressure waves 41 or planar acoustic pressure waves 42 or cylindrical acoustic pressure waves 44 that are minimally needed for successful treatment of the tissue condition 19, then the Adjusted Number of Total Treatments (ANTT) value is the following:

$$ANTT = 8 \cdot 1.04 \cdot 1.06 \cdot 1.04 \cdot 1.04 \cdot 1.05 \cdot 1.03 \cdot 1.03 \cdot 1.02 \cdot 1.04 \cdot 1.04 \cdot 1.04 \cdot 1.03 \cdot 1.04 \cdot 1.03 \cdot 1.03 \cdot 1.04 \cdot 1.03 \cdot 1.03 = 15.75 \approx 16$$
treatments.

It was seen before that the personalized/adjusted number of focused acoustic pressure shock waves 40 or radial acoustic pressure waves 41 or planar acoustic pressure waves 42 or cylindrical acoustic pressure waves 44 delivered in one treatment session can be determined via the questionnaire questions from FIGS. 8A-8E, FIGS. 9A-9E, FIGS. 10A-10E, FIGS. 11A-11E, and FIGS. 12A-12E. Also, the personalized/adjusted total number of treatment sessions can be determined via the questionnaire questions from FIGS. 13A-13G, FIGS. 14A-14G, and FIGS. 15A-15G. Similar adjustments for energy settings for the treatment using focused acoustic pressure shock waves 40 or radial acoustic pressure waves 41 or planar acoustic pressure waves 42 or cylindrical acoustic pressure waves 44 can be also made using the same approach of taking into account the characteristics/status of the wounds, and patient's comorbidities, existing therapies, and habits/lifestyle.

FIGS. 16A-16D present a preferable algorithm in other embodiments of the invention that can be used to adjust the energy settings when focused acoustic pressure shock waves 40 or radial acoustic pressure waves 41 or planar acoustic pressure waves 42 or cylindrical acoustic pressure waves 44 are used for the treatment of diabetic foot ulcers (DFUs), pressure sores/ulcers, arterial ulcers, venous ulcers, or burns based on different elements that take into account the characteristics/status of the wounds, and patient's comorbidities, existing therapies, and habits/lifestyle.

As a starting point for the algorithm used to personalize/adjust the energy setting for the treatments using focused acoustic pressure shock waves 40 or radial acoustic pressure waves 41 or planar acoustic pressure waves 42 or cylindrical acoustic pressure waves 44 is the basic/initial energy setting that is minimally necessary for successful treatment of the tissue condition 19. It is important to mention that the basic/initial energy setting are preferably specific for the treatment of each particular type of wound (DFU, pressure sore/ulcer, arterial ulcer, venous ulcer, burn wounds).

Figure 16A:
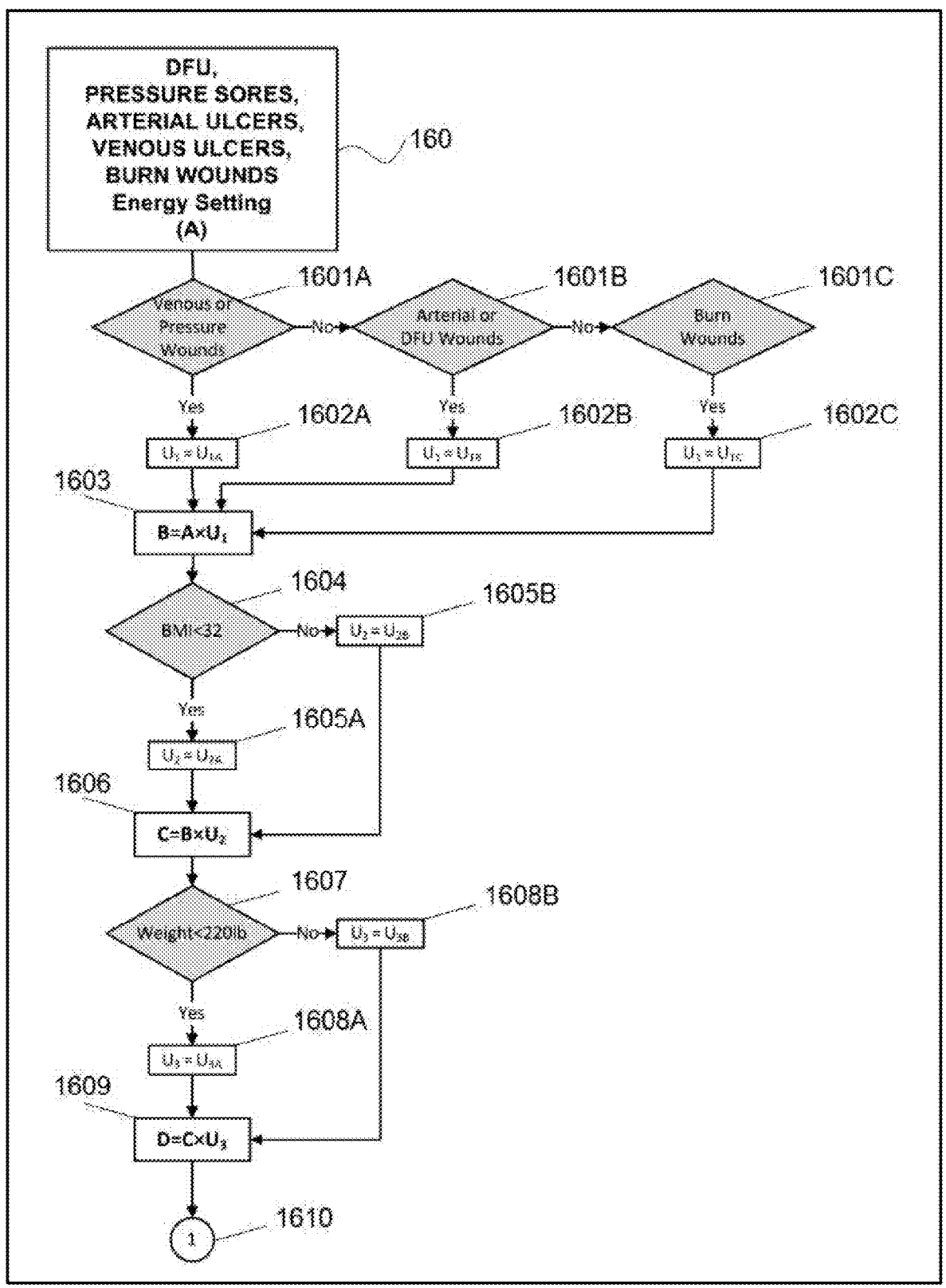
FIG. 16A is a flow diagram of the algorithm used to calculate the upgrade of energy setting when acoustic pressure shock waves are used for treatment of diabetic foot ulcers (DFUs), pressure sores/ulcers, arterial ulcers, venous ulcers, or burns when type of wound, body mass index (BMI), and patient weight are taken into account, according to one embodiment of the present invention.

In FIG. 16A the usual energy setting (UES) for DFUs, pressure sores, arterial and venous ulcers, and burn wounds 160 represents the starting point of the adjustment/optimization algorithm for energy setting for the treatments using focused acoustic pressure shock waves 40 or radial acoustic pressure waves 41 or planar acoustic pressure waves 42 or cylindrical acoustic pressure waves 44 for the treatment of diabetic foot ulcers (DFUs), pressure sores/ulcers, arterial ulcers, venous ulcers, and burn wounds. The first element used to alter the usual energy setting (UES) for DFU, pressure sores/ulcers, arterial ulcers, venous ulcers, and burn wounds treatment is the inquiry regarding the type of wound. Thus on the control console/unit display 2220, or artificial intelligence (A/I) device display 2740, or on the display of an interconnected device (see FIG. 2A for the medical treatment system 2000) as a desktop computer 28A, or a smart phone 28B, and/or tablet 28C, and/or laptop 28D is first displayed the inquiry for venous or pressure wounds 1601A. If the answer is "Yes" then the venous and pressure wounds modifying coefficient $U_{1A}$ 1602A will be used ($U_1=U_{1A}$). If the answer is "No", the inquiry for arterial or DFU wounds 1601B is displayed. If the answer is "Yes" then the arterial and DFU wounds modifying coefficient $U_{1B}$ 1602B will be used ($U_1=U_{1B}$). If the answer is "No", the inquiry for burn wounds 1601C is displayed. If the answer is "Yes" then burn wounds modifying coefficient $U_{1C}$ 1602C will be used ($U_1=U_{1C}$). Then the usual energy setting (UES) "A" is altered with the determined type of wound modifying coefficient "$U_1$", and thus the new energy setting becomes "B", which is now the updated energy setting based on type of wounds 1603.

The questionnaire from FIG. 16A continues with the inquiry on the body mass index (BMI). Thus the inquiry for body mass index (BMI) value 1604 is displayed (BMI<32). If the answer is "Yes" then the body mass index (BMI) modifying coefficient $U_{2A}$ 1605A will be used ($U_2=U_{2A}$). If the answer is "No" then the body mass index (BMI) modifying coefficient $U_{2B}$ 1605B will be used ($U_2=U_{2B}$). Then the energy setting "B" is altered with the determined body mass index (BMI) modifying coefficient "$U_2$", and thus the new energy setting becomes "C", which is now the updated energy setting based on obesity 1606.

The questionnaire from FIG. 16A continues with the inquiry on the patient's weight. Thus the inquiry for weight value 1607 is displayed (Weight<220 lb which is 99.8 Kg in metric system). If the answer is "Yes" then the weight modifying coefficient $U_{3A}$ 1608A will be used ($U_3=U_{3A}$). If the answer is "No" then the weight modifying coefficient $U_{3B}$ 1608B will be used ($U_3=U_{3B}$). Then the energy setting "C" is altered with the determined weight modifying coefficient "$U_3$", and thus the new energy setting becomes "D", which is now the updated energy setting based on weight 1609.

Figure 16B:
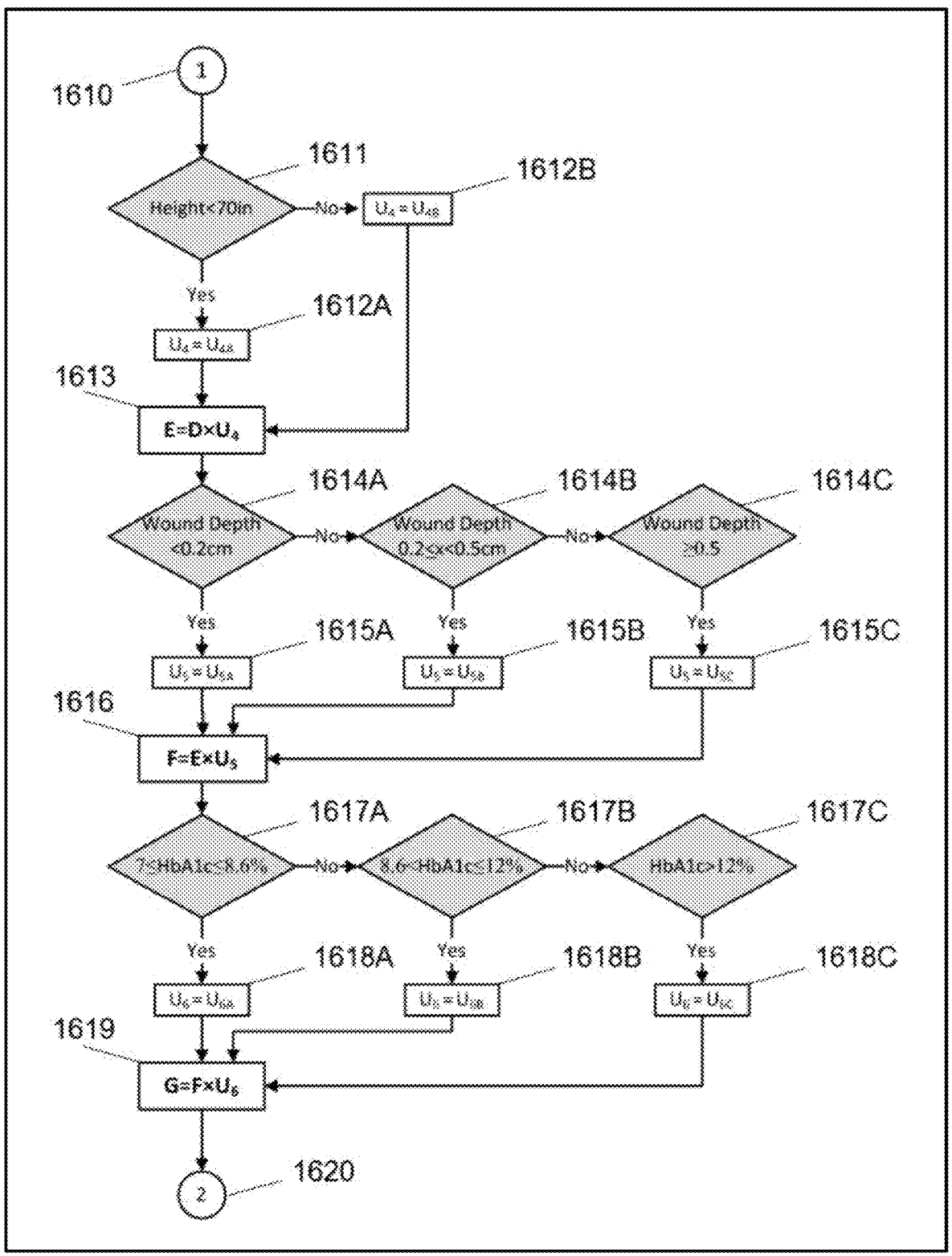
FIG. 16B is a flow diagram of the continuation of the algorithm presented in FIG. 16A used to calculate the upgrade of energy setting when acoustic pressure shock waves are used for treatment of diabetic foot ulcers (DFUs), pressure sores/ulcers, arterial ulcers, venous ulcers, or burns, when patient height, wound depth, and glycosylated hemoglobin A1c (HbA1c) are taken into account, according to one embodiment of the present invention.

The optimization continues on FIG. 16B and the continuation of the questionnaire flowchart from FIG. 16A to FIG. 16B is realized by the FIG. 16A to FIG. 16B connector 1610, which is seen on both FIG. 16A and FIG. 16B.

The questionnaire from FIG. 16B starts with the inquiry on the patient's height. Thus the inquiry for inquiry for height value 1611 is displayed (Height<70 in which is 177.8 cm in metric system). If the answer is "Yes" then the height modifying coefficient $U_{4A}$ 1612A will be used ($U_4=U_{4A}$). If the answer is "No" then the height modifying coefficient $U_{4B}$ 1612B will be used ($U_4=U_{4B}$). Then the energy setting "D" is altered with the determined height modifying coefficient "$U_4$", and thus the new energy setting becomes "E", which is now the updated energy setting based on height 1613.

The questionnaire from FIG. 16B continues with the inquiry on wound depth. Thus the inquiry for wound depth less than 0.2 cm 1614A is displayed. If the answer is "Yes" then the wound depth modifying coefficient $U_{5A}$ 1615A will be used ($U_5=U_{5A}$). If the answer is "No", the inquiry for wound depth between 0.2 and 0.5 cm 1614B is displayed. If the answer is "Yes" then the wound depth modifying coefficient $U_{5B}$ 1615B will be used ($U_8=U_{5B}$). If the answer is "No", the inquiry for wound depth in greater than 0.5 cm 1614C is displayed. If the answer is "Yes" then the wound depth modifying coefficient $U_{5C}$ 1615C will be used ($U_5=U_{5C}$). Then the energy setting "E" is altered with the determined wound depth modifying coefficient "$U_5$", and thus the new energy setting becomes "F", which is now the updated energy setting based on wound depth 1416.

The questionnaire from FIG. 16B continues with the inquiry on the value for glycated hemoglobin (HbA1c), which is an indication of diabetes presence. Thus the inquiry for glycated hemoglobin (HbA1c) between 7 and 8.6% 1617A is displayed. If the answer is "Yes" then the HbA1c modifying coefficient $U_{6A}$ 1618A will be used ($U_6=U_{6A}$). If the answer is "No", the inquiry for glycated hemoglobin (HbA1c) between 8.6 and 12% 1617B is displayed. If the answer is "Yes" then the HbA1c modifying coefficient $U_{6B}$ 1618B will be used ($U_6=U_{6B}$). If the answer is "No", the inquiry for glycated hemoglobin (HbA1c) larger than 12% 1617C is displayed. If the answer is "Yes" then the HbA1c modifying coefficient $U_{6C}$ 1618C will be used ($U_6=U_{6C}$). Then the energy setting "F" is altered with the determined HbA1c modifying coefficient "$U_6$", and thus the new energy setting becomes "G", which is now the updated energy setting based on diabetes presence 1619.

Figure 16C:
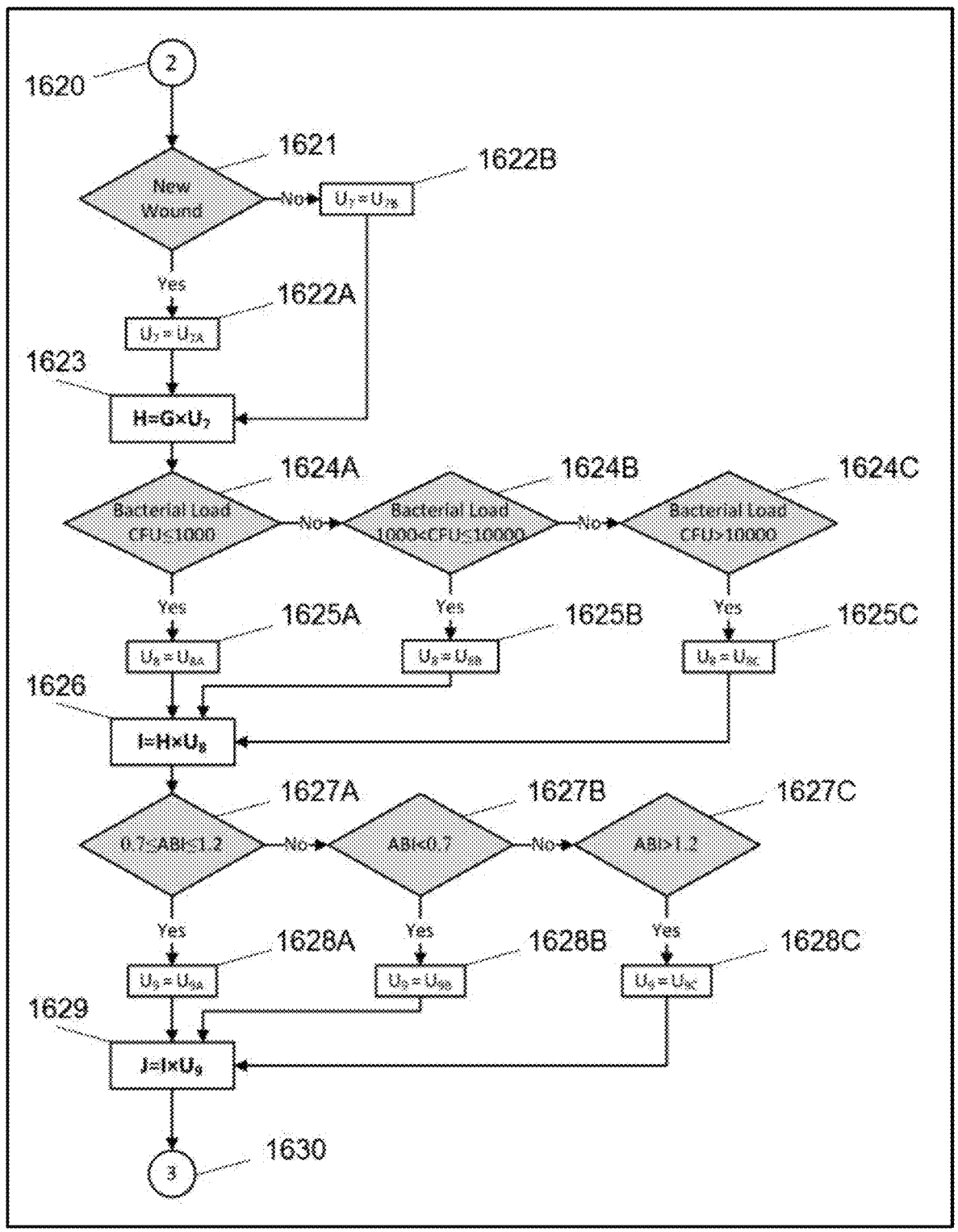
FIG. 16C is a flow diagram of the continuation of the algorithm presented in FIG. 16A and FIG. 16B used to calculate the upgrade of energy setting when acoustic pressure shock waves are used for treatment of diabetic foot ulcers (DFUs), pressure sores/ulcers, arterial ulcers, venous ulcers, or burns, when wound reoccurrence, bacterial load, and ankle-brachial index (ABI) are taken into account, according to one embodiment of the present invention.

The optimization continues on FIG. 16C and the continuation of the questionnaire flowchart from FIG. 16B to FIG. 16C is realized by the FIG. 16B to FIG. 16C connector 1620, which is seen on both FIG. 16B and FIG. 16C.

The questionnaire from FIG. 16C starts with the inquiry on new wound presence, which is an indication of recurrence. Thus the inquiry for new wound 1621 is displayed. If the answer is "Yes" then the new wound modifying coefficient $U_{7A}$ 1622A will be used ($U_7=U_{7A}$). If the answer is "No" then the new wound modifying coefficient $U_{7B}$ 1622B will be used ($U_7=U_{7B}$). Then the energy setting "G" is altered with the determined new wound modifying coefficient "$U_7$", and thus the new energy setting becomes "H", which is now the updated energy setting based on new wound presence 1623.

The questionnaire from FIG. 16C continues with the inquiry on bacterial colony forming units (CFU), which is an indication of bacterial load of the wound. Thus the inquiry for bacterial colony forming units (CFU) less than 1000 units 1624A is displayed. If the answer is "Yes" then the CFU modifying coefficient $U_{8A}$ 1625A will be used ($U_8=U_{8A}$). If the answer is "No", the inquiry for bacterial colony forming units (CFU) between 1000 and 10000 units 1624B is displayed. If the answer is "Yes" then the CFU modifying coefficient $U_{8B}$ 1625B will be used ($U_8=U_{8B}$). If the answer is "No", the inquiry for bacterial colony forming units (CFU) greater than 10000 units 1624C is displayed. If the answer is "Yes" then the CFU modifying coefficient $U_{8C}$ 1625C will be used ($U_8=U_{8C}$). Then the energy setting "H" is altered with the determined CFU modifying coefficient "$U_8$", and thus the new energy setting becomes "I", which is now the updated energy setting based on bacterial load 1626.

The questionnaire from FIG. 16C continues with the inquiry on ankle-brachial index (ABI), which is an indication on peripheral arterial disease. Thus the inquiry for ankle-brachial index (ABI) between 0.7 and 1.2 1627A is displayed. If the answer is "Yes" then the ABI modifying coefficient $U_{9A}$ 1628A will be used ($U_9=U_{9A}$). If the answer is "No", the inquiry for ankle-brachial index (ABI) less than 0.7 1627B is displayed. If the answer is "Yes" then the ABI modifying coefficient $U_{9B}$ 1628B will be used ($U_9=U_{9B}$). If the answer is "No", the inquiry for ankle-brachial index (ABI) greater than 1.2 1627C is displayed. If the answer is "Yes" then the ABI modifying coefficient $U_{9C}$ 1628C will be used ($U_9=U_{9C}$). Then the energy setting "I" is altered with the determined ABI modifying coefficient "$U_9$", and thus the new energy setting becomes "J", which is now the updated energy setting based on peripheral arterial disease 1629.

Figure 16D:
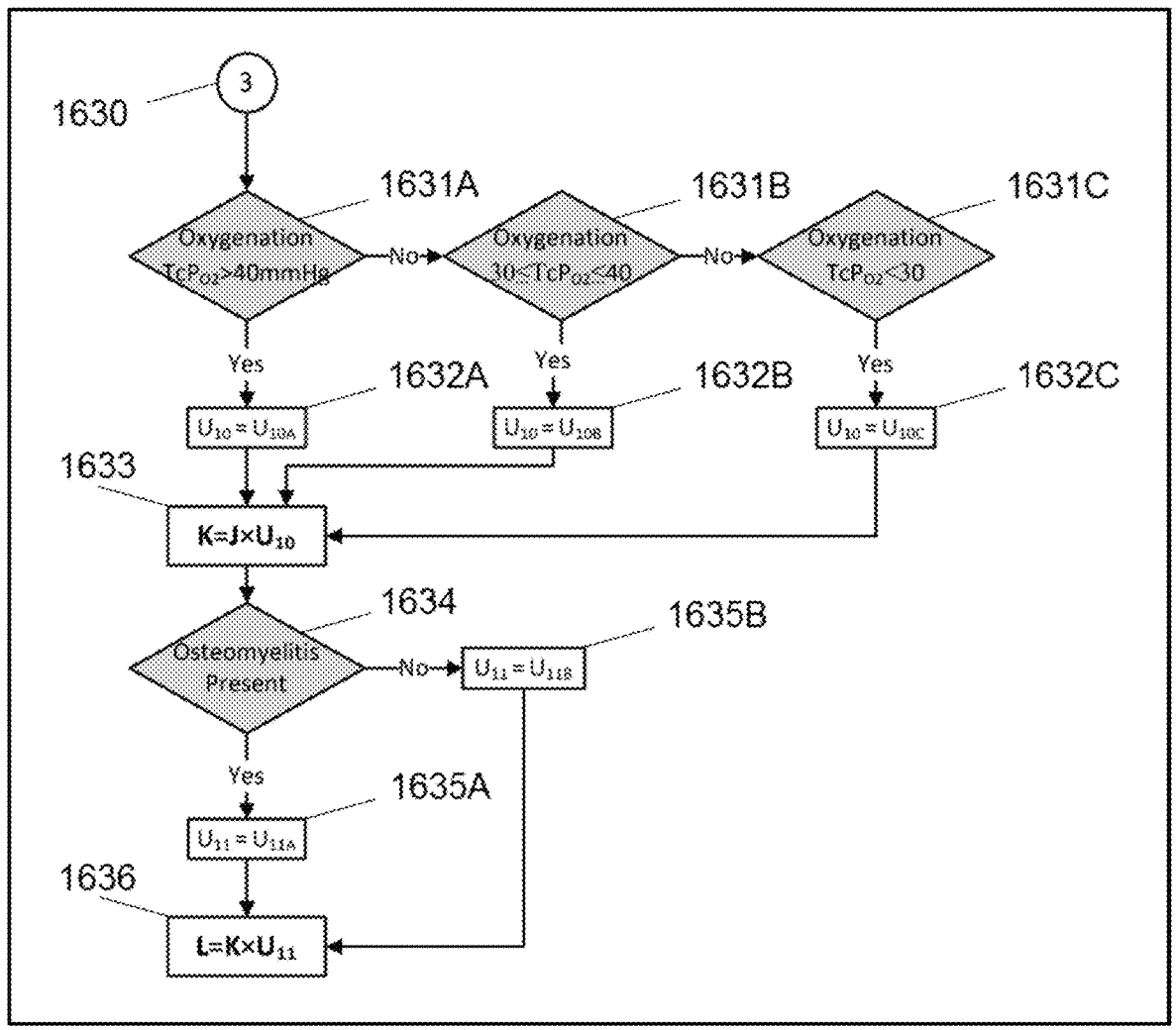
FIG. 16D is a flow diagram of the continuation of the algorithm presented in FIG. 16A, FIG. 16B, and FIG. 16C used to calculate the upgrade of energy setting when acoustic pressure shock waves are used for treatment of diabetic foot ulcers (DFUs), pressure sores/ulcers, arterial ulcers, venous ulcers, or burns, when area oxygenation ($T_cP_{O2}$—Transcutaneous Partial Pressure of Oxygen) and presence of bone osteomyelitis are taken into account, according to one embodiment of the present invention.

The optimization continues on FIG. 16D and the continuation of the questionnaire flowchart from FIG. 16C to FIG. 16D is realized by the FIG. 16C to FIG. 16D connector 1630, which is seen on both FIG. 16C and FIG. 16D.

The questionnaire from FIG. 16D starts with the inquiry on transcutaneous monitoring of oxygen ($T_cP_{O2}$), which is an indication on oxygenation of the wound. Thus the inquiry for transcutaneous monitoring of oxygen ($TcP_{O2}$) greater than 40 mmHg 1631A is displayed. If the answer is "Yes" then the $TcP_{O2}$ modifying coefficient $U_{10A}$ 1632A will be used ($U_{10}=U_{10A}$). If the answer is "No", the inquiry for transcutaneous monitoring of oxygen ($TcP_{O2}$) between 30 and 40 mmHg 1631B is displayed. If the answer is "Yes" then the $TcP_{O2}$ modifying coefficient $U_{10B}$ 1632B will be used ($U_{10}=U_{10B}$). If the answer is "No", the inquiry for transcutaneous monitoring of oxygen ($TcP_{O2}$) less than 30 mmHg 1631C is displayed. If the answer is "Yes" then the $TcP_{O2}$ modifying coefficient $U_{10C}$ 1632C will be used ($U_{10}=U_{10C}$). Then the energy setting "J" is altered with the determined transcutaneous monitoring of oxygen ($TcP_{O2}$) modifying coefficient "$U_{10}$", and thus the new energy setting becomes "K", which is now the updated energy setting based on tissue oxygenation 1633.

The questionnaire from FIG. 16D continues with the inquiry on comorbidities as osteomyelitis. Thus the inquiry for presence of osteomyelitis 1634 is displayed. If the answer is "Yes" then the osteomyelitis presence modifying coefficient $U_{11A}$ 1635A will be used ($U_{11}=U_{11A}$). If the answer is "No" then the osteomyelitis presence modifying coefficient $U_{11B}$ 1635B will be used ($U_{11}=U_{11B}$). Then the energy setting "K" is altered with the determined osteomyelitis presence modifying coefficient "$U_{11}$", and thus the new energy setting becomes "L", which is now the updated energy setting based on presence of osteomyelitis 1636.

In FIGS. 16A-16D the coefficients presented for energy setting for diabetic foot ulcers (DFUs), pressure sores/ulcers, arterial ulcers, venous ulcers, and burn wounds that can be used to adjust the energy setting based on inquiries for patient's comorbidities, existing therapies, habits/lifestyle and wound status are defined with general ranges and also with more preferable ranges and sometimes as a specific number.

In FIGS. 16A-16D the values for the coefficients are preferably as follows:

In FIG. 16A, coefficient $U_{1A}$ may be in the range from about 1.01 to 1.04, and preferably from about 1.02 to 1.03.

In FIG. 16A, coefficient $U_{1B}$ may be in the range from about 1.02 to 1.06, and preferably from about 1.03 to 1.05.

In FIG. 16A, coefficient $U_{1C}$ may be in the range from about 1.03 to 1.08, and preferably from about 1.04 to 1.06.

In FIG. 16A, coefficient $U_{2A}$ is preferably 1.00, because patients with a body mass index (BMI) below 32 should have a very good response to the acoustic pressure shock wave treatment and do not present any challenges from obesity point of view.

In FIG. 16A, coefficient $U_{2B}$ may be in the range from about 1.01 to 1.07, and preferably from about 1.02 to 1.07.

In FIG. 16A coefficient $U_{3A}$ is preferably 1.00, because patients with a weight below 220 lb/99.8 Kg should have a very good response to the acoustic pressure shock wave treatment and do not present any challenges from obesity point of view.

In FIG. 16A, coefficient $U_{3B}$ may be in the range from about 1.01 to 1.05, and preferably from about 1.02 to 1.04.

In FIG. 16B coefficient $U_{4A}$ is preferably 1.00 for a height below 70 in/177.8 cm.

In FIG. 16B, coefficient $U_{4B}$ may be in the range from about 1.00 to 1.03, and preferably from about 1.01 to 1.03.

In FIG. 16B, coefficient $U_{5A}$ may be in the range from about 1.01 to 1.04, and preferably from about 1.01 to 1.03.

In FIG. 16B, coefficient $U_{5B}$ may be in the range from about 1.02 to 1.06, and preferably from about 1.03 to 1.05.

In FIG. 16B, coefficient $U_{5C}$ may be in the range from about 1.03 to 1.08, and preferably from about 1.04 to 1.07.

In FIG. 16B, coefficient $U_{6A}$ may be in the range from about 1.01 to 1.04, and preferably from about 1.01 to 1.03.

In FIG. 16B, coefficient $U_{6B}$ may be in the range from about 1.02 to 1.07, and preferably from about 1.03 to 1.06.

In FIG. 16B, coefficient $U_{6C}$ may be in the range from about 1.03 to 1.10, and preferably from about 1.04 to 1.08.

In FIG. 16C coefficient $U_{7A}$ may be in the range from about 1.00 to 1.03, and preferably from about 1.01 to 1.02.

In FIG. 16C, coefficient $U_{7B}$ may be in the range from about 1.01 to 1.05, and preferably from about 1.02 to 1.05.

In FIG. 16C, coefficient $U_{8A}$ may be in the range from about 1.00 to 1.03, and preferably from about 1.01 to 1.02.

In FIG. 16C, coefficient $U_{8B}$ may be in the range from about 1.01 to 1.08, and preferably from about 1.02 to 1.07.

In FIG. 16C, coefficient $U_{8C}$ may be in the range from about 1.02 to 1.12, and preferably from about 1.03 to 1.10.

In FIG. 16C, coefficient $U_{9A}$ is preferably 1.00, because patients with an ankle-brachial index (ABI) between 0.7 and 1.2 should have a very good response to the acoustic pressure shock wave treatment.

In FIG. 16C, coefficient $U_{9B}$ may be in the range from about 1.01 to 1.04, and preferably from about 1.02 to 1.04.

In FIG. 16C, coefficient $U_{9C}$ may be in the range from about 1.01 to 1.06, and preferably from about 1.03 to 1.06.

In FIG. 16D, coefficient $U_{10A}$ is preferably 1.00, because patients with a $TcP_{O2}$ value greater than 40 mmHg is normal and the patients should have a very good response to the acoustic pressure shock wave treatment.

In FIG. 16D, coefficient $U_{10B}$ may be in the range from about 1.01 to 1.06, and preferably from about 1.02 to 1.05.

In FIG. 16D, coefficient $U_{10C}$ may be in the range from about 1.02 to 1.08, and preferably from about 1.03 to 1.06.

In FIG. 16D, coefficient $U_{11A}$ may be in the range from about 1.01 to 1.05, and preferably from about 1.02 to 1.04.

In FIG. 16D coefficient $U_{11B}$ is preferably 1.00 because patient without osteomyelitis should have a very good response to the acoustic pressure shock wave treatment.

A control console/unit 22 and associated acoustic pressure shock wave applicator/treatment apparatus 10 (see FIG. 2A) used for delivering a treatment for diabetic foot ulcers (DFUs), pressure sores/ulcers, arterial and venous ulcers, and burn wounds by means of the proposed adjustment algorithm for energy setting from FIGS. 16A-16D will use the following formula (where A=UES (usual energy setting) for the treatment of diabetic foot ulcers (DFUs), pressure sores/ulcers, arterial ulcers, venous ulcers, or burns wounds with focused acoustic pressure shock waves 40 or radial acoustic pressure waves 41 or planar acoustic pressure waves 42 or cylindrical acoustic pressure waves 44 and AES is the Adjusted Energy Setting):

$$AES = UES + U_1 \cdot U_2 \cdot U_3 \cdot U_4 \cdot U_5 \cdot U_6 \cdot U_7 \cdot U_8 \cdot U_9 \cdot U_{10} \cdot U_{11}.$$

For the largest values of these coefficients (worst situation) and usual energy setting (UES) used with focused acoustic pressure shock waves 40 or radial acoustic pressure waves 41 or planar acoustic pressure waves 42 or cylindrical acoustic pressure waves 44 for successful treatment of the tissue condition 19, then the Adjusted Energy Setting (AES) value is the following:

$$AES = UES + 1.08 \cdot 1.07 \cdot 1.05 \cdot 1.03 \cdot 1.08 \cdot 1.10 \cdot 1.05 \cdot 1.12 \cdot 1.06 \cdot 1.08 \cdot 1.05 = UES + 2.1 \approx UES + 2$$ (if the energy setting was $E2$ then the adjusted energy level will be $E4$).

The customized approaches can be also applied for other common skin conditions in a similar way as was exemplified for diabetic foot ulcers (DFUs), pressure sores/ulcers, arterial ulcers, venous ulcers, and burns for calculating adjusted dosage/number of focused acoustic pressure shock waves 40 or radial acoustic pressure waves 41 or planar acoustic pressure waves 42 or cylindrical acoustic pressure waves 44, adjusted number of treatments, or adjusted energy setting, based on patient's comorbidities and other aspects that might influence the successful outcome of the treatment the tissue condition 19. Thus the customized/personalized approach can be applied for calculating the adjusted dosage/number of focused acoustic pressure shock waves 40 or radial acoustic pressure waves 41 or planar acoustic pressure waves 42 or cylindrical acoustic pressure waves 44 for the treatment of skin discolorations (red birthmarks, hemangiomas, moles, freckles, melisma, and skin tags), chronic skin problems (eczema, psoriasis, acne, rosacea, porphyria, and pyoderma gangrenosum), acute skin problems (cold sores, plantar and palmer warts, blisters, chafing, corns and calluses, gangrene, rashes, dermatitis, cysts, skin lumps, urticarial, alopecia areata, vitiligo, varicose veins, spider veins, intertrigo, lice, scabies, bruises, epidermoid cysts, and keloids), skin infections (bacterial infections as leprosy, carbuncles, staph infection (impetigo), boils, pilonidal cysts, abscess, also fungal infections as fungal skin infections, tinea, athlete's foot, candidiasis, sporotrichosis, fungal nail infection, and viral infections as molluscum contagiosum, shingles, and chickenpox), skin cancer (melanoma and carcinoma), acute cuts, traumatic wounds, reconstructive skin flaps, surgery wounds, etc. Such an example is presented in FIGS. 17A-17E for the calculation of adjusted dosage for the treatment of tissue condition 19 using focused acoustic pressure shock waves 40 or radial acoustic pressure waves 41 or planar acoustic pressure waves 42 or cylindrical acoustic pressure waves 44.

The personalized treatment parameters for common skin conditions when focused acoustic pressure shock waves 40 or radial acoustic pressure waves 41 or planar acoustic pressure waves 42 or cylindrical acoustic pressure waves 44 are used can be determined using different factors. FIGS. 17A-17E present a preferable algorithm in another embodiment that can be used to adjust the dosage/number of focused acoustic pressure shock waves 40 or radial acoustic pressure waves 41 or planar acoustic pressure waves 42 or cylindrical acoustic pressure waves 44 used for the treatment of common skin conditions based on different elements that take into account the characteristics of the common skin condition, patient's comorbidities, existing therapies, and habits/lifestyle.

As a starting point for common skin conditions algorithm is the basic/initial number of focused acoustic pressure shock waves 40 or radial acoustic pressure waves 41 or planar acoustic pressure waves 42 or cylindrical acoustic pressure waves 44 that are minimally needed for successful treatment of the tissue condition 19.

Figure 17A:
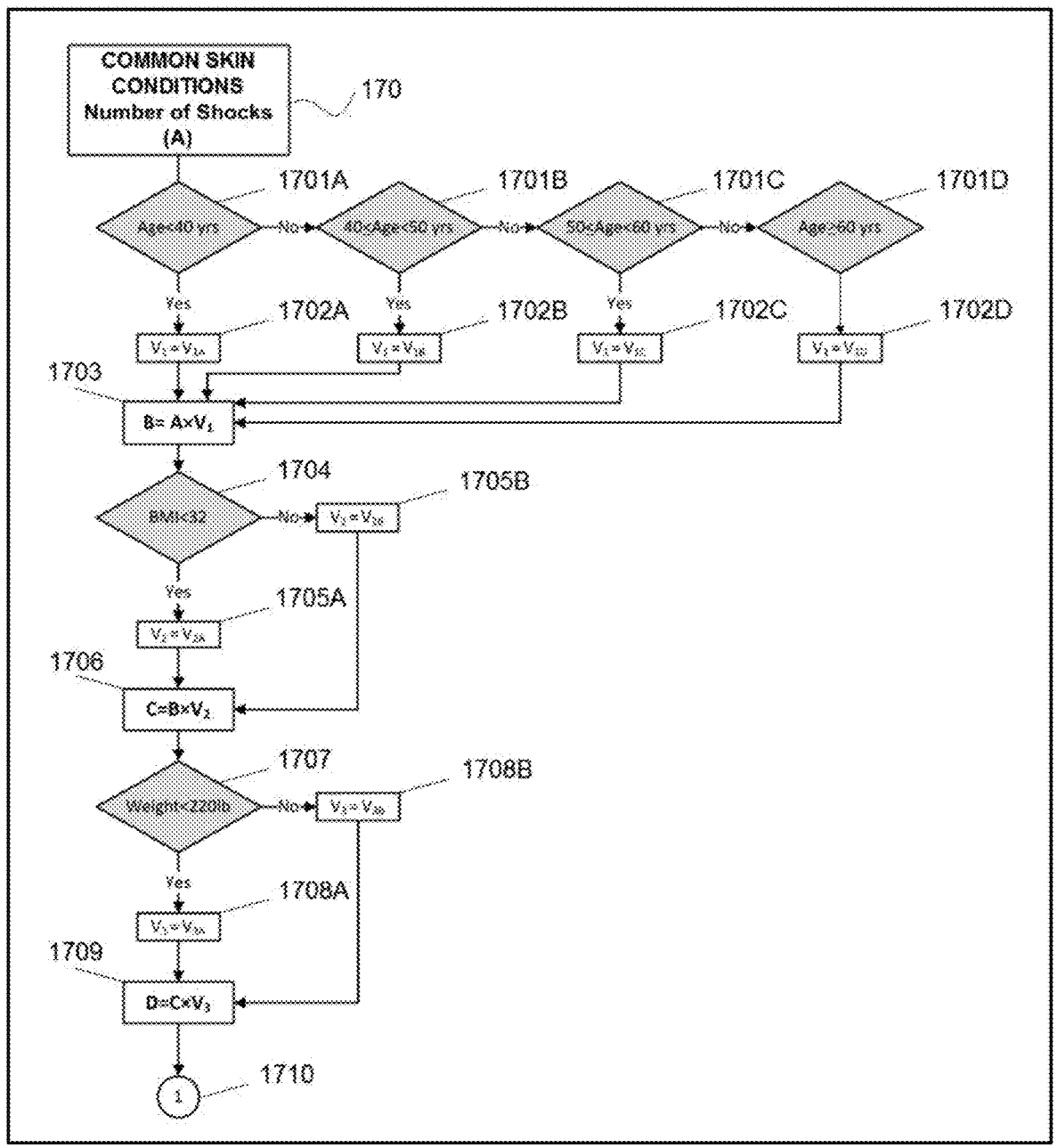
FIG. 17A is a flow diagram of the algorithm used to calculate the number of acoustic pressure shock waves to be used for common skin conditions when patient age, body mass index (BMI), and patient weight are taken into account, according to one embodiment of the present invention.

In FIG. 17A the basic/initial number of shocks for common skin conditions 170 represents the starting point of the adjustment/optimization algorithm for dosage/number of focused acoustic pressure shock waves 40 or radial acoustic pressure waves 41 or planar acoustic pressure waves 42 or cylindrical acoustic pressure waves 44 for the treatment of common skin conditions. The first element used to alter the basic/initial dosage used for common skin conditions treatment is the inquiry regarding the age of the patient. Thus on the control console/unit display 2220, or artificial intelligence (A/I) device display 2740, or on the display of an interconnected device (see FIG. 2A for the medical treatment system 2000) as a desktop computer 28A, or a smart phone 28B, and/or tablet 28C, and/or laptop 28D is first displayed the inquiry for age less than 40 years 1701A. If the answer is "Yes" then the age modifying coefficient $V_{1A}$ 1702A will be used ($V_1 = V_{1A}$). If the answer is "No", the inquiry for age between 40 and 50 years 1701B is displayed. If the answer is "Yes" then the age modifying coefficient $V_{1B}$ 1702B will be used ($V_1 = V_{1B}$). If the answer is "No", the inquiry for age between 50 and 60 years 1701C is displayed. If the answer is "Yes" then the age modifying coefficient $V_{1C}$ 1702C will be used ($V_1 = V_{1C}$). If the answer is "No", the inquiry for age older than 60 years 1701D is displayed and if the answer is "Yes" then the age modifying coefficient $V_{1D}$ 1702D will be used ($V_1=V_{1D}$). Then the basic/initial number of shocks for common skin conditions "A" is altered with the determined age modifying coefficient "$V_1$", and thus the new number of shocks becomes "B", which is now the updated number of shocks based on age 1703.

The questionnaire from FIG. 17A continues with the inquiry on the body mass index (BMI). Thus the inquiry for body mass index (BMI) value 1704 is displayed (BMI<32). If the answer is "Yes" then the body mass index (BMI) modifying coefficient $V_{2A}$ 1705A will be used ($V_2=V_{2A}$). If the answer is "No" then the body mass index (BMI) modifying coefficient $V_{2B}$ 1705B will be used ($V_2=V_{2B}$). Then the number of shocks "B" is altered with the determined body mass index (BMI) modifying coefficient "$V_2$", and thus the new number of shocks becomes "C", which is now the updated number of shocks based on obesity 1706.

The questionnaire from FIG. 17A continues with the inquiry on the patient's weight. Thus the inquiry for weight value 1707 is displayed (Weight<220 lb which is 99.8 Kg in metric system). If the answer is "Yes" then the weight modifying coefficient $V_{3A}$ 1708A will be used ($V_3=V_{3A}$). If the answer is "No" then the weight modifying coefficient $V_{3B}$ 1708B will be used ($V_3=V_{3B}$). Then the number of shocks "C" is altered with the determined weight modifying coefficient "$V_3$", and thus the new number of shocks becomes "D", which is now the updated number of shocks based on weight 1709.

Figure 17B:
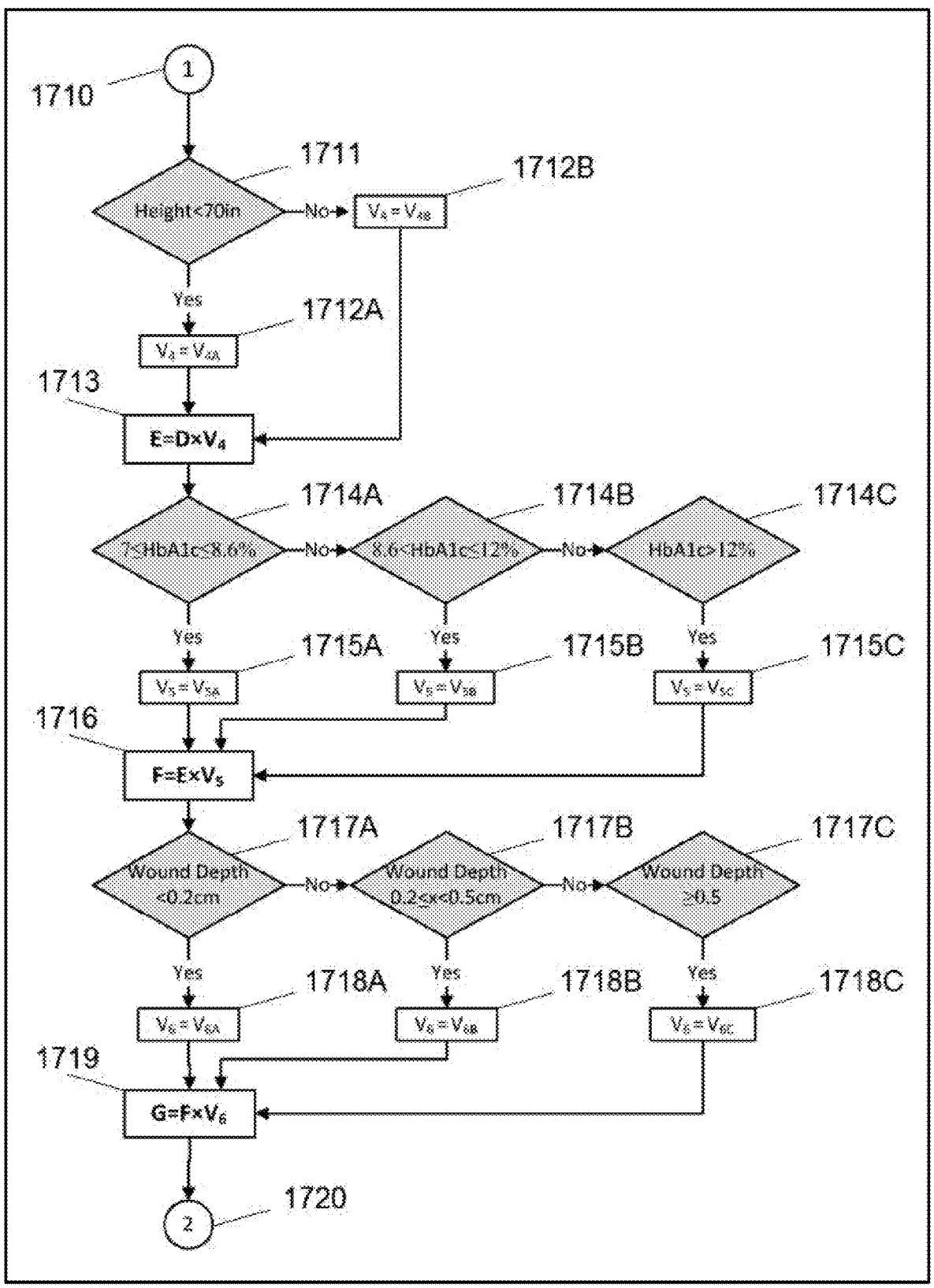
FIG. 17B is a flow diagram of the continuation of the algorithm presented in FIG. 17A used to calculate the number of acoustic pressure shock waves to be used for common skin conditions, when patient height, glycosylated hemoglobin A1c (HbA1c), and wound depth are taken into account, according to one embodiment of the present invention.

The optimization continues on FIG. 17B and the continuation of the questionnaire flowchart from FIG. 17A to FIG. 17B is realized by the FIG. 17A to FIG. 17B connector 1710, which is seen on both FIG. 17A and FIG. 17B.

The questionnaire from FIG. 17B continues with the inquiry on the patient's height. Thus the inquiry for inquiry for height value 1711 is displayed (Height<70 in which is 177.8 cm in metric system). If the answer is "Yes" then the height modifying coefficient $V_{4A}$ 1712A will be used ($V_4=V_{4A}$). If the answer is "No" then the height modifying coefficient $V_{4B}$ 1712B will be used ($V_4=V_{4B}$). Then the number of shocks "D" is altered with the determined height modifying coefficient "$V_4$", and thus the new number of shocks becomes "E", which is now the updated number of shocks based on height 1713.

The questionnaire from FIG. 17B continues with the inquiry on the value for glycated hemoglobin (HbA1c), which is an indication of diabetes presence. Thus the inquiry for glycated hemoglobin (HbA1c) between 7 and 8.6% 1714A is displayed. If the answer is "Yes" then the HbA1c modifying coefficient $V_{5A}$ 1715A will be used ($V_5=V_{5A}$). If the answer is "No", the inquiry for glycated hemoglobin (HbA1c) between 8.6 and 12% 1714B is displayed. If the answer is "Yes" then the HbA1c modifying coefficient $V_{5B}$ 1715B will be used ($V_5=V_{5B}$). If the answer is "No", the inquiry for glycated hemoglobin (HbA1c) larger than 12% 1714C is displayed. If the answer is "Yes" then the HbA1c modifying coefficient $V_{5C}$ 1715C will be used ($V_5=V_{5C}$). Then the number of shocks "E" is altered with the determined HbA1c modifying coefficient "$V_5$", and thus the new number of shocks becomes "F", which is now the updated number of shocks based on diabetes presence 1716.

The questionnaire from FIG. 17B starts with the inquiry on wound depth. Thus the inquiry for wound depth less than 0.2 cm 1717A is displayed. If the answer is "Yes" then the wound depth modifying coefficient $V_{6A}$ 1718A will be used ($V_6=V_{6A}$). If the answer is "No", the inquiry for wound depth between 0.2 and 0.5 cm 1717B is displayed. If the answer is "Yes" then the wound depth modifying coefficient $V_{6B}$ 1718B will be used ($V_6=V_{6B}$). If the answer is "No", the inquiry for wound depth greater than 0.5 cm 1717C is displayed. If the answer is "Yes" then the wound depth modifying coefficient $V_{6C}$ 1718C will be used ($V_6=V_{6C}$). Then the number of shocks "F" is altered with the determined wound depth modifying coefficient "$V_6$", and thus the new number of shocks becomes "G", which is now the updated number of shocks based on wound depth 1719.

Figure 17C:
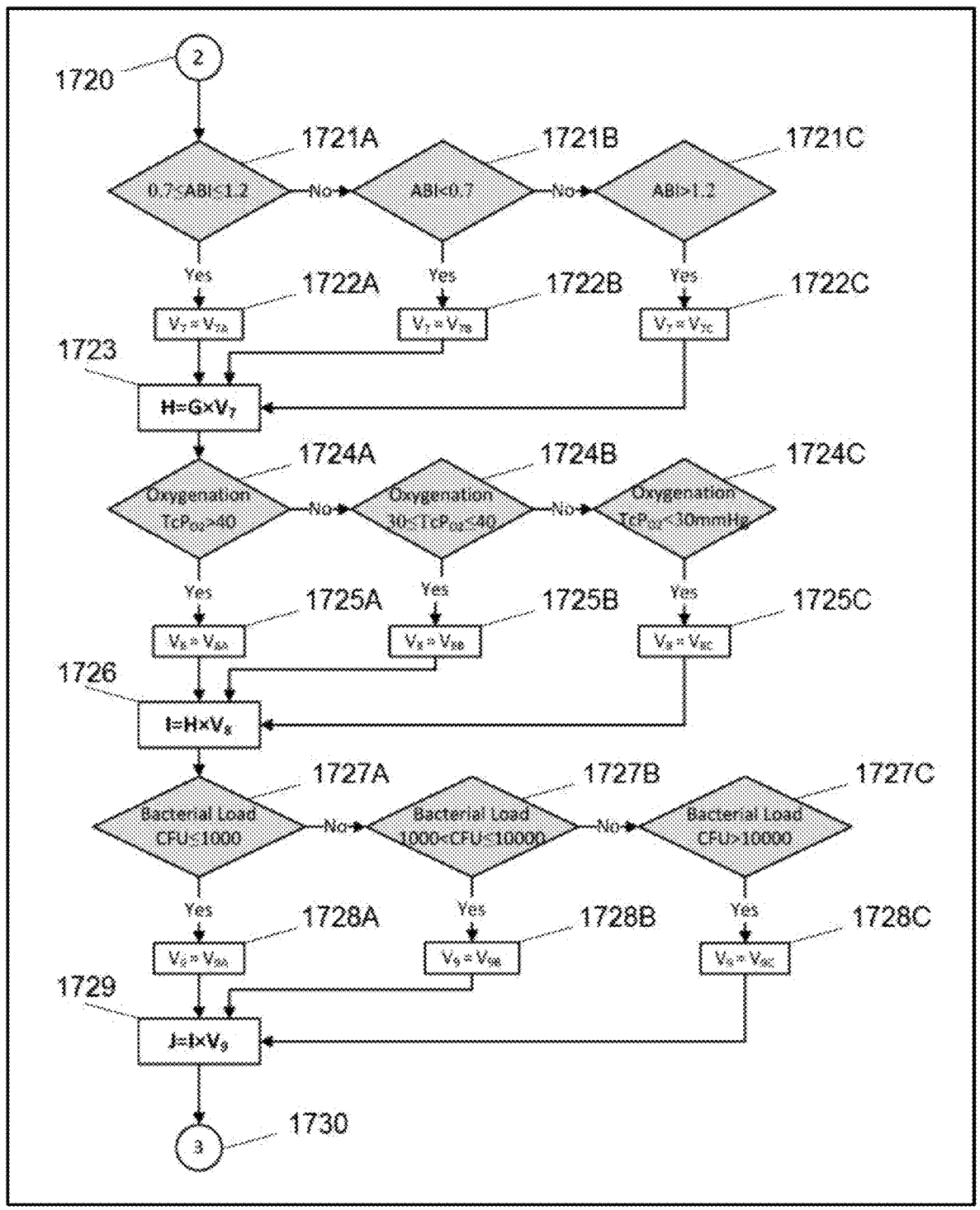
FIG. 17C is a flow diagram of the continuation of the algorithm presented in FIG. 17A and FIG. 17B used to calculate the number of acoustic pressure shock waves to be used for common skin conditions, when ankle-brachial index (ABI), area oxygenation ($T_cP_{O2}$—Transcutaneous Partial Pressure of Oxygen), and bacterial load are taken into account, according to one embodiment of the present invention.

The optimization continues on FIG. 17C and the continuation of the questionnaire flowchart from FIG. 17B to FIG. 17C is realized by the FIG. 17B to FIG. 17C connector 1720, which is seen on both FIG. 17B and FIG. 17C.

The questionnaire from FIG. 17C starts with the inquiry on ankle-brachial index (ABI), which is an indication on peripheral arterial disease. Thus the inquiry for ankle-brachial index (ABI) between 0.7 and 1.2 1721A is displayed. If the answer is "Yes" then the ABI modifying coefficient $V_{7A}$ 1722A will be used ($V_7=V_{7A}$). If the answer is "No", the inquiry for ankle-brachial index (ABI) less than 0.7 1721B is displayed. If the answer is "Yes" then the ABI modifying coefficient $V_{7B}$ 1722B will be used ($V_7=V_{7B}$). If the answer is "No", the inquiry for ankle-brachial index (ABI) greater than 1.2 1721C is displayed. If the answer is "Yes" then the ABI modifying coefficient $V_{7C}$ 1722C will be used ($V_7=V_{7C}$). Then the number of shocks "G" is altered with the determined ABI modifying coefficient "$V_7$", and thus the new number of shocks becomes "H", which is now the updated number of shocks based on peripheral arterial disease 1723.

The questionnaire from FIG. 17C continues with the inquiry on transcutaneous monitoring of oxygen ($T_cP_{O2}$), which is an indication on oxygenation of the wound. Thus the inquiry for transcutaneous monitoring of oxygen (TcP$_{O2}$) greater than 40 mmHg 1724A is displayed. If the answer is "Yes" then the TcP$_{O2}$ modifying coefficient $V_{8A}$ 1725A will be used ($V_8=V_{8A}$). If the answer is "No", the inquiry for transcutaneous monitoring of oxygen (TcP$_{O2}$) between 30 and 40 mmHg 1724B is displayed. If the answer is "Yes" then the TcP$_{O2}$ modifying coefficient $V_{8B}$ 1725B will be used ($V_8=V_{8B}$). If the answer is "No", the inquiry for transcutaneous monitoring of oxygen (TcP$_{O2}$) less than 30 mmHg 1724C is displayed. If the answer is "Yes" then the TcP$_{O2}$ modifying coefficient $V_{8C}$ 1725C will be used ($V_8=V_{8C}$). Then the number of shocks "H" is altered with the determined transcutaneous monitoring of oxygen (TcP$_{O2}$) modifying coefficient "$V_8$", and thus the new number of shocks becomes "I", which is now the updated number of shocks based on tissue oxygenation 1726.

The questionnaire from FIG. 17C continues with the inquiry on bacterial colony forming units (CFU), which is an indication of bacterial load of the wound. Thus the inquiry for bacterial colony forming units (CFU) less than 1000 units 1727A is displayed. If the answer is "Yes" then the CFU modifying coefficient $V_{9A}$ 1728A will be used ($V_9=V_{9A}$). If the answer is "No", the inquiry for bacterial colony forming units (CFU) between 1000 and 10000 units 1727B is displayed. If the answer is "Yes" then the CFU modifying coefficient $V_{9B}$ 1728B will be used ($V_9=V_{9B}$). If the answer is "No", the inquiry for bacterial colony forming units (CFU) greater than 10000 units 1727C is displayed. If the answer is "Yes" then the CFU modifying coefficient $V_{9C}$ 1728C will be used ($V_9=V_{9C}$). Then the number of shocks "I" is altered with the determined CFU modifying coefficient "$V_9$", and thus the new number of shocks becomes "J", which is now the updated number of shocks based on bacterial load 1729.

Figure 17D:
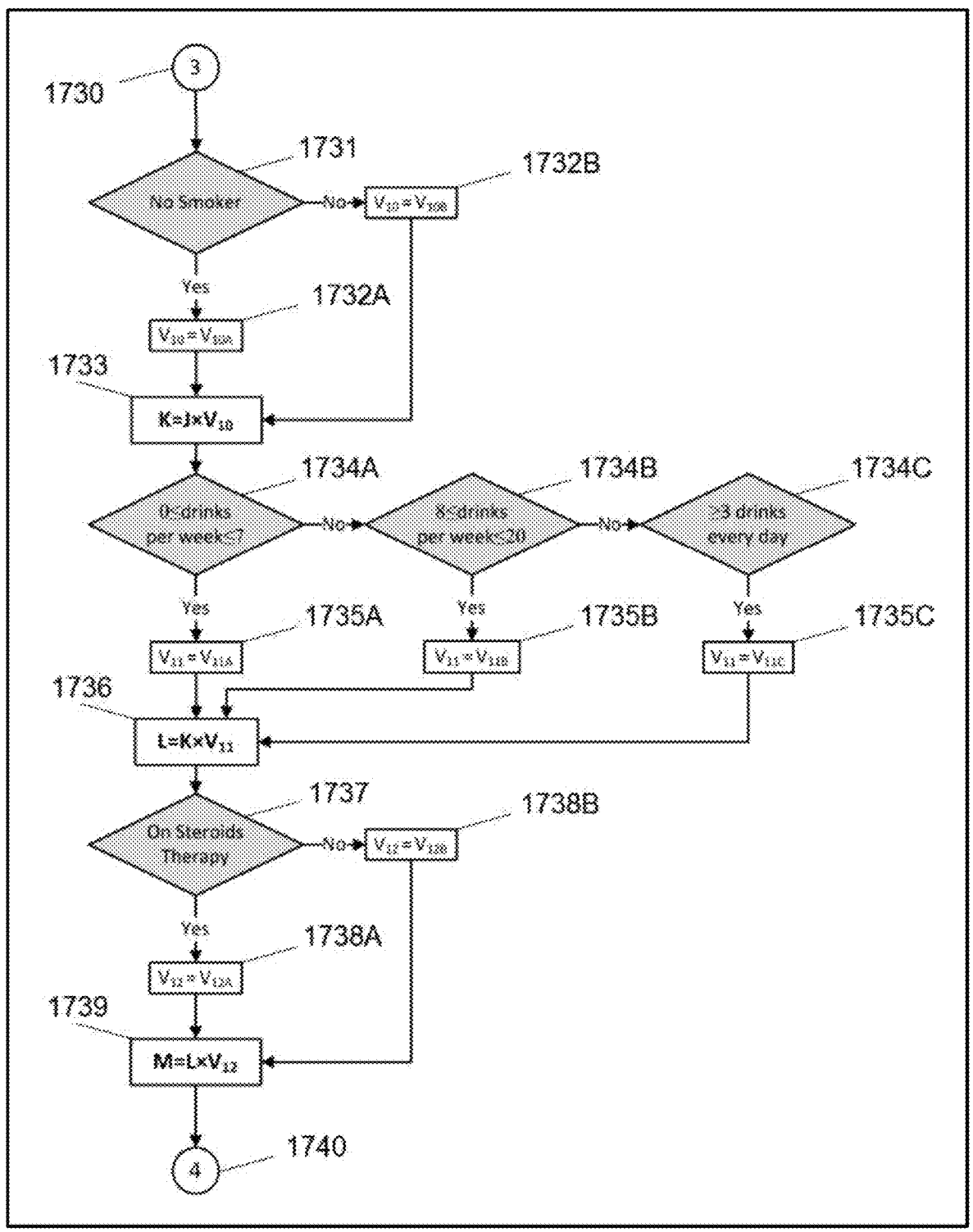
FIG. 17D is a flow diagram of the continuation of the algorithm presented in FIG. 17A, FIG. 17B, and FIG. 17C used to calculate the number of acoustic pressure shock waves to be used for common skin conditions, when smoker status, alcohol consumption, and patient possible steroids therapy are taken into account, according to one embodiment of the present invention.

The optimization continues on FIG. 17D and the continuation of the questionnaire flowchart from FIG. 17C to FIG.

17D is realized by the FIG. 17C to FIG. 17D connector 1730, which is seen on both FIG. 17C and FIG. 17D.

The questionnaire from FIG. 17D starts with the inquiry on smoking status. Thus the inquiry for smoking status 1731 is displayed. If the answer is "Yes" then the smoking status modifying coefficient $V_{10A}$ 1732A will be used ($V_{10}=V_{10A}$). If the answer is "No" then the smoking status modifying coefficient $V_{10B}$ 1732B will be used ($V_{10}=V_{10B}$). Then the number of shocks "J" is altered with the determined smoking status modifying coefficient "$V_{10}$", and thus the new number of shocks becomes "K", which is now the updated number of shocks based on smoking status 1733.

The questionnaire from FIG. 17D continues with the inquiry on drinking habit, which is indicated by the number of drinks over a certain period of time. Thus the inquiry for drinks less than 7 per week 1734A is displayed. If the answer is "Yes" then the drinking habit modifying coefficient $V_{11A}$ 1735A will be used ($V_{11}=V_{11A}$). If the answer is "No", the inquiry for drinks between 8 and 20 per week 1734B is displayed. If the answer is "Yes" then the drinking habit modifying coefficient $V_{11B}$ 1735B will be used ($V_{11}=V_{11B}$). If the answer is "No", the inquiry for drinks greater than 3 every day 1734 is displayed. If the answer is "Yes" then the drinking habit modifying coefficient $V_{11C}$ 1735C will be used ($V_{11}=V_{11}c$). Then the number of shocks "K" is altered with the determined drinking habit modifying coefficient "$V_{11}$", and thus the new number of shocks becomes "L", which is now the updated number of shocks based on drinking habit 1736.

The questionnaire from FIG. 17D continues with the inquiry on steroids therapy. Thus the inquiry for steroids therapy 1737 is displayed. If the answer is "Yes" then the steroids therapy modifying coefficient $V_{12A}$ 1738A will be used ($V_{12}=V_{12A}$). If the answer is "No" then the steroids therapy modifying coefficient $V_{12B}$ 1738B will be used ($V_{12}=V_{12B}$). Then the number of shocks "L" is altered with the determined steroids therapy modifying coefficient "$V_{12}$", and thus the new number of shocks becomes "M", which is now the updated number of shocks based on steroids therapy 1739.

Figure 17E:
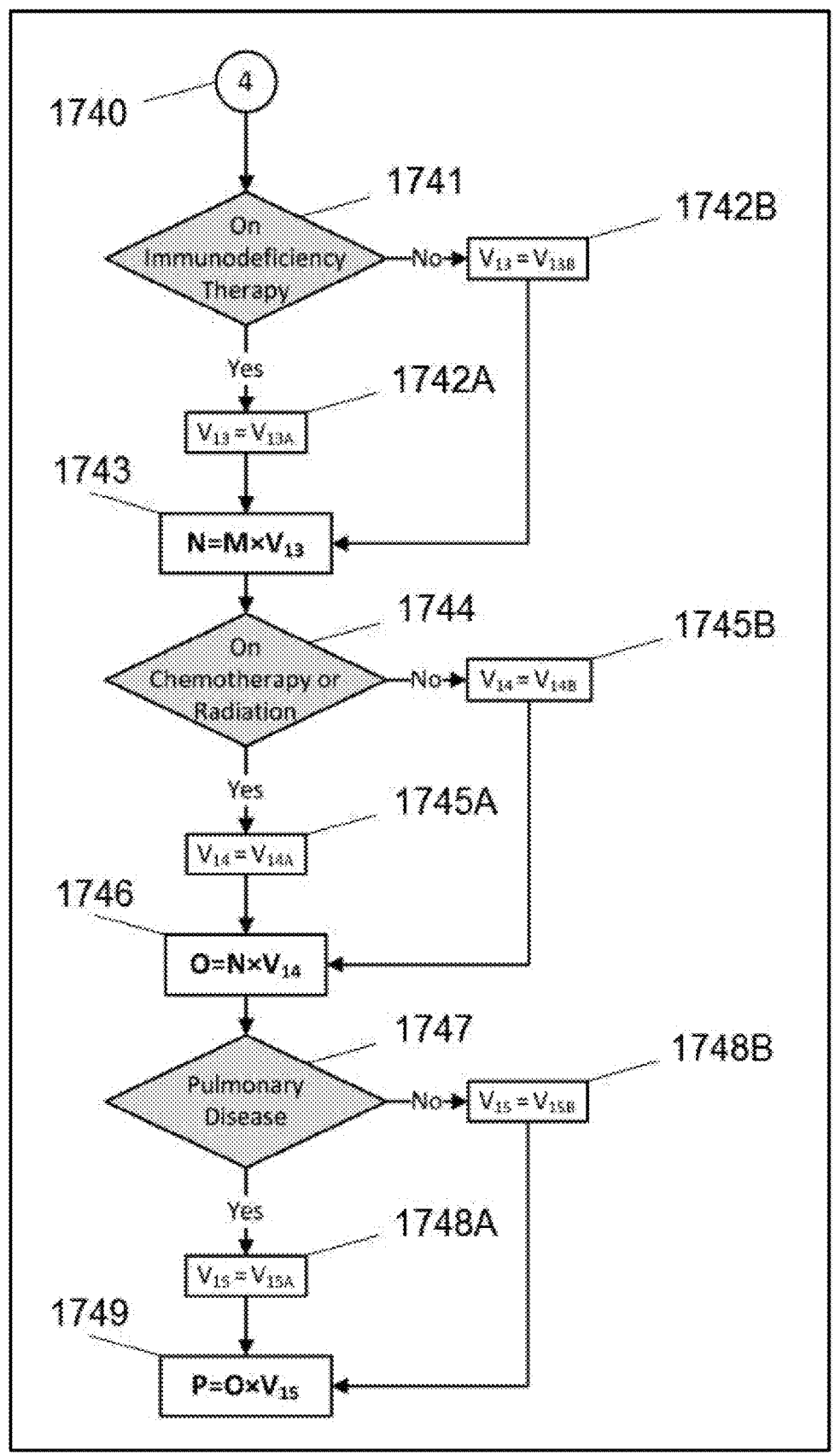
FIG. 17E is a flow diagram of the continuation of the algorithm presented in FIG. 17A, FIG. 17B, FIG. 17C, and FIG. 17D used to calculate the number of treatments with acoustic pressure shock waves for common skin conditions, when possible patient immunodeficiency therapy, possible chemotherapy or radiation therapy, and patient's possible pulmonary disease are taken into account, according to one embodiment of the present invention.

The optimization continues on FIG. 17E and the continuation of the questionnaire flowchart from FIG. 17D to FIG. 17E is realized by the FIG. 17D to FIG. 17E connector 1740, which is seen on both FIG. 17D and FIG. 17E.

The questionnaire from FIG. 17E starts with the inquiry on immunodeficiency therapy. Thus the inquiry for immunodeficiency therapy 1741 is displayed. If the answer is "Yes" then the immunodeficiency therapy modifying coefficient $V_{13A}$ 1742A will be used ($V_{13}=V_{13A}$). If the answer is "No" then the immunodeficiency therapy modifying coefficient $V_{13B}$ 1742B will be used ($V_{13}=V_{13B}$). Then the number of shocks "M" is altered with the determined immunodeficiency therapy modifying coefficient "$V_{13}$", and thus the new number of shocks becomes "N", which is now the updated number of shocks based on immunodeficiency therapy 1743.

The questionnaire from FIG. 17E continues with the inquiry on chemotherapy or radiation therapy. Thus the inquiry for chemotherapy or radiation therapy 1744 is displayed. If the answer is "Yes" then the chemotherapy or radiation therapy modifying coefficient $V_{14A}$ 1745A will be used ($V_{14}=V_{14A}$). If the answer is "No" then the chemotherapy or radiation therapy modifying coefficient $V_{14B}$ 1745B will be used ($V_{14}=V_{14B}$). Then the number of shocks "N" is altered with the determined chemotherapy or radiation therapy modifying coefficient "$V_{14}$", and thus the new number of shocks becomes "O", which is now the updated number of shocks based on chemotherapy and radiation therapy 1746.

The questionnaire from FIG. 17E continues with the inquiry on pulmonary disease. Thus the inquiry for pulmonary disease 1747 is displayed. If the answer is "Yes" then the pulmonary disease modifying coefficient $V_{15A}$ 1748A will be used ($V_{15}=V_{15A}$). If the answer is "No" then the pulmonary disease modifying coefficient $V_{15B}$ 1748B will be used ($V_{15}=V_{15B}$). Then the number of shocks "O" is altered with the determined pulmonary disease modifying coefficient "$V_{15}$", and thus the new number of shocks becomes "P", which is now the updated number of shocks based on pulmonary disease 1749.

In FIGS. 17A-17E the coefficients presented for common skin conditions that can be used to adjust the dosage based on inquiries for patient's comorbidities, existing therapies, habits/lifestyle and wound status are defined with general ranges and also with more preferable ranges and sometimes as a specific number.

In FIGS. 17A-17E the values for the coefficients are preferably as follows:

In FIG. 17A, coefficient $V_{1A}$ is preferably 1.00, because patients with age under 40 should have a very good response to the acoustic pressure shock wave treatment.

In FIG. 17A, coefficient $V_{1B}$ may be in the range from about 1.01 to 1.03, and preferably from about 1.02 to 1.03.

In FIG. 17A, coefficient $V_{1C}$ may be in the range from about 1.01 to 1.04, and preferably from about 1.02 to 1.04.

In FIG. 17A, coefficient $V_{1D}$ may be in the range from about 1.01 to 1.06, and preferably from about 1.03 to 1.05.

In FIG. 17A, coefficient $V_{2A}$ is preferably 1.00, because patients with a body mass index (BMI) below 32 should have a very good response to the acoustic pressure shock wave treatment and do not present any challenges from obesity point of view.

In FIG. 17A, coefficient $V_{2B}$ may be in the range from about 1.02 to 1.05, and preferably from about 1.03 to 1.04.

In FIG. 17A coefficient $V_{3A}$ is preferably 1.00, because patients with a weight below 220 lb/99.8 Kg should have a very good response to the acoustic pressure shock wave treatment and do not present any challenges from obesity point of view.

In FIG. 17A, coefficient $V_{3B}$ may be in the range from about 1.01 to 1.03, and preferably from about 1.02 to 1.03.

In FIG. 17B coefficient $V_{4A}$ is preferably 1.00 for a height below 70 in/177.8 cm.

In FIG. 17B, coefficient $V_{4B}$ may be in the range from about 1.00 to 1.02, and preferably from about 1.01 to 1.02.

In FIG. 17B, coefficient $V_{5A}$ is preferably 1.00, because patients with a HbA1c are controlling their diabetes and should have a very good response to the acoustic pressure shock wave treatment.

In FIG. 17B, coefficient $V_{5B}$ may be in the range from about 1.01 to 1.03, and preferably from about 1.02 to 1.03.

In FIG. 17B, coefficient $V_{5C}$ may be in the range from about 1.02 to 1.05, and preferably from about 1.03 to 1.05.

In FIG. 17B, coefficient $V_{6A}$ is preferably 1.00, because patients with very superficial wounds should have a very good response to the acoustic pressure shock wave treatment.

In FIG. 17B, coefficient $V_{6B}$ may be in the range from about 1.00 to 1.03, and preferably from about 1.01 to 1.02.

In FIG. 17B, coefficient $V_{6C}$ may be in the range from about 1.02 to 1.05, and preferably from about 1.04 to 1.05.

In FIG. 17C, coefficient $V_{7A}$ is preferably 1.00, because patients with an ankle-brachial index (ABI) between 0.7 and 1.2 should have a very good response to the acoustic pressure shock wave treatment.

In FIG. 17C, coefficient $V_{7B}$ may be in the range from about 1.00 to 1.03, and preferably from about 1.01 to 1.02.

In FIG. 17C, coefficient $V_{7C}$ may be in the range from about 1.01 to 1.04, and preferably from about 1.02 to 1.03.

In FIG. 17D, coefficient $V_{8A}$ is preferably 1.00, because patients with a $T_CP_{O2}$ value greater than 40 mmHg is normal and the patients should have a very good response to the acoustic pressure shock wave treatment.

In FIG. 17D, coefficient $V_{8B}$ may be in the range from about 1.01 to 1.04, and preferably from about 1.02 to 1.04.

In FIG. 17D, coefficient $V_{8C}$ may be in the range from about 1.02 to 1.05, and preferably from about 1.03 to 1.05.

In FIG. 17C, coefficient $V_{9A}$ is preferably 1.00, because patients with a colony forming units (CFU) of bacteria less than 1000 in the skin lesion should have a very good response to the acoustic pressure shock wave treatment.

In FIG. 17C, coefficient $V_{9B}$ may be in the range from about 1.01 to 1.04, and preferably from about 1.02 to 1.03.

In FIG. 17C, coefficient $V_{9C}$ may be in the range from about 1.04 to 1.08, and preferably from about 1.05 to 1.07.

In FIG. 17D coefficient $V_{10A}$ is preferably 1.00 because a non-smoker should have a very good response to the acoustic pressure shock wave treatment.

In FIG. 17D, coefficient $V_{10B}$ may be in the range from about 1.00 to 1.05, and preferably from about 1.02 to 1.04.

In FIG. 17D, coefficient $V_{11A}$ is preferably 1.00, because occasional drinking patients should have a very good response to the acoustic pressure shock wave treatment.

In FIG. 17D, coefficient $V_{11B}$ may be in the range from about 1.01 to 1.03, and preferably from about 1.02 to 1.03.

In FIG. 17D, coefficient $V_{11C}$ may be in the range from about 1.02 to 1.05, and preferably from about 1.03 to 1.04.

In FIG. 17D, coefficient $V_{12A}$ may be in the range from about 1.02 to 1.05, and preferably from about 1.03 to 1.04.

In FIG. 17D coefficient $V_{12B}$ is preferably 1.00 because a patient that is not on steroids therapy should have a very good response to the acoustic pressure shock wave treatment.

In FIG. 17E, coefficient $V_{13A}$ may be in the range from about 1.00 to 1.03, and preferably from about 1.01 to 1.02.

In FIG. 17E coefficient $V_{13B}$ is preferably 1.00 because a patient that is not on immunodeficiency therapy should have a very good response to the acoustic pressure shock wave treatment.

In FIG. 17E, coefficient $V_{14A}$ may be in the range from about 1.00 to 1.04, and preferably from about 1.02 to 1.04.

In FIG. 17E, coefficient $V_{14B}$ is preferably 1.00 because a patient that is not on chemotherapy or radiation therapy should have a very good response to the acoustic pressure shock wave treatment.

In FIG. 17E, coefficient $V_{15A}$ may be in the range from about 1.00 to 1.03, and preferably from about 1.01 to 1.02.

In FIG. 17E, coefficient $V_{15B}$ is preferably 1.00 because a patient without a pulmonary disease should have a very good response to the acoustic pressure shock wave treatment.

A control console/unit 22 and associated acoustic pressure shock wave applicator/treatment apparatus 10 (see FIG. 2A) used for delivering a treatment for common skin conditions by means of the proposed adjustment algorithm from FIGS. 17A-17E will use the following formula (where "A" is the initial number of focused acoustic pressure shock waves 40 or radial acoustic pressure waves 41 or planar acoustic pressure waves 42 or cylindrical acoustic pressure waves 44 delivered per treatment and "ATN" is the Adjusted Total Number of focused acoustic pressure shock waves 40 or radial acoustic pressure waves 41 or planar acoustic pressure waves 42 or cylindrical acoustic pressure waves 44 delivered per treatment):

$$\text{ATN} = A \cdot V_1 \cdot V_2 \cdot V_3 \cdot V_4 \cdot V_5 \cdot V_6 \cdot V_7 \cdot V_8 \cdot V_9 \cdot V_{10} \cdot V_{11} \cdot V_{12} \cdot V_{13} \cdot V_{14} \cdot V_{15}.$$

For the largest values for these coefficients (worst situation) and for example a number of A=500 is used as initial number of focused acoustic pressure shock waves 40 or radial acoustic pressure waves 41 or planar acoustic pressure waves 42 or cylindrical acoustic pressure waves 44 that are minimally needed for successful treatment of the tissue condition 19, then the Adjusted Total Number (ATN) value of focused acoustic pressure shock waves 40 or radial acoustic pressure waves 41 or planar acoustic pressure waves 42 or cylindrical acoustic pressure waves 44 delivered per treatment is the following:

$$\text{ATN} = 500 \cdot 1.06 \cdot 1.05 \cdot 1.03 \cdot 1.02 \cdot 1.05 \cdot 1.05 \cdot 1.04 \cdot 1.05 \cdot 1.08 \cdot 1.05 \cdot 1.05 \cdot 1.05 \cdot 1.03 \cdot 1.04 \cdot 1.03 = 970.96 \approx 971 \text{ shocks}.$$

Similar algorithms and principles, as the ones presented in the embodiments of this invention, can be used/applied to other medical treatments for soft, semi-hard, or hard tissues in the medical treatments using focused acoustic pressure shock waves 40 or radial acoustic pressure waves 41 or planar acoustic pressure waves 42 or cylindrical acoustic pressure waves 44 for tissue regeneration in general, abnormal organ functioning, infections, cartilage or muscle or skin or ligaments or tendon tears, erectile dysfunction (ED), bone fractures, bone fusion, bone spurs, heterotopic ossifications, calcifications, plaque formation on teeth, pain and inflammation management, tissue necrosis, autoimmune diseases, blood vessels plaques, cardiac and endovascular obstructions and occlusions, blood vessels restenosis after angioplasty or stenting, heart muscle ischemia, lymphedema, organs and tissue hyperplasia, adhesions between organs after surgeries in the abdominal or muscular or chest areas, capsular contracture around implants, implant infections, cellulite, body sculpting, spider veins, skin rejuvenation, scar tissue and fibrotic tissue, tissue spasm/contraction, peripheral nerves to reduce pain or promote nerve regeneration and repair, tissue growth and/or angiogenesis or vasculogenesis, auto-immune diseases such as Systemic Lupus Erythematosus or Scleroderma or Crohn's Disease or Dermatomyositis, cancer tumors or unwanted benign tissue, bacterial or abacterial prostatitis (chronic pelvic syndrome), interstitial cystitis, and the like.

All the algorithms presented in the various embodiments of this invention are may be carried out automatically by the control console/unit 22 and/or artificial intelligence (A/I) device 27, via the control console/unit processor 2200 and/or artificial intelligence (A/I) device processor 2700, respectively (see FIG. 2A and FIG. 2B) and then the output is used to automatically control performance of treatments with the acoustic pressure shock wave applicator/treatment apparatus 10.

Referring again to FIG. 2A, the control console/unit I/O (input/output) element 2230, and/or artificial intelligence (A/I) device processor 2700, or by using any devices that are interconnected with either the control console/unit processor 2200 or artificial intelligence (A/I) device processor 2700, as shown for the medical treatment system 2000, introduce data necessary to alter the initial/minimal dosages, and/or energy settings, and/or number of treatments. Exemplary interconnected devices, include a desktop computer 28A, or a smart phone 28B, or a tablet 28C, or a laptop 28D, or any other device that have input/output (I/O) and are communication capabilities, such as wireless connections like Bluetooth or Wi-Fi, or physical/cable connections. Also the patient's tissue condition 19 characteristics, comorbidities, biometrics, behavioral data necessary for the algorithms is taken/recorded via dedicated questions that are displayed on the control console/unit I/O (input/output) element 2230, and/or artificial intelligence (A/I) device I/O (input/output) element 2750, and/or on any devices interconnected as a desktop computer 28A, or a smart phone 28B, or a tablet 28C, or a laptop 28D, or any other device that has display, input/output (I/O), and wireless or physical/cable communication capability. Finally, this information is stored on the control console/unit memory 2210 and/or artificial intelligence (A/I) device memory 2760 in order to be used and processed by the control console/unit processor 2200 and/or artificial intelligence (A/I) device processor 2700, respectively.

The embodiments of this invention that show different optimization algorithms can be done automatically by the control console/unit 22 and/or artificial intelligence (A/I) device 27 and then used to perform treatments with the associated acoustic pressure shock wave applicator/treatment apparatus 10. Having almost the similar type of questions that were used for determining the adjusted number of treatments or adjusted energy settings or adjusted dosage/number of focused acoustic pressure shock waves 40 or radial acoustic pressure waves 41 or planar acoustic pressure waves 42 or cylindrical acoustic pressure waves 44 will allow the control console/unit display 2220, or artificial intelligence (A/I) device display 2740, or the interconnected device (see FIG. 2A for the medical treatment system 2000) as a desktop computer 28A, or a smart phone 28B, and/or tablet 28C, and/or laptop 28D to be used to simultaneously adjust all of these treatment factors (dosage, energy setting, and total number of treatments).

In other embodiments of the invention, other values may be used in place of coefficients to alter the initial focused acoustic pressure shock waves 40 or radial acoustic pressure waves 41 or planar acoustic pressure waves 42 or cylindrical acoustic pressure waves 44 known as dosage, and/or energy setting, and/or total number of treatments, including altering interim value/numbers for these parameters during processing of the algorithms based on inputs in response to patient questions. For example, a predetermined percentage may be used to alter the focused acoustic pressure shock waves 40 or radial acoustic pressure waves 41 or planar acoustic pressure waves 42 or cylindrical acoustic pressure waves 44 known as dosage, and/or energy setting, and/or total number of treatments instead of, but similar to, a coefficient. In other exemplary embodiments, a predetermined number of focused acoustic pressure shock waves 40 or radial acoustic pressure waves 41 or planar acoustic pressure waves 42 or cylindrical acoustic pressure waves 44 known as dosage, and/or predetermined energy setting, and/or predetermined total number of treatments may be added to the initial dosage, and/or energy setting, and/or total number of treatments, including added to interim numbers/values for these parameters, during processing of an algorithm to determine an adjusted dosage, and/or energy setting, and/or total number of treatments for a patient. It will be appreciated that such alternatives for altering dosage, and/or energy setting, and/or total number of treatments could be used alternatively or in combination with each other for any particular embodiment of algorithm processing in a treatment embodiment.

As described, the acoustic pressure waves used in the invention may be focused or non-focused and may be non-sinusoidal, sharp and high pressure waves having a relatively short distance in time between the crest and trough of the wave. However, in some embodiments, the pressure waves can be sinusoidal, ultrasonic focused or non-focused waves, or microwaves.

While the invention has been described in the associated embodiments with reference to exemplary structures and methods, the invention is not intended to be limited thereto, but to extend to modifications and improvements within the scope of equivalence of such claims to the invention.

What is claimed is:

1. A system for treating a tissue condition of a human or animal patient comprising:
    an electronic acoustic pressure shock wave applicator including a shock wave generation source enclosed within liquid by a coupling membrane;
    an electronic controller coupled to the acoustic pressure shock wave applicator and including a microprocessor and a non-transitory microprocessor-readable data storage medium having microprocessor-executable instructions for the microprocessor to adjust an initial treatment regimen based on type of tissue condition and treatment area or treatment volume, wherein the initial treatment regimen includes at least one of a number of shock waves per treatment, shock wave input energy per treatment and number of shock wave treatment sessions, to an adjusted individualized treatment regimen that changes the initial treatment regimen in response to inputs providing individualized patient parameters wherein each individualized patient parameter is selected from the group consisting of tissue condition state parameter, comorbidity parameter, physical characteristic parameter and lifestyle habit parameter of the patient, wherein said electronic controller is communicatively coupled for wireless or wired communication to the acoustic pressure shock wave applicator and causes the applicator to automatically generate the adjusted individualized treatment regimen to the patient; and
    an electronic input device receiving input data in response to questions from a patient questionnaire displayed to a user of the electronic input device and communicatively coupled for wireless or wired transmission of the input data to the electronic controller for determination of the individualized patient parameters and corresponding changes to the initial treatment regimen to arrive at the adjusted individualized treatment regimen, wherein the corresponding changes to the initial treatment regimen include automatic adjustment of the at least one of a number of shock waves per treatment, shock wave input energy per treatment and number of shock wave treatment sessions via multiplication with a coefficient value assigned to each individualized patient parameter to arrive at the adjusted individualized treatment regimen.

2. The system of claim 1, wherein the individualized patient parameters are selected from the group consisting of age, medical condition, disease condition, location of the tissue condition, body mass index, weight, height, glycated hemoglobin, ankle-brachial index, transcutaneous monitoring of oxygen measurement, age of wound, bacterial load colony forming unit measurement, smoker status, alcohol consumption, steroids therapy, presence of osteomyelitis, chemotherapy or radiation therapy, immunodeficiency therapy, lung disease, and good patient compliance.

3. The system of claim 2, wherein the tissue condition is a diabetic foot ulcer.

4. The system of claim 3, wherein the shock wave applicator generates acoustic pressure shock waves selected from the group consisting of focused, unfocused, planar, pseudo-planar, cylindrical, and radial extracorporeal acoustic pressure shock waves.

5. The system of claim 3, wherein the electronic controller is selected from the group consisting of an artificial intelligence device controller and a control console controller.

6. The system of claim 2, wherein the tissue condition is a skin condition.

7. The system of claim 6, wherein the skin condition is selected from the group consisting of a burn, wound, pressure ulcer, arterial ulcer, and venous ulcer.

8. The system of claim 7, wherein the shock wave applicator generates acoustic pressure shock waves selected from the group consisting of focused, unfocused, planar, pseudo-planar, cylindrical, and radial extracorporeal acoustic pressure shock waves.

9. The system of claim 2, wherein the shock wave applicator generates acoustic pressure shock waves selected from the group consisting of focused, unfocused, planar, pseudo-planar, cylindrical, and radial extracorporeal acoustic pressure shock waves.

10. The system of claim 2, wherein the electronic controller is selected from the group consisting of an artificial intelligence device controller and a control console controller.

11. The system of claim 2, wherein the tissue condition is a condition selected from the group consisting of tissue needing regeneration, abnormal organ functioning, infections, injuries to cartilage, muscle condition, skin condition, condition of ligaments or tendons, erectile dysfunction, bone fractures, bone fusion, bone spurs, heterotopic ossifications, calcifications, plaque formation on teeth, pain and inflammations, tissue necrosis, autoimmune diseases, blood vessels plaques, cardiac and endovascular obstructions and occlusions, blood vessels restenosis after angioplasty or stenting, heart muscle ischemia, lymphedema, organs and tissue hyperplasia, adhesions between organs after surgeries in abdominal, muscular or chest areas, capsular contracture around implants, implant infections, cellulite, body sculpting, spider veins, skin rejuvenation, scar tissue, fibrotic tissue, tissue spasm, tissue contraction, peripheral nerve condition to reduce pain or promote nerve regeneration and repair, tissue growth, angiogenesis, vasculogenesis, cancer tumors, unwanted benign tissue, bacterial or abacterial prostatitis, chronic pelvic syndrome, and interstitial cystitis.

12. The system of claim 2, wherein the tissue condition is a skin condition selected from the group consisting of diabetic foot ulcers, pressure sores, ulcers, arterial ulcers, venous ulcers, burns, birthmarks, hemangiomas, moles, freckles, melisma, skin tags, eczema, psoriasis, acne, rosacea, porphyria, pyodema gangrenosum, cold sores, plantar and palmer warts, blisters, chafing, corns and calluses, gangrene, rashes, dermatitis, cysts, skin lumps, urticarial, alopecia areata, vitiligo, varicose veins, spider veins, intertrigo, lice, scabies, bruises, epidermoid cysts, keloids, bacterial skin infections, leprosy, carbuncles, staph infection, impetigo, boils, pilonidal cysts, abscesses, fungal skin infections, tinea, athlete's foot, candidiasis, sporotrichosis, fungal nail infection, viral infections, molluscum contagiosum, shingles, chickenpox, skin cancer, melanoma, carcinoma, acute cuts, traumatic wounds, reconstructive skin flaps, and surgery wounds.

13. The system of claim 1, wherein the tissue condition is a diabetic foot ulcer.

14. The system of claim 13, wherein the shock wave applicator generates acoustic pressure shock waves selected from the group consisting of focused, unfocused, planar, pseudo-planar, cylindrical, and radial extracorporeal acoustic pressure shock waves.

15. The system of claim 13, wherein the electronic controller is selected from the group consisting of an artificial intelligence device controller and a control console controller.

16. The system of claim 1, wherein the tissue condition is a skin condition.

17. The system of claim 16, wherein the skin condition is selected from the group consisting of a burn, wound, pressure ulcer, arterial ulcer, and venous ulcer.

18. The system of claim 16, wherein the shock wave applicator generates acoustic pressure shock waves selected from the group consisting of focused, unfocused, planar, pseudo-planar, cylindrical, and radial extracorporeal acoustic pressure shock waves.

19. The system of claim 1, wherein the shock wave applicator generates acoustic pressure shock waves selected from the group consisting of focused, unfocused, planar, pseudo-planar, cylindrical, and radial extracorporeal acoustic pressure shock waves.

20. The system of claim 1, wherein the electronic controller is selected from the group consisting of an artificial intelligence device controller and a control console controller.

21. The system of claim 1, wherein the tissue condition is a condition selected from the group consisting of tissue needing regeneration, abnormal organ functioning, infections, injuries to cartilage, muscle condition, skin condition, condition of ligaments or tendons, erectile dysfunction, bone fractures, bone fusion, bone spurs, heterotopic ossifications, calcifications, plaque formation on teeth, pain and inflammations, tissue necrosis, autoimmune diseases, blood vessels plaques, cardiac and endovascular obstructions and occlusions, blood vessels restenosis after angioplasty or stenting, heart muscle ischemia, lymphedema, organs and tissue hyperplasia, adhesions between organs after surgeries in abdominal, muscular or chest areas, capsular contracture around implants, implant infections, cellulite, body sculpting, spider veins, skin rejuvenation, scar tissue, fibrotic tissue, tissue spasm, tissue contraction, peripheral nerve condition to reduce pain or promote nerve regeneration and repair, tissue growth, angiogenesis, vasculogenesis, cancer tumors, unwanted benign tissue, bacterial or abacterial prostatitis, chronic pelvic syndrome, and interstitial cystitis.

22. The system of claim 1, wherein the tissue condition is a skin condition selected from the group consisting of diabetic foot ulcers, pressure sores, ulcers, arterial ulcers, venous ulcers, burns, birthmarks, hemangiomas, moles, freckles, melisma, skin tags, eczema, psoriasis, acne, rosacea, porphyria, pyodema gangrenosum, cold sores, plantar and palmer warts, blisters, chafing, corns and calluses, gangrene, rashes, dermatitis, cysts, skin lumps, urticarial, alopecia areata, vitiligo, varicose veins, spider veins, intertrigo, lice, scabies, bruises, epidermoid cysts, keloids, bacterial skin infections, leprosy, carbuncles, staph infection, impetigo, boils, pilonidal cysts, abscesses, fungal skin infections, tinea, athlete's foot, candidiasis, sporotrichosis, fungal nail infection, viral infections, molluscum contagiosum, shingles, chickenpox, skin cancer, melanoma, carcinoma, acute cuts, traumatic wounds, reconstructive skin flaps, and surgery wounds.

23. A system for treating a tissue condition of a human or animal patient comprising:
an electronic acoustic pressure shock wave applicator including an acoustic pressure shock wave generation source enclosed within liquid by a coupling membrane;
an electronic controller coupled to the shock wave applicator and including a microprocessor and a non-transitory microprocessor-readable data storage medium having microprocessor-executable instructions for the microprocessor to increase an initial acoustic pressure shock waves dosage based on type of condition and treatment area or treatment volume to an adjusted individualized acoustic pressure shock waves dosage calculated through a plurality of dosage changes to the initial acoustic pressure shock waves dosage wherein each dosage change corresponds to an individualized patient parameter selected from the group consisting of a tissue condition state, comorbidity parameter, physical characteristic parameter and lifestyle habit parameter of the patient, wherein said electronic controller is communicatively coupled for wireless or wired communication to the acoustic pressure shock wave applicator and causes the applicator to automatically generate the adjusted individualized acoustic pressure shock waves dosage to the patient during treatment of the tissue condition; and
an electronic input device receiving data input in response to questions from a patient questionnaire displayed to a user of the electronic input device and communicatively coupled for wireless or wired transmission of the input data to the electronic controller for determination of the dosage changes corresponding to the individualized patient parameters, wherein the corresponding changes to the initial acoustic pressure shock waves dosage include automatic adjustment of the initial acoustic pressure shock waves dosage via multiplication with a coefficient value assigned to each individualized patient parameter to arrive at the adjusted individualized acoustic pressure shock wave dosage.

24. The system of claim 23, wherein the tissue condition is a diabetic foot ulcer.

25. The system of claim 23, wherein the tissue condition is a skin condition selected from the group consisting of diabetic foot ulcers, pressure sores, ulcers, arterial ulcers, venous ulcers, burns, birthmarks, hemangiomas, moles, freckles, melisma, skin tags, eczema, psoriasis, acne, rosacea, porphyria, pyodema gangrenosum, cold sores, plantar and palmer warts, blisters, chafing, corns and calluses, gangrene, rashes, dermatitis, cysts, skin lumps, urticarial, alopecia areata, vitiligo, varicose veins, spider veins, intertrigo, lice, scabies, bruises, epidermoid cysts, keloids, bacterial skin infections, leprosy, carbuncles, staph infection, impetigo, boils, pilonidal cysts, abscesses, fungal skin infections, tinea, athlete's foot, candidiasis, sporotrichosis, fungal nail infection, viral infections, molluscum contagiosum, shingles, chickenpox, skin cancer, melanoma, carcinoma, acute cuts, traumatic wounds, reconstructive skin flaps, and surgery wounds.

26. The system of claim 23, wherein the tissue condition is a condition selected from the group consisting of tissue needing regeneration, abnormal organ functioning, infections, injuries to cartilage, muscle condition, skin condition, condition of ligaments or tendons, erectile dysfunction, bone fractures, bone fusion, bone spurs, heterotopic ossifications, calcifications, plaque formation on teeth, pain and inflammations, tissue necrosis, autoimmune diseases, blood vessels plaques, cardiac and endovascular obstructions and occlusions, blood vessels restenosis after angioplasty or stenting, heart muscle ischemia, lymphedema, organs and tissue hyperplasia, adhesions between organs after surgeries in abdominal, muscular or chest areas, capsular contracture around implants, implant infections, cellulite, body sculpting, spider veins, skin rejuvenation, scar tissue, fibrotic tissue, tissue spasm, tissue contraction, peripheral nerve condition to reduce pain or promote nerve regeneration and repair, tissue growth, angiogenesis, vasculogenesis, cancer tumors, unwanted benign tissue, bacterial or abacterial prostatitis, chronic pelvic syndrome, and interstitial cystitis.

* * * * *